(12) United States Patent
Bueno Melendo et al.

(10) Patent No.: US 7,618,978 B2
(45) Date of Patent: Nov. 17, 2009

(54) AMIDES AS BACE INHIBITORS

(75) Inventors: Ana Belen Bueno Melendo, Madrid (ES); Shu-Hui Chen, Carmel, IN (US); Maria Rosario Gonzalez-Garcia, Madrid (ES); James Ray McCarthy, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 398 days.

(21) Appl. No.: 10/599,125

(22) PCT Filed: Apr. 8, 2005

(86) PCT No.: PCT/US2005/012189

§ 371 (c)(1),
(2), (4) Date: Sep. 20, 2006

(87) PCT Pub. No.: WO2005/108391

PCT Pub. Date: Nov. 17, 2005

(65) Prior Publication Data

US 2007/0225372 A1    Sep. 27, 2007

Related U.S. Application Data

(60) Provisional application No. 60/564,538, filed on Apr. 22, 2004.

(51) Int. Cl.
*A61K 31/445*    (2006.01)

(52) U.S. Cl. .................................... 514/278; 546/192
(58) Field of Classification Search .................. 546/192
See application file for complete search history.

(56) References Cited

U.S. PATENT DOCUMENTS

2007/0213331 A1    9/2007    Dally et al.

FOREIGN PATENT DOCUMENTS

| WO | WO 89/03842 | 5/1989 |
|----|----|----|
| WO | WO2004/024081 | 3/2004 |
| WO | WO 2004/043916 | 5/2004 |
| WO | WO 2005/014540 | 2/2005 |
| WO | WO2005/016876 A | 2/2005 |
| WO | WO 2005/108358 | 11/2005 |
| WO | WO 2006/034093 | 3/2006 |

*Primary Examiner*—James O Wilson
*Assistant Examiner*—Brian McDowell
(74) *Attorney, Agent, or Firm*—Elizabeth Dingess-Hammond; Robert D. Titus

(57) ABSTRACT

The present invention provides BACE inhibitors of Formula (I): methods for their use, and intermediates and methods for their preparation.

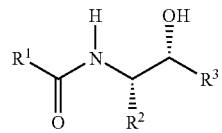

(I)

4 Claims, No Drawings

AMIDES AS BACE INHIBITORS

This application is a United States national phase entry, pursuant to 35 U.S.C. 371, of PCT/US2005/033277, filed Apr. 8, 2005, which claims benefit of U.S. provisional patent application Ser. No. 60/564,538, filed Apr. 22, 2004.

BACKGROUND OF THE INVENTION

Alzheimer's disease, characterized by cognitive and behavioral deterioration in its latter stages, has emerged as a significant social and financial concern. With a prevalence approaching 5.5% in the population above the age of 60, the cost for care of Alzheimer's disease patients has been estimated to be in excess of $100 billion annually. Although cholinesterase inhibitors are somewhat effective in reducing the symptoms of Alzheimer's disease, particularly when the disease is in its early phases, they are not at all effective in slowing or stopping the progression of the disease.

Neurofibrillary tangles and neuritic plaques are generally found in the brain regions associated with memory and cognition of those afflicted with Alzheimer's disease. These plaques are also found in the brains of individuals with Down's syndrome, Hereditary Cerebral Hemorrhage of the Dutch-Type, and other neurodegenerative disorders. The neuritic plaques are comprised primarily of amyloid β (Aβ) peptide, a neurotoxic and highly aggregatory peptide segment of amyloid precursor protein (APP). Aβ peptide is formed by the proteolytic cleavage of APP by β-secretase (BRACE) followed by at least one subsequent C-terminal cleavage by γ-secretase. As such, inhibition of BRACE is an attractive target for the treatment or prevention of Alzheimer's disease as well as other diseases characterized pathologically by amyloid plaques.

BRACE is a member of the pepsin sub-family of mammalian aspartic protease and, like its substrate APP, is a type I transmembrane protein. BRACE has been disclosed in the literature and is referred to also as "β-site APP-cleaving enzyme", "membrane aspartic protease of the pepsin family", "Asp-2", "β-secretase", "membrane-bound aspartic protease" and "Memapsin 2" (See: Ghosh, et al., *Current Medicinal Chemistry*, 9(11), 1135-1144 (2002)). Two isoforms of BRACE have been identified in humans, designated BACE1 and BACE2. It is believed that the BACE1 inhibitory activity is most important to inhibition of amyloid β (Aβ) peptide (Roggo, *Current Topics in Medicinal Chemistry*, 2, 359-370 (2002)). Currently described BRACE inhibitors are peptidomimetic transition state analogs, typically containing a hydroxyethyl moiety. Although many of these compounds are potent inhibitors of BRACE, their high molecular weights and low membrane permeability make them poor drug candidates. (See: Park and Lee, *Journal of the American Chemical Society*, 125(52), 16416-16422 (2003)). Additional compounds described as BRACE inhibitors are disclosed in WO 03/040096, WO 04/024081, WO 04/0039034, and WO 04/043916. Additional BRACE inhibitors are necessary to provide treatments for A-β peptide mediated disorders such as Alzheimer's disease. The present invention provides new inhibitors of BRACE.

BRIEF SUMMARY OF THE INVENTION

The present invention provides compounds of Formula I:

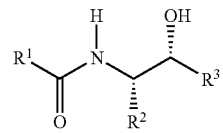

I where:

$R^1$ is $(C_3\text{-}C_7$ cycloalkyl$)_{0\text{-}1}(C_1\text{-}C_6$ alkyl$)$, $(C_3\text{-}C_7$ cycloalkyl$)_{0\text{-}1}(C_2\text{-}C_6$ alkenyl$)$, $(C_3\text{-}C_7$ cycloalkyl$)_{0\text{-}1}(C_2\text{-}C_6$ alkynyl$)$ or $C_3\text{-}C_7$ cycloalkyl, each optionally substituted with up to three groups independently selected from halo, hydroxy, thiol, cyano, trifluoromethyl, trifluoromethoxy, $C_1\text{-}C_7$ alkoxy, $C_3\text{-}C_7$ cycloalkoxy, oxo, and $NR^4R^5$, biphenyl optionally substituted with halo, hydrogen,

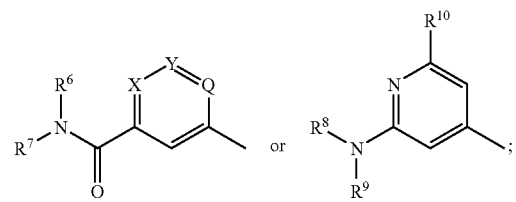

$R^2$ is $C_1\text{-}C_3$ alkyl, benzyl optionally monosubstituted in the phenyl ring with a substituent selected from the group consisting of halo, $C_1\text{-}C_6$ alkoxy optionally substituted in the alkyl chain with $C_3\text{-}C_7$ cycloalkyl, and $C_1\text{-}C_6$ alkylthio optionally substituted in the alkyl chain with $C_3\text{-}C_7$ cycloalkyl, or benzyl optionally disubstituted in the phenyl ring with a first substituent independently selected from halo and a second substituent independently selected from halo, $C_1\text{-}C_6$ alkoxy optionally substituted in the alkyl chain with $C_3\text{-}C_7$ cycloalkyl, and $C_1\text{-}C_6$ alkylthio optionally substituted in the alkyl chain with $C_3\text{-}C_7$ cycloalkyl;

$R^3$ is:

i) a piperidin-2-yl moiety of formula:

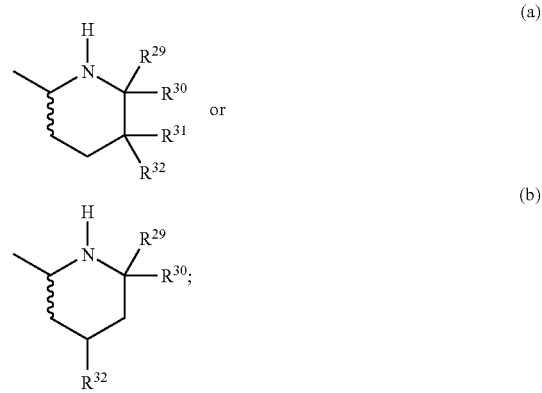

ii) a tetrahydropyridin-2-yl moiety of formula:

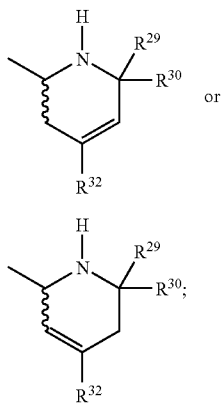

(c)

(d)

iii) a piperazin-2-yl moiety of formula:

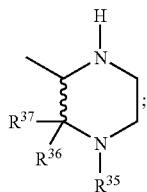

(e)

iv) homopiperidin-2-yl;
v) 1,2,3,4-tetrahydroisoquinolin-3-yl optionally substituted with one or two substituents selected from halo, $C_1$-$C_6$ alkyl, and $C_1$-$C_6$ alkoxy;
vi) 2-azabicyclo[2.2.2]oct-(5Z)ene-3-yl;
vii) 2-azabicyclo[2.2.1]hept-3-yl optionally substituted with $C_1$-$C_{10}$ alkyl optionally substituted with $C_1$-$C_4$ alkoxy; or
viii) 2-azabicyclo[2.2.2]oct-3-yl optionally substituted with oxo, or optionally substituted with one or two substituents independently selected from hydroxy, fluoro, and $C_1$-$C_6$ alkyl;

X is CH, N, or $N^+$—$O^-$;
Y is $CR^{11}$, N, or $N^+$—$O^-$;
Q is $CR^{12}$, N, or $N^+$—$O^-$;
$R^4$ is hydrogen, $C_1$-$C_6$ alkyl optionally substituted up to three times with fluoro, or phenyl;
$R^5$ is hydrogen, $C_1$-$C_6$ alkyl optionally substituted up to three times with fluoro, phenyl, —C(O)($C_1$-$C_6$ alkyl optionally substituted up to three times with fluoro), or —$SO_2$($C_1$-$C_6$ alkyl optionally substituted up to three times with fluoro);
$R^6$ and $R^7$ are independently selected from the group consisting of methyl, ethyl, and propyl;
$R^8$ is hydrogen or $C_1$-$C_6$ alkyl;
$R^9$ is $C_3$-$C_5$ cycloalkyl, sec-butyl, or —$CH_2R^{13}$;
$R^{10}$ is —$CF_2R^{14}$, —$OR^{15}$, —$CH_2C(O)CH_3$, —$S(O)_{1-2}R^{16}$, —$NR^{17}SO_2R^{18}$, ($C_1$-$C_3$ alkoxy)-carbonyl, phenyl optionally substituted with halo, 1,3-dioxolan-2-yl, 1,3-dioxan-2-yl, 1,1-dioxo-2,3,4,5-tetrahydroisothiazol-2-yl, or tetrazol-5-yl optionally substituted with $C_1$-$C_3$ alkyl;
$R^{11}$ is hydrogen, chloro, isobutyl, $CH_2R^{19}$, $CF_2R^{20}$, 1,1,1-trifluoro-2-hydroxyeth-2-yl, $C_2$-$C_4$ alkenyl optionally substituted with one or two fluorine atoms, $OR^{21}$, $C(O)R^{22}$, N(methyl)(methylsulfonyl), N(methyl)(acetyl), pyrrolidin-2-on-1-yl, methylsulfonyl, N,N-dimethylaminosulfonyl, phenyl optionally substituted with one or two substituents selected from the group consisting of hydroxymethyl, methoxy, fluoro, and methylsulfonyl, 1,3-dioxolan-2-yl, 1,3-dithiolan-2-yl, 1,3-oxathiolan-2-yl, 1,3-dioxan-2-yl, 1,3-dithian-2-yl, pyridinyl, thiazolyl, oxazolyl, or 1,2,4-oxadiazolyl optionally substituted with methyl;
$R^{12}$ is hydrogen or fluoro;
$R^{13}$ is ethynyl or cyclopropyl;
$R^{14}$ is hydrogen or methyl;
$R^{15}$ is difluoromethyl or methanesulfonyl;
$R^{16}$ is $C_1$-$C_4$ alkyl, $C_3$-$C_6$ cycloalkyl, phenyl, or —$NR^{25}R^{26}$;
$R^{17}$ is hydrogen, $C_1$-$C_3$ alkyl optionally substituted with up to 3 fluorine atoms, or $C_3$-$C_6$ cycloalkyl;
$R^{18}$ is $C_1$-$C_3$ alkyl or $C_3$-$C_6$ cycloalkyl;
$R^{19}$ is fluoro, hydroxy, or $C_1$-$C_3$ alkoxy;
$R^{20}$ is hydrogen, phenyl, or furyl;
$R^{21}$ is $C_1$-$C_3$ alkyl optionally substituted with one or two fluorine atoms;
$R^{22}$ is $C_1$-$C_3$ alkyl, $C_3$-$C_5$ cycloalkyl, $C_2$-$C_3$ alkenyl, $C_1$-$C_3$ alkoxy, $NR^{23}R^{24}$, pyrrolidin-1-yl optionally substituted with methyl or one or two fluorine atoms, piperidin-1-yl, phenyl, pyridinyl, or furyl;
$R^{23}$ is hydrogen or methyl;
$R^{24}$ is methyl, ethyl, or propyl;
$R^{25}$ is hydrogen or methyl;
$R^{26}$ is methyl; or
$R^{24}$ and $R^{26}$ taken together with the nitrogen atom to which they are attached form a pyrrolidine or piperidine ring;
$R^{29}$ is hydrogen or $C_1$-$C_6$ alkyl;
$R^{30}$ is hydrogen or $C_1$-$C_6$ alkyl;
$R^{29}$ and $R^{30}$ taken together with the carbon to which they are attached form a $C_3$-$C_6$ cycloalkyl ring;
$R^{31}$ is hydrogen, $C_1$-$C_6$ alkyl, $C_3$-$C_6$ cycloalkyl, or phenyl optionally monosubstituted with $C_1$-$C_6$ alkyl;
$R^{32}$ is hydrogen, $R^{33}$, or —$(CH_2)_{0-2}$—$OR^{33}$;
$R^{33}$ is $C_1$-$C_{10}$ alkyl optionally substituted with 1-6 fluorine atoms, $C_2$-$C_6$ alkenyl, $C_2$-$C_6$ alkynyl, or —$(CH_2)_{0-3}$—$R^{34}$;
$R^{34}$ is $C_3$-$C_7$ cycloalkyl or phenyl each optionally substituted with one or two substitutents independently selected from the group consisting of halo, $C_1$-$C_6$ alkyl, $C_1$-$C_6$ alkoxy, hydroxy, trifluoromethyl, and trifluoromethoxy, thienyl optionally substituted with halo, benzothienyl optionally substituted with halo, thiazolyl optionally substituted with $C_1$-$C_4$ alkyl, or adamantyl,
$R^{35}$ is —$(CH_2)_{0-6}$—$R^{34}$, —$C(O)$—$(CH_2)_{0-6}$—$R^{34}$, —$C(O)$—$(C_1$-$C_{10}$ alkyl), —$C(O)$—$(C_1$-$C_4$ alkoxy optionally substituted with phenyl), $C_1$-$C_{10}$ alkyl optionally substituted with 1-6 fluorine atoms, $C_2$-$C_{10}$ alkenyl, or $C_2$-$C_{10}$ alkynyl;
$R^{36}$ and $R^{37}$ are both hydrogen or, taken together with the carbon atom to which they are attached form a carbonyl group; or a pharmaceutically acceptable salt thereof; provided that: a) no more than one of X, Y, and Q may be N or $N^+$—$O^-$; and b) when X is CH, Y is $CR^{11}$, and Q is $CR^{12}$, then one of $R^{11}$ and $R^{12}$ is other than hydrogen.

The present invention also provides a method of treating Alzheimer's disease in a mammal comprising administering to a mammal in need of such treatment an effective amount of a compound of Formula I.

The present invention further provides a method of preventing the progression of mild cognitive impairment to Alzheimer's disease in a mammal comprising administering to a mammal in need of such treatment an effective amount of a compound of Formula I.

The present invention also provides a method of inhibiting BRACE in a mammal comprising administering to a mammal in need of such treatment an effective amount of a compound of Formula I.

The present invention also provides a method for inhibiting β-secretase mediated cleavage of amyloid precursor protein comprising administering to a mammal in need of such treatment an effective amount of a compound of Formula I.

The present invention further provides a method for the inhibition of production of A-β peptide comprising administering to a mammal in need of such treatment an effective amount of a compound of Formula I.

The present invention also provides a pharmaceutical formulation comprising a compound of Formula I, in combination with a pharmaceutically acceptable carrier, diluent, or excipient.

Furthermore, this invention provides the use of a compound of Formula I for the manufacture of a medicament for the treatment of Alzheimer's disease. This invention also provides the use of a compound of Formula I for the manufacture of a medicament for the prevention of the progression of mild cognitive impairment to Alzheimer's disease. The invention also provides the use of a compound of Formula I for the manufacture of a medicament for the inhibition of BRACE. The present invention also provides the use of a compound of Formula I for the manufacture of a medicament for the inhibition of β-secretase mediated cleavage of amyloid precursor protein. The invention further provides the use of a compound of Formula I for the manufacture of a medicament for the inhibition of production of A-β peptide.

Additionally, this invention provides a pharmaceutical formulation adapted for the treatment of Alzheimer's disease. Furthermore, this invention provides a pharmaceutical formulation adapted for the prevention of the progression of mild cognitive impairment to Alzheimer's disease. This invention also provides a pharmaceutical formulation adapted for the inhibition of BRACE.

Furthermore the present invention provides a pharmaceutical formulation adapted for the inhibition of β-secretase mediated cleavage of amyloid precursor protein. The present invention also provides a pharmaceutical formulation adapted for the treatment of conditions resulting from excessive levels of A-β peptide comprising a compound of Formula I or a pharmaceutically acceptable salt thereof in combination with one or more pharmaceutically acceptable excipients, carriers, or diluents.

This invention also provides intermediates of Formula II:

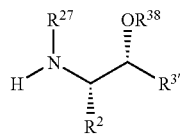

where:

$R^2$ is $C_1$-$C_3$ alkyl, benzyl optionally monosubstituted in the phenyl ring with a substituent selected from the group consisting of halo, $C_1$-$C_6$ alkoxy optionally substituted in the alkyl chain with $C_3$-$C_7$ cycloalkyl, and $C_1$-$C_6$ alkylthio optionally substituted in the alkyl chain with $C_3$-$C_7$ cycloalkyl, or benzyl optionally disubstituted in the phenyl ring with a first substituent independently selected from halo and a second substituent independently selected from halo, $C_1$-$C_6$ alkoxy optionally substituted in the alkyl chain with $C_3$-$C_7$ cycloalkyl, and $C_1$-$C_6$ alkylthio optionally substituted in the alkyl chain with $C_3$-$C_7$ cycloalkyl;

$R^3$ is:

ix) a piperidin-2-yl moiety of formula:

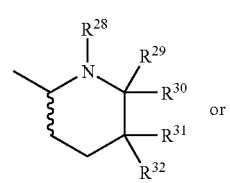

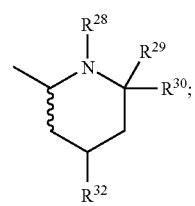

x) a tetrahydropyridin-2-yl moiety of formula:

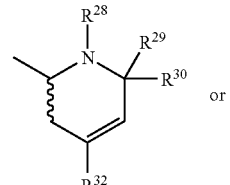

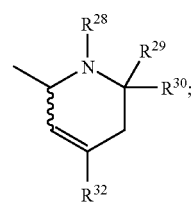

xi) a piperazin-2-yl moiety of formula:

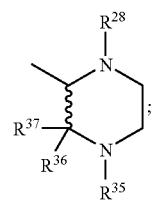

xii) homopiperidin-2-yl substituted in the 1-position with variable $R^{28}$;

xiii) 1,2,3,4-tetrahydroisoquinolin-3-yl substituted in the 1-position with variable $R^{28}$ and optionally further substituted with one or two substituents selected from halo, $C_1$-$C_6$ alkyl, and $C_1$-$C_6$ alkoxy;

xiv) 2-azabicyclo[2.2.2]oct-(5Z)ene-3-yl substituted in the 2-position with variable $R^{28}$;

xv) 2-azabicyclo[2.2.1]hept-3-yl substituted in the 2-position with variable $R^{28}$ and optionally further substituted with $C_1$-$C_{10}$ alkyl optionally substituted with $C_1$-$C_4$ alkoxy; or xvi) 2-azabicyclo[2.2.2]oct-3-yl substituted in the 2-position with variable $R^{28}$ and optionally further substituted with oxo, or optionally further substituted with one or two substituents independently selected from hydroxy, fluoro, and $C_1$-$C_6$ alkyl;

$R^{27}$ is hydrogen or a nitrogen protecting group;

$R^{28}$ is hydrogen or a nitrogen protecting group;

$R^{29}$ is hydrogen or $C_1$-$C_6$ alkyl;

$R^{30}$ is hydrogen or $C_1$-$C_6$ alkyl;

$R^{29}$ and $R^{30}$ taken together with the carbon to which they are attached form a $C_3$-$C_6$ cycloalkyl ring;

$R^{31}$ is hydrogen, $C_1$-$C_6$ alkyl, $C_3$-$C_6$ cycloalkyl, or phenyl optionally monosubstituted with $C_1$-$C_6$ alkyl;

$R^{32}$ is hydrogen, $R^{33}$, or —$(CH_2)_{0\text{-}2}$—$OR^{33}$;

$R^{33}$ is $C_1$-$C_{10}$ alkyl optionally substituted with 1-6 fluorine atoms, $C_2$-$C_6$ alkenyl, $C_2$-$C_6$ alkynyl, or —$(CH_2)_{0\text{-}3}$—$R^{34}$;

$R^{34}$ is $C_3$-$C_7$ cycloalkyl or phenyl each optionally substituted with one or two substitutents independently selected from the group consisting of halo, $C_1$-$C_6$ alkyl, $C_1$-$C_6$ alkoxy, hydroxy, trifluoromethyl, and trifluoromethoxy, thienyl optionally substituted with halo, benzothienyl optionally substituted with halo, thiazolyl optionally substituted with $C_1$-$C_4$ alkyl, or adamantyl;

$R^{35}$ is —$(CH_2)_{0\text{-}6}$—$R^{34}$, —$C(O)$—$(CH_2)_{0\text{-}6}$—$R^{34}$, —$C(O)$—$(C_1$-$C_{10}$ alkyl), —$C(O)$—$(C_1$-$C_4$ alkoxy optionally substituted with phenyl), $C_1$-$C_{10}$ alkyl optionally substituted with 1-6 fluorine atoms, $C_2$-$C_{10}$ alkenyl, or $C_2$-$C_{10}$ alkynyl;

$R^{36}$ and $R^{37}$ are both hydrogen or, taken together with the carbon atom to which they are attached form a carbonyl group;

$R^{38}$ is hydrogen or an oxygen protecting group; or an acid addition salt thereof; provided that when $R^2$ is unsubstituted benzyl and $R^3$ is a piperidinyl moiety of formula (f) or (g), then at least one of $R^{31}$ and $R^{32}$ is other than hydrogen when at least one of $R^{29}$ and $R^{30}$ is hydrogen.

This invention further provides intermediates of Formula III:

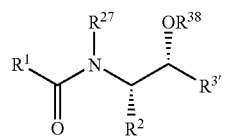

III where:

$R^1$ is $(C_3$-$C_7$ cycloalkyl$)_{0\text{-}1}(C_1$-$C_6$ alkyl), $(C_3$-$C_7$ cycloalkyl$)_{0\text{-}1}(C_2$-$C_6$ alkenyl), $(C_3$-$C_7$ cycloalkyl$)_{0\text{-}1}(C_2$-$C_6$ alkynyl) or $C_3$-$C_7$ cycloalkyl, each optionally substituted with up to three groups independently selected from halo, hydroxy, thiol, cyano, trifluoromethyl, trifluoromethoxy, $C_1$-$C_7$ alkoxy, $C_3$-$C_7$ cycloalkoxy, oxo, and $NR^4R^5$, biphenyl optionally substituted with halo, hydrogen,

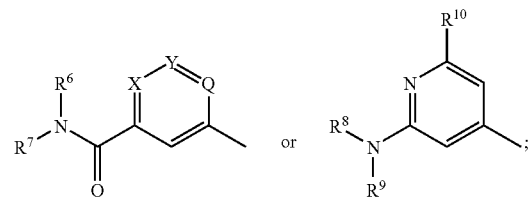

$R^2$ is $C_1$-$C_3$ alkyl, benzyl optionally monosubstituted in the phenyl ring with a substituent selected from the group consisting of halo, $C_1$-$C_6$ alkoxy optionally substituted in the alkyl chain with $C_3$-$C_7$ cycloalkyl, and $C_1$-$C_6$ alkylthio optionally substituted in the alkyl chain with $C_3$-$C_7$ cycloalkyl, or benzyl optionally disubstituted in the phenyl ring with a first substituent independently selected from halo and a second substituent independently selected from halo, $C_1$-$C_6$ alkoxy optionally substituted in the alkyl chain with $C_3$-$C_7$ cycloalkyl, and $C_1$-$C_6$ alkylthio optionally substituted in the alkyl chain with $C_3$-$C_7$ cycloalkyl;

$R^{3'}$ is:

ix) a piperidin-2-yl moiety of formula:

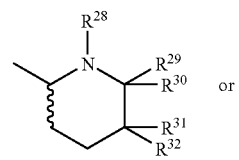

(f)

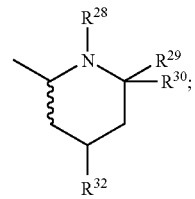

(g)

x) a tetrahydropyridin-2-yl moiety of formula:

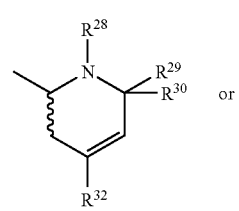

(h)

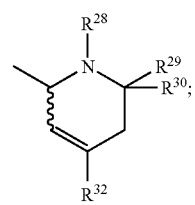

(j)

xi) a piperazin-2-yl moiety of formula:

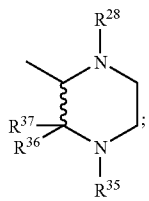

(k)

xii) homopiperidin-2-yl substituted in the 1-position with variable $R^{28}$;
xiii) 1,2,3,4-tetrahydroisoquinolin-3-yl substituted in the 1-position with variable $R^{28}$ and optionally further substituted with one or two substituents selected from halo, $C_1$-$C_6$ alkyl, and $C_1$-$C_6$ alkoxy;
xiv) 2-azabicyclo[2.2.2]oct-(5Z)ene-3-yl substituted in the 2-position with variable $R^{28}$;
xv) 2-azabicyclo[2.2.1]hept-3-yl substituted in the 2-position with variable $R^{28}$ and optionally further substituted with $C_1$-$C_{10}$ alkyl optionally substituted with $C_1$-$C_4$ alkoxy; or
xvi) 2-azabicyclo[2.2.2]oct-3-yl substituted in the 2-position with variable $R^{28}$ and optionally further substituted with oxo, or optionally further substituted with one or two substituents independently selected from hydroxy, fluoro, and $C_1$-$C_6$ alkyl;

X is CH, N, or $N^{30}$—O$^-$;
Y is $CR^{11}$, N, or $N^{30}$—O$^-$;
Q is $CR^{12}$, N, or $N^{30}$—O$^-$;
$R^4$ is hydrogen, $C_1$-$C_6$ alkyl optionally substituted up to three times with fluoro, or phenyl;
$R^5$ is hydrogen, $C_1$-$C_6$ alkyl optionally substituted up to three times with fluoro, phenyl, —C(O)($C_1$-$C_6$ alkyl optionally substituted up to three times with fluoro), or —SO$_2$($C_1$-$C_6$ alkyl optionally substituted up to three times with fluoro);
$R^6$ and $R^7$ are independently selected from the group consisting of methyl, ethyl, and propyl;
$R^8$ is hydrogen or $C_1$-$C_6$ alkyl;
$R^9$ is $C_3$-$C_5$ cycloalkyl, sec-butyl, or —CH$_2$R$^{13}$;
$R^{10}$ is —CF$_2$R$^{14}$, —OR$^{15}$, —CH$_2$C(O)CH$_3$, —S(O)$_{1-2}$R$^{16}$, —NR$^{17}$SO$_2$R$^{18}$, ($C_1$-$C_3$ alkoxy)-carbonyl, 1,3-dioxolan-2-yl, 1,3-dioxan-2-yl, 1,1-dioxo-2,3,4,5-tetrahydroisothiazol-2-yl, or tetrazol-5-yl optionally substituted with $C_1$-$C_3$ alkyl;
$R^{11}$ is hydrogen, chloro, isobutyl, CH$_2$R$^{19}$; CF$_2$R$^{20}$, 1,1,1-trifluoro-2-hydroxyeth-2-yl, $C_2$-$C_4$ alkenyl optionally substituted with one or two fluorine atoms, OR$^{21}$, C(O)R$^{22}$, N(methyl)(methylsulfonyl), N(methyl)(acetyl), pyrrolidin-2-on-1-yl, methylsulfonyl, N,N-dimethylaminosulfonyl, phenyl optionally substituted with one or two substituents selected from the group consisting of hydroxymethyl, methoxy, fluoro, and methylsulfonyl, 1,3-dioxolan-2-yl, 1,3-dithiolan-2-yl, 1,3-oxathiolan-2-yl, 1,3-dioxan-2-yl, 1,3-dithian-2-yl, pyridinyl, thiazolyl, oxazolyl, or 1,2,4-oxadiazolyl optionally substituted with methyl;
$R^{12}$ is hydrogen or fluoro;
$R^{13}$ is ethynyl or cyclopropyl;
$R^{14}$ is hydrogen or methyl;
$R^{15}$ is difluoromethyl or methanesulfonyl;
$R^{16}$ is $C_1$-$C_4$ alkyl, $C_3$-$C_6$ cycloalkyl, phenyl, or —NR$^{25}$R$^{26}$;
$R^{17}$ is hydrogen, $C_1$-$C_3$ alkyl optionally substituted with up to 3 fluorine atoms, or $C_3$-$C_6$ cycloalkyl;
$R^{18}$ is $C_1$-$C_3$ alkyl or $C_3$-$C_6$ cycloalkyl;
$R^{19}$ is fluoro, hydroxy, or $C_1$-$C_3$ alkoxy;
$R^{20}$ is hydrogen, phenyl, or furyl;
$R^{21}$ is $C_1$-$C_3$ alkyl optionally substituted with one or two fluorine atoms;
$R^{22}$ is $C_1$-$C_3$ alkyl, $C_3$-$C_5$ cycloalkyl, $C_2$-$C_3$ alkenyl, $C_1$-$C_3$ alkoxy, NR$^{23}$R$^{24}$, pyrrolidin-1-yl optionally substituted with methyl or one or two fluorine atoms, piperidin-1-yl, phenyl, pyridinyl, or furyl;
$R^{23}$ is hydrogen or methyl;
$R^{24}$ is methyl, ethyl, or propyl;
$R^{25}$ is hydrogen or methyl;
$R^{26}$ is methyl; or
$R^{25}$ and $R^{26}$ taken together with the nitrogen atom to which they are attached form a pyrrolidine or piperidine ring;
$R^{27}$ is hydrogen or a nitrogen protecting group;
$R^{28}$ is hydrogen or a nitrogen protecting group;
$R^{29}$ is hydrogen or $C_1$-$C_6$ alkyl;
$R^{30}$ is hydrogen or $C_1$-$C_6$ alkyl;
$R^{29}$ and $R^{30}$ taken together with the nitrogen to which they are attached form a $C_3$-$C_6$ cycloalkyl ring;
$R^{31}$ is hydrogen, $C_1$-$C_6$ alkyl, $C_3$-$C_6$ cycloalkyl, or phenyl optionally monosubstituted with $C_1$-$C_6$ alkyl;
$R^{32}$ is hydrogen, $R^{33}$, or —(CH$_2$)$_{0-2}$—OR$^{33}$;
$R^{33}$ is $C_1$-$C_{10}$ alkyl optionally substituted with 1-6 fluorine atoms, $C_2$-$C_6$ alkenyl, $C_2$-$C_6$ alkynyl, or —(CH$_2$)$_{0-3}$—R$^{34}$;
$R^{34}$ is $C_3$-$C_7$ cycloalkyl or phenyl each optionally substituted with one or two substitutents independently selected from the group consisting of halo, $C_1$-$C_6$ alkyl, $C_1$-$C_6$ alkoxy, hydroxy, trifluoromethyl, and trifluoromethoxy, thienyl optionally substituted with halo, benzothienyl optionally substituted with halo, thiazolyl optionally substituted with $C_1$-$C_4$ alkyl, or adamantyl;
$R^{35}$ is —(CH$_2$)$_{0-6}$—R$^{34}$, —C(O)—(CH$_2$)$_{0-6}$—R$^{34}$, —C(O)—($C_1$-$C_{10}$ alkyl), —C(O)—($C_1$-$C_4$ alkoxy optionally substituted with phenyl), $C_1$-$C_{10}$ alkyl optionally substituted with 1-6 fluorine atoms, $C_2$-$C_{10}$ alkenyl, or $C_2$-$C_{10}$ alkynyl;
$R^{36}$ and $R^{37}$ are both hydrogen or, taken together with the carbon atom to which they are attached form a carbonyl group;
$R^{38}$ is hydrogen or an oxygen protecting group; or an acid addition salt thereof provided that: a) no more than one of X, Y, and Q may be N or $N^{30}$—O$^-$; b) when X is CH, Y is $CR^{11}$, and Q is $CR^{12}$, then one of $R^{11}$ and $R^{12}$ is other than hydrogen; and c) at least one of $R^{27}$, $R^{28}$, and $R^{38}$ is other than hydrogen.

This invention also provides intermediates of Formula IV:

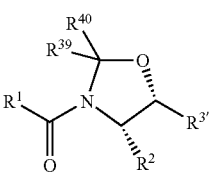

IV where:
$R^1$ is ($C_3$-$C_7$ cycloalkyl)$_{0-1}$($C_1$-$C_6$ alkyl), ($C_3$-$C_7$ cycloalkyl)$_{0-1}$($C_2$-$C_6$ alkenyl), ($C_3$-$C_7$ cycloalkyl)$_{0-1}$($C_2$-$C_6$ alkynyl) or $C_3$-$C_7$ cycloalkyl, each optionally substituted with up to three groups independently selected from halo, hydroxy, thiol, cyano, trifluoromethyl, trifluoromethoxy, $C_1$-$C_7$ alkoxy, $C_3$-$C_7$ cycloalkoxy, oxo, and NR$^4$R$^5$, biphenyl optionally substituted with halo, hydrogen,

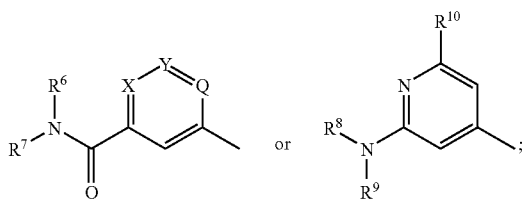 or 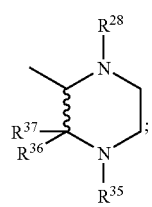

xi) a piperazin-2-yl moiety of formula:

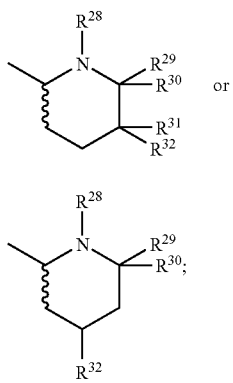

R² is C₁-C₃ alkyl, benzyl optionally monosubstituted in the phenyl ring with a substituent selected from the group consisting of halo, C₁-C₆ alkoxy optionally substituted in the alkyl chain with C₃-C₇ cycloalkyl, and C₁-C₆ alkylthio optionally substituted in the alkyl chain with C₃-C₇ cycloalkyl, or benzyl optionally disubstituted in the phenyl ring with a first substituent independently selected from halo and a second substituent independently selected from halo, C₁-C₆ alkoxy optionally substituted in the alkyl chain with C₃-C₇ cycloalkyl, and C₁-C₆ alkylthio optionally substituted in the alkyl chain with C₃-C₇ cycloalkyl;

R³' is:

ix) a piperidin-2-yl moiety of formula:

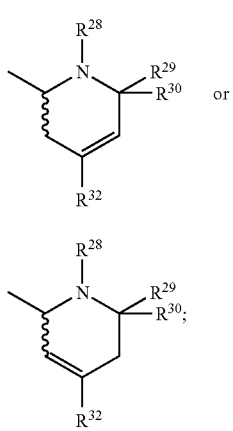

x) a tetrahydropyridin-2-yl moiety of formula:

xii) homopiperidin-2-yl substituted in the 1-position with variable R²⁸;
xiii) 1,2,3,4-tetrahydroisoquinolin-3-yl substituted in the 1-position with variable R²⁸ and optionally further substituted with one or two substituents selected from halo, C₁-C₆ alkyl, and C₁-C₆ alkoxy;
xiv) 2-azabicyclo[2.2.2]oct-(5Z)ene-3-yl substituted in the 2-position with variable R²⁸;
xv) 2-azabicyclo[2.2.1]hept-3-yl substituted in the 2-position with variable R²⁸ and optionally further substituted with C₁-C₁₀ alkyl optionally substituted with C₁-C₄ alkoxy; or
xvi) 2-azabicyclo[2.2.2]oct-3-yl substituted in the 2-position with variable R²⁸ and optionally further substituted with oxo, or optionally further substituted with one or two substituents independently selected from hydroxy, fluoro, and C₁-C₆ alkyl;

X is CH, N, or N⁺—O⁻;
Y is CR¹¹, N, or N⁺—O⁻;
Q is CR¹², N, or N⁺—O⁻;
R⁴ is hydrogen, C₁-C₆ alkyl optionally substituted up to three times with fluoro, or phenyl;
R⁵ is hydrogen, C₁-C₆ alkyl optionally substituted up to three times with fluoro, phenyl, —C(O)(C₁-C₆ alkyl optionally substituted up to three times with fluoro), or —SO₂(C₁-C₆ alkyl optionally substituted up to three times with fluoro);
R⁶ and R⁷ are independently selected from the group consisting of methyl, ethyl, and propyl;
R⁸ is hydrogen or C₁-C₆ alkyl;
R⁹ is C₃-C₅ cycloalkyl, sec-butyl, or —CH₂R¹³;
R¹⁰ is —CF₂R¹⁴, —OR¹⁵, —CH₂C(O)CH₃, —S(O)₁₋₂R¹⁶, —NR¹⁷SO₂R¹⁸, (C₁-C₃ alkoxy)-carbonyl, 1,3-dioxolan-2-yl, 1,3-dioxan-2-yl, 1,1-dioxo-2,3,4,5-tetrahydroisothiazol-2-yl, or tetrazol-5-yl optionally substituted with C₁-C₃ alkyl;
R¹¹ is hydrogen, chloro, isobutyl, CH₂R¹⁹; CF₂R²⁰,1,1,1-trifluoro-2-hydroxyeth-2-yl, C₂-C₄ alkenyl optionally substituted with one or two fluorine atoms, OR²¹, C(O)R²², N(methyl)(methylsulfonyl), N(methyl)(acetyl), pyrrolidin-2-on-1-yl, methylsulfonyl, N,N-dimethylaminosulfonyl, phenyl optionally substituted with one or two substituents selected from the group consisting of hydroxymethyl, methoxy, fluoro, and methylsulfonyl, 1,3-dioxolan-2-yl, 1,3-dithiolan-2-yl, 1,3-oxathiolan-2-yl, 1,3-dioxan-2-yl, 1,3-dithian-2-yl, pyridinyl, thiazolyl, oxazolyl, or 1,2,4-oxadiazolyl optionally substituted with methyl;
R¹² is hydrogen or fluoro;
R¹³ is ethynyl or cyclopropyl;
R¹⁴ is hydrogen or methyl;
R¹⁵ is difluoromethyl or methanesulfonyl;
R¹⁶ is C₁-C₄ alkyl, C₃-C₆ cycloalkyl, phenyl, or —NR²⁵R²⁶;
R¹⁷ is hydrogen, C₁-C₃ alkyl optionally substituted with up to 3 fluorine atoms, or C₃-C₆ cycloalkyl;

$R^{18}$ is $C_1$-$C_3$ alkyl or $C_3$-$C_6$ cycloalkyl;

$R^{19}$ is fluoro, hydroxy, or $C_1$-$C_3$ alkoxy;

$R^{20}$ is hydrogen, phenyl, or furyl;

$R^{21}$ is $C_1$-$C_3$ alkyl optionally substituted with one or two fluorine atoms;

$R^{22}$ is $C_1$-$C_3$ alkyl, $C_3$-$C_5$ cycloalkyl, $C_2$-$C_3$ alkenyl, $C^1$-$C_3$ alkoxy, $NR^{23}R^{24}$, pyrrolidin-1-yl optionally substituted with methyl or one or two fluorine atoms, piperidin-1-yl, phenyl, pyridinyl, or furyl;

$R^{23}$ is hydrogen or methyl;

$R^{24}$ is methyl, ethyl, or propyl;

$R^{25}$ is hydrogen or methyl;

$R^{26}$ is methyl; or $R^{25}$ and $R^{26}$ taken together with the nitrogen atom to which they are attached form a pyrrolidine or piperidine ring;

$R^{28}$ is hydrogen or a nitrogen protecting group;

$R^{29}$ is hydrogen or $C_1$-$C_6$ alkyl;

$R^{30}$ is hydrogen or $C_1$-$C_6$ alkyl;

$R^{29}$ and $R^{30}$ taken together with the nitrogen to which they are attached form a $C_3$-$C_6$ cycloalkyl ring;

$R^{31}$ is hydrogen, $C_1$-$C_6$ alkyl, $C_3$-$C_6$ cycloalkyl, or phenyl optionally monosubstituted with $C_1$-$C_6$ alkyl;

$R^{32}$ is hydrogen, $R^{33}$, or $-(CH_2)_{0-2}-OR^{33}$;

$R^{33}$ is $C_1$-$C_{10}$ alkyl optionally substituted with 1-6 fluorine atoms, $C_2$-$C_6$ alkenyl, $C_2$-$C_6$ alkynyl, or $-(CH_2)_{0-3}-R^{34}$;

$R^{34}$ is $C_3$-$C_7$ cycloalkyl or phenyl each optionally substituted with one or two substitutents independently selected from the group consisting of halo, $C_1$-$C_6$ alkyl, $C_1$-$C_6$ alkoxy, hydroxy, trifluoromethyl, and trifluoromethoxy, thienyl optionally substituted with halo, benzothienyl optionally substituted with halo, thiazolyl optionally substituted with $C_1$-$C_4$ alkyl, or adamantyl;

$R^{35}$ is $-(CH_2)_{0-6}-R^{34}$, $-C(O)-(CH_2)_{0-6}-R^{34}$, $-C(O)-(C_1$-$C_{10}$ alkyl), $-C(O)-(C_1$-$C_4$ alkoxy optionally substituted with phenyl), $C_1$-$C_{10}$ alkyl optionally substituted with 1-6 fluorine atoms, $C_2$-$C_{10}$ alkenyl, or $C_2$-$C_{10}$ alkynyl;

$R^{36}$ and $R^{37}$ are both hydrogen or, taken together with the carbon atom to which they are attached form a carbonyl group;

$R^{38}$ is hydrogen or an oxygen protecting group;

$R^{39}$ and $R^{40}$ are independently selected from methyl, ethyl, or propyl; or an acid addition salt thereof provided that no more than one of X, Y, and Q may be N or $N^+$—$O^-$.

DETAILED DESCRIPTION OF THE INVENTION

The general chemical terms used in the formulae above have their usual meanings. For example, the term "$C_1$-$C_3$ alkyl" includes methyl, ethyl, propyl, and isopropyl, and the terms "$C_1$-$C_6$ alkyl" and "$C_1$-$C_{10}$ alkyl" include methyl, ethyl, propyl, isopropyl, butyl, isobutyl, sec-butyl, tert-butyl, pentyl, neopentyl, and hexyl moieties.

The term "$C_3$-$C_5$ cycloalkyl" includes cyclopropyl, cyclobutyl, and cyclopentyl moieties, the term "$C_3$-$C_6$ cycloalkyl" includes cyclopropyl, cyclobutyl, cyclopentyl, and cyclohexyl, likewise, the term "$C_3$-$C_7$ cycloalkyl" includes cyclopropyl, cyclobutyl, cyclopentyl, cyclohexyl, and cycloheptyl moieties.

The term "$C_2$-$C_3$ alkenyl" includes ethenyl, prop-1-en-3-yl, prop-1-en-2-yl, and the like. The terms "$C_2$-$C_6$ alkenyl" and "$C_2$-$C_{10}$ alkenyl" include ethenyl, prop-1-en-3-yl, prop-1-en-2-yl, 2-methylprop-1-en-1-yl, and the like.

The terms "$C_2$-$C_6$ alkynyl" and "$C_2$-$C_{10}$ alkynyl" include ethynyl, prop-1-yn-3-yl, prop-1-yn-1-yl, 4-methylpent-2-yn-1-yl, and the like.

"Halo" includes fluoro, chloro, bromo, and iodo.

The terms "$C_1$-$C_3$ alkoxy" and "$C_1$-$C_7$ alkoxy" are a $C_1$-$C_3$ alkyl group or a $C_1$-$C_7$ alkyl group, respectively, bonded to an oxygen atom and include methoxy, ethoxy, isopropoxy, tert-butoxy, and the like. Similarly, the terms "$C_3$-$C_5$ cycloalkoxy" and "$C_3$-$C_7$ cycloalkoxy" are a $C_3$-$C_5$ cycloalkyl group or a $C_3$-$C_7$ cycloalkyl group, respectively, bonded through an oxygen atom and include cyclopropoxy, cyclobutoxy, cyclopentoxy, and the like.

The term "($C_3$-$C_7$ cycloalkyl)$_{0-1}$($C_1$-$C_6$ alkyl)" is taken to mean a $C_1$-$C_6$ alkyl moiety optionally substituted with one $C_3$-$C_7$ cycloalkyl moiety at any available carbon atom in the $C_1$-$C_6$ alkyl moiety. Similarly, "($C_3$-$C_7$ cycloalkyl)$_{0-1}$($C_2$-$C_6$ alkenyl)" and "($C_3$-$C_7$ cycloalkyl)$_{0-1}$($C_2$-$C_6$ alkynyl)" are taken to mean a $C_2$-$C_6$ alkenyl or $C_2$-$C_6$ alkynyl moiety optionally substituted at any available carbon atom in the $C_2$-$C_6$ alkenyl or $C_2$-$C_6$ alkynyl moiety.

The term "$C_1$-$C_6$ alkoxy optionally substituted in the alkyl chain with $C_3$-$C_7$ cycloalkyl" is taken to mean a $C_1$-$C_6$ alkoxy moiety optionally substituted with one $C_3$-$C_7$ cycloalkyl moiety at any available carbon atom in the $C_1$-$C_6$ alkoxy moiety. Similarly, the term "$C_1$-$C_6$ alkylthio optionally substituted in the alkyl chain with $C_3$-$C_7$ cycloalkyl" is taken to mean a $C_1$-$C_6$ alkylthio moiety optionally substituted with one $C_3$-$C_7$ cycloalkyl moiety at any available carbon atom in the $C_1$-$C_6$ alkylthio moiety.

The term "nitrogen protecting group" is taken to mean a moiety that is stable to projected reaction conditions and yet may be selectively removed by reagents and reaction conditions compatible with the regenerated amine. Such groups are well known by the skilled artisan and are described in the literature. (See, for example: Greene and Wuts, *Protective Groups in Organic Synthesis*, Third Edition, Chapter 7, John Wiley and Sons Inc., (1999)). Nitrogen protecting groups contemplated include:

a) suitable carbamates, such as:
1) $C_1$-$C_7$ alkyl carbamates including methyl, ethyl, tert-butyl, tert-amyl, diisopropylmethyl carbamates, and the like;
2) substituted ethyl carbamates, such as 2,2,2-trichloroethyl, 2-trimethylsilylethyl, 2-phenylethyl, 1,1-dimethyl-2-haloethyl, 1,1-dimethyl-2,2-dibromoethyl, 1,1-dimethyl-2,2,2-trichloro-ethyl, 2-(pyridin-2-yl)ethyl, 2-(pyridin-4-yl)ethyl, 2-methylthioethyl, 2-methylsulfonylethyl, 2-(p-toluenesulfonyl)ethyl, 2-phosphonioethyl, 1,1-dimethyl-2-cyanoethyl, 2-iodoethyl carbamates, and the like;
3) 1-adamantyl carbamate;
4) vinyl carbamate;
5) allyl carbamate;
6) 1-isopropylallyl carbamate;
7) cinnamyl carbamates, such as cinnamyl carbamate, 4-nitrocinnamyl, and the like;
8) 8-quinolinyl carbamate;
9) N-hydroxypiperidinyl carbamate;
10) $C_1$-$C_4$ alkyldithio carbamates;
11) Benzyl carbamates, such as benzyl, 4-methoxybenzyl, 4-nitrobenzyl, 4-halobenzyl, 4-cyanobenzyl, 4-decyloxybenzyl, 2,4-dichlorobenzyl, 3,5-dimethoxybenzyl, 2-nitrobenzyl, 3,4-dimethoxy-6-nitrobenzyl, phenyl (2-nitrophenyl)methyl, 4-methylsulfinylbenzyl, 9-anthrylmethyl, diphenylmethyl, 3-chloro-4-($C_2$-$C_6$ acyloxy)benzyl, 4-(dihydroxyboryl)benzyl carbamates, and the like;
12) 2-(1,3-dithianyl)methyl carbamate;
13) aryl carbamates, such as phenyl, nicotinyl, 4-(methylthio)phenyl, 2,4-di(methylthio)phenyl, 3-nitrophenyl carbamates, and the like;

14) 2-triphenylphosphonioisopropyl carbamate;
15) 5-benzisoxazolylmethyl carbamate;
16) 2-(trifluoromethyl)-6-chromonylmethyl carbamate;
17) S-benzyl thiocarbamate; and
18) $C_3$-$C_7$ cycloalkyl carbamates, such as cyclobutyl, cyclopentyl, 1-methylcyclohexyl, cyclopropylmethyl carbamates, and the like;

b) suitable ureas, such as:
1) phenothiazinyl-(10)-carbonyl;
2) N'-(p-toluenesulfonylaminocarbonyl); and
3) N'-phenylaminothiocarbonyl;

c) suitable formyl and acyl groups, such as:
1) formyl; and
2) acetyl groups, such as acetyl, chloroacetyl, trichloroacetyl, trifluoroacetyl, 4-chlorobutanoyl, phenylacetyl, 3-phenylpropanoyl, N-benzoylphenylalanyl, 2-nitrophenylacetyl, 2-nitrophenoxyacetyl, acetoacetyl, and the like;

d) suitable aroyl groups, such as:
1) picolinoyl;
2) 3-pyridinylcarbonyl;
3) benzoyl;
4) 4-phenylbenzoyl;
5) 2-nitrobenzoyl; and
6) 2-nitrocinnamoyl, and the like;

e) suitable cyclic imide groups, such as:
1) N-phthalimide;
2) N-dithiasuccinimide;
3) N-2,3-diphenylmaleimide; and
4) N-2,5-dimethylpyrrole, and the like;

f) allyl;
g) 3-acetoxypropyl;
h) suitable benzylic groups, such as benzyl, 2-methylbenzyl, α(X-methylbenzyl, and the like;
i) triphenylmethyl; and
j) suitable imine moieties, such as:
1) 1,1-dimethylthiomethyleneimine;
2) benzylidene imine; and
3) diphenylmethyleneimine, and the like.

The term "oxygen protecting group" is taken to mean a moiety that is stable to projected reaction conditions and yet may be selectively removed by reagents and reaction conditions compatible with the regenerated alcohol. Such groups are well known by the skilled artisan and are described in the literature. (See, for example: Greene and Wuts, *Protective Groups in Organic Synthesis*, Third Edition, Chapter 7, John Wiley and Sons Inc., (1999)). Oxygen protecting groups contemplated include:

a) methyl and substituted methyl groups such as methoxymethyl, methylthio-methyl, (phenyldimethylsilyl) methoxymethyl, benzyloxymethyl, p-methoxy-benzyloxymethyl, p-nitrobenzyloxy-methyl, o-nitrobenzyloxymethyl, (4-methoxyphenoxy) methyl, guiaiacolmethyl, tert-butoxymethyl, 4-pentenyloxymethyl, siloxymethyl, 2-methoxyethoxymethyl, 2,2,2-trichloroeth-oxymethyl, bis(2-chloroethoxy)methyl, 2-(trimethylsilyl)ethoxymethyl, 2-quinolinyl-methyl, 1-pyrenylmethyl, diphenylmethyl, triphenylmethyl, and the like;

b) tetrahydropyranyl and substituted tetrahydropyranyl groups such as 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydropyranyl-S,S-dioxide, and the like;

c) tetrahydrofuranyl and substituted tetrahydrofuranyl groups such as tetrahydrothiofuranyl and the like;

d) ethyl and substituted ethyl groups such as 1-ethoxyethyl, 1-(2-chloroethoxy)-ethyl, 1-[(2-trimethylsilyl)ethoxy]ethyl, 1-methyl-1-methoxy-ethyl, 1-methyl-1-benzyloxyethyl, 1-methyl-1-benzyloxy-2-fluoroethyl, 1-methyl-1-phenoxyethyl, 2,2,2-trichloroethyl, 1,1-dianisyl-2,2,2-trichloroethyl, 1,1,1,3,3,3-hexa-fluoro-2-phenylisopropyl, 2-trimethylsilylethyl, 2-(benzylthio)ethyl, 2-(phenylselenyl)ethyl, tert -butyl, and the like;

e) allyl;
f) propargyl;
g) substituted phenyl groups such as p-chlorophenyl, p-nitrophenyl, 2,4-dinitro-phenyl, 2,3,5,6-tetrafluoro-4-(trifluoromethyl)phenyl, and the like;

h) benzyl and substituted benzyl groups such as p-methoxybenzyl, 3,4-dimethoxybenzyl, o-nitrobenzyl, p-nitrobenzyl, p-halobenzyl, 2,6-dichloro-benzyl, p-cyanobenzyl, p-phenylbenzyl, 2,6-difluorobenzyl, p-acylamino-benzyl, p-azidobenzyl, 4-azido-3-chlorobenzyl, 2-trifluoromethylbenzyl, p-(methylsulfinyl)benzyl, and the like;

i) silyl groups such as trimethylsilyl, triethylsilyl, triisopropylsilyl, dimethyliso-propylsilyl, diethylisopropylsilyl, dimethylthexylsilyl, tert -butyldimethylsilyl, tert -butyldiphenylsilyl, tribenzylsilyl, tri- p-xylylsilyl, triphenylsilyl, diphenyl-methylsilyl, di- tert -butylmethylsilyl, tris(trimethylsilyl)silyl, (2-hydroxy-styryl)dimethylsilyl, (2-hydroxystyryl)diisopropylsilyl, tert -butylmethoxy-phenyl silyl, tert -butoxydiphenylsilyl, and the like;

j) formyl and benzoylformyl groups;
k) acetyl and substituted acetyl groups such as chloroacetyl, dichloroacetyl, trichloroacetyl, trifluoroacetyl, methoxyacetyl, triphenylmethoxyacetyl, phenoxyacetyl, p-chlorophenoxyacetyl, phenylacetyl, chlorodiphenylacetyl and the like;

l) pivaloyl;
m) crotonyl;
n) benzoyl and substituted benzoyl groups such as p-phenylbenzoyl, 2-chlorobenzoyl, 4-bromobenzoyl, 2,4,6-trimethylbenzoyl;

o) methoxycarbonyl and substituted methoxycarbonyl groups such as methoxymethoxycarbonyl, 9-flurenylmethoxycarbonyl, and the like;

p) ethoxycarbonyl and substituted ethoxycarbonyl groups such as 2,2,2-trichloroethoxycarbonyl, 1,1-dimethyl-2,2,2-trichloroethoxycarbonyl, 2-(trimethylsilyl)ethoxycarbonyl, 2-dansylethoxycarbonyl, 2-(4-nitrophenyl)-ethoxycarbonyl, 2-(2,4-dinitrophenyl)ethoxycarbonyl, 2-cyano-1-phenyl-ethoxycarbonyl, and the like;

q) isobutoxycarbonyl;
r) vinyloxycarbonyl;
s) allyloxycarbonyl;
t) substituted phenoxycarbonyl groups such as p-nitrophenoxycarbonyl, 2-iodophenoxycarbonyl, 2-chlorophenoxycarbonyl, 4-bromophenoxycarbonyl, 4-nitrophenoxycarbonyl, o-(dibromomethyl)phenoxycarbonyl, and the like;

u) benzyloxycarbonyl and substituted benzyloxycarbonyl groups such as p-methoxybenzyloxycarbonyl, 3,4-dimethoxybenzyloxycarbonyl, o-nitrobenzyl-oxycarbonyl, p-nitrobenzyloxycarbonyl, and the like; and v) sulfonyl groups such as methanesulfonyl, benzylsulfonyl, p-toluenesulfonyl, 2-[(4-nitrophenyl)ethyl]sulfonyl, and the like.

The term "inhibition of production of A-β, peptide" is taken to mean decreasing of excessive in vivo levels of A-β peptide in a mammal to normal or sub-normal levels.

The term "effective amount of a compound of Formula I" is taken to mean the dose or doses of a compound of Formula I required to inhibit BACE sufficiently to decrease in vivo levels of A-β peptide in a mammal to normal or sub-normal levels.

The term "treatment" includes treating one or more disease symptoms present in a patient as well as slowing, arresting, or reversing the progression of the disease.

The term "BACE" includes both BACE1 and BACE2.

Mild cognitive impairment has been defined as a potential prodromal phase of dementia associated with Alzheimer's disease based on clinical presentation and on progression of patients exhibiting mild cognitive impairment to Alzheimer's dementia over time. (Morris, et al, *Arch. Neurol.*, 58, 397-405 (2001); Petersen, et al., *Arch. Neurol.*, 56, 303-308 (1999)). The term "prevention of the progression of mild cognitive impairment to Alzheimer's disease" includes slowing, arresting, or reversing the progression of mild cognitive impairment to Alzheimer's disease in a patient.

Variables $R^3$ and $R^{3'}$ represent a variety of cyclic amines in Formulae I, II, III, and IV. For the sake of clarity and convenience, the following generic representations will be used interchangeably to represent the compounds of Formula I, Formula II, Formula III, and Formula IV respectively:

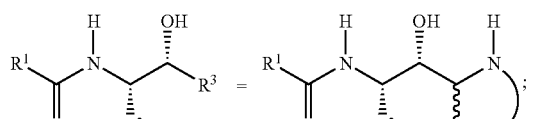

Equivalent Representations of Formula I

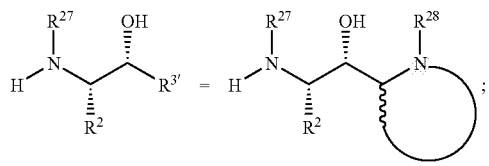

Equivalent Representations of Formula II

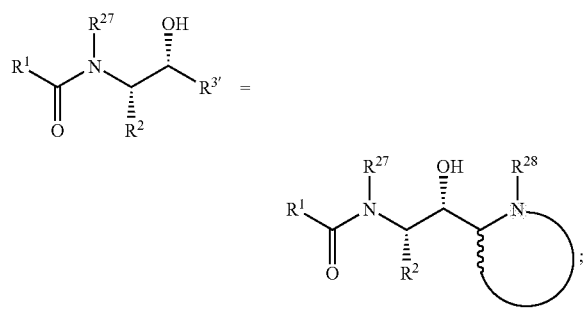

Equivalent Representations of Formula III

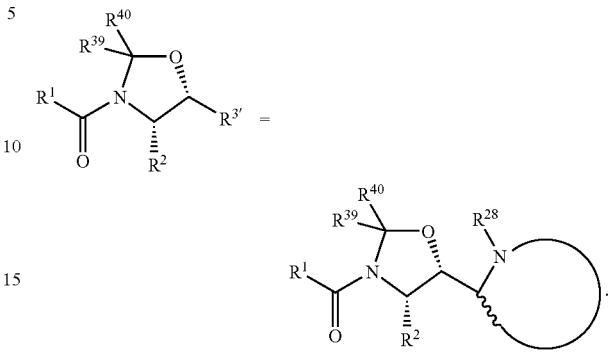

Equivalent Representations of Formula IV

The skilled artisan will appreciate that compounds of Formulae I, II, and III are comprised of a 1-amino-2-hydroxy-ethyl core that contains two chiral centers:

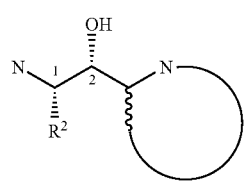

FIG. (1)

Although the present invention contemplates all individual enantiomers or diastereomers, as well as mixtures of the enantiomers and diastereomers of said compounds including racemates, the compounds with the absolute configuration at atoms labeled 1 and 2 as illustrated in figure (1) are preferred compounds of Formulae I, II, and III. The skilled artisan will also appreciate that the compounds of Formula IV comprise an oxazolidinyl ring that contains chiral centers corresponding to the atoms labeled 1 and 2 in figure (1). Although all individual enantiomers or diastereomers, as well as mixtures of the enantiomers and diastereomers of compounds of Formula IV including racemates are contemplated by the present invention, the compounds of Formula IV with the absolute configuration at atoms labeled 1 and 2 in figure (1) are preferred compounds of Formula IV. The skilled artisan will also appreciate that the point of attachment of the ring system corresponding to the moiety $R^3$ or $R^{3'}$ in compounds of Formulae I, II, III, and IV introduces a third chiral center into the compounds of the present invention. Although the present invention contemplates all individual enantiomers or diastereomers, as well as mixtures of the enantiomers and diastereomers of said compounds including racemates, it is preferred that compounds of the invention exist with the absolute configuration illustrated in figure (2).

FIG. (2)

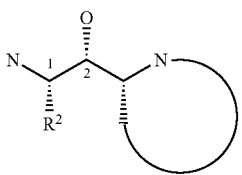

Additionally, the skilled artisan will appreciate that additional chiral centers may be created in the compounds of the invention by the selection of certain variables. The present invention contemplates all individual enantiomers or diastereomers, as well as mixtures of the enantiomers and diastereomers of said compounds including racemates. The skilled artisan will also appreciate that the Cahn-Ingold-Prelog (R) or (S) designations for all chiral centers will vary depending upon the substitution patterns of the particular compound. The single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques at any convenient point in the synthesis of compounds of the invention. Single enantiomers and diastereomers of compounds of the invention are a preferred embodiment of the invention.

It will be understood by the skilled reader that some or all of the compounds of Formulae I, II, III, and IV are capable of forming salts. In all cases, the pharmaceutically acceptable salts of all of the compounds are included in the names of them. The compounds of the present invention are amines, and accordingly react with any of a number of inorganic and organic acids to form pharmaceutically acceptable acid addition salts. Preferred pharmaceutically acceptable salts are those formed with hydrochloric acid and trifluoroacetic acid.

Although all of the compounds of Formula I are useful inhibitors of BACE, certain classes of compounds are preferred. The following paragraphs describe such preferred classes:

a) $R^1$ is hydrogen;
b) $R^1$ is $C_1$-$C_6$ alkyl;
c) $R^1$ is $C_1$-$C_4$ alkyl;
d) $R^1$ is $C_1$-$C_2$ alkyl;
e) $R^1$ is methyl optionally substituted with chloro or fluoro
f) $R^1$ is methyl;

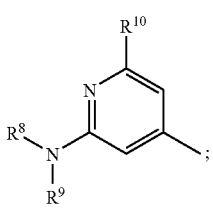

g) $R^1$ is R
h) $R^2$ is benzyl optionally mono- or difluorinated in the phenyl ring;
i) $R^2$ is benzyl;
j) $R^2$ is 3-fluorobenzyl;
k) $R^2$ is 3,5-difluorobenzyl;
l) $R^8$ is hydrogen;
m) $R^8$ is methyl;
n) $R^9$ is sec-butyl;
o) $R^{10}$ is —$NR^{17}SO_2R^{18}$ where $R^{17}$ and $R^{18}$ are both methyl;
p) The compound of Formula I is a free base;
q) The compound of Formula I is a pharmaceutically acceptable salt;
r) The compound of Formula I is the hydrochloride salt.

Preferred embodiments of the invention include all combinations of paragraphs a)-r). Other preferred compounds of Formula I are those where $R^1$ is ($C_3$-$C_7$ cycloalkyl)$_{0-1}$($C_1$-$C_6$ alkyl), ($C_3$-$C_7$ cycloalkyl)$_{0-1}$($C_2$-$C_6$ alkenyl), ($C_3$-$C_7$ cycloalkyl)$_{0-1}$($C_2$-$C_6$ alkynyl) or $C_3$-$C_7$ cycloalkyl, each optionally substituted with up to three groups independently selected from halo, hydroxy, thiol, cyano, trifluoromethyl, trifluoromethoxy, $C_1$-$C_7$ alkoxy, $C_3$-$C_7$ cycloalkoxy, oxo, and $NR^4R^5$, biphenyl optionally substituted with halo, hydrogen, or

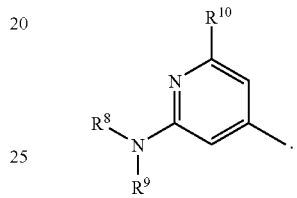

Especially preferred compounds of Formula I are those where $R^1$ is $C_1$-$C_6$ alkyl, $R^2$ is benzyl, 3-fluorobenzyl, or 3,5-difluorobenzyl, and $R^3$ is piperidin-2-yl (a) or (b), or piperazin-2-yl (e). Most preferred compounds of Formula I are those where $R^1$ is methyl, $R^2$ is benzyl, 3-fluorobenzyl, or 3,5-difluorobenzyl, and $R^3$ is piperidin-2-yl (a) or (b). Another group of especially preferred compounds of Formula I is where $R^1$ is methyl, $R^2$ is 3,5-difluorobenzyl, $R^3$ is piperidin-2-yl (a), $R^{29}$, $R^{30}$, and $R^{31}$ are hydrogen and $R^{32}$ is —$OR^{33}$, particularly cyclohexylmethoxy.

Although all of the compounds of Formula II are useful intermediates for the preparation of BACE inhibitors, certain of the compounds are preferred:

s) $R^2$ is benzyl optionally mono- or difluorinated in the phenyl ring;
t) $R^2$ is benzyl;
u) $R^2$ is 3-fluorobenzyl;
v) $R^2$ is 3,5-difluorobenzyl;
w) $R^{27}$ is hydrogen;
x) $R^{27}$ is a nitrogen protecting group;
y) $R^{27}$ is benzyl;
z) $R^{27}$ is 2-methylbenzyl;
aa) $R^{28}$ is hydrogen;
bb) $R^{28}$ is a carbamate protecting group;
cc) $R^{28}$ is tert-butoxycarbonyl;
dd) $R^{28}$ is benzyl;
ee) $R^{28}$ is α-methylbenzyl;
ff) one of $R^{27}$ and $R^{28}$ is hydrogen and the other is a nitrogen protecting group;
gg) $R^{27}$ is hydrogen and $R^{28}$ is tert-butoxycarbonyl, benzyl, or α-methylbenzyl;
hh) $R^{27}$ is hydrogen and $R^{28}$ is tert-butoxycarbonyl;
ii) $R^{27}$ is hydrogen and $R^{28}$ is α-methylbenzyl;
jj) both $R^{27}$ and $R^{28}$ are independently a nitrogen protecting group;
kk) $R^{27}$ is benzyl or 2-methylbenzyl and $R^{28}$ is tert-butoxycarbonyl, benzyl, or α-methylbenzyl;
ll) The compound of Formula II is a free base;
mm) The compound of Formula II is a salt.

Preferred embodiments of compounds of Formula II include all combinations of paragraphs s)-mm). Especially preferred compounds of Formula II are those where $R^{27}$ is hydrogen and $R^{28}$ is tert-butoxycarbonyl, benzyl, or α-methylbenzyl.

Although all of the compounds of Formula III are useful intermediates for the preparation of BACE inhibitors, certain of the compounds are preferred:

nn) $R^1$ is hydrogen;
oo) $R^1$ is $C_1$-$C_6$ alkyl;
pp) $R^1$ is $C_1$-$C_4$ alkyl;
qq) $R^1$ is $C_1$-$C_2$ alkyl;
rr) $R^1$ is methyl optionally substituted with chloro or fluoro;
ss) $R^1$ is methyl;
tt) $R^1$ is

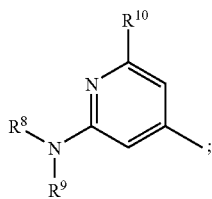

;

uu) $R^2$ is benzyl optionally mono- or difluorinated in the phenyl ring;
vv) $R^2$ is benzyl;
ww) $R^2$ is 3-fluorobenzyl;
xx) $R^2$ is 3,5-difluorobenzyl;
yy) $R^8$ is hydrogen;
zz) $R^8$ is methyl;
aaa) $R^9$ is sec-butyl;
bbb) $R^{10}$ is —$NR^{17}SO_2R^{18}$ where $R^{17}$ and $R^{18}$ are both methyl;
ccc) $R^{27}$ is hydrogen;
ddd) $R^{27}$ is a nitrogen protecting group;
eee) $R^{27}$ is benzyl;
fff) $R^{27}$ is 2-methylbenzyl;
ggg) $R^{28}$ is a carbamate protecting group;
hhh) $R^{28}$ is tert-butoxycarbonyl;
iii) $R^{28}$ is benzyl;
jjj) $R^{28}$ is α-methylbenzyl;
kkk) The compound of Formula III is a free base;
lll) The compound of Formula III is a salt.

Preferred embodiments of compounds of Formula III include all combinations of paragraphs nn)-lll). Other preferred compounds of Formula III are those where $R^1$ is $(C_3$-$C_7$ cycloalkyl$)_{0-1}$($C_1$-$C_6$ alkyl), $(C_3$-$C_7$ cycloalkyl$)_{0-1}$($C_2$-$C_6$ alkenyl), $(C_3$-$C_7$ cycloalkyl$)_{0-1}$ ($C_2$-$C_6$ alkynyl) or $C_3$-$C_7$ cycloalkyl, each optionally substituted with up to three groups independently selected from halo, hydroxy, thiol, cyano, trifluoromethyl, trifluoromethoxy, $C_1$-$C_7$ alkoxy, $C_3$-$C_7$ cycloalkoxy, oxo, and $NR^4R^5$, biphenyl optionally substituted with halo, hydrogen, or

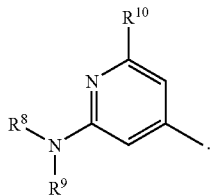

.

Especially preferred compounds of Formula III are those where $R^1$ is $C_1$-$C_6$ alkyl, $R^2$ is benzyl, 3-fluorobenzyl, or 3,5-difluorobenzyl, $R^{27}$ is hydrogen and $R^{28}$ is tert-butoxycarbonyl or α-methylbenzyl. Most preferred compounds of Formula III are those where $R^1$ is methyl, $R^2$ is benzyl, 3-fluorobenzyl, or 3,5-difluorobenzyl, $R^{27}$ is hydrogen and $R^{28}$ is tert-butoxycarbonyl or α-methylbenzyl.

Although all of the compounds of Formula IV are useful intermediates for the preparation of BACE inhibitors, certain of the compounds are preferred:

mmm) $R^1$ is hydrogen;
nnn) $R^1$ is $C_1$-$C_6$ alkyl;
ooo) $R^1$ is $C_1$-$C_4$ alkyl;
ppp) $R^1$ is $C_1$-$C_2$ alkyl;
qqq) $R^1$ is methyl optionally substituted with chloro or fluoro;
rrr) $R^1$ is methyl;
sss) $R^2$ is benzyl optionally mono- or difluorinated in the phenyl ring;
ttt) $R^2$ is benzyl;
uuu) $R^2$ is 3-fluorobenzyl;
vvv) $R^2$ is 3,5-difluorobenzyl;
www) $R^{28}$ is a carbamate protecting group;
xxx) $R^{28}$ is tert-butoxycarbonyl;
yyy) $R^{28}$ is benzyl;
zzz) $R^{28}$ is α-methylbenzyl;
aaaa) $R^{39}$ and $R^{40}$ are both methyl.

Preferred embodiments of compounds of Formula IV include all combinations of paragraphs mmm)—aaaa).

The compounds of Formula I are inhibitors of BACE. It is preferred the compound of Formula I selectively inhibits BACE1 relative to BACE2. Thus, the present invention also provides a method of inhibiting BACE in a mammal that comprises administering to a mammal in need of said treatment a BACE-inhibiting amount of a compound of Formula I. It is preferred that the mammal to be treated by the administration of the compounds of Formula I is human.

As inhibitors of BACE, the compounds of the present invention are useful for suppressing the production of A-β peptide, and therefore for the treatment of disorders resulting from excessive A-β peptide levels due to over-production and/or reduced clearance of A-β peptide. A further embodiment of the present invention is the use of a compound of Formula I for the manufacture of a medicament for treating a disease or condition capable of being improved or prevented by inhibition of BACE. The compounds of Formula I are therefore believed to be useful in treating or preventing Alzheimer's disease, mild cognitive impairment, Down's Syndrome, Hereditary Cerebral Hemorrhage with Amyloidosis of the Dutch-Type, cerebral amyloid antipathy, other degenerative dementias such as: dementias of mixed vascular and degenerative origin, dementia associated with Parkinson's disease, dementia associated with progressive supranuclear palsy, dementia associated cortical basal degeneration, and diffuse Lewy body type of Alzheimer's disease.

The compounds of the present invention may be prepared by a variety of procedures, some of which are illustrated in the Schemes below. It will be recognized by one of skill in the art that the individual steps in the following schemes may be varied to provide the compounds of Formula I. The particular order of steps required to produce the compounds of Formula I is dependent upon the particular compound being synthesized, the starting compound, and the relative liability of the substituted moieties. Some stereochemical centers have been specified and certain substituents have been eliminated in the following schemes for the sake of clarity and are not intended to limit the teaching of the schemes in any way. Furthermore, individual isomers, enantiomers, or diastereomers may be separated at any convenient point in the synthesis of compounds of Formula I. Additionally, the intermediates described in the following schemes contain a number of nitrogen and oxygen protecting groups (Pg). The variable "Pg" may be the same or different in each occurrence depending on the particular reaction conditions and the particular transformations to be performed.

The compounds of Formula I may be prepared as described in Scheme I where variables $R^1$, $R^2$, $R^{27}$, and $R^{28}$ are as previously defined:

added to the reaction mixture to facilitate the reaction. Alternatively, other carboxylic acid equivalents, including acylating agents, such as an appropriate acylimidazole, or a mixed anhydride, such as formic acetic anhydride, or an appropriate acid halide may be reacted directly with the amine of Formula II to provide the desired amide. The requisite carboxylic acids, carboxylic acid salts, acylating agents, and mixed anhydrides are either commercially available or may be prepared from commercially available materials by methods well known to the skilled artisan. (For example, See: *Comprehensive Organic Transformations*, Larock, VCH Publishers, Inc., New York, (1989); *Advanced Organic Chemistry*, March, Wiley Interscience, New York, Third Edition, (1985))

The conditions for deprotection of Formula III to provide compounds of Formula I depend on the nature of variables $R^{27}$, $R^{28}$ and $R^{38}$. The deprotection conditions are those well known to the skilled artisan and are described in the literature. (For example, see: Greene and Wuts, *Protective Groups in Organic Synthesis*, Third Edition, Chapter 7, John Wiley and Sons Inc., (1999)). Depending upon the nature of the protecting groups, they may all be removed in a single reaction, for example by treatment with acid or under hydrogenation conditions, or may be removed sequentially as necessary or

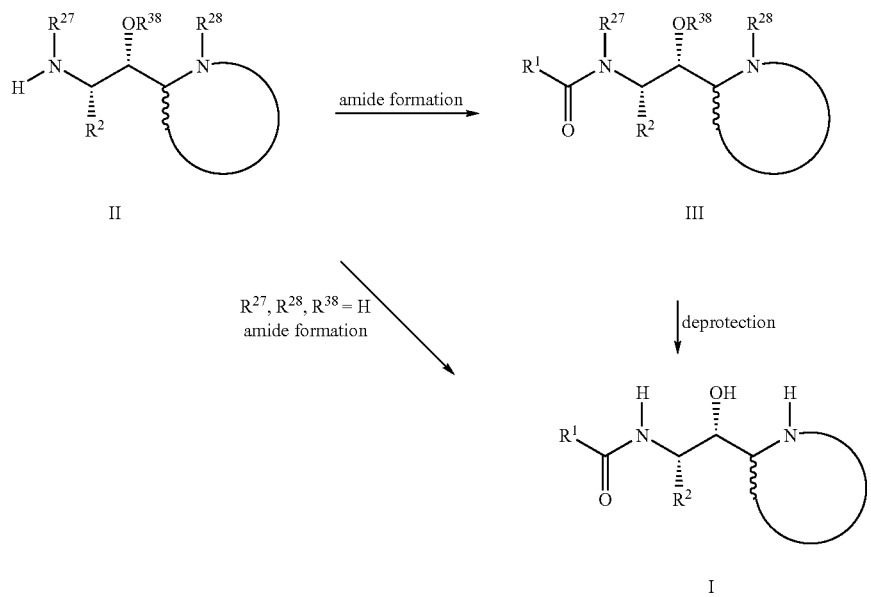

Scheme I

The amine of Formula II is reacted under standard amide forming conditions well known to the skilled artisan to provide compounds of Formula III (for example, see WO 03/040096 and WO 04/024081). An appropriate carboxylic acid of Formula $R^1$—COOH or an equivalent thereof, such as the sodium or, preferably, potassium carboxylate salt is reacted with a peptide coupling agent such as dicyclohexylcarbodiimide (DCC), 1-(3-dimethylaminopropyl)-3-ethylcarbodiimide hydrochloride (EDCI), or n-propylphosphonic anhydride, and an appropriate amine such as N-methylmorpholine or triethylamine, in a suitable solvent such as dichloromethane, dimethylformamide (DMF) or tetrahydrofuran (THF) to provide the compound of Formula III. If necessary or desired, an additive such as 4-(dimethylamino)pyridine and/or 1-hydroxybenzotriazole or equivalents thereof may be desired. The skilled artisan will appreciate that where $R^{27}$, $R^{28}$ and $R^{38}$ are hydrogen, no deprotection step is necessary. Further, if salts of compounds of the invention are desired, an appropriate free base of Formula I is simply reacted with an appropriate pharmaceutically acceptable acid in a suitable solvent under standard conditions to provide a pharmaceutically acceptable salt of a compound of Formula I. The skilled artisan will appreciate that, depending on the nature of variables $R^{27}$, $R^{28}$ and $R^{38}$, the deprotection and salt forming steps may occur simultaneously to provide a pharmaceutically acceptable salt of a compound of Formula I in a single step.

Intermediates of Formula II may be prepared as described in the following scheme where Pg and $R^{28'}$ represent nitrogen protecting groups and $R^2$ is as previously defined.

Scheme II

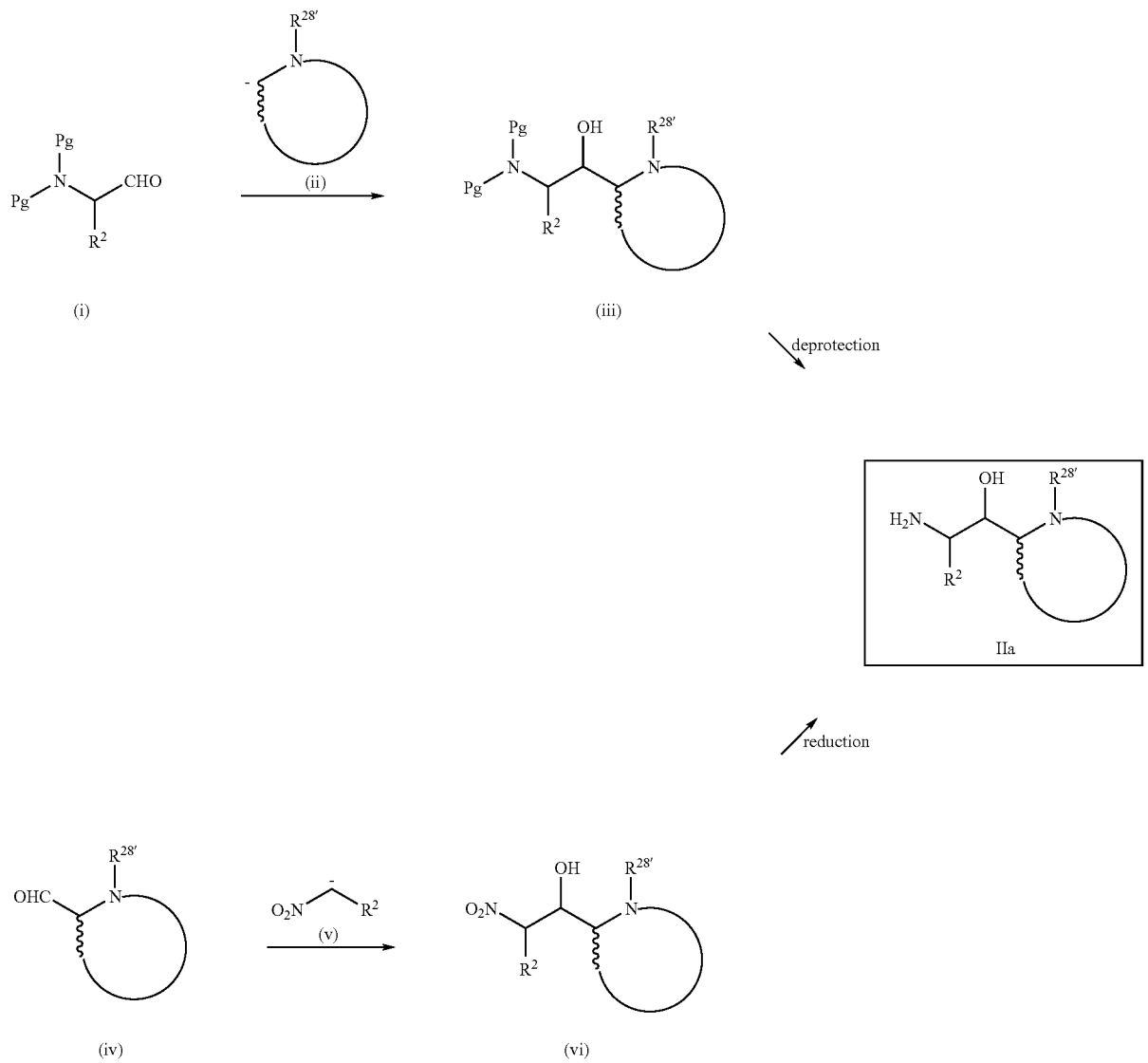

The N,N-diprotected aminoaldehyde (i) is reacted with the anion of an appropriately substituted cyclic amine (ii) at low temperature in a suitable solvent, for example tetrahydrofuran, to provide the N,N-diprotected aminoethanol (iii). The amine moiety is deprotected under standard conditions (For example, see: Greene and Wuts, *Protective Groups in Organic Synthesis*, Third Edition, Chapter 7, John Wiley and Sons Inc., (1999)) to provide the desired aminoethanol. Alternatively, aldehyde (iv) is reacted with the anion of an appropriately substituted nitroalkane (v) to provide the corresponding nitroethane (vi). The nitroethane is reduced to provide the desired aminoethanol under standard conditions. The requisite anions are prepared by treating the appropriately substituted cyclic amine or appropriately substituted nitroethane with a suitable base at low temperature. The requisite appropriately substituted cyclic amines, appropriately substituted nitroethanes, and appropriately substituted aldehydes are either commercially available or may be prepared from commercially available starting materials. (For example, see: *Comprehensive Organic Transformations*, Larock, Wiley-VCH Publishers, Inc., New York, (1999); *Advanced Organic Chemistry*, March, Wiley Interscience, New York, Third Edition, (1985))

A further alternative to Scheme II is to react the anion of an appropriately substituted pyridine with an N,N-diprotected aminoaldehyde (i). The pyridine moiety in the resulting N,N-diprotected aminoethanol must then be hydrogenated in an additional step, and the resulting piperidine nitrogen protected if necessary or desired, to provide the corresponding aminoethanols.

Intermediates of Formula II may also be prepared as described in Scheme III where variable $R^2$ and $R^{28'}$ are as previously defined.

Scheme III

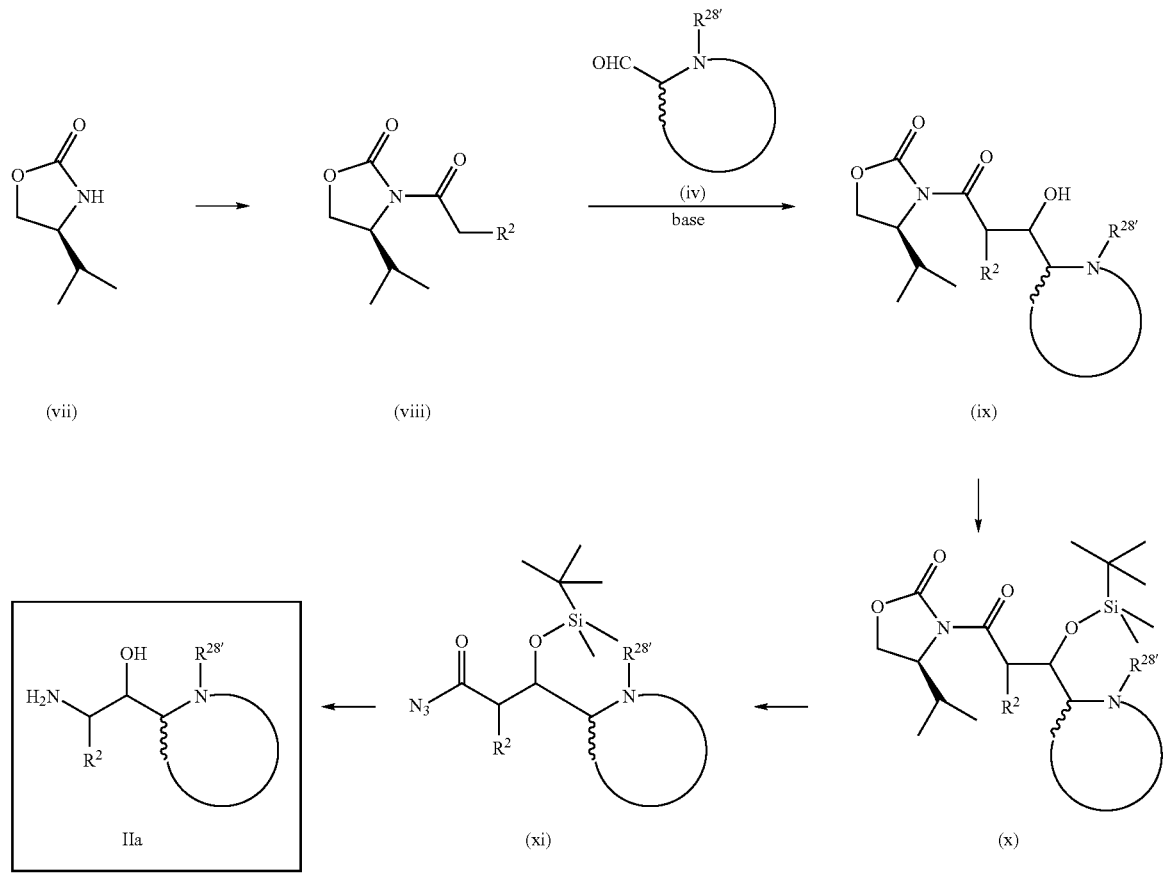

4-(S)-Isopropyloxazolidin-2-one (vii) is deprotonated with a suitable base, such as n-butyllithium in tetrahydrofuran, and then acylated with an appropriately substituted carboxylic acid derivative, such as an acid halide or acid anhydride, to provide the substituted amide (viii). This amide is deprotonated by reaction with a suitable base, such as N,N-diisopropylethylamine and reacted with aldehyde (iv) to provide the corresponding alcohol (ix). This alcohol is protected with an oxygen protecting group, preferably tert-butyldimethylsilyl, to provide the oxazolidin-2-one intermediate (x).

This intermediate is then reacted with basic hydrogen peroxide followed by treatment with a source of azide, such as diphenylphosphoryl azide, to provide the azidocarbonyl intermediate (xi). Treatment of the azidocarbonyl with benzyl alcohol followed by catalytic hydrogenation provides the desired amine (IIa).

Intermediates of Formula IIa where the cyclic amine moiety, $R^{3'}$, is a homopiperidine may be prepared as described in Scheme IV where Pg and $R^2$ are as previously defined.

Scheme IV

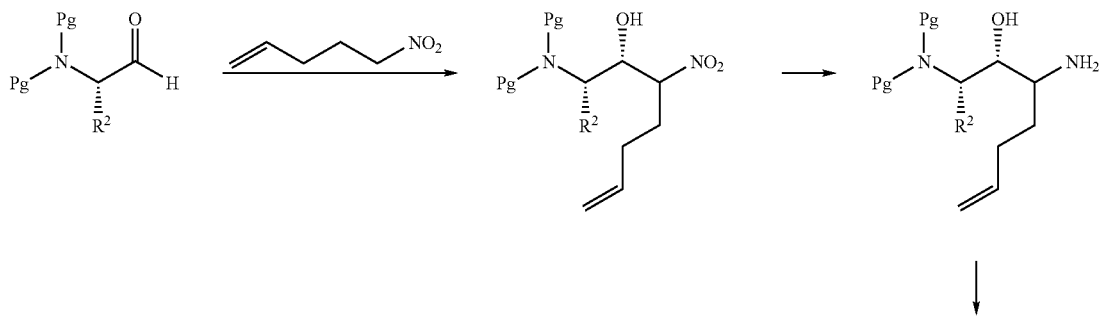

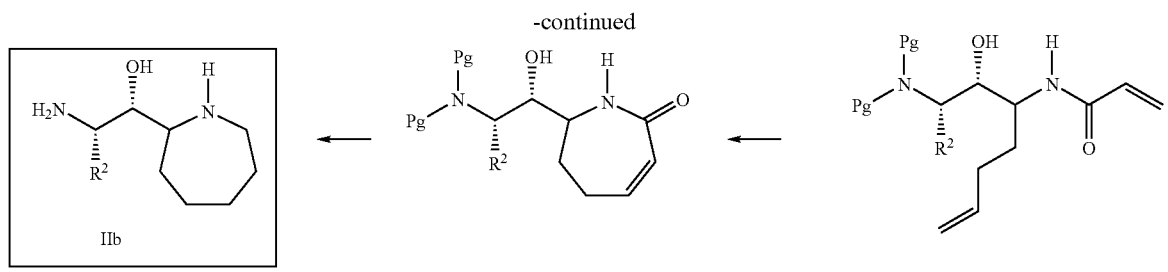

The anion of nitroalkene (xii) is reacted with diprotected aminoaldehyde (i) in a suitable solvent such as tetrahydrofuran to provide the nitroalcohol (xiii). This nitroalcohol is reduced to the corresponding aminoalcohol (xiv), which is then acylated with acryloyl chloride to provide the corresponding amide (xv). This amide is reacted with Grubb's catalyst to provide the 1,5,6,7-tetrahydroazepin-2-one (xvi). The carbonyl and double bond of this lactam are reduced by treatment with borane-dimethyl sulfide complex. The terminal amine is then deprotected to provide the aminoalcohol (IIb).

Intermediates useful for the preparation of certain compounds of Formula I where $R^3$ is a 5- or 6-monosubstituted piperidin-2-yl moiety or a 5,6-disubstituted piperidin-2-yl moiety may be prepared as illustrated in the following scheme where $R^1$, $R^2$, $R^{28'}$, $R^{39}$, and $R^{40}$ are as previously defined and the variable Pg is an oxygen protecting group.

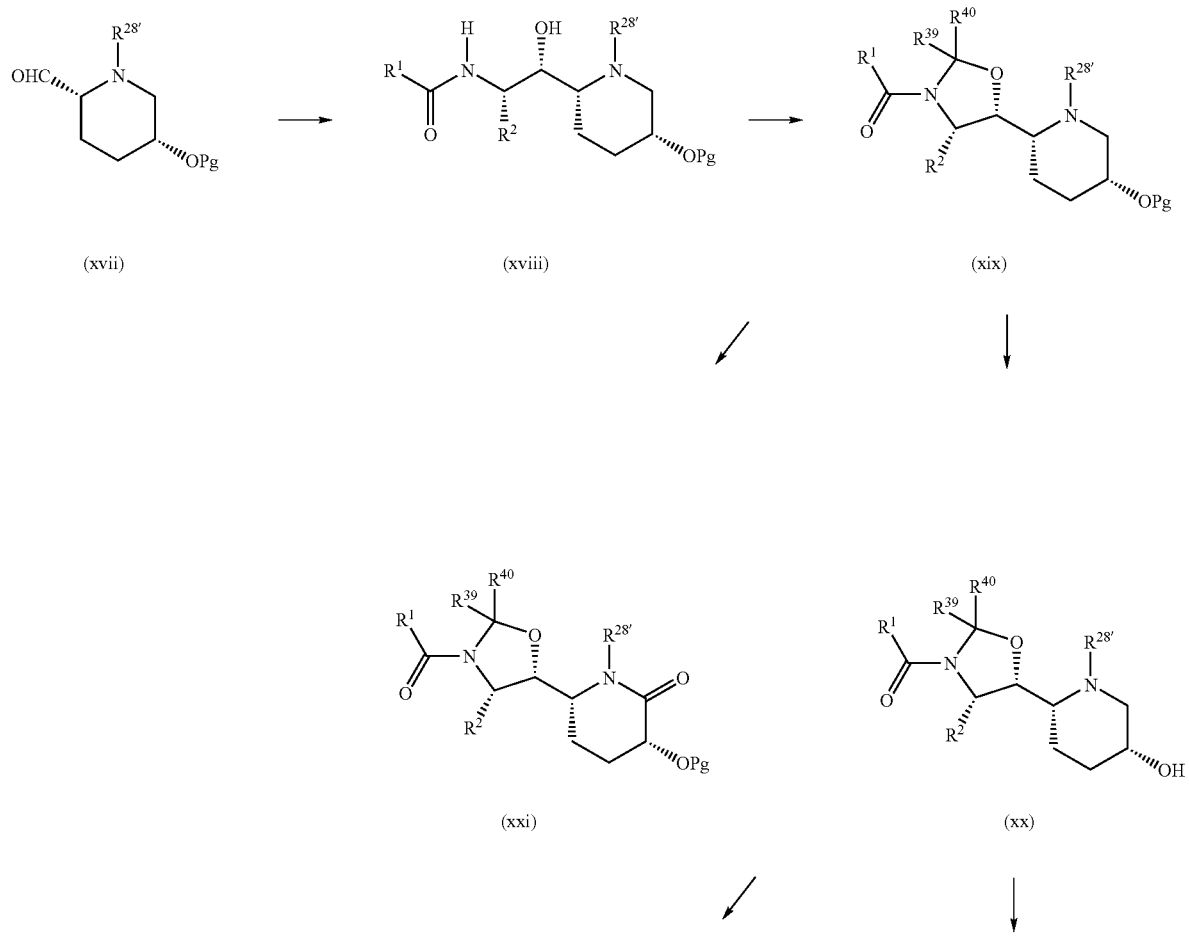

Scheme V

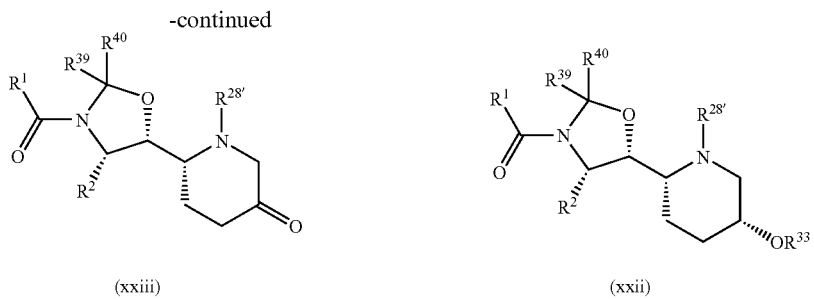

(xxiii)  (xxii)

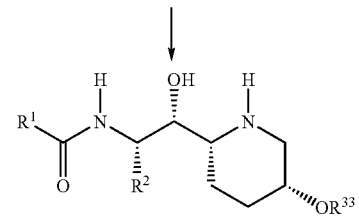

I(a)

An appropriately substituted 2-formylpiperidine (xvii) may be reacted as described in Schemes I and II to provide intermediate (xviii). The amide nitrogen and secondary alcohol moieties may be simultaneously protected by reaction with an appropriate enol ether, such as 2-methoxypropene, in the presence of acid to provide the corresponding oxazolidine (xix). Intermediate (xix) may be oxidized directly, for example with ruthenium (IV) oxide and sodium metaperiodate, to provide the protected hydroxyketone (xxi). Alternatively, intermediate (xix) may be deprotected to provide the corresponding alcohol (xx) and then oxidized under standard conditions to provide the corresponding ketone (xxiii). Ketone intermediates (xxi) and (xxiii) may be reacted with appropriate Grignard and Wittig reagents under a variety of conditions to provide further intermediates useful for the preparation of compounds of the invention. (For example, see: *Comprehensive Organic Transformations*, Larock, Wiley-VCH Publishers, Inc., New York, (1999); *Advanced Organic Chemistry*, March, Wiley Interscience, New York, Third Edition, (1985)) Intermediate alcohol (xx) may alternatively be reacted with an appropriate electrophile under standard conditions to provide intermediate (xxii). Deprotection of intermediate (xxii) under standard conditions provides compounds of Formula I(a) which represent a preferred embodiment of the present invention. Intermediates (xix), (xx), (xxi), (xxii), and (xxiii) represent further embodiments of the present invention.

The requisite aldehyde (xvii) may be prepared as described in the following scheme where variables $R^{28'}$ and Pg are as previously defined.

Scheme VI

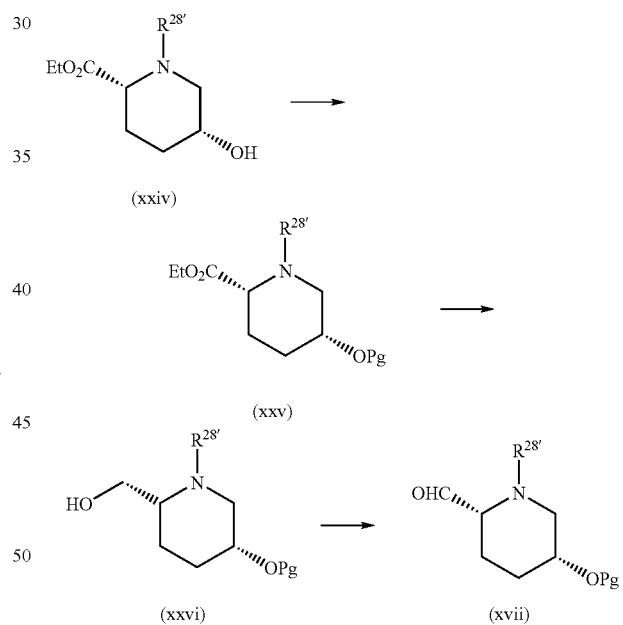

An appropriately N-protected 5-hydroxypiperidine-2-carboxylic acid ester (*Bioorg. Med. Chem. Lett.*, 12(10) 1387 (2002)) is reacted with an appropriate reagent to introduce a suitable oxygen protecting group to provide intermediate (xxv). The ester moiety is reduced under standard conditions, for example with a suitable hydride reducing agent such as lithium borohydride, to provide alcohol (xxvi), which is then oxidized under standard conditions, for example by reaction with sulfur trioxide complex in dimethylsulfoxide, to provide the desired aldehyde (xvii).

Intermediates useful for the preparation of compounds of Formula I where $R^3$ is the piperidin-2-yl moiety (b), the 1,2,3,6-tetrahydropyridin-2-yl moiety (c), or the 1,2,5,6-tetrahydropyridin-2-yl moiety (d) may be prepared as illustrated in the following scheme where $R^2$, $R^{29}$, and $R^{30}$ are as previously defined and the variable Pg is independently at each occurrence either a nitrogen or oxygen protecting group depending upon its point of attachment.

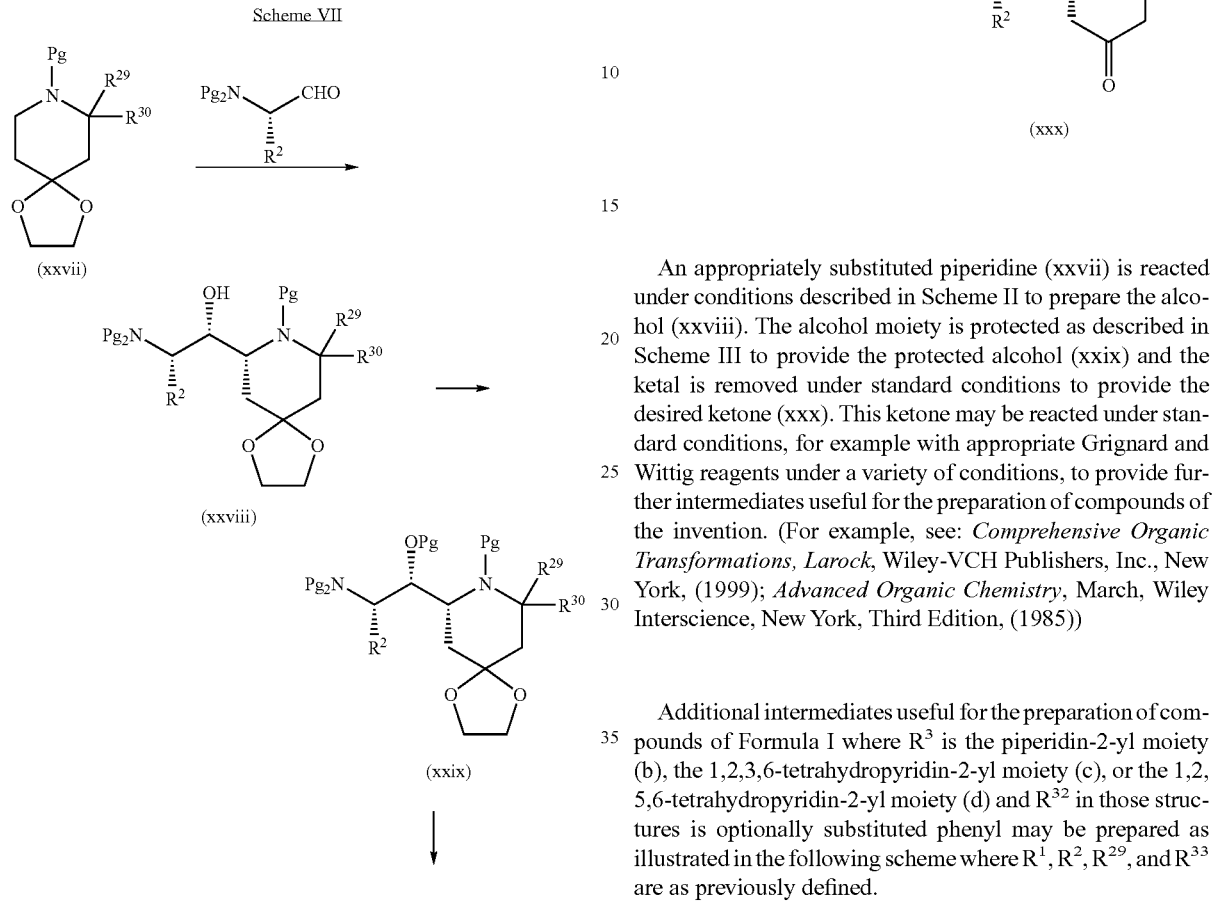

An appropriately substituted piperidine (xxvii) is reacted under conditions described in Scheme II to prepare the alcohol (xxviii). The alcohol moiety is protected as described in Scheme III to provide the protected alcohol (xxix) and the ketal is removed under standard conditions to provide the desired ketone (xxx). This ketone may be reacted under standard conditions, for example with appropriate Grignard and Wittig reagents under a variety of conditions, to provide further intermediates useful for the preparation of compounds of the invention. (For example, see: *Comprehensive Organic Transformations, Larock*, Wiley-VCH Publishers, Inc., New York, (1999); *Advanced Organic Chemistry*, March, Wiley Interscience, New York, Third Edition, (1985))

Additional intermediates useful for the preparation of compounds of Formula I where $R^3$ is the piperidin-2-yl moiety (b), the 1,2,3,6-tetrahydropyridin-2-yl moiety (c), or the 1,2,5,6-tetrahydropyridin-2-yl moiety (d) and $R^{32}$ in those structures is optionally substituted phenyl may be prepared as illustrated in the following scheme where $R^1$, $R^2$, $R^{29}$, and $R^{33}$ are as previously defined.

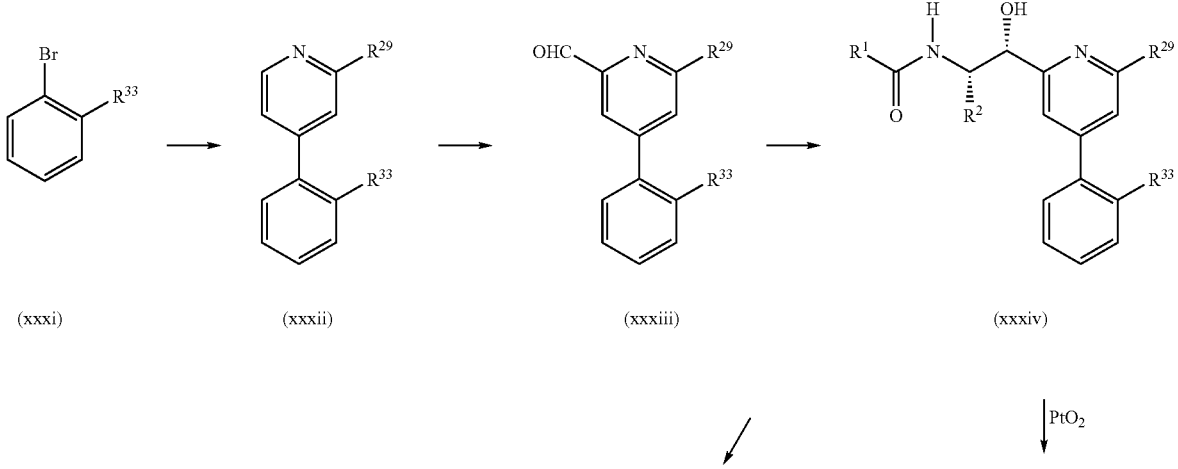

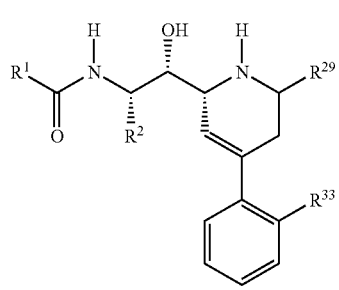

I(c)

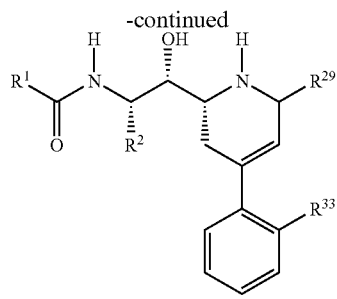

I(d)

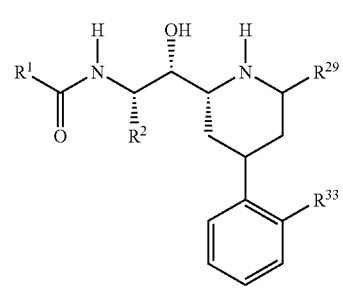

I(b)

An appropriate aryl halide (xxxi), preferably an aryl bromide, is reacted with a suitably substituted pyridine boronic acid in the presence of a palladium catalyst, such as tetrakis (triphenylphosphine) palladium(O), to provide a 4-arylpyridine (xxxii). This 4-arylpyridine is treated with a suitable base, such as methyllithium, and is then formylated under standard conditions to provide the aldehyde (xxxiii). This aldehyde is reacted as generally described in Schemes I and II to provide the intermediate compound (xxxiv). The pyridine ring is either hydrogenated completely in the presence of a suitable catalyst, such as platinum(II) oxide to provide compounds of Formula I(b), or compounds are treated with a suitable hydride reducing agent, such as sodium borohydride, in the presence of acid to provide the tetrahydropyridin-2-yl derivatives of Formula I(c) and I(d).

Intermediates useful for the preparation of compounds of Formula I where $R^3$ is the piperazinyl moiety (e) may be prepared as described in the following scheme where Pg, $R^1$, $R^2$, $R^{28}$, and $R^{35}$ are as previously defined.

The unprotected piperazine nitrogen of the aminoethanolamine (xxxv) is reacted with an appropriate electrophilic reagent, such as an appropriately substituted alkyl halide or acyl halide, under standard conditions to provide the corresponding intermediate of formula (xxxvi). Alternatively, the aminoethanolamine (xxxv) may be reacted with an appropriate carboxylic acid under standard peptide coupling conditions as previously described to provide the corresponding intermediate of formula (xxxvi). Intermediate (xxxvi) may then be completely deprotected to provide intermediate (xxxvii) where $R^{28}$=H and then reacted as previously described to provide compounds of Formula I(e). Alternatively, only the primary amine moiety of intermediate (xxxvi) is deprotected to provide intermediate (xxxvii) where $R^{28}$ is a nitrogen protecting group. This intermediate is then reacted with an appropriate reagent and deprotected as previously described

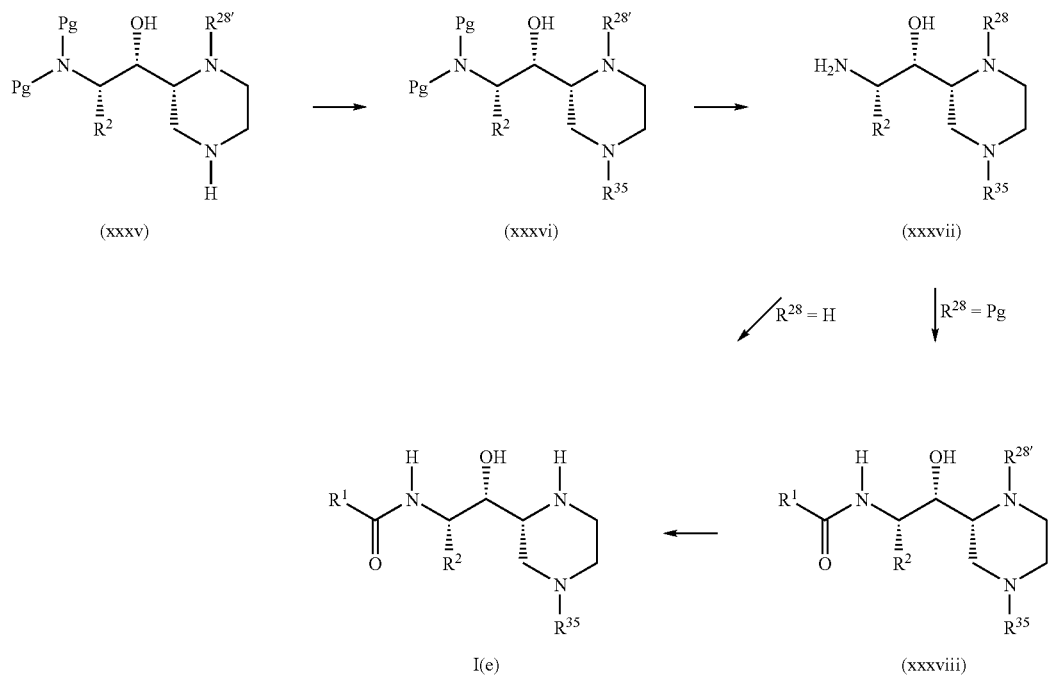

Preparation 1

2-(R)-[2-(S)-Amino-3-(3,5-difluorophenyl)-1-(S)-hydroxypropyl]-piperidine-1-carboxylic acid tert-butyl ester

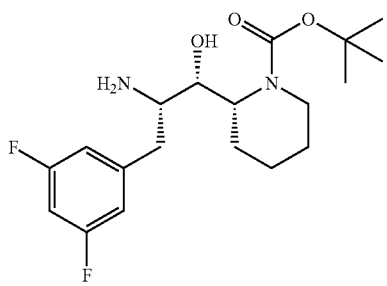

[2-(3,5-Difluorophenyl)-1-(S)-hydroxymethylethyl]-carbamic acid tert-butyl ester Dissolve commercially available 2-(S)-tert-butoxycarbonylamino-3-(3,5-difluorophenyl)propionic acid (5.995 g, 19.9 mmol) in ethylene glycol dimethyl ether (20 mL) and cool −20° C. Add 4-methylmorpholine (2.4 mL, 21.89 mmol) and stir 5 min, then add isobutyl chloroformate (2.9 mL, 21.89 mmol) dropwise and stir 5 min. Filter into −15° C. cooled flask with course frit, rinse with cold ethylene glycol dimethyl ether. Add sodium borohydride (1.129 g, 29.85 mmol) in water (9 mL) followed by water (500 mL), then warm to room temperature. Filter and dissolve solid in dichloromethane. Wash with saturated aqueous sodium chloride, dry (magnesium sulfate) and concentrate to give the title compound as a solid (4.57 g, 80%).

MS (ES): m/z=188.0 [M+H, prod-Boc].

2-(S)-Amino-3-(3,5-difluorophenyl)-propan-1-ol trifluoroacetate

Dissolve [2-(3,5-difluorophenyl)-1-(S)-hydroxymethylethyl]-carbamic acid tert-butyl ester (4.57 g, 15.9 mmol) in dichloromethane (20 mL). Add trifluoroacetic acid (20 mL) and stir 45 min and concentrate to give the title compound as a thick residue.

MS (ES): m/z=352.8 [M+H].

2-(S)-[Bis-(2-methylbenzyl)-amino]-3-(3,5-difluorophenyl)-propan-1-ol

Dissolve 2-(S)-amino-3-(3,5-difluorophenyl)-propan-1-ol trifluoroacetate (5.61 g, 15.9 mmol) in 10% aqueous ethanol (80 mL). Add potassium carbonate (8.79 g, 64 mmol) and 2-methylbenzyl bromide (4.7 mL, 35.0 mmol) and stir for 2 h. Dilute with dichloromethane (100 mL) and filter. Concentrate filtrate and partition in dichloromethane and water. Extract aqueous twice with dichloromethane, combine organics and wash with saturated aqueous sodium chloride, dry (magnesium sulfate) and concentrate. Purify (silica gel chromatography, eluting with hexanes and ethyl acetate) to give the title compound as a thick residue (4.30 g, 68%).

MS (ES): m/z=396.2 [M+H].

2-(S)-[Bis-(2-methylbenzyl)-amino]-3-(3,5-difluorophenyl)-propionaldehyde

Dissolve 2-(S)-[bis-(2-methylbenzyl)-amino]-3-(3,5-difluorophenyl)-propan-1-ol (1.34 g, 3.38 mmol) in DMSO (3 mL) and cool in an ice bath. Add triethylamine (1.9 mL, 13.51 mmol) followed by sulfur trioxide-pyridine complex (1.07 g, 6.76 mmol). Stir 30 min then slowly add water (1.5 mL). Dilute with ethyl acetate and wash with 5% aqueous citric acid (3×), saturated aqueous sodium chloride, dry (magnesium sulfate) and concentrate to give the title compound as a light yellow residue.

MS (ES): m/z=394.2 [M+H].

2-(S)-[Bis-(2-methylbenzyl)-amino]-3-(3,5-difluorophenyl)-1-pyridin-2-yl-propan-1-(S)-ol Dissolve 2-bromopyridine (0.485 mL, 5.07 mmol) in THF (30 mL) and cool to −78° C. Add n-butyllithium (2.0 mL, 2.5 M in hexanes). Slowly add 2-(S)-[bis-(2-methylbenzyl)-amino]-3-(3,5-difluorophenyl)-propionaldehyde (1.37 g, 3.3 mmol) in THF (10 mL) and stir 2 h. Quench reaction with saturated aqueous ammonium chloride. Warm to room temperature. Wash organic layer twice with 5% aqueous citric acid, saturated aqueous sodium chloride, dry (magnesium sulfate), concentrate and purify twice (silica gel chromatography, eluting with hexanes and ethyl acetate, and then dichloromethane and ethyl acetate) to give the title compound as a foam (0.636 g, 40%).

MS (ES): m/z=473.2 [M+H].

2-(S)-[Bis-(2-methylbenzyl)-amino]-3-(3,5-difluorophenyl)-1-(S/R)-piperidin-2-yl-propan-1-(R)-ol Add 2-(S)-[bis-(2-methylbenzyl)-amino]-3-(3,5-difluorophenyl)-1-pyridin-2-yl-propan-1-(S)-ol (0.55 g, 1.16 mmol), 5% platinum on carbon sulfided (215 mg), glacial acetic acid (1 mL) and methanol (25 mL) and stir under 1 atmosphere of hydrogen gas. Add filter agent, filter and concentrate. Add dichloromethane and wash with saturated aqueous sodium bicarbonate, dry (magnesium sulfate) and concentrate to give the title compound as a white foam (0.435 g, 78%).

MS (ES): m/z=479.3 [M+H].

2-(S)-[2-(S)-[Bis-(2-methylbenzyl)-amino]-3-(3,5-difluorophenyl)-1-(S)-hydroxypropyl]-piperidine-1-carboxylic acid tert-butyl ester and 2-(R)-[2-(S)-[Bis-(2-methylbenzyl)-amino]-3-(3,5-difluorophenyl)-1-(S)-hydroxypropyl]-piperidine-1-carboxylic acid tert-butyl ester Add di-tert-butyl dicarbonate (1.94 g, 8.9 mmol) to a solution of 2-(S)-[bis-(2-methylbenzyl)-amino]-3-(3,5-difluorophenyl)-1-(S/R)-piperidin-2-yl-propan-1-(R)-ol (0.425 g, 0.89 mmol) and triethylamine (0.43 mL, 3.1 mmol) in dichloromethane (20 mL). Stir 18 h at room temperature and wash with water (2×50 mL), saturated aqueous sodium chloride, dry (magnesium sulfate) and purify (silica gel chromatography, eluting with hexanes and ethyl acetate) to give the title compounds as a foam (0.042 g, 8%) of 2-(S)-[2-(S)-[bis-(2-methylbenzyl)-amino]-3-(3,5-difluorophenyl)-1-(S)-hydroxypropyl]-piperidine-1-carboxylic acid tert-butyl ester and (0.33 g, 64%) of 2-(R)-[2-(S)-[bis-(2-methylbenzyl)-amino]-3-(3,5-difluorophenyl)-1-(S)-hydroxypropyl]-piperidine-1-carboxylic acid tert-butyl ester.

MS (ES): m/z=579.3 [M+H].

2-(R)-[2-(S)-Amino-3-(3,5-difluorophenyl)-1-(S)-hydroxypropyl]-piperidine-1-carboxylic acid tert-butyl ester Add 2-(R)-[2-(S)-[bis-(2-methylbenzyl)-amino]-3-(3,5-difluorophenyl)-1-(S)-hydroxypropyl]-piperidine-1-carboxylic acid tert-butyl ester (0.33 g, 0.56 mmol), 20% palladium hydroxide on carbon (230 mg) and methanol (25 mL) and stir under 1 atmosphere of hydrogen gas for 18 h. Add filter agent, filter and concentrate to give the title compound as a foam (0.203 g, 98%).
MS (ES): m/z=371.2 [M+H].

Preparation 2

2-(R)-(2-(S)-Amino-1-(S)-hydroxy-3-phenylpropyl)-piperidine-1-carboxylic acid tert-butyl ester

2-(S)-Dibenzylamino-3-phenylpropionaldehyde

Dissolve 2-(S)-dibenzylamino-3-phenylpropan-1-ol (5.00 g, 15.08 mmol) in DMSO (15 mL) and cool in an ice bath. Add triethylamine (8.4 mL, 60.0 mmol) followed by sulfur trioxide-pyridine complex (4.80 g, 30.2 mmol), stir 30 min then slowly add water (15 mL). Dilute with ethyl acetate and wash with 5% aqueous citric acid (3×), saturated aqueous sodium chloride, dry (magnesium sulfate) and concentrate to give the title compound as a light yellow residue.
MS (ES): m/z=330.2 [M+H].

2-(S)-Dibenzylamino-3-phenyl-1-pyridin-2-yl-propan-1-(S)-ol

Dissolve 2-bromopyridine (2.73 mL, 28.63 mmol) in THF (150 mL) and cool to −78° C. Add n-butyllithium (12.0 mL, 2.5 M in hexanes). Slowly add 2-(S)-dibenzylamino-3-phenyl-propionaldehyde (4.71 g, 14.31 mmol) in THF (15 mL) and stir 30 min. Quench reaction with saturated aqueous ammonium chloride. Remove cold bath and warm to room temperature. Wash organic layer twice with 5% aqueous citric acid, saturated aqueous sodium chloride, dry (magnesium sulfate), concentrate and purify (silica gel chromatography, eluting with dichloromethane and ethyl acetate) to give the title compound as a residue (3.654 g, 62%).
MS (ES): m/z=409.3 [M+H].

2-(S)-Dibenzylamino-3-phenyl-1-piperidin-2-(R/S)-yl-propan-1-(R)-ol

Add 2-(S)-dibenzylamino-3-phenyl-1-pyridin-2-yl-propan-1-(S)-ol (1.05 g, 2.57 mmol), 5% platinum on carbon sulfided (215 mg), glacial acetic acid (2 mL) and methanol (40 mL) and stir 18 h under 1 atmosphere of hydrogen gas. Add filter agent, filter and concentrate. Add ethyl acetate and wash with saturated aqueous sodium bicarbonate, dry (magnesium sulfate) and concentrate to give the title compound as a white foam (1.005 g, 94%).
MS (ES): m/z=415.3 [M+H].

2-(S)-(2-(S)-Dibenzylamino-1-(S)-hydroxy-3-phenylpropyl)-piperidine-1-carboxylic acid tert-butyl ester and 2-(R)-(2-(S)-Dibenzylamino-1-(S)-hydroxy-3-phenylpropyl)-piperidine-1-carboxylic acid tert-butyl ester Add di-tert-butyl dicarbonate (4.7 g, 21.6 mmol) to a solution of 2-(S)-dibenzylamino-3-phenyl-1-piperidin-2-(R/S)-yl-propan-1-(R)-ol (0.895 g, 2.16 mmol) and triethylamine (1.05 mL, 7.55 mmol) in dichloromethane (20 mL). Stir 18 h at room temperature and wash with water (2×50 mL), saturated aqueous sodium chloride, dry (magnesium sulfate) and purify (silica gel chromatography, eluting with hexanes and ethyl acetate) to give the title compounds as a foam, 2-(S)-(2-(S)-dibenzylamnino-1-(S)-hydroxy-3-phenylpropyl)-piperidine-1-carboxylic acid tert-butyl ester (0.077 g, 7%) and 2-(R)-(2-(S)-dibenzylamino-1-(S)-hydroxy-3-phenylpropyl)-piperidine-1-carboxylic acid tert-butyl ester (0.521 g, 47%).
MS (ES): m/z=515.3 [M+H].

2-(R)-(2-(S)-Amino-1-(S)-hydroxy-3-phenylpropyl)-piperidine-1-carboxylic acid tert-butyl ester Add 2-(R)-(2-(S)-dibenzylamino-1-(S)-hydroxy-3-phenylpropyl)-piperidine-1-carboxylic acid tert-butyl ester (0.107 g, 0.21 mmol), 20% palladium hydroxide on carbon (60 mg) and methanol (5 mL) and stir 18 h under 1 atmosphere of hydrogen gas. Add filter agent, filter and concentrate to give the title compound as a foam.
MS (ES): m/z=335.2 [M+H].

Preparation 3

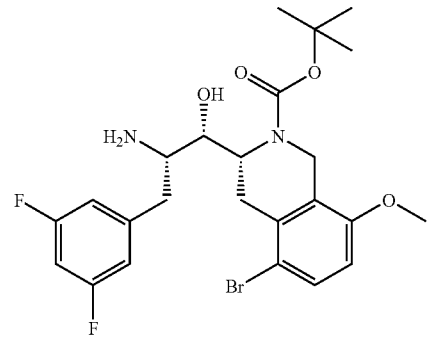

tert-Butyl 3(R)-[(1S,2S)-2-Amino-3-(3,5-difluorophenyl)-1-hydroxypropyl]-5-bromo-8-methoxy-3,4-dihydroisoquinoline-2(1H)-carboxylate

2-Bromo-5-hydroxy-(D)-phenylalanine

Slurry (D)-3-hydroxy-phenylalanine (3.00 g, 0.0166 mol) in acetic acid (300 mL) and add to bromine (0.930 mL, .0.0180 mol) in 30 mL of acetic acid over a period of 45 minutes at room temperature. Stir for 3 hours. Concentrate under reduced pressure and dissolve the residue in ethanol (120 mL). Add saturated aqueous sodium bicarbonate solution (1.5 g) and set in refrigerator to recrystallize. Collect six crops using less solvent each time. Combine crops to give the desired product as an off-white solid (1.87 g, 40%).
MS(ES): m/z=260 [M]

5-bromo-8-hydroxy-1,2,3,4-tetrahydroisoquinoline-3(R)-carboxylic acid

Slurry 2-bromo-5-hydroxy-(D)-phenylalanine (1.87 g, 0.00719 mol) in 0.05 M hydrochloric acid (10.7 mL) and add 37% formaldehyde solution in water (1.02 mL). Heat at 90° C. for one hour. Cool to room temperature, filter, and wash with water (2×) and acetone (2×) and dry in a vacuum oven to give the desired product (1.53 g, 75%) as a light pink solid.

MS(ES): m/z=272 [M]

Methyl 5-bromo-8-hydroxy-1,2,3,4-tetrahydroisoquinoline-3(R)-carboxylate

Slurry the 5-bromo-8-hydroxy-1,2,3,4-tetrahydroisoquinoline-3(R)-carboxylic acid (1.538 g, 0.005652 mol) in methanol (60 mL). Add sulfuric acid (305 uL, 0.00572 mol). Heat at 85° C. for 2.5 days. Cool the solution to room temperature and concentrate under reduced pressure to a volume of ~5 mL. Add ethyl acetate (100 mL) and neutralize with 10% aqueous potassium carbonate. Separate the layers and extract the aqueous layer with ethyl acetate (1×100 mL). Combine the organic layers and dry over magnesium sulfate. Concentrate the filtrate to give the desired product (1.65 g, 98%) as a light pink solid.

MS(ES): m/z=288 [M+2]

2-tert-Butyl 3-methyl 3(R)-5-bromo-8-hydroxy-3,4-dihydroisoquinoline-2,3(1H)-dicarboxylate To a solution of methyl (3R)-5-bromo-8-hydroxy-1,2,3,4-tetrahydroisoquinoline-3-carboxylate (1.64 g, 0.00573 mol) in tetrahydrofuran (28.0 mL, 0.345 mol) add di-tert-Butyldicarbonate (1.38 g, 0.00630 mol) and N,N-diisopropylethylamine (3.99 mL, 0.0229 mol). Stir the solution for 16 hours. Concentrate under reduced pressure and partition the residue between ethyl acetate (150 mL) and water (50 mL). Separate and wash the organic layer with 1N HCl solution (1×50 mL) and saturated aqueous sodium chloride (1×50 mL). Dry over magnesium sulfate. Purify (Biotage medium pressure chromatography using 25 to 30% ethyl acetate:hexanes as eluent) to give the desired product (1.29 g, 58%) as a white foam.

MS(ES): m/z=386 [M].

3(R)-5-Bromo-8-methoxy-3,4-dihydro-1H-isoquinoline-2,3-dicarboxylic acid 2-tert-butyl ester 3-methyl ester Dissolve the 2-tert-butyl 3-methyl 3(R)-5-bromo-8-hydroxy-3,4-dihydroisoquinoline-2,3(1H)-dicarboxylate (850 mg, 0.0022 mol) in acetone (6.00 mL, 0.0817 mol) and add potassium carbonate (304 mg, 0.00220 mol) and methyl iodide (1.30 mL, 0.0209 mol). Heat the reaction mixture to reflux and stir for 16 hours. Cool to room temperature and filter over a pad of filtering agent. Concentrate the filtrate and dissolve the residue in ethyl acetate and filter through a pad of filtering agent and repeat once more. Concentrate the filtrate to give the desired product (882 mg, 95%).

MS(ES): m/z=300 [M–100]

tert-Butyl 5-Bromo-3(R-(hydroxymethyl)-8-methoxy-3,4-dihydroisoquinoline-2(1H)-carboxylate Dissolve 3(R)-5-bromo-8-methoxy-3,4-dihydro-1H-isoquinoline-2,3-dicarboxylic acid 2-tert-butyl ester 3-methyl ester (880 mg, 0.0022 mol) in tetrahydrofuran (6.0 mL, 0.074 mol). Cool to 0° C. and add lithium borohydride (72 mg, 0.0033 mol). Stir for 60 hours. Add acetic acid (0.75 mL) slowly at 0° C. and add water (20 mL). Extract with ethyl acetate (1×100 mL) and wash with water (1×30 mL), saturated aqueous sodium bicarbonate (1×30 mL) and saturated aqueous sodium chloride (1×30 mL). Dry over magnesium sulfate and purify (Biotage medium pressure chromatography eluting with 40% ethyl acetate:hexanes) to give the desired product (710 mg, 82%) as a white foam.

MS(ES): m/z=272 [M–100]

tert-Butyl 5-Bromo-3(R)-formyl-8-methoxy-3,4-dihydroisoquinoline-2(1H)-carboxylate Dissolve the tert-butyl 5-bromo-3(R)-(hydroxymethyl)-8-methoxy-3,4-dihydroisoquinoline-2(1H)-carboxylate (710 mg, 0.0019 mol) in dimethylsulfoxide (2.00 mL) and cool to 0° C. Add triethylamine (1.06 mL, 0.00763 mol) and sulfur trioxide-pyridine complex (0.607 g, 0.00381 mol). Warm to room temperature over one hour. Dilute diethyl ether (100 mL) and extract (3×25 mL) with 5% aqueous citric acid, (1×25 mL) saturated aqueous sodium chloride, and dry over magnesium sulfate. Concentrate the filtrate to give the desired product (687 mg, 94%) as an off-white semi-solid.

MS(ES): m/z=370 [M].

tert-Butyl 5-Bromo-3(R)-[(1R,2S)-3-(3,5-difluorophenyl)-1-hydroxy-2-nitropropyl]-8-methoxy-3,4-dihydroisoquinoline-2(1H)-carboxylate Dissolve tert-butyl 5-bromo-3(R)-formyl-8-methoxy-3,4-dihydroisoquinoline-2(1H)-carboxylate (400.0 mg, 0.001080 mol) and 1-(3,5-difluorophenyl)-2-nitroethane (305 mg, 0.00162) in tetrahydrofuran (3.00 mL) and cool to 0° C. celsius. Add 1.00 M tetra-n-butylammonium fluoride in tetrahydrofuran (1.48 mL) and stir at 0° C. for 40 minutes. Dilute the reaction mixture with ethyl acetate (75 mL), water (20 mL) and saturated aqueous sodium chloride (5 mL). Shake well and separate the layers. Wash the organic layer with water (2×25 mL), saturated aqueous sodium chloride (1×25 mL) and dry over magnesium sulfate. Purify (Biotage medium pressure chromatography eluting with 10% ethyl acetate:hexanes) to give the desired product (234 mg, 37%) as a white solid.

MS(ES): m/z=557 [M].

Reduction

Dissolve tert-butyl 5-bromo-3(R)-[(1R,2S)-3-(3,5-difluorophenyl)-1-hydroxy-2-nitropropyl]-8-methoxy-3,4-dihydroisoquinoline-2(1H)-carboxylate (233 mg, 0.000418 mol) in methanol (5.00 mL). Cool to 0° C. and add nickel dichloride (86.9 mg, 0.000670 mol) and sodium tetrahydroborate (69.8 mg, 0.00184 mol) over one minute. Stir the resulting black slurry at 0° C. for 30 minutes then add water (0.5 mL) and concentrate under reduced pressure. Add water (10 mL) and ethyl acetate (25 mL) and filter through a filtering agent. Separate the filtrate layers and wash the organic layer with saturated aqueous sodium chloride (1×15 mL) and dry over magnesium sulfate. Purify (Biotage medium pressure chromatography eluting with 50% ethyl acetate:dichloromethane) to give the title compound (59.4 mg, 26%) as a white solid.

MS(ES): m/z=527 [M]

The compounds of Preparations 4-5 may be prepared essentially as described in Preparation 3 using an appropriately substituted 1-phenyl-2-nitromethane and 3-(R)-formyl-3,4-dihydro-1H-isoquinoline-2-carboxylic acid tert-butyl ester prepared essentially as described in WO 02/059117).

| Prep | Compound | MS [M + H] |
|---|---|---|
| 4 | 3-(R)-(2-(S)-Amino-1-(S)-hydroxy-3-phenylpropyl)-3,4-dihydro-1H-isoquinoline-2-carboxylic acid tert-butyl ester | 383.3 |
| 5 | 3-(R)-(2-(S)-Amino-1-(S)-hydroxy-3-(3,5-difluorophenyl)propyl)-3,4-dihydro-1H-isoquinoline-2-carboxylic acid tert-butyl ester | 419.2 |

Preparation 6

3-(2-(S)-amino-1-hydroxy-3-phenylpropyl)-1-methylpiperazin-2-one

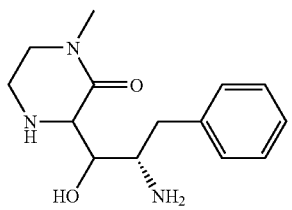

4-Benzyloxycarbonyl-1-methylpiperazin-2-one

Dissolve 4-benzyloxycarbonylpiperazin-2-one (2 g, 8.6 mmol) in THF (10 mL). Add sodium hydride (236 mg, 9.4 mmol, 60% dispersion in mineral oil) in one portion and stir at room temperature for 30 min. Add iodomethane (0.8 mL, 13 mmol) and stir at room temperature overnight. Concentrate, add ethyl acetate and wash with water. Separate organic layer, wash with saturated aqueous sodium chloride, dry (magnesium sulfate), concentrate and purify (silica gel chromatography, eluting with ethyl acetate) to give the title compound as a yellow oil (1.7 g, 82%).

MS (ES): m/z=249 [M+H].

3-(2-(S)-Dibenzylamino-1-hydroxy-3-phenylpropyl)-4-benzyloxycarbonyl-1-methylpiperazin-2-one Treat a solution of 4-benzyloxycarbonyl-1-methylpiperazin-2-one (1.4 g, 5.7 mmol) in THF (4 mL) cooled at –78° C. with lithium bis(trimethylsilyl)amide (1.0 M solution in THF, 5.7 mL, 5.7 mmol) dropwise and stir 30 min. Add 2-(dibenzylamino)-3-phenylpropanal (1 g, 3.1 mmol) in THF (2 mL) and stir at –78° C. for 45 min. Quench with saturated aqueous ammonium chloride solution. Separate organic layer and wash with water, saturated aqueous sodium chloride, dry (magnesium sulfate), concentrate and purify (silica gel chromatography, eluting with 1:1 hexanes:ethyl acetate) to provide the title compound as a mixture of four diastereoisomers which are separated by HPLC (normal phase, eluting with 85:15 hexanes:isopropanol) (828 mg, 45% total yield).

Isomer-1=run time 9.9 min, MS (ES): m/z=578 [M+H].
Isomer-2=run time 14.0 min, MS (ES): m/z=578 [M+H].
Isomer-3=run time 11.7 min, MS (ES): m/z=578 [M+H].
Isomer-4=run time 12.3 min, MS (ES): m/z=578 [M+H].

3-(2-(S)-Amino-1-hydroxy-3-phenylpropyl)-1-methylpiperazin-2-one

Treat a solution of 3-(2(S)-dibenzylamino-1-hydroxy-3-phenylpropyl)-4-benzyloxycarbonyl-1-methylpiperazin-2-one (Isomer-2) (210 mg, 0.36 mmol) in methanol (10 mL) with 20% palladium hydroxide on carbon (48 mg) in one portion and stir the mixture under 1 atmosphere of hydrogen gas for 24 h. Filter through a filtering agent, wash with methanol and concentrate to give the title compound as an oil.

MS (ES): m/z=264 [M+H].

The compounds of Preparation 7-9 may be prepared essentially as described in Preparation 6.

| Prep | Compound | MS [M + H] |
|---|---|---|
| 7 | 3-(2-(S)-amino-1-hydroxy-3-phenylpropyl)-1-methylpiperazin-2-one Isomer-1 | 264 |
| 8 | 3-(2-(S)-amino-1-hydroxy-3-phenylpropyl)-1-methylpiperazin-2-one Isomer-3 | 264 |
| 9 | 3-(2-(S)-amino-1-hydroxy-3-phenylpropyl)-1-methylpiperazin-2-one Isomer-4 | 264 |

Preparation 10

2-(R)-[(1S,2S)-2-Acetylamino-3-(3,5-difluorophenyl)-1-hydroxypropyl]-piperidine-1-carboxylic acid tert-butyl ester

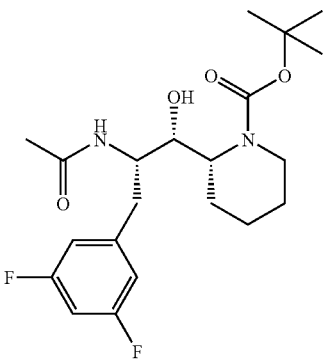

(2-(R)-[(1S,2S)-2-Acetylamino-3-(3,5-difluorophenyl)-1-hydroxypropyl]-piperidine-1-carboxylic acid tert-butyl ester Add 1-acetylimidazole (0.035 g, 0.315 mmol) and triethylamine (0.04 mL, 0.286 mmol) to solution of 2-(R)-[2-(S)-amino-3-(3,5-difluorophenyl)-1-(S)-hydroxypropyl]-piperidine-1-carboxylic acid tert-butyl ester (0.106 mg, 0.286 mmol) in dichloromethane (10 mL) and stir 18 h at room temperature. Dilute with ethyl acetate and wash with 1 N hydrochloric acid (3×), saturated aqueous sodium bicarbonate, saturated aqueous sodium chloride, dry (magnesium sulfate), concentrate and purify (silica gel chromatography, eluting with dichloromethane and ethyl acetate) to give the title compound as a white solid (0.089 g, 76%).

MS (ES): m/z=411.2 [M−H].

The compound of Preparation 11 may be prepared essentially as described in Preparation 10 beginning with the appropriate amine.

| Prep | Compound | MS [M + H] |
|---|---|---|
| 11 | 2-(R)-((1S,2S)-2-Acetylamino-1-hydroxy-3-phenylpropyl)-piperidine-1-carboxylic acid tert-butyl ester | 377.2 |

Preparation 12

2-(S)-sec-butylamino-6-(methanesulfonyl-methylamino)-isonicotinic acid potassium salt 2-(S)-sec-Butylamino-6-chloro-isonicotinic acid methyl ester Add to a 300 mL autoclave reactor 2,6-dichloroisonicotinic acid methyl ester (20 g, 0.09707 mol), palladium acetate (2.18 g, 0.009707 mol, 0.), rac-2,2'-bis(diphenylphosphino)-1,1'-binaphthyl (6.04 g, 0.009707 mol), cesium carbonate (37.95 g, 0.1165 mol) and (S)-(+)-2-sec-butylamine (8.52 g, 0.1165 mol) in toluene (200 mL). Flush with nitrogen 3 times and heat to 90° C. for 23 h. Cool to room temperature, filter, concentrate the filtrate and purify (silica gel chromatography) to give the title compound as a yellow solid (11.3 g, 48%).

m.p. 62.3-63.0° C., $^1$H NMR (500 MHz, DMSO) δ 7.07 (s, 1H), 6.84 (s, 1H), 4.72 (br s, 1H), 3.95 (s, 3H), 3.74 (m, 1H), 1.59 (m, 2H) 1.24 (d, J=6.5 Hz, 3H), 0.99 (t, J=7 Hz, 3H).

(S)-(+)-2-sec-Butylamino-6-methanesulfonylamino-isonicotinic acid methyl ester

Add to a 300 mL of autoclave reactor (s)-(+)-2-sec-butylamino-6-chloro-isonicotinic acid methyl ester (12.46 g, 0.05134 mol), bis(dibenzylideneacetone)palladium (0) (2.35 g, 0.002567 mol), 2-di-tert-butylphosphino biphenyl (1.53 g, 0.005134 mol) and sodium methanesulfonamide (12.02 g, 0.1027 mol) in toluene (250 mL). Flush with nitrogen 3 times and heat to 99° C. for 24 h. Filter and dissolve the filter cake in water (400 mL). Extract the aqueous layer with chloroform (3×200 mL), dry (magnesium sulfate) and concentrate. Dissolve the crude product in dichloromethane (20 mL) and precipitate out by adding hexanes (400 mL) to give a solid (7.18 g, 46%).

m.p. 118.6-123.0° C., $^1$H NMR (500 MHz, DMSO) δ 6.87 (s, 1H), 6.69 (s, 1H), 4.83 (br, 1H), 3.94 (s, 3H), 3.74 (m, 1H), 3.27 (s, 1H), 1.60 (m, 2H) 1.25 (d, J=7 Hz, 3H),0.99 (t, J=7 Hz, 3H).

(S)-(+)-2-sec-Butylamino-6-(methanesulfonyl-methylamino)-isonicotinic acid methyl ester Treat a mixture of (s)-(+)-2-sec-butylamino-6-methanesulfonylamino-isonicotinic acid methyl ester (13.63 g, 0.04523 mol) and potassium carbonate (12.50 g, 0.09046 mol) in DMF (42 mL) with iodomethane (7.90 g, 0.05563 mol). Stir at room temperature for 18 h, and add water (200 mL). The aqueous layer was extracted with methyl tert-butyl ether (5×150 mL). Wash the combined organic layers with 1 N lithium chloride (5×100 mL), dry (magnesium sulfate) and concentrate to give the title compound as a solid (13.19 g, 92%).

$^1$H NMR (500 MHz, DMSO) δ 7.00 (d, J=7.5 Hz, 1H) 6.84 (s, 1H), 6.77 (s, 1H), 3.85 (s, 3H), 3.80 (m, 1H), 3.26 (s, 3H), 3.21 (s, 3H), 1.54 (m, 2H) 1.13 (m, 3H), 0.99 (t, J=5.5 Hz, 3H).

(S)-(+)-2-sec-butylamino-6-(methanesulfonyl-methylamino)-isonicotinate potassium salt Heat a mixture of (S)-(+)-2-sec-butylamino-6-(methanesulfonyl-methylamino)-isonicotinic acid methyl ester (12.66 g, 0.04014 mol) and potassium hydroxide (2.7 g, 0.04817 mol, 1.2 eq) until dissolved. Dilute with water (62 mL) and was heat to reflux for 3 h. Cool to room temperature and add 1 N HCl (8 mL). Concentrate and add dichloromethane (300 mL) and stir well. Filter and concentrate filtrate to give the title compound as a yellow solid (13.62 g, 100%).

m.p. 78-83° C. $^1$H NMR (500 MHz, DMSO) δ 6.72 (s, 1H), 6.67 (s, 1H), 6.30 (d, J=7 Hz, 1H) 3.73 (m, 1H), 3.18 (s, 3H), 3.17 (s, 3H), 1.55 (q, 1H) 1.45 (q, 1H), 1.12 (d, J=5 Hz, 3H), 0.89 (t, J=7.5 Hz, 3H).

Preparation 13

2-[1-(S)-Phenylethyl]-2-aza-(1R,4R)-bicyclo[2.2.2]oct-(5Z)ene-3-(R)-carboxylic acid ethyl ester

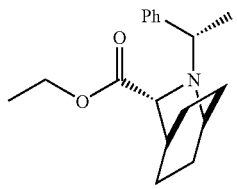

(S)-(1-phenyl-ethylimino) acetic acid ethyl ester

Treat a solution of neat (S)-α-methylbenzylamine (7.5 mL, 59 mmol) in dichloromethane (300 mL) at 0° C. with ethyl glyoxalate solution (50% in toluene, 11.5 mL). Add 4Å molecular sieves (20 g) to the above solution. Stir the reaction mixture at 0° C. for 2 h. Filter the solids off, concentrate and purify (silica gel chromatography, eluting with 20:80 to 70:30 ethyl acetate:hexanes) to give the title compound (11.1 g, 97%)

2-[1-(S)-Phenylethyl]-2-aza-(1R,4R)bicyclo[2.2.2]oct-(5Z)ene-3-(R)-carboxylic acid ethyl ester and
2-[1-(S)-Phenplethyl]-2-aza-(1S,4S)-bicyclo[2.2.2]oct-(5Z)-ene-3-(S)-carboxylic acid ethyl ester Treat a solution of (S)-(1-phenyl-ethylimino)-acetic acid ethyl ester (2.05 g, 10 mmol) in dichloromethane (50 mL) at −78° C. with trifluoroactetic acid (0.53 mL, 11 mmol), boron trifluoride diethyl etherate (1.39 mL, 11 mmol), followed by 1,3-cyclohexadiene (1.05 mL, 11 mmol). Stir the reaction mixture at -78° C. for 2 h and at −20° C. overnight. Quench the reaction with saturated aqueous sodium bicarbonate. Extract the products with dichloromethane (100 mL). Wash the organic layer with saturated aqueous sodium bicarbonate, saturated aqueous sodium chloride, dry (magnesium sulfate), concentrate and purify (silica gel chromatography, eluting with 10:90 ethyl acetate:hexanes) to give the title compound 2-[1-(S)-phenylethyl]-2-aza-(1R,4R)-bicyclo[2.2.2]oct-(5Z)ene-3-(R)-carboxylic acid ethyl ester (1.22 g, 43%) as Isomer

Preparation 14

(5R,6S)-Dihydroxy-2-[1-(S)-phenylethyl]-2-aza-(1R, 4S)-bicyclo[2.2.2]octane-3-(R)-carboxylic acid ethyl ester

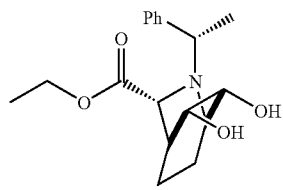

Treat a solution of 2-[1-(S)-phenylethyl]-2-aza-(1R,4R)-bicyclo[2.2.2]oct-(5Z)ene-3-(R)-carboxylic acid ethyl ester (1.22 g, 4.28 mmol) in THF (20 mL) at 0° C. with a THF solution of osmium tetroxide (109 mg, 0.43 mmol), followed by 4-methylmorpholine N-oxide (601 mg, 5.14 mmol). Stir the reaction at 0° C. for 1 h and at room temperature overnight. Quench the reaction with 10% aqueous sodium sulfite (20 mL), dilute the reaction mixture with ethyl acetate (100 mL), dry (magnesium sulfate), concentrate and purify (silica gel chromatography, eluting with 20:80 to 1:1 ethyl acetate:hexanes) to give the title compound (0.8 g, 58%).

Preparation 15

(5S,6R)-Difluoro-2-[1-(S)-phenylethyl]-2-aza-(1R, 4S)-bicyclo[2.2.2]octane-3-(R)-carboxylic acid ethyl ester

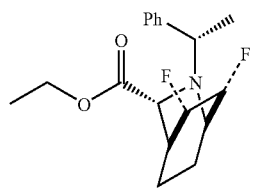

Treat a solution of (5R,6S)-dihydroxy-2-[1-(S)-phenylethyl]-2-aza-(1R,4S)-bicyclo[2.2.2]octane-3-(R)-carboxylic acid ethyl ester (800 mg, 2.50 mmol) in dichloromethane (16 mL) at -10° C. with (diethylamino)sulfur trifluoride (0.786 mL, 6.0 mmol) for 1 h and at room temperature overnight. Quench the reaction with ice and saturated aqueous sodium bicarbonate. Extract with dichloromethane (100 mL), dry (magnesium sulfate), concentrate and purify (silica gel chromatography, eluting with 15:85 ethyl acetate:hexanes) to give the, title compound (480 mg, 60%).

Preparation 16

5-(S)-Hydroxy-2-[1-(S)-phenylethyl]-2-aza-(1R,4S)-bicyclo[2.2.2]octane-3-(R)-carboxylic acid ethyl ester

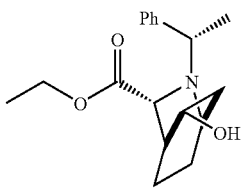

Add a solution of 2-[1-(S)-phenylethyl]-2-aza-(1R,4R)-bicyclo[2.2.2]oct-(5Z)ene-3-(R)-carboxylic acid ethyl ester (1.1 g, 3.86 mmol) in THF (5 mL) to a THF solution of boron trifluoride-methyl sulfide complex solution at 0° C. Stir the reaction at 0° C. for 1 h, room temperature for 2 h and 30° C. for 30 min. Treat the reaction mixture with water (0.2 mL), 1 N NaOH (0.70 mL), THF (1.5 mL), ethanol (0.4 mL), 30% hydrogen peroxide (0.4 mL). Stir the reaction mixture at room temperature for 1 h. Extract the product with ethyl acetate, dry (magnesium sulfate), concentrate and purify (silica gel chromatography, eluting with 30:70 to 60:40 ethyl acetate:hexanes) to give the title compound (0.36 g, 30%).

Preparation 17

5-Oxo-2-[1-(S)-phenylethyl]-2-aza-(1R,4S)-bicyclo[2.2.2]octane-3-(R)-carboxylic acid ethyl ester

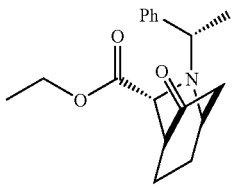

Treat a solution of 5-(S)-hydroxy-2-[1-(S)-phenylethyl]-2-aza-(1R,4S)-bicyclo[2.2.2]octane-3-(R)-carboxylic acid ethyl ester (252 mg, 0.83 mmol) in dichloromethane (10 mL) with Dess-Martin reagent (528 mg, 1.25 mmol) at room temperature for 2 h. Quench the reaction with 10% aqueous sodium sulfite solution and extract the product with ethyl acetate (50 mL), dry (magnesium sulfate), concentrate and purify (silica gel chromatography, eluting with 30:70 to 60:40 ethyl acetate:hexanes) to give the title compound (120 mg, 48%).

Preparation 18

5-(R)-Fluoro-2-[1-(S)-phenylethyl]-2-aza-(1R,4S)-bicyclo[2.2.2]oetane-3-(R)-carboxylic acid ethyl ester

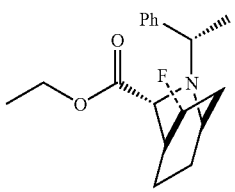

Treat a solution of 5-(S)-hydroxy-2-[1-(S)-phenylethyl]-2-aza-(1R,4S)-bicyclo[2.2.2]octane-3-(R)-carboxylic acid ethyl ester (102 mg, 0.34 mmol) in dichloromethane (10 mL) at 0° C. with (diethylamino)sulfur trifluoride (53 µL, 0.40 mmol) for 2h. Quench the reaction with ice. Extract the product with dichloromethane (50 mL), dry (magnesium sulfate), concentrate and purify (silica gel chromatography, eluting with 10:90 to 20:80 ethyl acetate:hexanes) to give the title compound (36 mg, 34%).

Preparation 19

5,5-Difluoro-2-[1-(S)-phenylethyl]-2-aza-(1R,4S)-bicyclo[2.2.2]octane-3-(R)-carboxylic acid ethyl ester

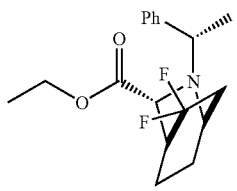

Treat a solution of 5-oxo-2-[1-(S)-phenylethyl]-2-aza-(1R,4S)-bicyclo[2.2.2]octane-3-(R)-carboxylic acid ethyl ester (102 mg, 0.34 mmol) in dichloromethane (10 mL) at 0° C. with (diethylamino)sulfur trifluoride (111 µL, 0.85 mmol) for 1 h. Stir the reaction at room temperature overnight. Quench the reaction with ice and extract the product with ethyl acetate (50 mL), dry (magnesium sulfate), concentrate and purify (silica gel chromatography, eluting with 10:90 to 20:80 ethyl acetate:hexanes) to give the title compound (40 mg, 37%).

Preparation 20

3-(R)-[2-(S)-Amino-1-(S)-hydroxy-3-phenylpropyl]-2-aza-(1R,4R)-bicyclo[2.2.2]octane-2-carboxylic acid tert-butyl ester 2-Aza-(1R,4R)-bicyclo[2.2.2]octane-2,3-dicarboxylic acid 2-tert-butyl ester 3-(R)-ethyl ester Add di-tert-butyl dicarbonate (478 mg, 2.2 mmol) to an ethanol (10 mL) and ethyl acetate (5 mL) solution of 2-[1-(S)-phenylethyl]-2-aza-(1R,4R)-bicyclo[2.2.2]oct-(5Z)ene-3-(R)-carboxylic acid ethyl ester (570 mg, 2 mmol). Cool the reaction to −78° C. and add 10% palladium on carbon (424 mg, 0.40 mmol) to the reaction mixture and stir under an atmosphere of hydrogen gas (1 atm) overnight at room temperature. Filter the catalyst, concentrate the filtrate and purify (silica gel chromatography, eluting with 10:90 to 15:85 ethyl acetate:hexanes) to give the title compound (355 mg, 62%).

3-(R)-Hydroxymethyl-2-aza-(1R,4R)-bicyclo[2.2.2]octane-2-carboxylic acid tert-butyl ester Treat a solution of 2-aza-(1R,4R)-bicyclo[2.2.2]octane-2,3-dicarboxylic acid 2-tert-butyl ester 3-(R)-ethyl ester (600 mg, 2.12 mmol) in dichloromethane (10 mL) at −78° C. with diisobutylaluminum hydride (1.0 M in dichloromethane, 5.3 mL, 5.3 mmol). Stir the reaction at −78° C. for 2 h and at room temperature overnight. Quench the reaction with a saturated aqueous sodium tartrate solution (30 mL over 30 min). Extract with ethyl acetate (75 mL) and purify (silica gel chromatography, eluting with 20:80 to 60:40 ethyl acetate:hexanes) to give the title compound (380 mg, 74%) along with 3-formyl-2-aza-bicyclo[2.2.2]octane-2-carboxylic acid tert-butyl ester (68 mg, 13%).

3-(R)-Formyl-2-aza-(1R,4R)-bicyclo[2.2.2]octane-2-carboxylic acid tert-butyl ester Treat a solution of 3-(R)-hydroxymethyl-2-aza-(1R,4R)-bicyclo[2.2.2]octane-2-carboxylic acid tert-butyl ester (570 mg, 2.37 mmol) in dichloromethane (16 mL) with Dess-Martin reagent (1.20 g, 2.84 mmol) at room temperature for 1.5 h. Quench the reaction with 10% aqueous sodium sulfite solution. Extract with ethyl acetate (75 mL), wash the organic layer with saturated aqueous sodium chloride, dry (magnesium sulfate), concentrate and purify (silica gel chromatography, eluting with 15:85 ethyl acetate:hexanes) to give the title compound (390 mg, 68%).

3-(R-[1-(R)-Hydroxy-2-(S)-nitro-3-phenylpropyl]-2-aza-(1R,4R)-bicyclo[2.2.2]octane-2-carboxylic acid tert-butyl ester (7a) and 3-(R)-[1-(S)-Hydroxy-2-(S)-nitro-3-phenylpropyl]-2-aza-(1R,4R)-bicyclo[2.2.2] octane-2-carboxylic acid tert-butyl ester Dissolve 3-(R)-formyl-2-aza-(1R,4R)-bicyclo[2.2.2]octane-2-carboxylic acid tert-butyl ester (70 mg, 0.3 mmol) in anhydrous THF (0.7mL) and cool to 0° C. Add a solution of tetrabutylammonium fluoride (1.0 M solution in THF, 0.03 mL) and then dropwise add 1-phenyl-2-nitroethane (66 mg. 0.43 mmol) to the mixture at 0° C. Maintain the reaction at the same temperature with stirring under nitrogen gas. Dilute the mixture with ethyl acetate (20 mL) after 4 h and wash with saturated aqueous sodium chloride solution, extract the organic layer, dry (magnesium sulfate), concentrate and purify (silica gel chromatography, eluting with 0:100 to 2:98 ethyl acetate:dichloromethane) to give the two isomers: Isomer 1 (22% yield) eluting with $R_f$=0.4 and Isomer 2 (15% yield) eluting with $R_f$=0.2.

Isomer 1: MS (ES): m/z=389.2 [M−H], Isomer2: MS (ES): m/z=389.0 [M−H].

3-(R)-[2-(S)-Amino-1-(S)-hydroxy-3-phenylpropyl]-2-aza-(1R,4R)-bicyclo[2.2.2]octane-2-carboxylic acid tert-butyl ester Dissolve 3-(R)-[1-(R)-hydroxy-2-(S)-nitro-3-phenylpropyl]-2-aza-(1R,4R)-bicyclo[2.2.2]octane-2-carboxylic acid tert-butyl ester (60 mg, 0.15 mmol) in methanol (3 mL). Add nickel (II) chloride (29.7 mg. 0.23 mmol) to the mixture at room temperature with vigorous stirring for 2 h. Cool the solution to 0° C. and add sodium borohydride (29 mg, 0.77 mmol). After 5 min at the same temperature, quench the reaction with water (3 mL) and concentrate. Dilute the residue with ethyl acetate and wash the organic layer with water, extract the organic layer and dry (magnesium sulfate). Filter and concentrate to obtain the crude title compound which is used in the next step without further purification.

MS (ES): m/z=361.3 [M+H].

The compounds of Preparation 21-23 may be prepared essentially as described in Preparation 20 with Preparations 22-23 using cyclopentadiene essentially as described in Preparation 13.

| Prep | Compound | MS [M + H] |
|---|---|---|
| 21 | 3-(R)-[2-(S)-Amino-1-(R)-hydroxy-3-phenylpropyl]-2-aza(1R,4R)-bicyclo[2.2.2]octane-2-carboxylic acid tert-butyl ester | 361.2 |
| 22 | 3-(2-Amino-1-hydroxy-3-phenylpropyl)-2-azabicyclo[2.2.1]heptane-2-carboxylic acid tert-butyl ester-Isomer 1 | 347.3 |
| 23 | 3-(2-Amino-1-hydroxy-3-phenylpropyl)-2-azabicyclo[2.2.1]heptane-2-carboxylic acid tert-butyl ester-Isomer 2 | 347.2 |

Preparation 24

2-((2S)-2-Amino-1-hydroxy-3-phenylpropyl)-6-ethylpiperidine-1-carboxylic acid tert-butyl ester 2-Ethylpiperidine-1-carboxylic acid tert-butyl ester Stir 2-ethylpiperidine (11.8 mL, 88.3 mmol) and di-tert-butyl-dicarbonate (23.1 g, 105.96 mmol) in saturated aqueous sodium bicarbonate (100 mL) and 1,4-dioxane (100 mL) at room temperature overnight. Extract with ethyl acetate; wash the combined organic layers with 5% aqueous potassium bisulfate, water, saturated aqueous sodium chloride, dry (magnesium sulfate), concentrate and purify (silica gel chromatography, eluting with 90:10 hexanes:ethyl acetate) to give the title compound (12 g, 64%).
$^1$H-NMR (CDCl$_3$, 300 MHz) δ 0.83 (t, J=7.26 Hz, 3H), 1.43 (s, 9H), 1.20-1.80 (m, 6H), 2.64-2.78 (m, 1H), 3.95 (br d, 1H), 4.09 (br s, 1H).

2-((2S)-2-Dibenzylamino-1-hydroxy-3-phenylpropyl)-6-ethylpiperidine-1-carboxylic acid tert-butyl ester Add N,N,N',N'-tetrametlhylethylenediamine (1.4 mL, 9.11 mmol), then sec-butyllithium (1.4 M in cyclohexane, 7.2 mL, 10.1 mmol) to 2-ethylpiperidine-1-carboxylic acid tert-butyl ester in diethyl ether (18 mL) at −78° C. under a nitrogen atmosphere. Warm to −35° C. and stir for 1 h. Cool to −78° C. and add (2S)-2-(dibenzylamino)-3-phenylpropanal (3.0 g, 9.11 mmol) in diethyl ether (4 mL) and stir for 30 min. Quench at −78° C. with water, warm to room temperature and extract with diethyl ether. Combine the organic layers, dry (magnesium sulfate) and concentrate. Separate the two major diastereomers of 2-((2S)-2-dibenzylaniino-1-hydroxy-3-phenylpropyl)-6-ethylpiperidine-1-carboxylic acid tert-butyl ester using normal-phase preparative HPLC (Kromasil Si 60, 10 μm, 80×180 mm; 98:2 Hexane:Acetone; 130 mL/min).
Isomer 1: MS (ES): m/z=543 [M+H].
Isomer 2: MS (ES): m/z=543 [M+H].

2-((2S)-2-Amino-1-hydroxy-3-phenylpropyl)-6-ethylpiperidine-1-carboxylic acid tert-butyl ester Stir 2-((2S)-2-dibenzylamino-1-hydroxy-3-phenylpropyl)-6-ethylpiperidine-1-carboxylic acid tert-butyl ester-Isomer 2 (0.7 g, 1.23 mmol) and 20% palladium hydroxide (0.2 g, 50% wet) in methanol (10 mL) under a balloon of hydrogen gas at room temperature for 2 days. Filter the suspension through a pad of filtering agent, wash with methanol and concentrate to give the title compound (0.4 g, 95%).
MS (ES): m/z=363 [M+H].

The compound of Preparations 25-27 may be prepared essentially as described in Preparation 24.

| Prep | Compound | MS [M + H] |
|---|---|---|
| 25 | 2-((2S)-2-Amino-1-hydroxy-3-phenylpropyl)-6-ethylpiperidine-1-carboxylic acid tert-butyl ester (Isomer 1) | 363 |
| 26 | 2-((2S)-2-Amino-1-hydroxy-3-phenylpropyl)-6-methylpiperidine-1-carboxylic acid tert-butyl ester (Isomer 1) | 349 |
| 27 | 2-((2S)-2-Amino-1-hydroxy-3-phenylpropyl)-6-methylpiperidine-1-carboxylic acid tert-butyl ester (Isomer 2) | 349 |

Preparation 28

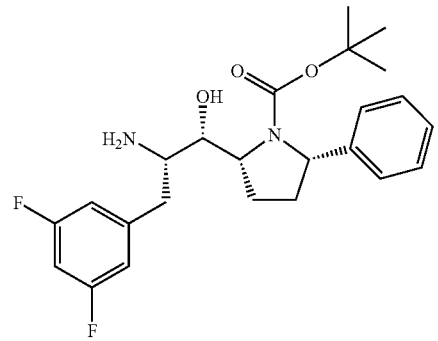

(2R,5 S)-2-[(1S,2S)-2-Amino-3-(3,5-difluorophenyl)-1-hydroxypropyl]-5-phenyl-pyrrolidine-1-carboxylic acid tert-butyl ester (2R,5S)-2-Hydroxymethyl-5-phenylpyrrolidine-1-carboxylic acid tert-butyl ester To an ice cold solution of commercially available (2R,5S)-5-phenyl-pyrrolidine-1,2-dicarboxylic acid 1-tert-butyl ester (1.00 g, 3.45 mmol) in 1,2-dimethoxyethane (5 mL) is added 4-methylmorpholine (0.4 mL, 3.795 mmol) and isobutyl chloroformate (0.50 mL, 3.795 mmol). Stir 15 min and filter into cold flask. Add sodium borohydride (0.196 g, 5.17 mmol) in water (3 mL), followed by addition of water (50 mL). Extract product with ethyl acetate (3×50 mL) and wash with saturated aqueous sodium chloride, dry (magnesium sulfate) and purify on silica gel to give the title compound (0.886 g, 93%).
MS (ES): m/z=278.3 [M+H].

(2R,5S)-2-[(1S,2S)-2-Amino-3-(3 5-difluorophenyl)-1-hydroxy-propyl]-5-phenyl-pyrrolidine-1-carboxylic acid tert-butyl ester The title compound may be prepared from (2R,5S)-2-hydroxymethyl-5-phenylpyrrolidine-1-carboxylic acid tert-butyl ester essentially as described in Preparation 1 (sulfur trioxide-pyridine oxidation step) and Preparation 20 (Henry reaction step and sodium borohydride nitro reduction step).
MS (ES): m/z=433.3 [M+H].

The compound of Preparation 29 may be prepared essentially as described in Preparation 28 starting with commercially available piperazine-1,2-(R)-4-tricarboxylic acid 4-benzyl ester 1-tert-butyl ester and reacting the intermediate aldehyde with 1,3-difluoro-5-(2-nitroethyl)-benzene followed by sodium borohydride reduction.

| Prep | Compound | MS [M + H] |
|---|---|---|
| 29 | 2-(R)-[2-(R,S)-Amino-3-(3,5-difluorophenyl)-1-(S)-hydroxypropyl]-piperazine-1,4-dicarboxylic acid 4-benzyl ester 1-tert-butyl ester | 506.2 |

Preparation 30

2-(R)-[(2-(R)-Amino-1-(S)-hydroxy-3-phenylpropyl)]-piperazine-1-carboxylic acid tert-butyl ester 4-Benzyl-2-(R)-[(2-(R)-dibenzylamino-1-(S)-hydroxy-3-phenylpropyl)]-piperazine-1-carboxylic acid-tert-butyl ester Dissolve commercially available tert-butyl 4-benzyl-1-piperazinecarboxylate (2.9 g, 10.4 mmol) in diethyl ether (75 mL) under argon and cool to −78° C. Add tetramethylethylene diamine (1.8 mL, 11.7 mmol) and sec-butyllithium (9 mL, 11.7 mmol) dropwise at −78° C. React for 1.5 h and add 2-(S)-dibenzylamino-3-phenylpropionaldehyde (2.6 g, 7.9 mmol) in diethyl ether (18 mL) dropwise over 10 min. Stir for 45 min. Add saturated aqueous ammonium chloride solution and ethyl acetate and let warm to room temperature, separate the layers, extract the aqueous layer with ethyl acetate, wash the organic layer with saturated aqueous sodium chloride solution, dry (magnesium sulfate), concentrate and purify (silica gel chromatography, eluting with 4:1 hexanes:ethyl acetate) to give the title compound (the first spot to elute) as a white solid (1.45 g, 30%) and a second diastereomer (the second spot to elute) as a white solid (1.1 g, 23%).

(2-(R)-(2-(R -Amino-1-(S)-hydroxy-3-phenylpropyl)-piperazine-1-carboxylic acid tert-butyl ester Dissolve 4-benzyl-2-(R)-(2-(R)-dibenzylamino-1-(S)-hydroxy-3-phenylpropyl)-piperazine-1-carboxylic acid tert-butyl ester (1.1 g, 1.8 mmol) in methanol (18 mL) and add 10% palladium on carbon (184 mg) and acetic acid (1 mL, 18 mmol). Stir under 1 atmosphere of hydrogen overnight, filter through a filtering agent wash with methanol and concentrate. Load onto a SCX cartridge (5 g), elute with methanol followed by 2 N ammonia in methanol to give the title compound as a yellow solid (573 mg, 95% yield).

Preparation 31

4-Acetyl-2-(R)-(2-(R)-amino-1-(S)-hydroxy-3-phenylpropyl)-piperazine-1-carboxylic acid tert-butyl ester 2-(R)-[2-(R)-(Benzhydrylidene-amino)-1-(S)-hydroxy-3-phenylpropyl]-piperazine-1-carboxylic acid tert-butyl ester Dissolve 2-(R)-(2-(R)-amino-1-(S)-hydroxy-3-phenylpropyl)-piperazine-1-carboxylic acid tert-butyl ester (98 mg, 0.29 mmol) in dry dichloromethane and add benzophenoneimine (0.083 ml, 0.49 mmol) by syringe, stir overnight, and purify (silica gel chromatography, eluting with ethyl acetate and 98:2 ethyl acetate:triethylamine) to obtain (144 mg, 95% yield) of the title compound (144 mg, 95%) as a colorless oil.

4-Acetyl-2-(R)-[2-(R)-(benzhydrylidene-amino)-1-(S)-hydroxy-3-phenylpropyl]-piperazine-1-carboxylic acid tert-butyl ester Dissolve 2-(R)-[2-(R)-(benzhydrylidene-amino)-1-(S)-hydroxy-3-phenylpropyl]-piperazine-1-carboxylic acid tert-butyl ester (144 mg, 0.29 mmol)) in dry dichloromethane (3 mL). Add 1-acetylimidazole (48 mg, 0.43 mmol) and triethylamine (0.081 mL, 0.58 mmol) and stir for 2 h. Dilute with ethyl acetate and wash with 1 N HCl and saturated aqueous sodium bicarbonate, dry (magnesium sulfate), and concentrate to give the title compound which is used in the next step without further purification.

4-Acetyl-2-(R)-(2-(R)-amino-1-(S)-hydroxy-3-phenylpropyl)-piperazine-1-carboxylic acid tert-butyl ester Dissolve 4-acetyl-2-(R)-[2-(R)-(benzhydrylidene-amino)-1-(S)-hydroxy-3-phenylpropyl]-piperazine-1-carboxylic acid tert-butyl ester (66 mg, 0.12 mmol) in methanol (1 mL) and add 10% palladium on carbon (12 mg). Stir under 1 atmosphere of hydrogen gas overnight, filter through a filtering agent, wash with methanol and concentrate to give the title compound that may be used without further purification.

Preparation 32

2-(R)-(2-(R)-Amino-1-(S)-hydroxy-3-phenylpropyl)-4-(3-methylbutyl)-piperazine-1-carboxylic acid tert-butyl ester 2-(R)-[2-(R)-(Benzhydrylidene-amino)-1-(S)-hydroxy-3-phenylpropyl]-4-(3-methyl -butyl)-piperazine-1-carboxylic acid tert-butyl ester Dissolve (2-(R)-[2-(R)-(benzhydrylidene-amino)-1-(S)-hydroxy-3-phenylpropyl]-piperazine-1-carboxylic acid tert-butyl ester (167 mg, 0.33 mmol) in 1,2-dichloroethane (2.5 mL) and add 3-methylbutyraldehyde (0.042 mL, 0.41 mmol). After 5 min, add sodium triacetoxyborohydride (100 mg, 0.47 mmol) and stir for 1 h. Add saturated aqueous sodium bicarbonate solution (5 mL) and stir for 10 min. Add ethyl acetate and separate the layers. Extract the aqueous layer with ethyl acetate, combine the organic layers, wash the organic layer with saturated aqueous sodium chloridesolution, dry (magnesium sulfate), concentrate and purify (silica gel chromatography, eluting with ethyl acetate) to give the title compound as a colorless oil (165 mg, 87%).

2-(R)-(2-(R)-Amino-1-(S)-hydroxy-3-phenyl-propyl)-4-(3-methylbutyl)-piperazine-1-carboxylic acid tert-butyl ester Dissolve 2-(R)-[2-(R)-(benzhydrylidene-amino)-1-(S)-hydroxy-3-phenylpropyl]-4-(3-methyl-butyl)-piperazine-1-carboxylic acid tert-butyl ester in methanol (3 mL) and add 10% palladium on carbon (29 mg). Stir under 1 atmosphere of hydrogen gas for 24 h and filter through a filtering agent, wash with methanol and concentrate to give the title compound which is used without further purification.

Preparation 33

3-(2-(S)-amino-1-(S)-hydroxy-3-(S)-phenylpropyl)-1-(p-methoxybenzyl)-piperazin-2-one 4-Benzyloxycarbonyl-1-(p-methoxybenzyl)-piperazin-2-one Add to a solution of 4-benzyloxycarbonyl-piperazin-2-one (2 g, 8.6 mmol) in dry THF (10 mL/mmol) under nitrogen, sodium hydride (236 mg, 9.4 mmol, 60% dispersion in mineral oil) in one portion and stir at room temperature for 30 min. Add p-methoxybenzyl chloride (1.86 mL, 13 mmol) and stir at room temperature overnight. Concentrate, add ethyl acetate, wash with water, saturated aqueous sodium chloride, dry (magnesium sulfate), concentrate and purify (silica gel chromatography, eluting with 1:1 hexanes:ethyl acetate) to give the title compound as an oil (1.6 g, 54%).

MS (ES): m/z 355=[M+H].

3-(2-(S)-Dibenzylamino-1-hydroxy-3-phenylpropyl)-4-benzyloxycarbonl-1-(p-methoxybenzyl)piperazin-2-one Cool a solution of 4-benzyloxycarbonyl-1-(-methoxybenzyl)-piperazin-2-one (1.9 g, 5.5 mmol) in dry THF (4 mL/mmol) to −78° C. under nitrogen. Add lithium bis(trimethylsilyl)amide (1.0 M solution in THF, 5.5 mL, 5.5 mmol) dropwise and stir 30 min. Add 2-(dibenzylamino)-3-phenyl-propanal (1 g, 3.1 mmol) in dry THF (2 mL/mmol) and stir at −78° C. for 45 min. Quench with saturated aqueous ammonium chloride solution. Separate organic layer and wash with water, saturated aqueous sodium chloride, dry (magnesium sulfate), concentrate and purify (silica gel chromatography eluting with 100% hexanes to 1:1 hexanes:ethyl acetate) to provide a mixture of four diastereoisomers (908 mg, 43%). Separation of the isomers by Chiralpak AD (250×50 mn) HPLC (eluting with ethanol:acetonitrile 95:5 at 230 nm) provides:

Isomer-1=run time 8.7 min, MS(ES): m/z=684 [M+H].
Isomer-2=run time 13.7 min, MS(ES): m/z=684 [M+H].
Isomer-3=run time 9.8 min, MS(ES): m/z=684 [M+H].
Isomer-4=run time 11.8 min, MS(ES): m/z=684 [M+H].

Deprotection

Add palladium hydroxide (172-mg) in one portion to a solution of 3(S)-(2-(S)-dibenzylamino-1-(S)-hydroxy-3-phenylpropyl)-4-benzyloxycarbonyl-1-(p-methoxybenzyl)-piperazin-2-one Isomer-1 (240 mg, 0.35 mmol) in methanol (10 mL/mmol) and stir the mixture under 1 atmosphere of hydrogen gas for 24 h. Filter through a filtering agent, wash with methanol and concentrate to give the title compound as an oil (Isomer-1) (110 mg, 85%).

MS (ES): m/z 370=[M+H].
Follow same procedure for Isomer-2, 3 and 4:
MS (ES): m/z 370=[M+H] (Isomer-2).
MS (ES): m/z 370=[M+H] (Isomer-3).
MS (ES): m/z 370=[M+H] (Isomer-4).

Preparation 34

3-(2-(S)-amino-1(S)-hydroxy-3-(S)-phenylpropyl)-1-propylpiperazin-2-one

4-Benzyloxycarbonyl-1-allylpiperazin-2-one

Add to a solution of 4-benzyloxycarbonylpiperazin-2-one (1.6 g, 6.8 mmol) in dry THF (10 mL/mmol) under nitrogen, sodium hydride (188 mg, 7.4 mmol, 60% dispersion in mineral oil) in one portion and stir at room temperature for 30 min. Add allyl iodide (0.9 mL, 10 mmol) and stir at room temperature overnight. Concentrate, add ethyl acetate and wash with water, saturated aqueous sodium chloride solution, dry (magnesium sulfate), concentrate and purify (silica gel chromatography, eluting with 1:1 hexanes/ethyl acetate) to give the title compound as an oil (1.3 g, 72%).

MS (ES): m/z 275 =[M+H].

3-(2-(S)-Dibenzylamino-1-hydroxy-3-phenylpropyl)-4-benzyloxycarbonyl-1-allylpiperazin-2-one Add to a solution of 4-benzyloxycarbonyl-1-allylpiperazin-2-one (1.1 g, 4.0 mmol) in dry THF (4 mL/mmol) at −78° C. under nitrogen lithium bis(trimethylsilyl)amide (1.OM solution in THF, 4.0 mL, 4.0 mmol) dropwise and stir 30 min. Add 2-(dibenzylamino)-3-phenylpropanal (732 mg, 2.2 mmol) in dry THF (2 mL/mmol) and stir at −78° C. for 45 min. Quench with saturated aqueous ammonium chloride solution. Separate organic layer and wash with water, saturated aqueous sodium chloride solution, dry (magnesium sulfate), concentrate and purify (silica gel chromatography, eluting with 100% hexanes to 1:1 hexanes:ethyl acetate) to give a mixture of four diastereoisomers (836 mg, 62%). Separate the isomers by normal phase HPLC (95:5 hexanes:isopropanol 95/5) to provide:

Isomer-1=run time 7.9 min, MS (ES): m/z 604=[M+H].
Isomer-2=run time 10.0 min, MS (ES): m/z 604=[M+H].

3-(S)-(2-(S)-amino-1-(S)-hydroxy-3-phenylpropyl)-1-propylpiperazin-2-one

To a solution of 3-(S)-(2-(S)-dibenzylamino-1-(S)-hydroxy-3-phenylpropyl)-4-benzyloxycarbonyl-1-propylpiperazin-2-one Isomer-2 (215 mg, 0.35 mmol) in methanol (10 mL/mmol) add palladium hydroxide (172 mg) in one portion and stir the mixture under 1 atmosphere of hydrogen gas for 24 h. Filter through a filtering agent, wash with methanol and concentrate to give the title compound as an oil (Isomer-2) (94 mg, 91%).

MS (ES): m/z 292=[M+H].

Preparation 35

4-(4-methylpentanoyl)-2-(R)-(2-(R)-acetylamino-1-(S)-hydroxy-3-phenylpropyl)-piperazine-1-carboxylic acid tert-butyl ester 2-(R)-(2-(R)-Acetylamino-1-(S)-hydroxy-3-phenylpropyl)-piperazine-1-carboxylic acid tert-butyl ester Dissolve 2-(R)-(2-(R)-amino-1-(S)-hydroxy-3-phenylpropyl)-piperazine-1-carboxylic acid tert-butyl ester (232 mg, 0.69 mmol) in 7 ml of dry $CH_2Cl_2$ and add N-acetyl-N-(2-trifluoromethyl-phenyl)-acetamide (Tetrahedron Letters, 38(21), 3751 (1997)) (162 mg, 0.66 mmol). Stir at room temperature overnight. Subject reaction mixture to silica gel chromatography, eluting ethyl acetate/triethylamine 98:2 to obtain 122 mg of the title compound (60% yield based on 79% conversion) and 50 mg of starting amine.

4-(4-methylpentanoyl)-2-(R)-(2-(R)-acetylamino-1-(S)-hydroxy-3-phenylpropyl)-piperazine-1-carboxylic acid tert-butyl ester Dissolve 2-(R)-(2-(R)-Acetylamino-1-(S)-hydroxy-3-phenyl-propyl)-piperazine-1-carboxylic acid tert-butyl ester (122 mg, 0.32 mmol) in 3 ml of dry $CH_2Cl_2$. Add 4-methylpentanoic acid (0.04 ml, 0.32 mmol), EDCI (73.6 mg, 0.38 mmol), HOBT (51.8 mg, 0.38 mmol), triethylamine (0.13 ml, 0.96 mmol) and dimethylaminopyridine (3.9 mg, 0.032 mmol), and stir at room temperature overnight. Dilute with $CH_2Cl_2$, and wash with 5% $NaHCO_3$ followed by saturated aqueous sodium chloride. Dry organic layer with $MgSO_4$ and remove the solvent under reduced pressure. Subject residue to silica gel chromatography, eluting with ethyl acetate/methanol 9:1 to obtain 74 mg (48% yield) of a white solid.

Preparation 36

2-(R)-(2-(R)-Amino-1-(S)-hydroxy-3-phenylpropyl)-4-(5-methylhexanoyl)-piperazine-1-carboxylic acid tert-butyl ester 2-(R)-[2-(R)-(Benzhydrylidene-amino)-1-(S)-hydroxy-3-phenylpropyl]-4-(5-methyl -hexanoyl)-piperazine-1-carboxylic acid tert-butyl ester Dissolve (2-(R)-[2-(R)-(benzhydrylidene-amino)-1-(S)-hydroxy-3-phenylpropyl]-piperazine-1-carboxylic acid tert-butyl ester (110 mg, 0.22 mmol) in 2.2 ml of dichloromethane and react with 5-methylhexanoic acid (28.6 mg, 0.22 mmol), EDCI (50.6 mg, 0.26 mmol), HOBT (35.6 mg, 0.26 mmol), triethylamine (0.09 ml, 0.66 mmol) and dimethylaminopyridine (2.6 mg, 0.02 mmol). Stir at room temperature overnight. Dilute with $CH_2Cl_2$, and wash with 5%$NaHCO_3$ and saturated aqueous sodium chloride. Dry organic layers with $MgSO_4$ and remove the solvent under reduced pressure. Subject residue to silica gel chromatography, eluting with hexanes/ethyl acetate/triethylamine 67:32:1 to obtain 103 mg (76% yield) of the desired product.

2-(R)-(2-(R)-Amino-1-(S)-hydroxy-3-phenyl-propyl)-4-(5-methylhexanoyl)-piperazine-1-carboxylic acid tert-butyl ester Dissolve 2-(R)-[2-(R)-(Benzhydrylideneamino)-1-(S)-hydroxy-3-phenyl-propyl]-4-(5-methylhexanoyl)-piperazine-1-carboxylic acid tert-butyl ester (103 mg, 0.17 mmol) in 2 ml of methanol and add palladium (10% on C, 30 mg). Stir under 1 atmosphere of $H_2$ for 24 h and filter through celite, eluting with methanol. Concentrate to dryness to provide the title compound.

The compounds of Preparations 37-39 may be prepared essentially as described in Preparation 36.

| Prep | Compound | MS [M + H] |
|---|---|---|
| 37 | 2-(R)-(2-(R)-Amino-1-(S)-hydroxy-3-phenylpropyl)-4-(2-propyl-pentanoyl)-piperazine-1-carboxylic acid tert-butyl ester | |

-continued

| Prep | Compound | MS [M + H] |
|---|---|---|
| 38 | 2-(R)-(2-(R)-Amino-1-(S)-hydroxy-3-phenylpropyl)-4-(3-methoxy-benzoyl)-piperazine-1-carboxylic acid tert-butyl ester | |
| 39 | 2-(R)-(2-(R)-Amino-1-(S)-hydroxy-3-phenylpropyl)-4-(5-cyclohexyl-pentanoyl)-piperazine-1-carboxylic acid tert-butyl ester | |

Preparation 40

4-[2-(3-Methyl-butyl)-phenyl]-3-oxo-piperazine-1-carboxylic acid tert-butyl ester 1-Bromo-2-(3-methyl-butyl)-benzene Charge a Schlenck flask with palladium dibenzylidene acetone (88 mg, 0.16 mmol) and tri-o-furyl phosphine (72 mg, 0.31 mmol), purge with nitrogen and add 2 ml of dry THF. Stir until the deep purple solution turns to greenish yellow and add 1-iodo-2-bromobenzene (0.8 ml. 6.2 mmol) followed by 3-methyl-butyl zinc (0.5 M solution in THF, 30 ml, 15 mmol). Stir at room temperature for 4 hours. Add silica gel, concentrate under reduced pressure, load residue onto a flash silica gel column, and elute with hexane to obtain the desired compound as a colorless liquid (1.1 g, 75%).

1-Iodo-2-(3-methyl-butyl)-benzene

Charge a pressure tube with sodium iodide (734 mg, 4.9 mmol), copper iodide (23 mg, 0.12 mmol), trans-N,N'-dimethyl-cyclohexane-1,2-diamine (34 mg, 0.24 mmol) dissolved in 0.5 ml of pentanol, and 1-bromo-2-(3-methyl-butyl)-benzene dissolved in 0.5 ml of pentanol. Purge with nitrogen, cap the tube, and heat at 130° C. for 3 days. Subject to silica gel chromatography, eluting with hexane to obtain the desired compound as a colorless liquid (587 mg, 84%).

Coupling

Charge a pressure tube with copper iodide (16 mg, 0.08 mmol), potassium phosphate (717 g, 3.4 mmol), trans-1,2-diaminocyclohexane (0.020 ml, 0.17 mmol), 1-Iodo-2-(3-methyl-butyl)-benzene (462 mg, 1.7 mmol), and 3-oxo-piperazine-1-carboxylic acid tert-butyl ester (405 g, 2.02 mmol). Purge with nitrogen and add 2 ml of dry 1,4-dioxane. Cap the tube and stir at 120° C. overnight. Filter through CELITE™, eluting with EtOAc and concentrate under reduced pressure. Subject residue to silica gel chromatography, eluting with hexane followed by EtOAc/hexane 1:1 to give the title compound as a yellow solid (172 mg, 29%).

Preparation 41

2-(S)-[2-(S)-Amino-3-(3,5-difluoro-phenyl)-1-(S)-hydroxy-propyl]-4-(4-methoxy-phenyl)-3-oxo-piperazin-1-carboxylic acid tert-butyl ester 4-(4-Methoxy-phenyl)-3-oxo-piperazine-1-carboxylic acid tert-butyl ester Charge in a pressure tube copper iodide (42 mg, 0.22 mmol), potassium phosphate (1.6 g, 7.5 mmol), trans-1,2-diaminocyclohexane (0.053 ml, 0.44 mmol), p-methoxyphenyl iodide (868 mg, 3.7 mmol) and 3-oxo-piperazine-1-carboxylic acid tert-butyl ester (1.05 g, 4.7 mmol). Purge with nitrogen and add 6 ml of dry toluene. Cap the tube and stir at 100° C. overnight. Filter through celite eluting with EtOAc and concentrate. Purify in a silica gel cartridge (20 g) eluting with EtOAc/hexane 1:1 followed by 100% EtOAc to give the title compound as a white solid (1.03 g, 90%).

2-(S)-[2-(S)-Dibenzylamino-3-(S)-(3,5-difluoro-phenyl)-1-hydroxy-propyl]-4-(4-methoxy-phenyl)3-oxo-piperazine-1-carboxylic acid tert-butyl ester Treat a solution of 4-(4-methoxy-phenyl)-3-oxo-piperazine-1-carboxylic acid tert-butyl ester (1.8 g, 6.1 mmol) in THF (18 mL) cooled at −78° C. with lithium bis(trimethylsilyl)amide (1.0 M solution in THF, 6.1 mL, 6.1 mmol) drop-wise and stir 30 min. Add 2-(dibenzylamino)-3-(3,5-difluorophenyl)-propanal (1.5 g, 4.1 mmol) in THF (8 mL) and stir at −78° C. for 45 min. Quench with saturated aqueous ammonium chloride solution. Separate the organic layer and wash with water and saturated aqueous sodium chloride, dry (magnesium sulfate), concentrate and purify (silica gel chromatography, eluting with hexane:ethyl acetate 4:1 followed by 2:1 followed by 1:1) to provide isomer A as a foamy yellow solid (718 mg, 26%) and isomer B as a yellow foamy solid (635 mg, 23%).
Isomer-A MS (ES): m/z=672 [M+H].
Isomer-B MS (ES): m/z=672 [M+H]

2-(S)-[2-(S)-Amino-3-(3,5-difluoro-phenyl)-1-(S)-hydroxy-propyl]-4-(4-methoxy-phenyl)-3-oxo-piperazin-1-carboxylic acid tert-butyl ester Treat a solution of 2-(S)-[2-(S)-dibenzylamino-3-(S)-(3,5-difluoro-phenyl)-1-hydroxy-propyl]-4-(4-methoxy-phenyl)-3-oxo-piperazine-1-carboxylic acid tert-butyl ester (isomer A from previous preparation) (718 mg, 1.08 mmol) in methanol (11 mL). Add acetic acid (0.65 ml, 10.8 mmol) and 10% palladium on carbon (108 mg) in one portion and stir the mixture under 1 atmosphere of hydrogen gas overnight. Add more 10% palladium on carbon (20 mg) and stir for 7 hours. Filter through a filtering agent, wash with methanol and concentrate to give the title compound as an oil.
MS (ES): m/z=492 [M+H].
The compound of Preparation 42 may be prepared essentially as described in Preparation 41.

| Prep | Compound | MS [M + H] |
|---|---|---|
| 42 | 2-(S)-(2-(S)-Amino-3-phenyl-1-(S)-hydroxy-propyl)-4-(4-methoxy-phenyl)-3-oxo-piperazin-1-carboxylic acid tert-butyl ester | 434 |

Preparation 43

2-(S)-[2-(S)-Amino-3-(3,5-difluoro-phenyl)-1-(S)-hydroxy-propyl]-4-[2-(3-methyl-butyl)-phenyl]-3-oxo-piperazine-1-carboxylic acid tert-butyl ester

1-Bromo-2-(3-methyl-butyl)-benzene

Charge a Schlenck flask with palladium dibenzylidene acetone (88 mg, 0.16 mmol) and tri-o-furyl phosphine (72 mg, 0.31 mmol), purge with nitrogen and add 2 ml of dry THF. Stir for 2 minutes, until the deep purple solution turns to greenish yellow and add 1-iodo-2-bromo benzene (0.8 ml, 6.2 mmol) followed by 3-methyl-butyl zinc (0.5 M solution in THF, 30 ml, 15 mmol). React at rt for 4 hours. Add silica gel, concentrate, load onto a flash chromatography column and elute with hexane to obtain the title compound as a colorless liquid (1.1 g, 75%).

1-Iodo-2-(3-methyl-butyl)-benzene

Charge a pressure tube with sodium iodide (734 mg, 4.9 mmol) and copper iodide (23 mg, 0.12 mmol). Add trans-N, N'-dimethyl-cyclohexane-1,2-diamine (34 mg, 0.24 mmol) dissolved in 0.5 ml of pentanol. Add 1-bromo-2-(3-methyl-butyl)-benzene dissolved in 0.5 ml of pentanol. Purge with nitrogen, cap the tube and heat at 130° C. for 3 days. Load onto a silica gel cartridge eluting with hexane to obtain the title compound as a colorless liquid (587 mg, 84%).

4-[2-(3-Methyl-butyl)-phenyl]-3-oxo-piperazine-1-carboxylic acid tert-butyl ester Charge in a pressure tube copper iodide (16 mg, 0.08 mmol), potassium phosphate (717 g, 3.4 mmol), trans-1,2-diaminocyclohexane (0.020 ml, 0.17 mmol), 1-Iodo-2-(3-methyl-butyl)-benzene (462 mg, 1.7 mmol) and 3-oxo-piperazine-1-carboxylic acid tert-butyl ester (405 g, 2.02 mmol). Purge with nitrogen and add 2 ml of dry 1,4-dioxane. Cap the tube and stir at 120° C. overnight. Filter through celite eluting with EtOAc and concentrate. Purify in a silica gel cartridge (10 g) eluting with hexane followed by EtOAc/hexane 1:1 to give the title compound as a yellow solid (172 mg, 29%).

2-(S)-[2-(S)-Amino-3-(3,5-difluoro-phenyl)-1-(S)-hydroxy-propyl]-4-[2-(3-methyl -butyl)-phenyl]-3-oxo-piperazine-1-carboxylic acid tert-butyl ester The title is prepared by reacting 4-[2-(3-methyl-butyl)-phenyl]-3-oxo-piperazine-1-carboxylic acid tert-butyl ester with 2-(dibenzylamino)-3-(3,5-difluorophenyl)-propanal essentially as described in Preparation 41.
MS(ES): m/z=532 [M+H]

Preparation 44

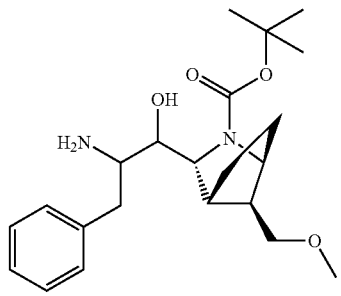

3-(2-Amino-1-hydroxy-3-phenylpropyl)-7-methoxymethyl-2-azabicyclo [2.2.1]heptane-2-carboxylic acid tert-butyl ester

7-Methoxymethyl-2-(1-phenylethyl)-2-azabicyclo [2.2.1]hept-5-ene-3-carboxylic acid ethyl ester Add molecular sieves (3 Å, 12.0 g), (S)-(−)-α-methylbenzylamine (6.4 mL, 50.0 mmol) to a solution of ethylglyoxalate (10.3 mL, 50.0 mmol) in dichloromethane (200 mL) cooled in an ice bath. Stir the mixture at 0° C. for 2 h, and then cool to −78° C. Add trifluoroacetic acid (4.10 mL, 55.0 mmol), boron trifluoride etherate (6.90 mL, 55.0 mmol), and 5-methoxymethyl-1,3-cyclopentadiene (60.0 mmol, prepared in situ by adding cyclopentadienylsodium (2.0 M in THF, 30.0 mL, 60.0 mmol) to a solution of chloromethyl methyl ether (5.70 mL, 75.0 mmol) in tetrahydrofuran (30 mL) at −55° C.) with a 5 min interval between each addition. Stir for 2 h at −78° C. and refrigerate (−20° C.) overnight. Quench the reaction with saturated aqueous sodium bicarbonate solution (200 mL) and stir the mixture vigorously for 15 min. Separate the layers, dry the organic layer (magnesium sulfate), concentrate, and purify (silica gel chromatography 10:90 to 30:70 ethyl acetate:hexanes) to give the title compound (3.95 g, 25%).

7-Methoxyrethyl-2-aza-bicyclo[2.2.1]heptane-2,3-dicarboxylic acid 2-tert-butyl ester 3-ethyl ester Chill a mixture of 7-methoxymethyl-2-(1-phenylethyl)-2-azabicyclo[2.2.1]hept-5-ene-3-carboxylic acid ethyl ester (2.10 g, 6.66 mmol), di-tert-butyldicarbonate (1.60 g, 7.32 mmol) in an ice bath. Flush the flask with nitrogen for 5 min, and slowly add 10% palladium on carbon (1.42 g). Stir the mixture under hydrogen (1 atmosphere) for 2 h, filter off catalyst through a filtering agent and wash solid with ethyl acetate. Concentrate and purify (silica gel chromatography, eluting with 20:80 to 30:70 ethyl acetate:hexanes) to give the title compound (1.53 g, 73%).

MS (ES): m/z=214.1 [M+H-Boc].

3-Hydroxymethyl-7-methoxymethyl-2-azabicyclo[2.2.1]heptane-2-carboxylic acid tert-butyl ester Add di-isobutylalluminium hydrate (1 M in hexanes, 14.6 mL, 14.6 mmol) to a solution of 7-methoxymethyl-2-azabicyclo[2.2.1]heptane-2,3-dicarboxylic acid 2-tert-butyl ester 3-ethyl ester (1.53 g, 4.88 mmol) in dichloromethane (20 mL) cooled in an ice bath. Stir the mixture at room temperature for 3 h. Quench with saturated aqueous sodium tartrate and stir until the solution becomes clear. Extract the mixture with ethyl acetate (3×50 mL), wash the combined extract with saturated aqueous sodium tartrate, dry (magnesium sulfate), concentrate and purify (silica gel chromatography, eluting with 1:1 ethyl acetate:hexanes) to give the title compound (0.780 g, 59%).

MS (ES): m/z=172.1 [M+H-Boc].

3-Formyl-7-methoxymethyl-2-azabicyclo[2.2.1]heptane-2-carboxylic acid tert-butyl ester Chill a solution of 3-hydroxymethyl-7-methoxymethyl-2-azabicyclo[2.2.1]heptane-2-carboxylic acid tert-butyl ester (0.780 g, 2.87 mmol) in dichloromethane (20 mL) in an ice bath and add Dess-Martin periodinate (1.46 g, 3.44 mmol). Stir the mixture at room temperature for 2 h and quench with 10% aqueous sodium sulfite. Extract the mixture with dichloromethane (3×20 mL). Wash the organic extracts with saturated aqueous sodium chloride, dry (magnesium sulfate), concentrate and purify (silica gel chromatography, eluting with 25:75 ethyl acetate:hexanes) to give the title compound (0.780 g, 100%).

3-(1-Hydroxy-2-nitro-3-phenylpropyl)-7-methoxymethyl-2-azabicyclo[2.2.1]heptane-2-carboxylic acid tert-butyl ester Add 1-phenyl-2-nitroethane (0.350 g, 2.23 mmol) to a solution of 3-formyl-7-methoxymethyl-2-aza-bicyclo[2.2.1]heptane-2-carboxylic acid tert-butyl ester (0.400 g, 1.48 mmol) in anhydrous tetrahydrofaran (5 mL) cooled in an ice bath. Add tetrabutylammonium fluoride (1.0 M in tetrahydrofuran, 1.48 mL, 1.48 mmol) and stir the mixture in an ice bath for 1 h. Dilute the mixture with ethyl acetate, and wash the solution with saturated aqueous sodium chloride, dry (magnesium sulfate), concentrate and purify (silica gel chromatography, eluting with 20:80 to 30:70 ethyl acetate:hexanes) to give the title compound (0.320 g, 51%).

3-(2-Amino-1-hydroxy-3-phenylpropyl)-7-methoxymethyl-2-azabicyclo[2.2.1]heptane-2-carboxylic acid tert-butyl ester Cool a mixture of 3-(1-hydroxy-2-nitro-3-phenylpropyl)-7-methoxymethyl-2-azabicyclo[2.2.1]heptane-2-carboxylic acid tert-butyl ester (0.320 g, 0.761 mmol) and nickel (II) chloride (0.150 g, 1.14 mmol) in methanol (10 mL) in a water bath and slowly add sodium borohydride (0.115 g, 3.04 mmol). After 5 min, quench the reaction with water and concentrate. Add ethyl acetate and water, then filter through a filtering agent and wash solid with ethyl acetate. Separate the layers and wash organic layer with saturated aqueous sodium chloride, dry (magnesium sulfate) and concentrate to give the title compound (0.243 g, 82%).

MS (ES): m/z=391.3 [M+H].

The compound of Preparation 45 may be prepared essentially as described in Preparation 44 starting with (S)-α-methylbenzylamine and (R)-(−)-α-phellandrene.

| Prep | Compound | MS [M + H] |
|---|---|---|
| 45 | 3-(2-Amino-1-hydroxy-3-phenylpropyl)-7-isopropyl-5-methyl-2-azabicyclo[2.2.2]octane-2-carboxylic acid tert-butyl ester | 417.4 |

Preparation 46

3,5-Difluorophenyl nitroethane

1-(3,5-Difluorophenyl)-2-nitroethanol

Add nitromethane (200 mL, 2.5 eq) to a suspension of potassium carbonate (30 g) and 3,5-difluorobenzaldehyde (200 g) in tetrahydrofuran (600 mL) at room temperature. Stir at room temperature overnight, filter, wash with ethyl acetate and concentrate to give the title compound as a crude oil (330 g) which is used in the next step without further purification.

1,3-Difluoro-5-(2-nitrovinyl)-benzene

Add acetic anhydride (160 mL) to a solution of 1-(3,5-difluorophenyl)-2-nitroethanol (330 g) and 4-dimethylaminopyridine (18 g) in dichloromethane (1000 mL), at room temperature using a water bath to keep the temperature below 35° C. Add acetic acid over 30 min and stir the reaction mixture overnight. Dilute with dichloromethane (660 mL) and wash with 2% aqueous HCl, saturated aqueous sodium chloride, saturated aqueous sodium bicarbonate, dry (magnesium sulfate) and concentrate. Wash the crude with hexanes to give the title compound (220 g).

3,5-Difluorophenyl nitroethane

Add portionwise sodium borohydride (12 g) over 1.5 h to a solution of 1,3-difluoro-5-(2-nitrovinyl)-benzene (100 g) in a mixture of dimethylsulfoxide (400 mL) and acetic acid (80 mL) at room temperature using a water bath to keep the temperature below 30° C. Dilute with ethyl acetate (1000 mL) and wash with water (600 mL), saturated aqueous sodium bicarbonate (2×600 mL), saturated aqueous sodium chloride (600 mL), dry (magnesium sulfate) concentrate and purify (silica gel chromatography, eluting with 3:97 ethyl acetate: hexanes) to give the title compound a pale yellow solid (63 g, 62%).

Preparation 47

(S)-2-sec-Butylamino-6-(cyclopropanesulfanyl-methylamino)-isonicotinic acid

Cyclopropanesulfonic Acid Methylamide

Dissolve cyclopropylsulfonyl chloride (1.0 g, 7.1 mmol) in dichloromethane (8 mL). Cool to 0° C. and slowly add methylamine (2.0 M solution in THF, 10.7 mL, 21 mmol). Stir for 5 min and add triethylamine dropwise (1.4 mL, 11 mmol). Stir from 0° C. to room temperature overnight. Filter, concentrate the organic layer and purify (silica gel chromatography, eluting with 0:100 to 25:75 ethy acetate:hexanes) to give the title compound.

MS (ES): m/z=134 [M−H].

Sodium Cyclopropanesulfonic Acid Methylamide

Dissolve cyclopropanesulfonic acid methylamide in THF (10 mL) and cool to 0° C. Slowly add sodium hydride (208 mg, 60% suspension in mineral oil) into the solution and stir from 0° C. to room temperature for 3 h. Concentrate and use the solid in the next step without further purification.

(S)-2-sec-Butylamino-6-chloro-isonicotinic acid methyl ester

Dissolve 2,6-dichloro-isonicotinic methyl ester (2.0 g, 10 mmol), palladium (II) acetate (224.0 mg, 1.0 mmol), racemic 2,2'-bis(diphenylphosphino)-1,1'-binaphthyl (632 mg, 1.0 mmol) and cesium carbonate (3.96 g, 12 mmol) in toluene (20 mL) in a previously degassed sealed vessel. Flush the mixture with nitrogen gas. Add (S)-(+)-sec-butylamine (1.2 mL, 12 mmol) to the solution and heat the sealed mixture overnight at 100° C. Cool to room temperature and dilute with diethyl ether and filter through a filtering agent. Concentrate the filtrate and purify (silica gel chromatography, eluting with 0:100 to 10:90 ethyl acetate:hexanes) to give the title compound (73%).

MS (ES): m/z=243 [M+H].

(S)-2-sec-Butylamino-6-(cyclopropanesulfonyl-methylamino)-isonicotinic acid methyl ester Dissolve (S)-2-sec-butylamino-6-chloro-isonicotinic acid methyl ester (880 mg, 3.6 mmol), tris(dibenzylideneacetone)dipalladium (0) (164 mg, 0.18 mmol), 2-(di-tert-butylphosphino)biphenyl (107 mg, 0.36 mmol) in toluene (18 mL) and THF (2 mL) in a previously nitrogen-filled sealed vessel. Add sodium cyclopropanesulfonic acid methylamide (700 mg, 4.42 mmol) into the mixture under nitrogen and flush the reactants again with nitrogen before sealing and heating overnight at 100° C. Cool the reaction to room temperature and dilute with ethyl acetate and diethyl ether and filter through a filtering agent. Concentrate and purify (silica gel chromatography, eluting with 0:100 to 08:92 ethyl acetate:hexanes) to give the title compound.

MS (ES): m/z=342 [M+H].

(S)-2-sec-Butylamino-6-(cyclopropanesulfonyl-methylamino)-isonicotinic acid

Dissolve (S)-2-sec-butylamino-6-(cyclopropanesulfonyl-methylamino)-isonicotinic acid methyl ester (600 mg, 1.97 mmol) in methanol (18 mL). Slowly add 2 N NaOH (3 mL) and stir overnight at room temperature. Acidify the mixture to about pH=6 with 5 N HCl and concentrate. Dilute with ethyl acetate (30 mL) and wash the organic layer with saturated aqueous sodium chloride solution, dry (magnesium sulfate) and concentrate to give the title compound.

MS (ES): m/z=328 [M+H].

The compounds of Preparation 48-54 may be prepared essentially as described in Preparation 47 starting with the corresponding sulfonyl chlorides and amines.

| Prep | Compound | MS (ES) [M + H] |
|---|---|---|
| 48 | (S)-2-sec-Butylamino-6-(cyclopropyl-methanesulfonylamino)-isonicotinic acid | 328 |
| 49 | (S)-2-sec-Butylamino-6-(propane-2-sulfonylamino)-isonicotinic acid | 316 |
| 50 | (S)-2-sec-Butylamino-6-[methyl-(propane-2-sulfonyl)-amino]-isonicotinic acid | 330 |
| 51 | (S)-2-sec-Butylamino-6-(ethyl-methanesulfonylamino)-isonicotinic acid | 316 |
| 52 | (S)-2-sec-Butylamino-6-[(2-fluoroethyl)-methanesulfonylamino]-isonicotinic acid | 334 |
| 53 | (S)-2-sec-Butylamino-6-[(2,2-difluoroethyl)-methanesulfonylamino]-isonicotinic acid | 352 |
| 54 | (S)-2-sec-Butylamino-6-[(2,2,2-trifluoroethyl)-methanesulfonylamino]-isonicotinic acid | 370 |

Preparation 55

(S)-2-sec-Butylamino-6-[1,3]dioxan-2-yl-isonicotinic acid

2-Chloro-6-vinyl-isonicotinic acid methyl ester

Add methyl 2,6-dichloro-isonicotinate (3.8 g, 18.4 mmol), tetrakis(triphenylphosphine)palladium (0) (1.15 g, 0.99 mmol), triphenyhlphosphine (524 mg, 2 mmol) in toluene (40 mL) to a previously nitrogen-filled sealed vessel. Flush the reactants with nitrogen again. Add tributyl(vinyl)tin (6.98 mL, 24.0 mmol) and heat the sealed mixture at 95° C. overnight. Cool to room temperature, dilute with diethyl ether and filter through a filtering agent. Wash the organic filtrate with saturated ammonium chloride, saturated sodium bicarbonate and saturated aqueous sodium chloride. Dry (magnesium sulfate), concentrate and purify (silica gel chromatography, eluting with 5:95 to 10:90 ethyl acetate:hexanes) to give the title compound (70%).

2-Chloro-6-formyl-isonicotinic acid methyl ester

Dissolve 2-chloro-6-vinyl-isonicotinic acid methyl ester (1.6 g, 8 mmol) in dichloromethane (10 mL) and flush the reaction vessel with oxygen gas. Cool to −78° C. and pass positive pressure of ozone through the solution for 15 min until blue color appears. Quench with excess dimethylsulfide (1.5 mL) and warm to room temperature overnight. Concentrate and purify (silica gel chromatography, eluting with 0:100 to 10:90 ethyl acetate:hexanes) to give the title compound.

2-Chloro-6-[1,3]dioxan-2-yl-isonicotinic acid methyl ester

Dissolve 2-chloro-6-formyl-isonicotinic acid methyl ester (200 mg, 1.0 mmol) in THF (8 mL). Add Amberlyst® 15 ion exchange resin (0.3 g) and dropwise 1,3-propanediol (0.1 mL, 1.5 mmol). Stir at room temperature for two days. Filter, concentrate and purify (silica gel chromatography, eluting with 0:100 to 10:90 ethyl acetate:hexanes) to give the title compound (88%).

(S)-2-sec-Butylamino-6-[1,3]dioxan-2-yl-isonicotinic acid methyl ester

Dissolve 2-chloro-6-[1,3]dioxan-2-yl-isonicotinic acid methyl ester (150 mg, 0.6 mmol), palladium (II) acetate (7.0 mg, 0.03 mmol), racemic 2,2'-bis(diphenylphosphino)-1,1'-binaphthyl (20 mg, 0.03 mmol) and cesium carbonate (482 mg, 1.3 mmol) in toluene (2 mL) in a previously degassed sealed vessel. Flush the mixture with nitrogen gas. Add (S)-(+)-sec-butylamine (0.074 mL, 0.74 mmol) and heat the sealed mixture overnight at 100° C. Cool to room temperature, dilute with diethyl ether and filter through filtering agent. Concentrate the filtrate and purify (silica gel chromatography, eluting with 0:100 to 20:80 ethyl acetate:hexanes) to give the title compound (68%).

(S)-2-sec-Butylamino-6-[1,3]dioxan-2-yl-isonicotinic acid

Dissolve (S)-2-sec-butylamino-6-[1,3]dioxan-2-yl-isonicotinic acid methyl ester (100 mg, 0.35 mmol) in methanol (4 mL). Slowly add 1 N lithium hydroxide (0.46 mL) and stir overnight at room temperature. Acidify the mixture to about pH=6 with 5 N HCl and concentrate. Dilute with ethyl acetate (15 mL), wash the organic layer with saturated aqueous sodium chloride, dry (magnesium sulfate) and concentrate to give the title compound.
MS (ES): m/z=281 [M+H].
The compound of Preparation 56 may be prepared essentially as described in Preparation 55.

| Prep | Compound | MS (ES) [M + H] |
|---|---|---|
| 56 | (S)-2-sec-Butylamino-6-[1,3]dioxolan-2-yl-isonicotinic acid | 267 |

Preparation 57

(S)-2-sec-Butylamino-6-difluoromethyl-isonicotinic acid

2-Chloro-6-vinyl-isonicotinic acid methyl ester

Add methyl 2,6-dichloroisonicotinate (3.8 g, 18.4 mmol), tetrakis(triphenylphosphine)palladium (0) (1.15 g, 0.99 mmol), triphenyhlphosphine (524 mg, 2 mmol) and toluene (40 mL) in a previously nitrogen-filled sealed vessel. Flush the reactants with nitrogen again. Add tributyl(vinyl)tin (6.98 mL, 24.0 mmol) under nitrogen and heat the sealed mixture at 95° C. overnight with vigorous stirring. Cool the reaction to room temperature, dilute with diethyl ether and filter through a filtering agent. Wash the organic filtrate with saturated aqueous ammonium chloride, saturated aqueous sodium bicarbonate, saturated aqueous sodium chloride, dry (magnesium sulfate), concentrate and purify (silica gel chromatography, eluting with 5:95 to 10:90 ethyl acetate:hexanes) to give the title compound (70%).

2-Chloro-6-formyl-isonicotinic acid-methyl ester

Dissolve 2-chloro-6-vinyl-isonicotinic acid methyl ester (1.6 g, 8 mmol) in dichloromethane (10 mL) and flush the reaction vessel with oxygen gas. Cool to −78° C. and pass positive pressure of ozone through the solution for 15 min until sky blue color appears. At the same temperature quench the reaction with excess dimethylsulfide (1.5 mL) and warm up to room temperature overnight. Concentrate and purify (silica gel chromatography, eluting with 0:100 to 10:90 ethyl acetate:hexanes) to give the title compound.

2-Chloro-6-difluoromethyl-isonicotinic acid methyl ester

Dissolve 2-chloro-6-formyl-isonicotinic acid methyl ester (386 mg, 1.93 mmol) in dichloromethane (2 mL) and cool to 0° C. Add (diethylamino)sulfur trifluoride (0.625 mL, 4.8 mmol) dropwise and stir overnight while warming up to room temperature. Quench the reaction by water and dilute further with dichloromethane (10 mL). Extract the organic layer and dry (magnesium sulfate). Concentrate and purify (silica gel chromatography, eluting with 5:95 ethyl acetate:hexanes) to give the title compound as an oil (47%).

(S)-2-sec-Butylamino-6-difluoromethyl-isonicotinic acid methyl ester

Dissolve 2-chloro-6-difluoromethyl-isonicotinic acid methyl ester (200 mg, 0.9 mmol), palladium (II) acetate (20.0 mg, 0.09 mmol), racemic 2,2'-bis(diphenylphosphino)-1,1'-binaphthyl (56 mg, 0.09 mmol) and cesium carbonate (438 mg, 1.35 mmol) in toluene (3 mL) in a previously degassed sealed vessel. Flush the mixture with nitrogen gas. Add (S)-(+)-sec-butylamine (0.108 mL, 1.08 mmol) to the solution under nitrogen and heat the sealed mixture overnight at 100° C. Cool the reaction to room temperature. Dilute with diethyl ether and filter through a filtering agent. Concentrate the filtrate and purify (silica gel chromatography, eluting with 10:90 acetate:hexanes) to give the title compound as an oil (60%).

(S)-2-sec-Butylamino-6-difluoromethyl-isonicotinic acid

Dissolve 2-sec-butylamino-6-difluoromethyl-isonicotinic acid methyl ester (140 mg, 0.54 mmol) in methanol (2 mL and THF (10 mL). Slowly add 1 N aqueous lithium hydroxide (0.7 mL) and stir overnight at room temperature. Acidify the mixture to about pH=6 by 5 N HCl and concentrate to near dryness. Dilute with ethyl acetate (20 mL) and wash the organic layer with saturated aqueous sodium chloride. Dry (magnesium sulfate) and concentrate to give the title compound as a solid.

Preparation 58

(S)-2-sec-Butylamino-6-(1,1-difluoroethyl)-isonicotinic acid

2-Acetyl-6-chloro-isonicotinic acid methyl ester

Add methyl 2,6-dichloroisonicotinate (3.0 g, 15.0 mmol), trans-dichlorobis(triphenylphosphine)palladium (II) (105 mg, 0.15 mmol) and toluene (10 mL) in a previously nitrogen filled sealed vessel. Flush the reactants with nitrogen again. Add tributyl(1-ethoxyvinyl)tin (5.57 mL, 16.5 mmol) under nitrogen and heat the sealed mixture at 100° C. overnight with vigorous stirring. Cool the reaction to room temperature, dilute with diethyl ether and filter through a filtering agent. Concentrate to near dryness and dilute the residue with THF (10 mL). Add dropwise 5 N HCl (5 mL) and stir the mixture overnight. Concentrate to near dryness and extract the organic material by diethyl ether, partitioning with water. Dry (magnesium sulfate), concentrate and purify (silica gel chromatography, eluting with 0:100 to 10:90 ethyl acetate:hexanes) to give the title compound as a solid over two steps (47%).

2-Chloro-6-(1,1-difluoroethyl)-isonicotinic acid methyl ester

Dissolve 2-acetyl-6-chloro-isonicotinic acid methyl ester (410 mg, 1.9 mmol) in dichloromethane (4 mL) and cool to 0° C. Add (diethylamino)sulfur trifluoride (0.55 mL, 4.2 mmol) dropwise and stir over night while warming up to room temperature. Quench the reaction using water and dilute further with dichloromethane (10 mL). Extract the organic layer and dry (magnesium sulfate). Concentrate and purify (silica gel chromatography, eluting with 5:95 ethyl acetate:hexanes) to give the title compound as an oil (45%).

(S)-2-sec-Butylamino-6-(1,1-difluoroethyl)-isonicotinic acid methyl ester

Dissolve 2-chloro-6-(1,1-difluoroethyl)-isonicotinic acid methyl ester (200 mg, 0.85 mmol), palladium (II) acetate (20.0 mg, 0.09 mmol), racemic 2,2'-bis(diphenylphosphino)-1,1'-binaphthyl (56 mg, 0.09 mmol) and cesium carbonate (414 mg, 1.27 mmol) in toluene (3 mL) in a previously degassed sealed vessel. Flush the mixture with nitrogen gas. Add (S)-(+)-sec-butylamine (0.10 mL, 1.02 mmol) to the solution under nitrogen and heat the sealed mixture overnight at 100° C. Cool the reaction to room temperature. Dilute with diethyl ether and filter through a filtering agent. Concentrate the filtrate and purify (silica gel chromatography, eluting with 0:100 to 5:95 ethyl acetate:hexanes) to give the title compound as an oil (86%).

(S)-2-sec-Butylamino-6-(1,1-difluoroethyl)-isonicotinic acid

Dissolve (S)-2-sec-butylamino-6-(1,1-difluoroethyl)-isonicotinic acid methyl ester (200 mg, 0.73 mmol) in methanol (3 mL). Slowly add 1 N lithium hydroxide (1.0 mL) and stir overnight at room temperature. Acidify the mixture to about pH=6 by 5 N HCl and concentrate to near dryness. Dilute with ethyl acetate (20 mL) and wash the organic layer with saturated aqueous sodium chloride. Dry (magnesium sulfate) and concentrate to give the title compound as a solid (95%).

MS (ES): m/z=259 [M+H].

Preparation 59

(S)-2-sec-Butylamino-6-(2-oxopropyl)-isonicotinic acid

2-Chloro-6-(2-oxopropyl)-isonicotinic acid methyl ester

Add methyl 2,6-dichloroisonicotinate (3.0 g, 15.0 mmol), trans-dichlorobis(tri-o-tolylphosphine)palladium (II) (196 mg, 0.25 mmol), tributyltin methoxide (2.4 g, 7.5 mmol) and toluene (20 mL) in a previously nitrogen filled sealed vessel. Flush the reactants with nitrogen again. Add isopropenyl acetate (0.85 mL, 7.75 mmol) under nitrogen and heat the sealed mixture at 100° C. overnight with vigorous stirring. Cool the reaction to room temperature, dilute with diethyl ether and filter through a filtering agent. Concentrate and purify (silica gel chromatography, eluting with 0:100 to 20:80 ethyl acetate:hexanes) to give the title compound (29%).

(S)-2-sec-Butylamino-6-(2-oxopropyl)-isonicotinic acid methyl ester

Dissolve 2-chloro-6-(2-oxopropyl)-isonicotinic acid methyl ester (200 mg, 0.88 mmol), palladium (II) acetate (2.0 mg, 0.009 mmol), racemic 2,2'-bis(diphenylphosphino)-1,1'-binaphthyl (8.2 mg, 0.014 mmol) and cesium carbonate (458 mg, 1.23 mmol) in toluene (2 mL) in a previously degassed sealed vessel. Flush the mixture with nitrogen gas. Add (S)-(+)-sec-butylamine (0.105 mL, 1.0 mmol) to the solution under nitrogen and heat the sealed mixture overnight at 100° C. Cool the reaction to room temperature. Dilute with diethyl ether and filter through a filtering agent. Concentrate the filtrate and purify (silica gel chromatography, 0:100 to 20:80 ethyl acetate:hexanes) to give the title compound (22%).

MS (ES): m/z=265 [M+H].

(S)-2-sec-Butylamino-6-(2-oxopropyl)-isonicotinic acid

Dissolve (S)-2-sec-butylamino-6-(2-oxopropyl)-isonicotinic acid methyl ester (50 mg, 0.19 mmol) in THF (2 mL). Slowly add 1 N lithium hydroxide (0.28 mL) and stir overnight at room temperature. Acidify the mixture to about pH=6 by 5 N HCl and concentrate to near dryness. Dilute with ethyl acetate (10 mL) and wash the organic layer with saturated aqueous sodium chloride. Dry (magnesium sulfate) and concentrate to give the title compound as a solid.

MS (ES): m/z=251 [M+H].

Preparation 60

(S)-2-sec-Butylamino-6-(2,2-difluoropropyl)-isonicotinic acid

2-Chloro-6-(2,2-difluoropropyl)-isonicotinic acid methyl ester

Dissolve 2-chloro-6-(2-oxopropyl)-isonicotinic acid methyl ester (760 mg, 3.3 mmol in dichloromethane (5 mL) and cool to 0° C. Add (diethylamino)sulfur trifluoride (1.1 mL, 8.3 mmol) dropwise and stir over night while warming up to room temperature. Quench with water and dilute further with dichloromethane (20 mL). Extract the organic layer and dry (magnesium sulfate), concentrate and purify (silica gel chromatography, eluting with 0:100 to 5:95 ethyl acetate:hexanes) to give the title compound as an oil (18%).

(S)-2-sec-Butylamino-6-(2,2-difluoropropyl)-isonicotinic acid methyl ester

Dissolve 2-chloro-6-(2,2-difluoropropyl)-isonicotinic acid methyl ester (150 mg, 0.6 mmol), palladium (II) acetate (224.0 mg, 1.0 mmol), racemic 2,2'-bis(diphenylphosphino)-1,1'-binaphthyl (37 mg, 0.06 mmol) and cesium carbonate (293 mg, 0.9 mmol) in toluene (2 mL) in a previously degassed sealed vessel. Flush the mixture with nitrogen gas. Add (S)-(+)-sec-butylamine (0.07 mL, 0.72 mmol) to the solution under nitrogen and heat the sealed mixture overnight at 100° C. Cool the reaction to room temperature. Dilute with diethyl ether and filter through a filtering agent. Concentrate the filtrate and purify (silica gel chromatography, eluting with 0:100 to 5:95 ethyl acetate:hexanes) to give the title compound as an oil (58%).

(S)-2-sec-Butylamino-6-(2,2-difluoropropyl)-isonicotinic acid

Dissolve (S)-2-sec-butylamino-6-(2,2-difluoropropyl)-isonicotinic acid methyl ester (100 mg, 0.34 mmol) in THF (3 mL). Slowly add 1 N lithium hydroxide (0.52 mL) and stir overnight at room temperature. Acidify the mixture to about pH=6 by 5 N HCl and concentrate to near dryness. Dilute with ethyl acetate (20 mL) and wash the organic layer with saturated aqueous sodium chloride, dry (magnesium sulfate) and concentrate to give the title compound as a solid.

Preparation 61

2-Acetyl-(S)-6-sec-butylamino-isonicotinic acid

2-Acetyl-(S)-6-sec-butylamino-isonicotinic acid methyl ester

Dissolve 2-acetyl-6-chloro-isonicotinic acid methyl ester (300 mg, 1.4 mmol), palladium (II) acetate (16 mg, 0.07 mmol), racemic 2,2'-bis(diphenylphosphino)-1,1'-binaphthyl (46 mg, 0.07 mmol) and cesium carbonate (781 mg, 2.1 mmol) in anhydrous toluene (3 mL) in a previously degassed sealed vessel. Flush the mixture with nitrogen gas. Add (S)-(+)-sec-butylamine (0.16 mL, 1.68 mmol) to the solution under nitrogen and heat the sealed mixture overnight at 100° C. Cool the reaction to room temperature. Dilute with diethyl ether and filter through a filtering agent. Concentrate the filtrate and purify (silica gel chromatography, eluting with 0:100 to 5:95 ethyl acetate:hexanes) to give the title compound as a solid (17%).

2-Acetyl-(S)-6-sec-butylamino-isonicotinic acid

Dissolve 2-acetyl-(S)-6-sec-butylamino-isonicotinic acid methyl ester (60 mg, 0.24 mmol) in THF (3 mL). Slowly add 1 N lithium hydroxide (0.3 mL) and stir overnight at room temperature. Acidify the mixture to about pH=6 by 5 N HCl and concentrate to near dryness. Dilute with ethyl acetate (15 mL) and wash the organic layer with saturated aqueous sodium chloride, dry (magnesium sulfate) and concentrate to give the title compound as a solid (96%).

MS (ES): m/z=237 [M+H].

Preparation 62

(S)-6-sec-Butylaminopyridine-2,4-dicarboxylic acid 2-ethyl ester

2-Chloro-6-(1-ethoxyvinyl)-isonicotinic acid methyl ester

Add methyl 2,6-dichloroisonicotinate (2.06 g, 10 mmol), tetrakis(triphenylphosphine)palladium (0) (578 mg, 0.5 mmol), triphenylphosphine (263 mg, 1 mmol) and toluene (25 mL) in a previously nitrogen filled sealed vessel. Flush the reactants with nitrogen again. Add tributyl(1-ethoxyvinyl)tin (4.05 mL, 12.0 mmol) under nitrogen and heat the sealed mixture at 100° C. overnight with vigorous stirring. Cool the reaction to room temperature, dilute with diethyl ether and filter through a filtering agent. Wash the organic filtrate with saturated aqueous ammonium chloride, saturated aqueous sodium bicarbonate and saturated aqueous sodium chloride respectively. Dry (magnesium sulfate), concentrate and purify (silica gel chromatography, eluting with 5:95 to 10:90 ethyl acetate:hexanes) to give the title compound.

6-Chloropyridine-2,4-dicarboxylic acid 2-ethyl ester 4-methyl ester

Dissolve 2-chloro-6-(1-ethoxyvinyl)-isonicotinic acid methyl ester (4.8 g, 20 mmol) in dichloromethane (40 mL) and flush the reaction vessel with oxygen gas. Cool to −78° C. and pass positive pressure of ozone through the solution for 10 min until sky blue color appears. At the same temperature quench the reaction with excess dimethylsulfide (6 mL) and warm up to room temperature overnight. Concentrate and purify (silica gel chromatography, eluting with 0:100 to 10:90 ethyl acetate:hexanes) to give the title compound.

(S)-6-sec-Butylaminopyridine-2,4-dicarboxylic acid 2-ethyl ester 4-methyl ester Dissolve 6-chloropyridine-2,4-dicarboxylic acid 2-ethyl ester 4-methyl ester (2.8 g, 11.5 mmol), palladium (II) acetate (258.0 mg, 1.15 mmol), racemic 2,2'-bis(diphenylphosphino)-1,1'-binaphthyl (716 mg, 1.15 mmol) and cesium carbonate (5.6 g, 17.2 mmol) in toluene (25 mL) in a previously degassed sealed vessel. Flush the mixture with nitrogen gas. Add (S)-(+)-sec-butylamine (1.38 mL, 13.8 mmol) to the solution under nitrogen and heat the sealed mixture overnight at 100° C. Cool the reaction to room temperature. Dilute with diethyl ether and filter through a filtering agent. Concentrate the filtrate and purify (silica gel chromatography, eluting with 0:100 to 10:90 ethyl acetate:hexanes) to give the title compound as an oil (72%).

(S)-6-sec-Butylaminopyridine-2,4-dicarboxylic acid 2-ethyl ester 4-methyl ester alternatively may be prepared by the following procedure

2-Chloro-6-methoxy-isonicotinic acid methyl ester

Mix commercially available 2-chloro-6-methoxy-isonicotinic acid (17 g, 90.6 mmol), concentrated sulfuric acid (0.85 mL) in methanol (150 mL) and reflux overnight. Cool the mixture to room temperature, filter and dry the solid under vacuum to give the title compound (15.5 g). Concentrate filtrate and dilute with ethyl acetate (150 mL). Wash with sodium bicarbonate solution, water, dry (sodium sulfate) and concentrate to give additional title compound (1.7 g) (17.2 g, 93% combined yield).

MS (ES): m/z=202 [M+H].

6-Methoxypyridine-2,4-dicarboxylic acid 2-ethyl ester 4-methyl ester

Add 2-chloro-6-methoxy-isonicotinic acid methyl ester (5 g, 24.8 mmol), palladium acetate (4.157 g, 18.5 mmol), 1,4-bis(diphenylphosphino)butane (1.038 g, 2.43 mmol), ethanol (127 mL), triethylamine (18 mL, 129 mmol) with DMSO (150 mL) to a pressure vessel. Seal the pressure vessel and purge with nitrogen. Pressurize the reaction mixture with carbon monoxide (690 KPa), seal the vessel, agitate the reaction and heat to 80° C. for 19 h. Cool to room temperature, filter the reaction mixture through a filtering agent and concentrate. Dissolve the residue in water (200 mL) and extract with hexanes (3×150 mL) and concentrate to give 6-methoxypyridine-2,4-dicarboxylic acid 2-ethyl ester 4-methyl ester (3.5 g). Extract the aqueous layer with ethyl acetate (3×150 mL) and wash the combined ethyl acetate layers with water, aqueous sodium bicarbonate solution, saturated aqueous sodium chloride, dry (sodium sulfate), concentrate, and purify (silica gel chromatography, eluting with ethyl acetate and hexanes) to give additional title compound (2.1 g) (5.6 g, 95% combined yield).

MS (ES): m/z=240 [M+H].

6-Chloropyridine-2,4-dicarboxylic acid 2-ethyl ester 4-methyl ester

Mix 6-methoxypyridine-2,4-dicarboxylic acid 2-ethyl ester 4-methyl ester (239 mg, 1.0 mmol), phosphorous oxychloride (0.46 mL, 4.93 mmol) in DMF (1.9 mL) and heat to 85° C. for 24 h. Cool to room temperature and quench with saturated aqueous sodium acetate solution (5 mL). Extract with ethyl acetate, wash with water, dry (sodium sulfate), concentrate and purify (silica gel chromatography, eluting with ethyl acetate and hexanes) to give the title compound (190 mg, 78%).

MS (ES): m/z=244 [M+H].

(S)-6-sec-Butylaminopyridine-2,4-dicarboxylic acid 2-ethyl ester 4-methyl ester Add 6-chloropyridine-2,4-dicarboxylic acid 2-ethyl ester 4-methyl ester (2.44 g, 10 mmol), palladium acetate (224 mg, 1.0 mmol), racemic-2,2'-bis(diphenylphosphino)-1,1'-binaphthyl (623 mg, 1.0 mmol), cesium carbonate (4.95 g, 15.2 mmol) in toluene (70 mL) in a sealed tube. Degas the tube for 5 min with nitrogen, add (S)-sec-butylamine (1.2 mL, 11.8 mmol) and seal the tube. Heat to 80° C. overnight. Cool to room temperature and filter the mixture through a filtering agent. Wash with ethyl acetate. Dissolve the solid in water and extract with ethyl acetate. Combine all organic solutions, concentrate and purify (silica gel chromatography, eluting with ethyl acetate and hexanes) to give the title compound (2.5 g, 90%).

MS (ES): m/z=281 [M+H].

(S)-6-sec-Butylaminopyridine-2,4-dicarboxylic acid 2-ethyl ester

Dissolve (S)-6-sec-butylaminopyridine-2,4-dicarboxylic acid 2-ethyl ester 4-methyl ester (990 mg, 3.5 mmol) in THF (35 mL) and dropwise add 1 N lithium hydroxide solution (3.5 mL). Stir at room temperature for 2 h and acidify the mixture to about pH=4 by 5 N HCl and concentrate to near dryness. Dilute with ethyl acetate (20 mL) and wash the organic layer with saturated sodium chloride solution, dry (magnesium sulfate) and concentrate to give a 2:1 ratio of crude title compound to starting material which is used in the next step without further purification.

Preparation 63

(S)-2-sec-Butylamino-6-cyano-isonicotinic acid

(S)-2-sec-Butylamino-6-cyano-isonicotinic acid methyl ester

Dissolve (S)-2-sec-butylamino-6-chloro-isonicotinic acid methyl ester (800 mg, 0.34 mmol), tris(dibenzylideneacetone)dipalladium (0) (120 mg, 0.13 mmol), 1,1'-bis(diphenylphosphino)ferrocene (146 mg, 0.26 mmol), zinc dust (52 mg) and zinc (II) cyanide (387 mg, 3.3 mmol) in N,N-dimethylacetamide (6.6 mL) ) in a previously nitrogen-filled sealed vessel. Flush the reactants with nitrogen before sealing and heat for 6 h at 130° C. Cool to room temperature, dilute with ethyl acetate and wash with 2 N ammonium hydroxide. Wash the organic layer with saturated aqueous sodium chloride, dry (magnesium sulfate), concentrate and purify (silica gel chromatography, eluting with 0:100 to 05:95 ethyl acetate:hexanes) to give the title compound.

(S)-2-sec-Butylamino-6-cyano-isonicotinic acid

Dissolve (S)-2-sec-butylamino-6-cyano-isonicotinic acid methyl ester (250 mg, 0.93 mmol) in methanol (3 mL). Slowly add 2 N NaOH (1.5 mL) and stir overnight at room temperature. Acidify to about pH=6 with 5 N HCl and concentrate. Dilute with ethyl acetate (20 mL) and wash the organic layer with saturated aqueous sodium chloride, dry (magnesium sulfate) and concentrate to give the title compound.

MS (ES): m/z=220 [M+H].

Preparation 64

(S)-2-sec-Butylamino-6-methanesulfonyl-isonicotinic acid

(S)-2-sec-Butylamino-6-methylsulfanyl-isonicotinic acid methyl ester

Add toluene (20 mL), (S)-2-sec-butylamino-6-chloro-isonicotinic acid methyl ester (2.01 g, 8.29 mmol), palladium acetate (186 mg, 0.83 mmol), racemic 2,2'-bis(diphenylphosphino)-1,1'-binaphthyl (516 mg, 0.83 mmol), cesium carbonate (5.40 g, 16.6 mmol), and sodium thiomethoxide (1.16 g, 16.6 mmol) to a sealed vessel flushed with nitrogen. Heat the sealed vessel at 90° C. overnight. Cool to room temperature and filter the solution through a filtering agent and concentrate the filtrate. Purify the residue (silica gel chromatography, eluting with ethyl acetate:hexanes 90:10) to give the title compound (1.4 g, 66%).

MS (ES): m/z=255 [M+H].

(S)-2-sec-Butylamino-6-methanesulfonyl-isonicotinic acid methyl ester

Chill a solution of (S)-2-sec-butylamino-6-methylsulfanyl-isonicotinic acid methyl ester (1.22 g, 4.80 mmol) in dichloromethane (20 mL) in an ice bath and add 3-chloroperbenzoic acid (2.74 g, 15.9 mmol). Stir at room temperature for 3 h and partition the solution between dichloromethane and saturated sodium bicarbonate. Extract the aqueous layer with dichloromethane (2×30 mL). Combine the organic extract, wash with water, saturated aqueous sodium chloride, dry (magnesium sulfate), concentrate and purify (silica gel, eluting with ethyl acetate:hexanes 25:75) to give the title compound (1.02 g, 74%).

MS (ES): m/z=287 [M+H].

(S)-2-sec-Butylamino-6-methanesulfonyl-isonicotinic acid

Chill a solution of (S)-2-sec-butylamino-6-methanesulfonyl-isonicotinic acid methyl ester (1.02 g, 3.57 mmol) in THF (10 mL) in an ice bath. Add 1 N lithium hydroxide (5.4 mL, 5.4 mmol) and stir the solution at room temperature for 3 h. Add 1 N HCl until about pH=2. Concentrate and partition the residue between ethyl acetate and water. Separate the layers and extract the aqueous layer with ethyl acetate (2×30 mL). Wash the combined extract with saturated aqueous sodium chloride, dry (magnesium sulfate) and concentrate to give the title compound.

MS (ES): m/z=273 [M+H].

Preparation 65

(S)-2-sec-Butylamino-6-propanesulfonyl-isonicotinic acid

2-Chloro-6-propylsulfanyl-isonicotinic acid methyl ester

Add 2,6-dichloroisonicotinic acid methyl ester (4.12 g, 20.0 mmol), toluene (40 mL), palladium acetate (448 mg, 2.0 mmol), racemic 2,2'-bis(diphenylphosphino)-1,1'-binaphthyl (1.25 g, 2.0 mmol) and cesium carbonate (7.82 g, 24.0 mmol) into a sealed vessel flushed with nitrogen. Slowly add propanethiol (2.2 mL, 24 mmol,). Heat and stir the reaction mixture at 80° C. for 18 h. Cool to room temperature, dilute with diethyl ether and filter through a filtering agent. Concentrate the filtrate and purify (silica gel chromatography, 2:98 to 5:95 ethyl acetate:hexane) to give the title compound (55%).

2-Chloro-6-propanesulfonyl-isonicotinic acid methyl ester

Add a suspension of potassium peroxymonosulfate (35.6 g, 57.7 mmol) in water (80 mL) to a cooled solution of 2-chloro-6-propylsulfanyl-isonicotinic acid methyl ester (4.71 g, 19.2 mmol) in methanol (40 mL) and THF (40 mL). Stir the mixture at room temperature for 3 days. Dilute the mixture with water and extract with dichloromethane (3×100 mL). Wash the combined extracts with water, dry (magnesium sulfate), concentrate and purify (silica gel chromatograpy, eluting with 20:80 ethyl acetate:hexanes) to give the title product (2.75 g, 52%).

(S)-2-sec-Butylamino-6-propanesulfonyl-isonicotinic acid methyl ester

Add 2-chloro-6-propanesulfonyl-isonicotinic acid methyl ester (2.70 g, 9.71 mmol), toluene (40 mL), palladium acetate (218 mg, 0.97 mmol), racemic 2,2'-bis(diphenylphosphino)-1,1'-binaphthyl (605 mg, 0.97 mmol), cesium carbonate (4.75 g, 14.6 mmol), and (S)-sec-butylamine (1.46 mL, 14.6 mmol) to a sealed vessel flushed with nitrogen. Heat and stir the sealed vessel at 90° C. overnight. Cool to room temperature, filter through a pad of filtering agent, concentrate and purify (silica gel chromatography, eluting with 20:80 to 30:70 ethyl acetate:hexanes) to give the title compound (2.47 g, 81%).

MS (ES): m/z =315 [M+H].

(S)-2-sec-Butylamino-6-propanesulfonyl-isonicotinic acid

Add 2 N NaOH (6.0 mL, 12.0 mmol) to a solution of (S)-2-sec-butylamino-6-propanesulfonyl-isonicotinic acid methyl ester (2.47 g, 7.87 mmol) in methanol (10 mL) at 0° C. Stir the mixture at room temperature for 3 h, acidify the solution to about pH =2 and concentrate to one half of the solvent. Partition the residue between ethyl acetate and water. Extract the aqueous layer with ethyl acetate (2×50 mL). Wash the combined extracts with saturated aqueous sodium chloride, dry (magnesium sulfate) and concentrate to give the title compound (90%).

MS (ES): m/z =301 [M+H].

Preparation 66

(S)-2-sec-Butylamino-6-isopropanesulfonyl-isonicotinic acid

Add 2-Chloro-6-isopropylsulfonyl-isonicotinic acid methyl ester

Add sodium isopropylthiolate (0.89 g, 10.0 mmol, (prepared from treatment of isopropanethiol with 0.95 equivalent of sodium hydride) slowly to a solution of methyl 2,6-dichloroisonicotinate (2.06 g, 10.0 mmol) in DMF (10 mL) at 0° C. Stir the mixture at room temperature overnight. Partition the mixture between diethyl ether (30 mL) and water (30 mL) and extract the aqueous layer with diethyl ether (2×30 mL). Wash the combined extracts with 5% aqueous lithium hydroxide solution, dry (magnesium sulfate) and concentrate. The crude material is used directly in the next step reaction without further purification.

2-Chloro-6-isopropanesulfonyl-isonicotinic acid methyl ester

Add 3-chloroperbenzoic acid (5.32 g, 30.8 mmol) to a solution of 2-chloro-6-isopropylsulfanyl-isonicotinic acid methyl ester (2.37 g, 9.63 mmol) in dichloromethane (50 mL) at 0° C. Stir the mixture at room temperature for 4 h and partition the mixture between dichloromethane and aqueous saturated sodium bicarbonate. Extract the aqueous layer with dichloromethane (2×50 mL) and wash the combined organic extracts with water, saturated aqueous sodium chloride, dry (magnesium sulfate), concentrate and purify (silica gel chromatography, eluting with 25:75 ethyl acetate:hexanes) to give the title compound (1.26 g, 47%).

(S)-2-sec-Butylamino-6-isopropanesulfonyl-isonicotinic acid methyl ester

Add 2-chloro-6-isopropanesulfonyl-isonicotinic acid methyl ester (1.26 g, 4.53 mmol), toluene (20 mL), palladium acetate (102mg, 0.453 mmol.), racemic 2,2'-bis(diphenylphosphino)-1,1'-binaphthyl (282 mg, 0.453 mmol) and cesium carbonate (2.21 g, 6.80 mmol) to a sealed vessel flushed with nitrogen. Slowly add (S)-sec-butylamine (0.68 mL, 6.80 mmol) to the mixture. Heat and stir the sealed vessel at 90° C. overnight. Cool to room temperature, concentrate and purify (silica gel chromatography, eluting with 20:80 to 70:30 ethyl acetate:hexanes) to give the title compound.

(S)-2-sec-Butylamino-6-isopropanesulfonyl-isonicotinic acid

Add 2 N NaOH (7.0 mL, 14.0 mmol) to a solution of 2-sec-butylamino-6-isopropanesulfonyl-isonicotinic acid methyl ester (1.46 g, 4.65 mmol) in methanol (10 mL) at 0° C. Stir the mixture at room temperature for 3 h and acidify the solution to about pH =2 and concentrate the solvent to one half volume. Partition the residue between ethyl acetate and water, and extract the aqueous layer with ethyl acetate (2×50 mL). Wash the combined organic extracts with saturated aqueous sodium chloride, dry (magnesium sulfate) and concentrate to give the title compound in 90% yield.

MS (ES): m/z =301 [M+H].

The compounds of Preparation 67-68 may be prepared essentially as described in

Preparation 66.

| Prep | Compound | MS (ES) [M + H] |
|---|---|---|
| 67* | (S)-2-sec-Butylamino-6-cyclopropanesulfonyl-isonicotinic acid | 299 |
| 68** | (S)-2-sec-Butylamino-6-cyclopentanesulfonyl-isonicotinic acid | 327 |

*Sodium cyclopropylthiolate Add solid sulfur (0.47 g, 15.0 mmol) to a solution of cyclopropylmagnesium bromide (0.8 M, 20.0 mL, 16.0 mmol) in THF (20 mL) at 0° C. according to the reference J. Am. Chem. Soc., 114(9), 3499, (1992). Heat at 50° C. for 3 h and cool to 0° C. Add lithium aluminum hydride (0.49 g, 13.0 mmol) slowly and reflux for 30 min. Cool the reaction mixture in an ice bath and quencch with water (1 mL), 5% aqueous sulfuric acid (5 mL), and then dilute with diethyl ether (10 mL). Separate the layers and extract the aqueous layer with diethyl ether (2 × 20 mL). Wash the combined extract with 5% aqueous sulfuric acid, aqueous saturated sodium bicarbonate, aqueous saturated ammonium chloride, saturated aqueous sodium chloride, dry (magnesium sulfate), and concentrate the filtrate to one half volume. Add sodium hydride (0.44 g, 11.0 mmol), 60% dispersion in mineral oil) to the solution with cooling and stir at room temperature overnight. Concentrate and dry the residue in vaccum to give the title product
**Sodium cyclopentylthiolate is prepared from cyclopentyl mercaptan by reaction with 0.95 equivalent of sodium hydride in THF.

Preparation 69

2-(Propane-2-sulfonyl)-6-prop-2-ynylamino-isonicotinic acid

2-Chloro-6-isopropanesulfonyl-isonicotinic acid methyl ester

Add 3-chloroperbenzoic acid (5.32 g, 30.8 mmol) to a solution of 2-chloro-6-isopropylsulfonyl-isonicotinic acid methyl ester (2.37 g, 9.63 mmol) in dichloromethane (50 mL) at 0° C. Stir the mixture at room temperature for 4 h. Partition the mixture between dichloromethane and aqueous saturated sodium bicarbonate. Extract the aqueous layer with dichloromethane (2×50 mL) and wash the combined extracts with water, saturated aqueous sodium chloride, dry (magnesium sulfate), concentrate and purify (silica gel chromatography, eluting with 25:75 ethyl acetate:hexanes) to give the title product as a white solid (1.26 g, 47%).

2-(Propane-2-sulfonyl)-6-prop-2-ynylamino-isonicotinic acid methyl ester

Add THF (10 mL), 2-chloro-6-iso-propanesulfonyl-isonicotinic acid methyl ester (0.50 g, 1.80 mmol), N,N-diisopropylethylamine (0.470 mL, 2.70 mmol), and propargylamine (0.740 mL, 10.8 mmol) to a sealed vessel flushed with nitrogen. Heat and stir the reaction at 80° C. overnight. Cool to room temperature, concentrate and purify (silica gel chromatography, eluting with 20:80 to 30:70 ethyl acetate:hexanes) to give the title product (0.102 g, 19%).

MS (ES): m/z =297 [M+H].

2-(Propane-2-sulfonyl)-6-prop-2-ynylamino-isonicotinic acid

Add 1 N lithium hydroxide (0.52 mL, 0.52 mmol) to a solution of 2-(propane-2-sulfonyl) -6-prop-2-ynylamino-isonicotinic acid methyl ester (0.102 g, 0.344 mmol) in THF (2 mL) at 0° C. Stir the mixture at room temperature for 3 h and acidify the solution to about pH =2 and concentrate the solvent to one half volume. Partition the residue between ethyl acetate and water, and extract the aqueous layer with ethyl acetate (2×10 mL). Wash the combined organic extract with saturated aqueous sodium chloride, dry (magnesium sulfate) and concentrate to give the title compound (85%).

MS (ES): m/z =283 [M+H].

The compounds of Preparation 70-72 may be prepared essentially as described in

Preparation 69.

| Prep | Compound | MS (ES) [M + H] |
|---|---|---|
| 70 | 2-Cyclopropylamino-6-isopropanelsulfonyl-isonicotinic acid | 283 |
| 71 | 2-Cyclopropyl-methylamino-6-isopropanelsulfony-isonicotinic acid | 299 |
| 72 | 2-Cyclobutylamino-6-isopropanelsulfonyl-isonicotinic acid | 299 |

Preparation 73

2-Cyclopropylamino-6-cyclopropanesulfonyl-isonicotinic acid tert-Butyl-2,6-dichloroisonicotinate Add 2,6-dichloro-isonicotinic acid (2.00 g, 10.4 mmol) in dichloromethane (25 mL) and THF (5 mL) to a flask equipped with a gas condenser. Cool to 0° C. and slowly add concentrated sulfuric acid. Condense isobutylene gas via a condenser filled with dry ice in acetone until total volume of the solution increases by about 20 mL. Stir the mixture at room temperature overnight and pour into a cold solution of sodium carbonate. Separate the layers and extract the aqueous layer with dichloromethane (2×50 mL). Wash the combined organic extract with water, dry (magnesium sulfate) and concentrate to give the title compound (1.02 g, 40%).

2-Chloro-6-cyclopropylsulfonyl-isonicotinic acid tert-butyl ester

Add sodium cyclopropylthiolate (0.554 g, 5.76 mmol (prepared from treatment of isopropanethiol with 0.95 equivalent of sodium hydride) slowly to a solution of tert-butyl 2,6- dichloroisonicotinate (1.30 g, 5.24 mmol) in DMF (5 mL) at 0° C. Stir at room temperature and partition the mixture between diethyl ether (20 mL) and water (20 mL) and extract the aqueous layer with diethyl ether (2×20 mL). Wash the combined extract with 5% aqueous lithium hydroxide solution, dry (magnesium sulfate) and concentrate to give the title compound as a crude residue which is used directly in the next reaction without further purification.

2-Chloro-6-cyclopropanesulfonyl-isonicotinic acid tert-butyl ester

Add 3-chloroperbenzoic acid (1.66 g, 9.6 mmol) to a solution of 2-chloro-6-cyclopropylsulfonyl-isonicotinic acid tert-butyl ester (0.785 g, 2.74 mmol) in dichloromethane (20 mL) at 0° C. Stir at room temperature overnight and partition the mixture between dichloromethane and saturated aqueous sodium bicarbonate and extract the aqueous layer with dichloromethane (2×20 mL). Wash the combined extract with water, saturated aqueous sodium chloride, dry (magnesium sulfate) and purify (silica gel chromatography, eluting with 15:85 ethyl acetate:hexanes) to give the title compound (0.193 g, 22%).

2-Cyclopropylamino-6-cyclopropanesulfonyl-isonicotinic acid tert-butyl ester Add 2-chloro-6-cyclopropanesulfonyl-isonicotinic acid tert-butyl ester (0.190 g, 0.607 mmol), palladium acetate (0.020 g, 0.091 mmol), racemic 2,2'-bis(diphenylphosphino)-1,1'-binaphthyl (0.057 g, 0.091 mmol), cesium carbonate (0.297 g, 0.911 mmol), and (S)-sec-butylamine (0.063 mL, 0.911 mmol) in toluene (5 mL) to a sealed tube flushed with nitrogen. Heat and stir the reaction mixture at 90° C. for 18 h. Cool and filter the mixture through a pad of filtering agent, concentrate and purify (silica gel chromatography, eluting with 20:80 ethyl acetate:hexanes) to give the title compound (0.120 g, 59%).

MS (ES): m/z =339 [M+H].

2-Cyclopropylamino-6-cyclopropanesulfonyl-isonicotinic acid

Add trifluoroacetic acid (2 mL) to a solution of 2-cyclopropylamino-6-cyclopropanesulfonyl-isonicotinic acid tert-butyl ester (0.120 g, 0.355 mmol) in dichloromethane (2 mL) at 0° C. Stir the solution at room temperature for 3 h, concentrate and dry the title compound (0.076 g, 54%).

MS (ES): n/z =283 [M+H].

Preparation 74

(S)-2-sec-Butylamino-6-(methanesulfonyl-methylamino)-isonicotinic acid

(S)-2-sec-Butylamino-6-methane-sulfonylamino-isonicotinic acid methyl ester

Add 2-sec-butylamino-6-chloro-isonicotinic acid methyl ester (500 mg, 2.07 mmol), toluene (10 mL), tris(dibenzylideneacetone)dipalladium(0) (95 mg, 0.104 mmol), 2-(di-tert-butylphosphino)biphenyl (62 mg, 0.207 mmol), and methanesulfonamide sodium salt (363 mg, 3.11 mmol) to a sealed flask flushed with nitrogen. (Prepare methanesulfonamide sodium salt by adding sodium hydride (2.0 g, 50.0 mmol, 60% dispersion in mineral oil) slowly to a solution of methanesulfonamide (5.0 g, 52.6 mmol) and THF (80 mL) at 0° C.) Stir the mixture at room temperature overnight. Concentrate and dry the residue under vacuum. Heat and stir the sealed flask at 100° C. for 18 h. Cool to room temperature, filter through a pad of filtering agent, wash with dichloromethane, concentrate the filtrate and purify (silica gel chromatography, eluting with 20:80 to 25:75 ethyl acetate:hexanes) to give the title compound (475 mg, 76%).

MS (ES): in/z=302 [M+H].

(S)-2-sec-Butylamino-6-(methanesulfonyl-methylamino)-isonicotinic acid methyl ester Add sodium hydride (47 mg, 1.18 mmol, 60% dispersion in mineral oil) to a solution of (S)-2-sec-butylamino-6-methanesulfonylamino-isonicotinic acid methyl ester (356 mg, 1.18 mmol) in DMF (5 mL) at 0° C. Stir for 10 min, add iodomethane (0.11 mL, 1.77 mmol) dropwise. Stir the mixture at room temperature for 2 h, cool and quench the reaction with an ammonium chloride solution. Extract the mixture with ethyl acetate (3×30 mL) and wash the combined extract with water, saturated aqueous sodium chloride, dry (magnesium sulfate), concentrate and purify (silica gel chromatography, eluting with 20:80 ethyl acetate:hexanes) to give the title compound (320 mg, 86%).

MS (ES): m/z =316 [M+H].

(S)-2-sec-Butylamino-6-(methanesulfonyl-methylamino)-isonicotinic acid

Add 1 N lithium hydroxide (19.5 mL, 19.5 mmol) to a solution of (S)-2-sec-butylamino-6-(methanesulfonyl-methylamino)-isonicotinic acid methyl ester (2.45 g, 7.77 mmol) in THF (10 mL) at 0° C. After 2 h at room temperature, acidify the mixture to about pH =2 and concentrate. Extract the residue with ethyl acetate (3×40 mL), wash the combined extracts with saturated aqueous sodium chloride, dry (magnesium sulfate) and concentrate to give the title compound as a yellow solid (2.23 g, 95%).

MS(ES): m/z=302 [M+H].

The compound of Preparation 75 may be prepared essentially as described in Preparation 74.

| Prep | Compound | MS (ES) [M + H] |
|---|---|---|
| 75 | (S)-2-sec-Butylamino-6-methane-sulfonylamino-isonicotinic acid | 288 |

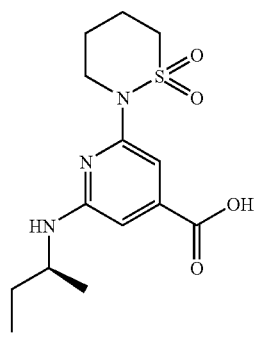

Preparation 76

(S)-2-sec-Butylamino-6-(1,1-dioxo-1λ$^6$-[1,2]thiazinan-2-yl)-isonicotinic acid

4-Chlorobutanesulfonyl chloride

Add anhydrous sodium sulfite (16.8 g, 130 mmol) to a solution of 4-chlorobutyl acetate (20.0 g, 133 mmol) in water (50 mL) and reflux the mixture for 20 h. Cool to room temperature and add concentrated HC1 (19.0 mL) and reflux for 1 h. Cool the mixture to room temperature, neutralize to about pH =7. Concentrate to about one half the volume, filter away the sodium chloride. Concentrate and dry to give the title compound.

4-Chlorobutanesulfonamide

Chill a suspension of 4-chlorobutanesulfonyl chloride (5.0 g, 26.2 mmol) in dichloromethane (50 mL) and add phosphorous pentachloride (12.0 -g, 55.0 mmol) portionwise. Stir the mixture at room temperature for 4 h and filter away the precipitate. Bubble ammonia gas into the filtrate at 0° C. for 1 h. Stir the mixture for 1 h, filter away the ammonium chloride, concentrate and purify (silica gel chromatography, eluting with 30:70 to 40:60 ethyl acetate:hexanes) to give the title compound (1.18 g, 26%).

[1,2]thiazinane 1,1-dioxide, sodium salt

Add sodium (0.157 g, 6.84 mmol) to 50 mL of degassed anhydrous ethanol. After dissolution of sodium, add 4-chlorobutanesulfonamide (1.18 g, 6.84 mmol) into the solution and reflux for 2 h. Cool and filter through a filtering agent, concentrate the filtrate and add ethyl acetate. Filter the mixture through a pad of silica gel and wash with ethyl acetate. Concentrate the filtrate and dry. Convert [1,2]thiazinane 1,1-dioxide to the title compound by treatment with 0.95 equivalent of sodium hydride in THF, concentrate and dry.

2-sec-Butylamino-6-(1,1-dioxo-1λ$^6$-[1,2]thiazinan-2-yl)-isonicotinic acid methyl ester Add 2-sec-butylamino-6-chloro-isonicotinic acid methyl ester (1.0 g, 4.13 mmol), tris(dibenzylideneacetone)dipalladium(0) (0.189 g, 0.207 mmol), 2-(di-tert-butylphosphino)biphenyl (0.123 g, 0.413 mmol) and the sodium salt of [1,2]thiazinane 1,1-dioxide (0.844 g, 5.37 mmol) in toluene (10 mL) to a sealed flask flushed with nitrogen. Heat and stir the sealed flask at 100° C. for 18 h. Cool to room temperature and filter through a bed of filtering agent, and wash with dichloromethane. Concentrate the filtrate and purify (silica gel chromatography, eluting with 20:80 to 30:70 ethyl acetate:hexanes) to give the title compound (0.533 g, 38%).

MS (ES): m/z =342 [M+H].

2-sec-Butylamino-6-(1,1-dioxo-1λ$^6$[1,2]thiazinan-2-yl)-isonicotinic acid

Add 1 N lithium hydroxide (4.0 mL, 3.88 mmol) to a solution of 2-sec-butylamino-6-(1,1-dioxo-1λ$^6$-[1,2]thiazinan-2-yl)-isonicotinic acid methyl ester (0.590 g, 1.80 mmol) in THF (5 mL) at 0° C. Stir for 2 h at room temperature and acidify the mixture to about pH =2 and concentrate. Extract the residue with ethyl acetate (3×40 mL) and wash the combined extract with saturated aqueous sodium chloride, dry (magnesium sulfate) and concentrate to give the title compound (0.377 g, 74%).

MS (ES): m/z =328 [M+H].

The compound of Preparation 77 may be prepared essentially as described in Preparation 76.

| Prep | Compound | MS (ES) [M + H] |
|---|---|---|
| 77 | (S)-2-sec-Butylamino-6-(1,1-dioxo-1λ$^6$-isothiazolidin-2-yl)-isonicotinic acid | 314 |

Preparation 78

(S)-2-sec-Butylamino-6-dimethylsulfamoyl-isonicotinic acid

2-Benzylsulfanyl-6-chloro-isonicotinic acid methyl ester

Add sodium hydride (0.80 g, 20.0 mmol, 60% dispersion in mineral oil) slowly to a solution of methyl 2,6-dichloroisonicotinate (4.12 g, 20.0 mmol) in DMF at 0° C. Stir the mixture at room temperature overnight and partition between diethyl ether (50 mL) and water (50 mL). Extract the aqueous layer with diethyl ether (2×30 mL) and wash the combined extract with 5% aqueous lithium hydroxide. Dry (magnesium sulfate), concentrate and purify (silica gel chromatography, eluting with 3:97 ethyl acetate:hexanes) to give the title compound (5.03 g, 86%). 2-Chloro-6-dimethylsulfamoyl-isonicotinic acid methyl ester Bubble chlorine gas for 30 min into a solution of 2-benzylsulfanyl-6-chloro-isonicotinic acid methyl ester (2.50 g, 8.50 mmol) in water (5 mL) and glacial acetic acid (30 mL) at 0° C. Concentrate and suspend the residue in THF and add dimethylamine in methanol (2.0 M in methanol, 10.6 mL, 21.2 mmol) with cooling. After stirring at room temperature overnight, filter through a filtering agent and partition the filtrate between ethyl acetate (50 mL) and water (50 mL). Extract aqueous layer with ethyl acetate (2×50 mL) and wash the combined extract with water, saturated aqueous sodium chloride, dry (magnesium sulfate) and filter the filtrate through a pad of silica gel and concentrate to give the title product that is used directly in the next reaction without further purification.

(S)-2-sec-Butylamino-6-dimethylsulfamoyl-isonicotinic acid methyl ester

Add toluene (20 mL), 2-chloro-6-dimethylsulfamoyl-isonicotinic acid methyl ester (2.49 g, 8.93 mmol), palladium acetate (0.201 g, 0.893 mmol), racemic 2,2'-bis(diphenylphosphino)-1,1'-binaphthyl (0.556 g, 0.893 mmol) and cesium carbonate (4.36 g, 13.4 mmol) to a sealed vessel flushed with nitrogen. Slowly add (S)-sec-butylamine (1.36 mL, 13.4 mmol) to the mixture. Heat and stir the sealed vessel at 90° C. overnight. Cool to room temperature, filter through a pad of filtering agent, concentrate and purify (silica gel chromatography, eluting with 20:80 to 30:70 ethyl acetate:hexanes) to give the title compound (1.43 g, 51%).

MS (ES): m/z =326 [M+H].

(S)-2-sec-Butylamino-6-dimethylsulfamoyl-isonicotinic acid

Add 1 N lithium hydroxide (11.4 mL, 11.4 mmol) to a solution of (S)-2-sec-butylamino-6-dimethylsulfamoyl-isonicotinic acid methyl ester (1.43 g, 4.54 mmol) and THF (10 mL) at 0° C. Stir the mixture overnight, acidify the solution to about pH =2 and concentrate solvent to one half volume. Partition the residue between ethyl acetate and water, and extract the aqueous layer with ethyl acetate-(2×30 mL). Wash the combined organic extract with saturated aqueous sodium chloride, dry (magnesium sulfate) and concentrate to give the title compound.

MS (ES): m/z=302 [M+H].

The compounds of Preparation 79-80 may be prepared essentially as described in Preparation 78.

| Prep | Compound | MS (ES) [M + H] |
|---|---|---|
| 79 | (S)-2-sec-Butylamino-6-methylsulfamoyl-isonicotinic acid | 288 |
| 80 | (S)-2-sec-Butylamino-6-(pyrrolidine-1-sulfonyl)-isonicotinic acid | 328 |

Preparation 81

6-Cyclobutylaminopyridine-2,4-dicarboxylic acid 2-ethyl ester

2-Chloro-6-(1-ethoxyvinyl)-isonicotinic acid methyl ester

Add 2,6-dichloro-isonicotinic acid methyl ester, tetrakis(triphenylphosphine)palladium(0) (0.763 g, 0.66 mmol), triphenylphosphine (0.346 g, 1.32 mmol), tributyl(1-ethoxyvinyl)tin (5.0 g, 13.9 mmol) and toluene (30 mL), to a sealed flask flushed with nitrogen. Heat at 100° C. overnight and cool to room temperature. Filter the mixture through a filtering agent, concentrate and purify (silica gel chromatography eluting with 25:75 ethyl acetate:hexanes) to give the title compound (84%).

6-Chloropyridine-2,4-dicarboxylic acid 2-ethyl ester 4-methyl ester

Chill a solution of 2-chloro-6-(1-ethoxyvinyl)-isonicotinic acid methyl ester (2.47 g, 10.2 mmol) in dichloromethane (20 mL) at -78° C. and bubble ozone into it for 15 min until light blue in color. Quench with dimethylsulfide and stir at room temperature for 3 h. Concentrate and purify (silica gel chromatography, eluting with 15:85 ethyl acetate:hexanes) to give the title compound (1.44 g, 58%).

MS (ES).: m/z =244 [M+H].

6-Cyclobutylaminopyridine-2,4-dicarboxylic acid 2-ethyl ester 4-methyl ester

Add 6-chloropyridine-2,4-dicarboxylic acid 2-ethyl ester 4-methyl ester (0.500 g, 2.05 mmol), palladium acetate (0.0461 g, 0.205 mmol), racemic 2,2'-bis(diphenylphosphino)-1,1'-binaphthyl (0.128 g, 0.205 mmol), cesium carbonate (0.801 g, 2.46 mmol) and toluene (5 mL), to a sealed vessel flushed with nitrogen. Slowly add cyclobutylamine (0.210 mL, 2.46 mmol) and heat and stir the sealed vessel at 90° C. overnight. Cool to room temperature, filter through a pad of filtering agent, concentrate and purify (silica gel chromatography, eluting with 10:90 to 20:80 ethyl acetate:hexanes) to give the title compound (0.223 g, 39%).

MS (ES): m/z =279 [M+H].

6-Cyclobutylaminopyridine-2,4-dicarboxylic acid 2-ethyl ester

Add 1 N lithium hydroxide (0.80 mL, 0.802 mmol) to a solution of 6-cyclobutylaminopyridine-2,4-dicarboxylic acid 2-ethyl ester 4-methyl ester (0.223 g, 0.802 mmol) in THF (2 mL) at 0° C. Stir for 1 h, acidify the solution to about pH =2, concentrate the solvent to one half volume. Partition the residue between ethyl acetate and water, and extract the aqueous layer with ethyl acetate (2×15 mL). Wash the combined organic extracts with saturated aqueous sodium chloride, dry (magnesium sulfate) and concentrate to give the title compound.

MS (ES): m/z =279 [M+H].

Preparation 82

2-sec-Butylamino-6-(propane-1-sulfinyl)-isonicotinic acid 2-sec-Butylamino-6-propylsulfanyl-isonicotinic acid methyl ester Add 2-chloro-6-propylsulfanyl-isonicotinic acid methyl ester (1.35 g, 5.49 mmol) palladium acetate (0.123 g, 0.549 mmol, 0.1eq.), racemic 2,2'-bis(diphenylphosphino)-1,1'-binaphthyl (0.342 g, 0.549 mmol, 0.1 eq.), cesium carbonate (2.68 g, 8.24 mmol, 1.5 eq.) and toluene (20 mL) into a sealed vessel flushed with nitrogen. Slowly add (S)-sec-butylamine (0.824 mL, 8.24 mmol) and heat and stir the reaction mixture at 90° C. for 18 h. Cool the reaction mixture to room temperature, dilute with ether and filter through a filtering agent. Concentrate the filtrate and purify (silica gel chromatography, eluting with the 5:95 to 10:90 ethyl acetate:hexanes) to give the title compound (55%).

MS (ES): m/z =284 [M+H].

(S)-2-sec-Butylamino-6-(propane-1-sulfinyl)-isonicotinic acid methyl ester

Add sodium perborate monohydrate (0.133 g, 1.33 mmol) to a cooled solution of (S)-2-sec-butylamino-6-propylsulfanyl-isonicotinic acid methyl ester (0.396 g, 1.40 mmol) in acetic acid (4 mL). Stir at room temperature overnight and concentrate. Dissolve the residue in ethyl acetate and wash the solution with aqueous sodium bicarbonate, saturated aqueous sodium chloride, dry (magnesium sulfate), concentrate and purify (silica gel chromatography, eluting with 30:70 ethyl acetate:hexanes) to give the title compound (0.230 g, 55%).

(S)-2-sec-Butylamino-6-(propane-1 -sulfinyl)-isonicotinic acid

Add 1 N lithium hydroxide (1.15 mL, 1.15 mmol) to a solution of (S)-2-sec-butylamino-6-propane-1-sulfinyl)-isonicotinic acid methyl ester (0.229 g, 0.767 mmol) in THF (2 mL) at 0° C. Stir at room temperature for 3 h, acidify the solution to about pH 2 and concentrate to one half of the solvent. Partition the residue between ethyl acetate and water. Extract the aqueous layer with ethyl acetate (2×10 mL). Wash the combine organic extract with saturated aqueous sodium chloride, dry (magnesium sulfate) and concentrate to give the title compound (95%).

MS (ES): m/z =283 [M−H].

The compound of Preparation 83 may be prepared essentially as described in Preparation 82 using sodium thiomethoxide with 3-chloroperbenzoic acid as the oxidant.

| Prep | Compound | MS (ES) [M + H] |
|---|---|---|
| 83 | (S)-2-sec-Butylamino-6-(methane-1-sulfinyl)-isonicotinic acid | 257 |

Preparation 84

(S)-2-sec-Butylamino-6-(2-fluorophenyl)-isonicotinic acid (S)-2-sec-Butylamino-6-(2-fluorophenyl)-isonicotinic acid methyl ester Add (S)-2-sec-butylamino-6-chloroisonicotinic acid methyl ester (1.40 g, 5.75 mmol), 2-fluorophenylboronic acid (1.0 g, 7.15 mmol), tetrakis(triphenylphosphine)palladium (0) (0.664 g, 0.575 mmol), potassium carbonate (2.38 g, 17.3 mmol) and 1,4-dioxane (25 mL) to a sealed flask flushed with nitrogen. Heat and stir the mixture overnight and cool to room temperature. Filter the mixture through a filtering agent, concentrate and purify (silica gel chromatography, eluting with 4:96 ethyl acetate:hexanes) to give the title compound (1.31 g, 75%).

MS (ES): m/z =303 [M+H].

(S)-2-sec-Butylamino-6-(2-fluorophenyl)-isonicotinic acid

Chill a solution of (S)-2-sec-butylamino-6-(2-fluorophenyl)-isonicotinic acid methyl ester (1.31 g, 4.32 mmol) in methanol (5 mL) and THF (5 mL). Ada 2 N NaOH (6.50 mL, 13.0 mmol) stir at room temperature for 3 h, and acidify the solution to about pH=2 and concentrate to one half of the solvent. Partition the residue between ethyl acetate and water. Extract the aqueous layer with ethyl acetate (2×30 mL). Wash the combined organic extracts with saturated aqueous sodium chloride, dry (magnesium sulfate) and concentrate to give the title compound (80%).

MS (ES): m/z =289 [M+H].

Preparation 85

2-Cyclopropylamino-6-(methanesulfonyl-methylamino)-isonicotinic acid

2-Chloro-6-methane-sulfonylamino-isonicotinic acid methyl ester

Add methyl 2, 6-dichloro-isonicotinate (2.06 g, 10.0 mmol), toluene (10 mL), tris(dibenzylideneacetone)dipalladium(0) (0.458 g, 0.50 mmol), 2-(di-tert-butylphosphino)biphenyl (0.298 g, 1.00 mmol), and methanesulfonamide sodium salt (1.17 g, 10.0 mmol) to a sealed flask flushed with nitrogen. Heat and stir the sealed flask at 100° C. for 18 h. Cool the mixture to room temperature and filter through a pad of filtering agent, and wash the solid with dichloromethane. Concentrate and purify (silica gel chromatography, eluting with 20:80 to 30:70 ethyl acetate:hexanes) to give the title compound(1.31 g, 50%).

2-Chloro-6-(methanesulfonyl-methylamino)-isonicotinic acid methyl ester

Add sodium hydride (257 mg, 6.43 mmol, 60% dispersion in mineral oil) at 0° C. to a solution of 2-chloro-6-methanesulfonylamino-isonicotinic acid methyl ester (1.31 g, 4.95 mmol) in DMF (10 mL). After stirring at 0° C. for 15 min, add iodomethane (0.4 mL, 6.43 mmol). Stir the reaction at 0° C. for 1 h and at room temperature for 2 h. Quench the reaction with ice and extract the reaction mixture with ethyl acetate. Wash the organic layer with saturated aqueous sodium chloride, dry (sodium sulfate), concentrate and purify (silica gel chromatography, eluting with 30:70 ethyl acetate:hexanes) to give the title compound (1.0 g,72%).

2-Cyclopropylamino-6-(methanesulfonyl-methylamino)-isonicotinic acid methylester Add palladium acetate (29 mg, 0.13 mmol), racemic 2,2'-bis(diphenylphosphino)-1,1'-binaphthyl (81 mg, 0.13 mmol), cesium carbonate (531 mg, 1.63 mmol), toluene (10 mL), and 2-chloro-6-(methanesulfonyl-methylamino)-isonicotinic acid methyl ester (347 mg, 1.25 mmol) to a sealed tube. After degassing the reaction vessel with nitrogen, add cyclopropylamine (0.114 mL, 1.63 mmol) to the reaction mixture. Heat the reaction vessel at 90° C. overnight. Cool to room temperature and filter the solids through a filtering agent. Wash with ethyl acetate. Concentrate the combined filtrates and purify (silica gel chromatography, eluting with 30:70 ethyl acetate:hexanes) to give the title compound (261 mg 70%).

2-Cyclopropylamino-6-(methanesulfonyl-methylamino)-isonicotinic acid

Treat a solution of 2-cyclopropylamino-6-(methanesulfonyl-methylamino)-isonicotinic acid methyl ester (261 mg, 0.87 mmol) in methanol (8 mL) with 1 N NaOH (1.3 mL, 1.31 mmol) at room temperature. Stir for 5 h, acidify with 1 N HCl to about pH=3. Extract the reaction mixture with ethyl acetate, dry (sodium sulfate) and concentrate to give the title compound (226 mg, 91%).

MS (ES): m/z=286 [M+H].

Preparation 86

(S)-2-sec-Butylamino-6-(2H-tetrazol-5-yl)-isonicotinic acid (S)-2-sec-Butylamino-6-cyano-isonicotinic acid methyl ester Add 2-sec-butylamino-6-chloro-isonicotinic acid methyl ester (1.22 g, 5.0 mmol), tris(dibenzylideneacetone)dipalladium (183 mg, 0.2 mmol), 1,1'-bis(diphenylphosphino)ferrocene (222 mg, 0.4 mmol), zinc cyanide (587 mg, 5.0 mmol), and zinc dust (78 mg, 1.2 mmol) in N,N-dimethylacetamide (10 mL) and heat in a sealed tube at 120° C. overnight. Cool to room temperature, filter through a filtering agent, concentrate and purify (silica gel chromatography, eluting with 10:90 to 15:85 ethyl acetate:hexanes) to give the title compound (703 mg, 59%).

MS (ES): m/z=234 [M+H].

(S)-2-sec-Butylamino-6-(2H-tetrazol-5-yl)-isonicotinic acid methyl ester

Heat a suspension of (S)-2-sec-butylamino-6-cyano-isonicotinic acid methyl ester (932 mg, 4.0 mmol), sodium azide (780 mg, 12 mmol), and triethylamine hydrochloride (1.65 g, 12 mmol) in toluene (13 mL) at 90° C. for 2 days. Cool to room temperature and extract with water (3×30 mL), acidify the combined aqueous layers to about pH=2 using 1 N HCl, extract the desired product with ethyl acetate (4×50 mL), dry (sodium sulfate) and concentrate to give the title compound (720 mg, 65%).
MS (ES): m/z=277 [M+H].

(S)-2-sec-Butylamino-6-(2H-tetrazol-5-yl)-isonicotinic acid

Treat a solution of (S)-2-sec-butylamino-6-(2H-tetrazol-5-yl)-isonicotinic acid methyl ester (250 mg, 0.91 mmol) in methanol (4 mL) at room temperature with 2 N NaOH (1.36 mL, 2.72 mmol). Stir overnight, acidify with 1 N HCl to about pH=3, concentrate and lyophilize to give the title compound.
MS (ES): m/z=261 [M−H].

Preparation 87

(S)-2-sec-Butylamino-6-(2-ethyl-2H-tetrazol-5-yl)-isonicotinic acid

(S)-2-sec-Butylamino-6-(1-ethyl-1H-tetrazol-5-yl)-isonicotinic acid

(S)-2-sec-Butylamino-6-(2-ethyl-2H-tetrazol-5-yl)-isonicotinic acid methyl ester

(S)-2-sec-Butylamino-6-(1-ethyl-1H-tetrazol-5-yl)-isonicotinic acid methyl ester Treat a solution of (S)-2-sec-butylamino-6-(2H-tetrazol-5-yl)-isonicotinic acid methyl ester (720 mg, 2.61 mmol) in DMF (10 mL) with potassium carbonate (541 mg, 3.92 mmol) and iodoethane (0.364 mL, 3.92 mL) at room temperature. Dilute with ethyl acetate (100 mL), wash with water (twice), saturated aqueous sodium chloride, dry (sodium sulfate) and concentrate to give approximately a 1:1 mixture of the two title compounds which are used directly in the next step without further purification.
MS (ES): m/z=303 [M−H].

(S)-2-sec-Butylamino-6-(2-ethyl-2H-tetrazol-5-yl)-isonicotinic acid

(S)-2-sec-Butylamino-6-(1-ethyl-1H-tetrazol-5-yl)-isonicotinic acid

Dissolve the crude product mixture of (S)-2-sec-butylamino-6-(2-ethyl-2H-tetrazol-5-yl)-isonicotinic acid methyl ester and (S)-2-sec-butylamino-6-(1-ethyl-1H-tetrazol-5-yl)-isonicotinic acid methyl ester (approximately 2.61 mmol) in methanol (10 mL) and treat with 2 N NaOH (1.95 mL, 3.9 mmol) overnight. Acidify the reaction mixture to about pH=3 and extract with ethyl acetate (3×50 mL). Dry (sodium sulfate), and concentrate to give the title compounds as a crude mixture.
MS (ES): m/z=289 [M−H].

Preparation 88

(S)-2-sec-Butylamino-6-(2-methyl-2H-tetrazol-5-yl)-isonicotinic acid

(S)-2-sec-Butylamino-6-(2-methyl-2H-tetrazol-5-yl)-isonicotinic acid methyl ester Treat a solution of (S)-2-sec-butylamino-6-(2H-tetrazol-5-yl)-isonicotinic acid methyl ester (350 mg, 1.26 mmol) in ethyl acetate (8 mL) with trimethyloxonium tetrafluoroborate at room temperature for 3 h. Dilute with ethyl acetate (50 mL) and wash with saturated sodium bicarbonate and saturated aqueous sodium chloride. Dry (sodium sulfate) and concentrate to give the title compound which is used directly in the next step without further purification.
MS (ES): m/z=291 [M+H].

(S)-2-sec-Butylamino-6-(2-methyl-2H-tetrazol-5-yl)-isonicotinic acid

Treat a solution of (S)-2-sec-butylamino-6-(2-methyl-2H-tetrazol-5-yl)-isonicotinic acid methyl ester (250 mg, 0.86 mmol) in methanol (5 mL) with 2 N NaOH (0.64 mL, 1.29 mmol). Stir at room temperature overnight, acidify the reaction to about pH=3 using 1 N HCl. Extract the reaction mixture with ethyl acetate (3×25 mL). Wash the combined organic layers with saturated aqueous sodium chloride, dry (sodium sulfate) and concentrate to give the title compound.
MS (ES): m/z=277 [M+H].

Preparation 89

(S)-2-sec-Butylamino-isonicotinic acid

(S)-2-sec-Butylamino-isonicotinic acid methyl ester

Degas with nitrogen a suspension containing 2-chloro-isonicotinic acid methyl ester (2.15 g, 12.5 mmol), palladium acetate (281 mg, 1.25 mmol), racemic 2,2'-bis(diphenylphosphino)-1,1'-binaphthyl (780 mg, 1.25 mmol), cesium carbonate (4.95 g, 15 mmol), and (S)-sec-butylamine (1.5 mL, 15 mmol) in toluene (30 mL) and heat in a sealed tube at 90° C. overnight. Cool to room temperature and filter the solids through a filtering agent. Wash with ethyl acetate (30 mL), concentrate and purify (silica gel chromatography, eluting with 15:85 to 30:70 ethyl acetate:hexanes) to give the title compound.

(S)-2-sec-Butylamino-isonicotinic acid

Treat a solution of (S)-2-sec-butylamino-isonicotinic acid methyl ester (2.69 g, 12.5 mmol) in methanol (35 mL) with 1 N NaOH (15 mL, 15 mmol) at room temperature for 5 hr. Acidify to about pH=3 with 1 N HCl. Concentrate and redissolve the residue in a 1:1 CH$_3$CN:water solution and lyophilize to give the title compound.
MS (ES):. m/z=193 [M−H].

Preparation 90

(S)-2-sec-Butylamino-6-difluoromethoxy-isonicotinic acid

2-Chloro-6-methoxy-isonicotinic acid ethyl ester

Treat an ethanol suspension of 2-chloro-6-methoxy-isonicotinic acid (3.75 g, 20 mmol) at 0° C. with thionyl chloride for 30 min. Heat at 70° C. overnight. Cool to room temperature, concentrate, dissolve the residue in ethyl acetate (200 mL), wash the organic layer with saturated aqueous sodium bicarbonate solution, saturated aqueous sodium chloride solution, dry (magnesium sulfate) and concentrate to give the title compound (4.2 g, 98%).

(S)-2-sec-Butylamino-6-methoxy-isonicotinic acid ethyl ester

Add (S)-sec-butyl amine (1.18 mL, 11.8 mmol) to a suspension of 2-chloro-6-methoxy-isonicotinic acid ethyl ester (1.69 g, 7.86 mmol), palladium acetate (0.088 g, 0.4 mmol), racemic 2,2'-bis(diphenylphosphino)-1,1'-binaphthyl (0.250 g, 0.4 mmol), and cesium carbonate (3.8 g, 11.8 mmol) in toluene (20 mL) at room temperature and stir 15 h at 80° C. Cool to room temperature, filter through a filtering agent, concentrate and purify (silica gel chromatography, eluting with 5:95 ethyl acetate:hexanes to give the title compound (1.85 g, 93%).

MS (ES): m/z=253 [M+H].

(S)-2-sec-Butylamino-6-hydroxy-isonicotinic acid ethyl ester

Treat sodium iodide (5.58 g, 36.7 mmol) and (S)-2-sec-butylamino-6-methoxy-isonicotinic acid ethyl ester (1.85 g, 7.3 mmol) in acetonitrile (30 mL) with chlorotrimethylsilane (4.66 mL, 36.7 mmol) and stir at reflux for 38 h. Quench with methanol (10 mL), stir for 24 h, and concentrate. Dissolve residue in ethyl acetate, wash with water, saturated aqueous sodium chloride, dry (magnesium sulfate), concentrate and purify (silica gel chromatography, eluting with 70:30 to 100:0 ethyl acetate:hexanes) to give the title compound (0.98 g, 56%).

MS (ES): m/z=239 [M+H].

(S)-2-sec-Butylamino-6-difluoromethoxy-isonicotinic acid ethyl ester

Add cesium carbonate (0.352 g, 1.08 mmol) to (S)-2-sec-butylamino-6-hydroxy-isonicotinic acid ethyl ester (0.172 g, 0.72 mmol) in butan-2-one (10 mL) ((Bioorg. Med. Chem. Lett., 12, 2149-2152 (2002)). Heat at 70° C. for 30 min and add chlorodifluoroacetic acid methyl ester (0.24 mL, 2.16 mmol) in three equal portions over 3 h. Heat for 3 days at 70° C. Add again chlorodifluoroacetic acid methyl ester (0.24 mL, 2.16 mmol) in three equal portions over 3 h and stir at room temperature for 24 h. Concentrate and dissolve the crude mixture in ethyl acetate and filter. Purify (silica gel chromatography, eluting with 2:98 to 6:92 ethyl acetate:hexanes) to give the title compound (0.135 g, 65%). MS (ES): m/z=289 [M+H].

(S)-2-sec-Butylamino-6-difluoromethoxy-isonicotinic acid

Add 2 N NaOH (0.67 mL) to (S)-2-sec-butylamino-6-difluoromethoxy-isonicotinic acid ethyl ester in ethanol (5 ML). Stir 3 h and acidify to about pH=4 with 1 N HCl and extract with ethyl acetate. Wash organic layer with saturated aqueous sodium chloride, dry (magnesium sulfate) and concentrate to give the title compound (0.1 g, 85%).

MS (ES): m/z=261 [M+H].

Preparation 91

2-Methanesulfonyl-6-(methylpropylamino)-isonicotinic acid

2-Chloro-6-methanesulfonyl-isonicotinic acid methyl ester

Stir a mixture of 2,6-dichloro-isonicotinic acid methyl ester (20 g, 90.0 mmol) and sodium methyl thiolate (6.4 g, 90.9 mmol) in DMF (90 mL overnight at room temperature. Partition the reaction between of diethyl ether (50 mL) and water (100 mL). Extract the organics with diethyl ether (2×25 mL). Wash the combined organic layers with 5% aqueous lithium chloride solution, dry (magnesium sulfate) and concentrate to give an oil (19.12 g). Dissolve in dichloromethane (100 mL) and cool the solution in a wet ice/acetone bath. Add peracetic acid (15 mL) dropwise. Remove the ice bath and stir overnight. Quench the reaction with water (100 mL) and solid sodium bisulfite to a negative starch iodide endpoint. Separate the organic layer, dry (magnesium sulfate) and concentrate. Crystallize by the addition of hexanes to give a white solid. Filter the slurry, wash with hexanes, and dry under vacuum to give the title compound (13.7 g) as a white crystalline solid. Recover a second crop of the title compound (6 g) from the filtrate (19.7 g, 83% total yield).

2-Methanesulfonyl-6-(methylpropylamino)-isonicotinic acid methyl ester

Add methylpropylamine (0.21 mL, 2.0 mmol) to a suspension of 2-chloro-6-methanesulfonyl-isonicotinic acid methyl ester (0.25 g, 1.0 mmol), palladium acetate (0.022 g, 0.1 mmol), racemic 2,2'-bis(diphenylphosphino)-1,1'-binaphthyl (0.062 g, 0.1 mmol), and cesium carbonate (0.325 g, 1.0 mmol) in toluene (5 mL) at room temperature and stir 18 h at 80° C. Cool, filter through a filtering agent and purify (silica gel chromatography, eluting with 20:80 to 40:60 ethyl acetate:hexanes) to give the title compound (0.181 g, 63%).

2-Methanesulfonyl-6-(methylpropylamino)-isonicotinic acid

Add 2 N NaOH (0.95 mL) to 2-methanesulfonyl-6-(methylpropylamino)-isonicotinic acid methyl ester (0.181 g, 0.63 mmol) in methanol (5 mL). Stir 3 h, acidify to about pH=3 using 1 N HCl, extract into ethyl acetate, wash organic layer with saturated aqueous sodium chloride, dry (magnesium sulfate) and concentrate to give the title compound (0.14 g, 85%).

MS (ES): m/z=273 [M+H].

Preparation 92

2-Cyclobutylamino-6-methanesulfonyl-isonicotinic acid

2-Cyclobutylamino-6-methanesulfonyl-isonicotinic acid methyl ester

Add cyclobutylamine (0.13 mL, 1.5 mmol) to a suspension of 2-chloro-6-methanesulfonyl-isonicotinic acid methyl ester (0.25 g, 1.0 mmol), palladium acetate (0.022 g, 0.1 mmol), racemic 2,2'-bis(diphenylphosphino)-1,1'-binaphthyl (0.062 g, 0.1 mmol), and cesium carbonate (0.325 g, 1.0 mmol) in toluene (5 mL) at room temperature and heat for 16 h at 80° C. Cool, filter through a filtering agent, concentrate and purify (silica gel chromatography, eluting with 15:85 to 40:60 ethyl acetate:hexanes) to give the title compound (0.255 g, 90%).

2-Cyclobutylamino-6-methanesulfonyl-isonicotinic acid

Add 2 N NaOH (1.26 mL) to 2-cyclobutylamino-6-methanesulfonyl-isonicotinic acid methyl ester (0.24 g 0.85 mmol) in methanol (5 mL). Stir 3 h, acidify to about pH=3 with 1 N HCl, extract into ethyl acetate, wash organic layer with saturated aqueous sodium chloride, dry (magnesium sulfate) and concentrate to give the title compound (0.19 g, 86%).

MS (ES): m/z=271 [M+H].

The compounds of Preparations 93-94 may be prepared essentially as described in Preparation 92 beginning with the appropriate amine.

| Prep | Compound | MS (ES) [M + H] |
|------|----------|-----------------|
| 93 | 2-Pyrrolidin-1-yl-6-methanesulfonyl-isonicotinic acid | 271 |
| 94 | 2-Cyclopropylamino-6-methanesulfonyl-isonicotinic acid | |

Preparation 95

2-(Methanesulfonyl-methylamino)-6-(methylpropylamino)-isonicotinic acid

2-Chloro-6-(methylpropylamino)-isonicotinic acid methyl ester

Mix 2,6-dichloro-isonicotinic acid methyl ester (5 g, 24.2 mmol), methylpropyl-amine (3.2 g, 23.06 mmol), cesium carbonate (10 g, 31.2 mmol), racemic-2,2'-bis(diphenylphosphino)-1,1'-binaphthyl (1.5 g, 2.43 mmol), and palladium acetate (0.27 g, 1.21 mmol) in toluene (50 mL). Degas with argon, seal the vessel and heat at 80° C. for 16 h. Cool to room temperature and dilute with diethyl ether (50 mL). Filter through a filtering agent, concentrate, and purify (silica gel chromatography, eluting with 0:100 to 20:80 ethyl acetate:hexanes to give the title compound as an oil (795 mg, 13.5%).

$^1$H NMR (CDCl$_3$) δ 7.00 (s, 1H), 6.93 (s, 1H), 3.92 (s, 3H), 3.49 (t, J=7.2 Hz, 2H), 3.09 (s, 3H), 1.69-1.59 (m, 2H), 0.94 (t, J=7.6 Hz, 3H).

2-Methanesulfonylamino-6-(methylpropylamino)-isonicotinic acid methyl ester Dissolve methane sulfonamide (951 mg, 10 mmol) in THF (30 mL). Add sodium hydride (380 mg, 9.5 mmol, 60% dispersion in mineral oil) and reflux for 3 h, cool to room temperature and concentrate. Charge a sealed flask with sodium methansulfonamide (478 mg, 4.09 mmol), 2-chloro-6-(methylpropylamino)-isonicotinic acid methyl ester (79 mg, 3.27 mmol), biphenyl-2-yl-di-tert-butylphosphane (98 mg, 0.33 mmol), and tris(dibenzylideneacetone)dipalladium (0) (150 mg, 0.16 mmol) in toluene (7 mL). Degas with argon, seal the vessel and heat at 100° C. for 16 h. Cool to room temperature, dilute with ethyl acetate, wash with water, aqueous sodium chloride, concentrate and purify (silica gel chromatography, eluting with 0:100 to 50:50 ethyl acetate:hexanes) to give the title compound as an oil (870 mg, 88%).

MS (ES): m/z=302 [M+H].

2-(methanesulfonyl-methylamino)-6-(methylpropylamino)-isonicotinic acid methyl ester Dissolve 2-methanesulfonylamino-6-(methylpropylamino)-isonicotinic acid methyl ester (87 mg, 2.89 mmol) and iodomethane (0.27 mL, 4.33 mmoles) in DMF (10 mL). Add potassium carbonate (639 mg, 4.62 mmol) and tetrabutylammonium bromide (93 mg, 0.98 mmol) and stir at room temperature 1 h. Dilute with ethyl acetate (80 mL), wash with 10% aqueous potassium carbonate (2×15 mL), 0.1 N citric acid (2×15 mL), 1 N lithium chloride (2×15 mL) and saturated aqueous sodium chloride (15 mL).

Concentrate organic layer and purify (silica gel chromatography, eluting with 10:90 to 40:60 ethyl acetate:hexanes to give the title compound (796 mg, 87%).

MS (ES): m/z=316 [M+H].

2-(methanesulfonyl-methylamino)-6-(methylpropylamino)-isonicotinic acid

Dissolve 2-(methanesulfonyl-methylamino)-6-(methylpropylamino)-isonicotinic acid methyl ester (796 mg, 2.52 mmoles) in THF (35 mL) and add 1 N lithium hydroxide (12.6 mmoles). Stir at room temperature for 16 h, acidify with 5 N HCl (2.6 mL), and partition between diethyl ether and water. Wash the diethyl ether layer with saturated aqueous sodium chloride, dry (magnesium sulfate) and concentrate to give the title compound as a yellow solid (650 mg, 85%).

MS (ES): m/z=302 [M+H].

Preparation 96

2-Benzenesulfonyl-6-(S)-sec-butylamino)-isonicotinic acid

2-benzenesulfonyl-6-chloro-isonicotinic acid methyl ester

Mix 2,6-dichloro-isonicotinic acid methyl ester (1 g, 4.85 mmol) and sodium thiophenoxide (0.64 g, 4.85 mmol) in DMF (10 mL) at room temperature for 4 h. Quench with water and extract with dichloromethane. Dry the dichloromethane layer over magnesium sulfate and concentrate. Dissolve the residue in chloroform (30 mL) and add neutral alumina (6 g) and potassium peroxymonosulfate (11.92 g, 19.39 mmol). Reflux for 16 h, concentrate and purify (silica gel chromatography, eluting with 0:100 to 20:80 ethyl acetate:hexanes) to give the title compound as a white solid (1.4 g, 93%).

MS (ES): m/z=312 [M+H].

2-Benzenesulfonyl-6-(S)-sec-butylamino)-isonicotinic acid

In a sealed tube mix 2-benzenesulfonyl-6-chloro-isonicotinic acid methyl ester (1.4 g, 4.49 mmol), palladium acetate (0.1 g, 0.45 mmol), cesium carbonate (2.19 g, 6.74 mmol), (S)-sec-butylamine (0.36 g, 4.94 mmoles) and racemic 2,2'-bis(diphenylphosphino)-1,1'-binaphthyl (0.28 g. 0.45 mmol) in toluene (50 mL). Degas with argon, seal the flask and heat at 80° C. for 16 h. Cool to room temperature and partition between diethyl ether and water. Dry the organic layer over magnesium sulfate, concentrate and purify (silica gel chromatography, eluting with 0:100 to 20:80 ethyl acetate:hexanes) to give the methyl ester (490 mg, 31%) as an oil. Dissolve the oil in THF (14 mL) and add 1 N lithium hydroxide (7 mL). Stir vigorously at room temperature for 4 h and concentrate. Partition the residue between diethyl ether and 1

N HCl, dry the organic layer (magnesium sulfate) and concentrate to give the title compound as a white solid (430 mg, 91%).

MS (ES): m/z=335 [M+H].

Preparation 97

2-sec-Butylamino-6-methanesulfonyloxy-isonicotinic acid

2-Benzyloxy-6-chloro-isonicotinic acid methyl ester

Add sodium hydride (1.15 g, 28.75 mmol 60% in mineral oil) to a suspension of 2,6-dichloroisonicotinic acid (2 g, 10.42 mmol) at 0° C. in DMF (40 mL). Warm to room temperature and stir for 10 min. Add benzyl alcohol (1.35 mL, 13.045 mmol) dropwise and heat to 80° C. for 1 h. Cool to room temperature, add diiodomethane (2 mL) and stir for 30 min. Pour into saturated aqueous sodium chloride and partition between ethyl acetate and water. Dry (magnesium sulfate), concentrate and purify (silica gel chromatography, eluting with 5:95 ethyl acetate:hexanes) to give the title compound as a colorless oil (2.3 g, 79%).

MS (ES): m/z=278 [M+H].

2-Benzyloxy-6-sec-butylamino-isonicotinic acid methyl ester

Degas a sealed tube for 5 min and add a suspension 2-benzyloxy-6-chloro-isonicotinic acid methyl ester (1 g, 3.604 mmol), palladium acetate (100 mg, 0.445 mmol), racemic 2,2'-bis-diphenylphosphanyl-[1,1']binaphthalenyl (307 mg, 0.493 mmol), cesium carbonate (1.2 g, 3.683 mmol) and (R)-sec-butylamine (0.5 mL, 1.387 mmol) in toluene (14 mL). Heat to 105° C. and stir for 20 h. Cool to room temperature, concentrate and purify (silica gel chromatography, eluting with 3:97 ethyl acetate:hexanes) to give the title compound.

MS (ES): m/z=315 [M+H].

2-sec-Butylamino-6-hydroxy-isonicotinic acid

Treat a solution of 2-benzyloxy-6-sec-butylamino-isonicotinic acid methyl ester (340 mg, 1.036 mmol) in methanol (15 mL) and ethyl acetate (5 mL) with 10% Pd/C (150 mg). Stir the mixture under a balloon containing hydrogen gas for 2.5 h. Filter through a filtering agent, wash with ethyl acetate and concentrate to give the title compound which is used directly in the next step without further purification.

MS (ES): m/z=225 [M+H].

2-sec-Butylamino-6-methanesulfonyloxy-isonicotinic acid methyl ester

Add methanesulfonyl chloride (0.1 mL, 1.292 mmol) to a solution of 2-sec-butylamino-6-hydroxy-isonicotinic acid (242 mg, 1.016 mmol) and triethyl amine (0.25 mL, 1.793 mmol) in dichloromethane (15 mL) at 0° C. Stir at room temperature for 15 min, dilute with dichloromethane, wash with saturated aqueous sodium chloride, dry (magnesium sulfate), concentrate and purify (silica gel chromatography, eluting with 15:85 ethyl acetate:hexanes) to give the title compound as a white solid (240 mg, 75%).

MS (ES): m/z =303 [M+H].

2-sec-Butylamino-6-methanesulfonyloxy-isonicotinic acid

Add 1 N lithium hydroxide (2 mL) to a solution of 2-sec-butylamino-6-methanesulfonyloxy-isonicotinic acid methyl ester (235 mg, 0.743 mmol) in THF (15 mL) at 0° C. Warm to room temperature and stir for 12 h. Acidify with 5% aqueous HCl to about pH=3, extract with ethyl acetate, dry (magnesium sulfate), and concentrate to give the title compound.

MS (ES): m/z=289 [M+H].

Preparation 98

6-Fluoro-N,N-dipropyl-isophthalamic acid

3-Bromo-4-fluoro-N,N-dipropylbenzamide

Combine 3-bromo-4-fluorobenzoic acid (5.0 g, 22.8 mmol) with 1-(3-dimethylaminopropyl)-3-ethylcarbodiimide (4.4 g, 22.8 mmol) and N-hydroxy-succinimide (2.6 g, 22.8 mmol) in dichloromethane (75 mL) and stir at room temperature for 30 min. Add N,N-dipropylamine (4.7 mL, 34.3 mmol) and triethylamine (8.0 mL, 57.1 mol) and stir at room temperature overnight. Dilute with ethyl acetate and wash with 1 N HCl, saturated aqueous potassium carbonate, saturated aqueous sodium chloride, dry (magnesium sulfate), concentrate and purify (silica gel chromatography, eluting with 30:70 ethyl acetate:hexanes) to give the title compound.

$^1$HNMR (CDCl$_3$) δ 0.79-0.99 (m, 6H), 1.56-1.68 (m, 4H), 3.17-3.44 (m, 4H), 7.14 (t, 1H)), 7.26-7.31 (m, 1H)), 7.56-7.58 (m, 1H).

3-Cyano-4-fluoro-N,N-diprgpylbenzamide

Combine 3-bromo-4-fluoro-N,N-dipropylbenzamide (1.0 g, 3.3 mmol) with copper cyanide (0.45 g, 5.0 mmol) in DMF (5 mL) and heat at reflux until all starting material is consumed. Cool to room temperature and partition between ethyl acetate and saturated aqueous sodium bicarbonate. Separate the organic layer and wash with saturated aqueous sodium bicarbonate, saturated sodium chloride solution, dry (magnesium sulfate), concentrate and purify (silica gel chromatography, eluting with 20:80 ethyl acetate:hexanes) to give the title compound.

$^1$HNMR (CDCl$_3$) δ 0.79-0.99 (m, 6H), 1.66-1.69 (m, 4H)), 3.15-3.45 (m, 4H)), 7.27 (t, 1H), 7.60-7.65 (m, 2H).

6-Fluoro-N,N-dipropyl-isophthalamic acid

Dissolve 3-cyano-4-fluoro-N,N-dipropylbenzamide (0.52 g, 2.1 mmol) in a 3:1 solution of concentrated sulfuric acid:water (5 mL). Heat at 150° C. until no starting material remains. Cool to room temperature, pour into water and extract with ethyl acetate. Wash the organic layer with saturated aqueous sodium chloride solution, dry (magnesium sulfate) and concentrate to give the title compound that is used without further purification.

MS (ES): m/z=268.0 =[M+H].

Preparation 99

5-(Methyl-propylcarbamoyl)-isophthalic acid monoethyl ester 5-(Methyl-propylcarbamoyl)-isophthalic acid diethyl ester Stir a solution of diethyl 1,3,5-benzene tricarboxylate (2.47 g, 9.28 mmol), 1-hydroxybenzotriazole (1.38 g, 10.2 mmol), 1-(3-dimethylaminopropyl)-3-ethylcarbodiimide hydrochloride (EDCI) (1.96 g, 10.2 mmol), N-methylpropylamine (1.04 mL, 10.2 mmol) in dichloromethane (50 mL) at room temperature overnight. Dilute with dichloromethane (300 mL) and extract the solution with 0.1 N citric acid (2×50 mL), saturated aqueous sodium bicarbonate (50 mL), and saturated aqueous sodium chloride (50 mL). Dry (magnesium sulfate), concentrate and purify (silica gel chromatography, eluting with 50:50 ethyl acetate:hexanes) to give the title compound (2.02 g, 68%).

MS (ES): m/z=322 [M+H].

5-(Methyl-propylcarbamoyl)-isophthalic acid monoethyl ester

Stir a solution of 5-(methyl-propylcarbamoyl)-isophthalic acid diethyl ester (2.02 g, 6.3 mmol), NaOH (0.25 g, 6.3 mmol) and ethanol (32 mL) at room temperature overnight. Add 0.2 N HCl (60 mL) and extract with ethyl acetate (2×50 mL). Dry (magnesium sulfate), concentrate and purify (silica gel chromatography, eluting with 50:50 ethyl acetate:hexanes with 1% acetic acid then 100% ethyl acetate with 1% acetic acid) to give the title compound as an oil (1.4 g, 75%).

MS (ES): m/z=294 [M+H].

Preparation 100

3-Ethylcarbamoyl-5-(methyl-propylcarbamoyl)-benzoic acid

3-Ethylcarbamoyl-5-(methyl-propylcarbamoyl)-benzoic acid ethyl ester

Stir a solution of 5-(methyl-propylcarbamoyl)-isophthalic acid monoethyl ester (146 mg, 0.5 mmol), 1-hydroxybenzotriazole (74 mg, 0.55 mmol), 1-(3-dimethylamninopropyl)-3-ethylcarbodiimide hydrochloride (110 mg, 0.55 mmol), ethylamine (2 N in THF, 0.275 mL, 0.55 mmol) in 0.75 mL DMF at room temperature overnight. Dilute with dichloromethane (15 mL) and wash with water (5 mL), 0.1 N aqueous citric acid (5 mL), saturated aqueous sodium bicarbonate (5 mL), and saturated aqueous sodium chloride (5 mL). Dry (magnesium sulfate) and concentrate to give the title compound (157 mg, 100%).

MS (ES): m/z=321 [M+H].

3-Ethylcarbamoyl-5-(methyl-propylcarbamoyl)-benzoic acid

Stir a solution of 3-ethylcarbamoyl-5-(methyl-propylcarbamoyl)-benzoic acid ethyl ester (157 mg, 0.5 mmol), 1 N aqueous lithium hydroxide (2.45 mL, 2.45 mmol) and THF (2.45 mL) at room temperature overnight. Dilute the reaction with water and extract with dichloromethane. Acidify the aqueous with 5 N HCl, extract the aqueous with dichloromethane and dry (magnesium sulfate) and concentrate to give the title compound (106 mg, 74%).

MS (ES): m/z=293 [M+H].

Preparation 101

3,5-Bis(methyl-propylcarbamoyl)-benzoic acid

3,5-Bis(methyl-propylcarbamoyl)-benzoic acid ethyl ester

Stir a solution of 5-(methyl-propylcarbamoyl)-isophthalic acid monoethyl ester (146 mg, 0.5 mmol), 1-hydroxybenzotriazole (68 mg, 0.5 mmol), 1-(3-dimethylaminopropyl)-3-ethylcarbodiimide hydrochloride (96 mg, 0.5 mmol), N-methylpropylamine (51 µL, 0.5 mmol) in dichloromethane (2.5 mL) at room temperature overnight. Dilute with dichloromethane (15 mL) and wash with water (5 mL), 0.1 N citric acid (5 mL), saturated aqueous sodium bicarbonate (5 mL), and saturated aqueous sodium chloride (5 mL). Dry (magnesium sulfate) and concentrate to give the title compound (157 mg, 90%)

MS (ES): m/z=349 [M+H].

3,5-Bis(methyl-propylcarbamoyl)-benzoic acid

Stir a solution of 3,5-bis(methyl-propylcarbamoyl)-benzoic acid ethyl ester (157 mg, 0.45 mmol), 1 N lithium hydroxide (2.25 mL, 2.25 mmol) and THF (2.25 mL) for 2 h at room temperature. Dilute the reaction with water (10 mL) and extract with dichloromethane (10 mL). Acidify the aqueous with 5 N HCl, extract the aqueous with dichloromethane, dry (magnesium sulfate) and concentrate to give the title compound (119 mg, 82%).

MS (ES): m/z=321 [M+H].

Preparation 102

5-(Methyl-propylcarbamoyl)-isophthalic acid monoisopropyl ester

5-(Methyl-propylcarbamoyl)-isophthalic acid 1-ethyl ester 3-isopropyl ester

Sonicate a mixture of 5-(methyl-propyl-carbamoyl)-isophthalic acid monoethyl ester (146 mg, 0.5 mmol), isopropanol (0.75 mL) and concentrated sulfuric acid (25 µL) then stir the resulting solution at room temperature for one month. Add 1-hydroxybenzotriazole (68 mg, 0.5 mmol), 1-(3-dimethylaminopropyl)-3-ethylcarbodiimide hydrochloride (96 mg, 0.5 mmol), and triethylamine (100 µL). Stir overnight at room temperature. Add dichloromethane (25 mL) and wash with 0.1 N citric acid (5 mL), saturated aqueous sodium bicarbonate (10 mL), saturated aqueous sodium chloride (10 mL), dry (magnesium sulfate) and concentrate (149 mg, 89%).

MS (ES): m/z=336 [M+H].

5-(Methyl-propylcarbamoyl)-isophthalic acid monoisopropyl ester

Stir a solution of 5-(methyl-propylcarbamoyl)-isophthalic acid 1-ethyl ester 3-isopropyl ester (149 mg, 0.4 mmol) in 0.2 N NaOH in 1:10 water:isopropanol (2.2 mL) overnight. Add 1 N lithium hydroxide (0.44 mL) and stir for 1 h at room temperature. Dilute with water and extract with dichloromethane. Acidify the aqueous with 5 N HCl, extract the aqueous with dichloromethane, dry (magnesium sulfate) and concentrate to give the title compound (79 mg, 56%).

MS (ES): m/z=308 [M+H].

Preparation 103

5-Difluoromethyl-N-methyl-N-propyl-isophthalamic acid

5-Hydroxymethyl-isophthalic acid monoethyl ester

Add a solution of diethyl-5-(hydroxymethyl)-isophthalate (5 g, 19.8 mmol) in acetone (88 mL) to a solution of NaOH (792 mg, 19.8 mmol) in ethanol (12 mL). After 4 h collect precipitate. Dissolve the precipitate in water (200 mL), add 5

5-Hydroxymethyl-N-methyl-N-propyl-isophthalamic acid ethyl ester

Stir a solution of 5-hydroxymethyl-isophthalic acid monoethyl ester (1.9 g, 8.4 mmol), N-methylpropylamine (947 µl, 9.2 mmol), 1-hydroxybenzotriazole (1.24 g, 9.2 mmol), and 1-(3-dimethylaminopropyl)-3-ethylcarbodiimide hydrochloride (1.77 g, 9.2 mmol) in a mixture of dichloromethane (12 mL) and DMF (12 mL) at room temperature for 1.5 h. Concentrate and purify (silica gel chromatography, eluting with 50:50 ethyl acetate:hexanes) to give the title compound (950 mg, 40% yield).

MS (ES): m/z=280 [M+H].

5-Formyl-N-methyl-N-propyl-isophthalamic acid ethyl ester

Add a solution of 5-hydroxymethyl-N-methyl-N-propyl-isophthalamic acid ethyl ester (600 mg, 2.15 mmol) dropwise to a mixture of Dess-Martin periodinane (1.06 g, 2.5 mmol) in dichloromethane (6.5 mL). Stir the exothermic reaction mixture (32° C.) for 20 min without additional heat. To the reaction mixture add diethyl ether (12 mL) and saturated aqueous sodium bicarbonate (12 mL). Separate the layers and wash the aqueous layer with diethyl ether (2×12 mL). Combine the organics and wash with saturated aqueous sodium bicarbonate (12 mL), saturated aqueous sodium chloride (12 mL), dry (magnesium sulfate), concentrate, and purify (silica gel chromatography, eluting with 50:50 ethyl acetate:hexanes) to give the title compound as an oil (0.54 g, 91%).

MS (ES): m/z=278 [M+H].

5-Difluoromethyl-N-methyl-N-propyl-isophthalamic acid ethyl ester

Add a solution of bis(2-methoxyethyl) aminosulfar trifluoride (161 mg, 0.73 mmol) in dichloromethane (88 µL) to a solution of 5-formyl-N-methyl-N-propyl-isophthalamic acid ethyl ester (120 mg, 0.43 mmol) in dichloromethane (130 µL). Place the reaction under nitrogen, add ethanol (3.5 µL) and stir the reaction at room temperature for 48 h. Pour the reaction into saturated aqueous sodium bicarbonate and extract with dichloromethane. Dry (magnesium sulfate), concentrate and purify (silica gel chromatography, eluting with 50:50 ethyl acetate:hexanes) to give the title compound (68 mg, 53%).

MS (ES): m/z=300 [M+H].

5-Difluoromethyl-N-methyl-N-propyl-isophthalamic acid

Stir a solution of 5-difluoromethyl-N-methyl-N-propyl-isophthalarnic acid ethyl ester (68 mg, 0.23 mmol), 1 N lithium hydroxide (1.15 mL) and THF (1.15 mL) at room temperature over the weekend. Add water and extract with dichloromethane. Acidify the aqueous with 5 N HCl (240 µL), extract with dichloromethane, dry (magnesium sulfate) and concentrate to give the title compound (61 mg, 100%).

Preparation 104

5-Fluoromethyl-N-methyl-N-propyl-isophthalamic acid

5-Fluoromethyl-N-methyl-N-propyl-isophthalamic acid ethyl ester

Add bis(2-methoxyethyl) aminosulfur trifluoride (220 mg, 1.0 mmol) to a polypropylene tube (5 mL), seal, cool to −78° C., add a solution of 5-hydroxymethyl-N-methyl-N-propyl-isophthalamic acid ethyl ester (250 mg, 0.9 mmol) in dichloromethane (1 mL) in 0.2 mL increments. Stir at −78° C. for 3 h then at room temperature overnight. Pour the reaction into saturated aqueous sodium bicarbonate. Extract with dichloromethane, dry (magnesium sulfate), concentrate and purify (silica gel chromatography, eluting with 50:50 ethyl acetate:hexanes) to give the title compound (73 mg, 29%).

MS (ES): m/z=282 [M+H].

5-Fluoromethyl-N-methyl-N-propyl-isophthalamic acid

Stir a solution of 5-fluoromethyl-N-methyl-N-propyl-isophthalamic acid ethyl ester (73 mg, 0.26 mmol), 1 N lithium hydroxide (1.3 mL, 1.3 mmol) and THF (1.3 mL) at room temperature overnight. Add water (10 mL) and extract with dichloromethane (3×10 mL). Acidify the aqueous with 5 N HCl (260 µL), extract with dichloromethane (3×10 mL), dry (magnesium sulfate) and concentrate to give the title compound (56 mg, 85%).

Preparation 105

N-Methyl-N-propyl-5-vinyl-isophthalamic acid

5-Bromo-isophthalic acid monomethyl ester

Add a solution of NaOH pellets (3.66 g, 91.5 mmol) in methanol (200 mL) to dimethyl-5-bromoisophthalate (25 g) and stir the resulting solution overnight at room temperature. Add water (300 mL) and extract with dichloromethane (3×200 mL). Acidify the aqueous with 5 N HCl (20 mL), filter the precipitate and dry to give a mixture of the title compound and 5-bromo-isophthalic acid in about a 6:4 ratio by LCMS (18.2 g crude).

5-Bromo-N-methyl-N-propyl-isophthalamic acid methyl ester

Add N-methylpropylamine (5.14 g, 70.4 mmol) to a mixture of 5-bromo-isophthalic acid monomethyl ester and 5-bromo-isophthalic acid (18.2 g), 1-hydroxybenzotriazole (9.5 g, 70.4 mmol), and 1-(3-dimethylaminopropyl)-3-ethylcarbodiimide hydrochloride (13.5 g, 70.4 mmol) in dichloromethane (200 mL). Stir the solution for 2 h at room temperature. Add saturated aqueous ammonium chloride (100 mL) and acidify the mixture with 1 N HCl. Filter away the precipitate, extract the filtrate with dichloromethane, wash the organic extracts with 1 N HCl, saturated aqueous sodium bicarbonate, saturated aqueous sodium chloride, dry (magnesium sulfate), concentrate and purify (silica gel chromatography, eluting with 30:70 ethyl acetate:hexanes) to give the title compound as an oil (10.1 g, 46%).

MS (ES): m/z=315 [M+H].

N-Methyl-N-propyl-5-vinyl-isophthalamic acid methyl ester

Dissolve 5-bromo-N-methyl-N-propyl-isophthalamic acid methyl ester (2.7 g, 8.6 mmol) in toluene (16 mL) and place the solution under nitrogen. Add in sequence 2,6-di-tert-butyl-4-methylphenol (a few crystals), tetrakis(triphenylphosphine)palladium (0) (185 mg, 0.16 mmol), and tributylvinyl tin (3 g, 9.5 mmol) and reflux for 4 h. Filter through a filtering agent and concentrate. Add diethyl ether (70 mL) and 20% aqueous potassium fluoride (70 mL) and stir vigorously. Collect the diethyl ether layer and extract with diethyl ether two additional times. Concentrate and purify (silica gel chromatography, eluting with 0:100 to 50:50 ethyl acetate:hexanes) to give the title compound (1.58 g, 70%).

N-Methyl-N-propyl-5-vinyl-isophthalamic acid

Stir a solution of N-methyl-N-propyl-5-vinyl-isophthalamic acid methyl ester (78 mg, 0.3 mmol), 1 N lithium hydroxide (1.5 mL, 1.5 mmol), and THF (1.5 mL) at room temperature overnight. Add water and extract with ethyl acetate. Acidify the aqueous with 5 N HCl, extract with ethyl acetate, dry (magnesium sulfate) and concentrate to give the title compound (52 mg, 70%).

Preparation 106

N-Methyl-5-oxazol-2-yl-N-propyl-isophthalamic acid

N-Methyl-5-oxazol-2-yl-N-propyl-isophthalamic acid methyl ester

Add n-butyllithium (1.6 M in hexanes, 1.25 mL, 2.01 mmol) dropwise to a solution of oxazole (126 mg, 1.83 mmol) in THF (12.6 mL) at −78° C. Stir for 30 min at −78° C. and add a solution of zinc chloride (747 mg, 5.49 mmol) in diethyl ether (5.5 mL) and stir at 0° C. for 1 h. Add a solution of 5-iodo-N-methyl-N-propyl-isophthalamic acid methyl ester (330 mg, 0.91 mmol) in THF (5.1 mL) followed by tetrakis(triphenylphosphine)palladium (0) (105 mg, 0.091 mmol) and heat to reflux for 30 min. Add ethyl acetate (40 mL), wash with water (2×20 mL), dry (magnesium sulfate), concentrate and purify (silica gel chromatography, eluting with 50:50 ethyl acetate:hexane) to give the title compound (225 mg, 82%).

MS (ES): m/z=303 [M+H].

N-Methyl-5-oxazol-2-yl-N-propyl-isophthalamic acid

Stir a solution of N-methyl-5-oxazol-2-yl-N-propyl-isophthalamic acid methyl ester (225 mg, 0.74 mmol) in 1 N lithium hydroxide (3.0 mL, 3.0 mmol) and THF (3.0 mL) at room temperature for 3 h. Add water (40 mL) and extract with ethyl acetate (40 mL). Acidify the aqueous with 5 N HCl, extract with ethyl acetate (2×40 mL), dry (magnesium sulfate) and concentrate to give the title compound (213 mg, 100%).

Preparation 107

N-Methyl-5-(3-methyl-[1,2,4]oxadiazol-5-yl)-N-propyl-isophthalamic acid

N-Methyl-5-(3-methyl-[1,2,4]oxadiazol-5-yl)-N-propyl-isophthalamic acid ethyl ester Stir a solution of 5-(methyl-propyl-carbamoyl)-isophthalic acid monoethyl ester (330 mg, 1.13 mmol), acetamideoxime (117 mg, 1.58 mmol), and 1-(3-dimethylaminopropyl)-3-ethylcarbodiimide hydrochloride (303 mg, 1.58 mmol) in dichloromethane (20 mL) at room temperature overnight. Concentrate and purify (silica gel chromatography, eluting with 2:98 methanol:dichloromethane). Concentrate and add THF (30 mL) and 1 N tetrabutylammonium fluoride in THF (43 µL, 0.043 mmol). Reflux the solution for 30 min and concentrate. Add ethyl acetate, extract with saturated aqueous sodium chloride, dry (magnesium sulfate) concentrate and purify (silica gel chromatography, eluting with 50:50 ethyl acetate:hexanes) to give the title compound (135 mg, 36%).

MS (ES): m/z=332 [M+H].

N-Methyl-5-(3-methyl-[1,2,4]oxadiazol-5-yl)-N-propyl-isophthalamic acid

Stir a solution of N-methyl-5-(3-methyl-[1,2,4]oxadiazol-5-yl)-N-propyl-isophthalamic acid ethyl ester (135 mg, 0.4 mmol), 1 N lithium hydroxide (1.6 mL, 1.6 mmol) and THF (1.6 mL) at room temperature overnight. Add 1 N HCl (20 mL) and extract with ethyl acetate (3×20 mL). Dry (magnesium sulfate) and concentrate to give the title compound.

Preparation 108

N-Methyl-5-oxazol-5-yl-N-propyl-isophthalamic acid

N-Methyl-5-oxazol-5-yl-N-propyl-isophthalamic acid

Heat a solution of 5-formyl-N-methyl-N-propyl-isophthalamic acid ethyl ester (300 mg, 1.08 mmol), tosylmethyl isocyanide (254 mg, 1.3 mmol), and sodium methoxide (193 mg, 3.57 mmol) in methanol (3.1 mL) at 40° C. for 1 h. Add water to the hot solution and extract with dichloromethane and ethyl acetate. Acidify the aqueous with 5 N HCl, extract with dichloromethane, dry (magnesium sulfate), concentrate and purify (silica gel chromatography, eluting with 0:100 to 4:96 methanol:dichloromethane) to give the title compound (203 mg, 65%).

MS (ES): m/z=289 [M+H].

Preparation 109

5-(2,2-Difluorovinyl)-N-methyl-N-propyl-isophthalamic acid

Toluene-4-sulfonic acid 2,2-Difluorovinyl ester

Add n-butyllithium (1.6 M in hexanes, 4.9 mL, 7.8 mmol) dropwise over 5 min to a solution of 2,2,2-trifluoroethyl-p-toluene sulfonate (1.0 g, 3.9 mmol) in THF (20 mL) at −78° C. Stir for 30 min, add acetic acid (225 µL, 3.9 mmol) and stir for 30 min. Warm to room temperature, add ethyl acetate and extract with saturated aqueous ammonium chloride, and saturated aqueous sodium bicarbonate. Dry (magnesium sulfate), concentrate and purify (silica gel chromatography, eluting with 0:100 to 15:85 ethyl acetate:hexanes) to give the title compound as an oil (430 mg, 47%).

5-(2,2-Difluorovinyl)-N-methyl-N-propyl-isophthalamic acid ethyl ester

Add n-butyllithium (1.6 M in hexanes, 4.5 mL, 7.4 mmol) dropwise to a mixture of zirconocene dichloride (1.05 g, 3.6 mmol) in dry THF (15 mL) at −78° C. and stir for 1 h. Add a solution of toluene-4-sulfonic acid 2,2-difluorovinyl ester (420 mg, 1.8 mmol) in THF (3.6 mL) dropwise. Stir at −78° C. for 5 min and at room temperature for 3 h. Add triphenyl phosphine (79 mg, 0.3 mmol) and tris(dibenzylidineacetone)dipalladium(0) (34 mg, 0.036 mmol), stir for 10 min, add 5-iodo-N-methyl-N-propyl-isophthalamic acid methyl ester (722 mg, 2.0 mmol) and zinc iodide (1.35 g, 4.3 mmol). Reflux the reaction for 1 h and stir at room temperature overnight. Add pH=7 phosphate buffer (400 mL) and ethyl acetate (250 mL). Separate the layers and wash with saturated aqueous ammonium chloride (2×100 mL), saturated aqueous sodium bicarbonate (2×100 mL), dry (magnesium sulfate), concentrate and purify (silica gel chromatography, eluting with 25:75 ethyl acetate:hexanes) to give the title compound (187 mg, 35%).

MS (ES): in/z=298 [M+H].

5-(2,2-Difluorovinyl)-N-methyl-N-propyl-isophthalamic acid

Stir a solution of 5-(2,2-difluorovinyl)-N-methyl-N-propyl-isophthalamic acid ethyl ester (187 mg, 0.63 mmol), 1 N lithium hydroxide (2.5 mL, 2.5 mmol) and THF (2.5 mL) at room temperature overnight. Partition the reaction between ethyl acetate and water. Acidify the aqueous with 5 N HCl and extract with ethyl acetate. Dry (magnesium sulfate), concentrate and purify (silica gel chromatography, eluting with 2:98 to 6:94 methanol:dichloromethane with 1% acetic acid) to give the title compound (78 mg, 44%).

MS (ES): m/z=284 [M+H].

Preparation 110

N-Methyl-5-(2-methylpyrrolidine-1-carbonyl)-N-propyl-isophthalamic acid

N-Methyl-5-(2-methylpyrrolidine-1-carbonyl)-N-propyl-isophthalamic acid ethyl ester Add 2-methyl pyrrolidine (204 mg, 2.4 mmol) to a solution of 5-(methyl-propylcarbamoyl)-isophthalic acid monoethyl ester (640 mg, 2.18 mmol) in dichloromethane (8 mL) followed by 1-hydroxybenzotriazole (20 mg, 0.15 mmol) and diisopropyl carbodiimide (375 μL, 2.4 mmol). Stir the solution at room temperature over the weekend. Add ethyl acetate (25 mL) and wash with saturated aqueous ammonium chloride (2×10 mL), saturated aqueous sodium bicarbonate (10 mL), saturated aqueous sodium chloride (10 mL), dry (sodium sulfate), concentrate and purify (silica gel chromatography, eluting with 50:50 ethyl acetate:hexanes) to give the title compound as an oil (218 mg, 28%).

MS (ES): m/z=361 [M+H].

N-Methyl-5-(2-methylpyrrolidine-1-carbonyl)-N-propyl-isophthalamic acid

Stir a solution of N-methyl-5-(2-methylpyrrolidine-1-carbonyl)-N-propyl-isophthalamic acid ethyl ester (218 mg, 0.6 mmol), 1 N lithium hydroxide (2.4 mL, 2.4 mmol) and THF (2.4 mL) at room temperature overnight. Add 50 mL water and extract with dichloromethane (3×10 mL). Acidify the aqueous with 1 N HCl (3 mL) and extract with dichloromethane (3×10 mL). Dry (sodium sulfate) and concentrate to give the title compound (216 mg, 100%).

MS (ES): m/z=333 [M+H].

Preparation 111

5-(3,3-Difluoropyrrolidine-1-carbonyl)-N-methyl-N-propyl-isophthalamic acid

3,3-Difluoropyrrolidine-1-carboxylic acid tert-butyl ester

Add ethanol (270 μL) to a solution of 3-oxopyrrolidine-1-carboxylic acid tert-butyl ester (3.36 g, 18.2 mmol), and bis(2-methoxyethyl) aminosulfur trifluoride (6.85 g, 31 mmol) in dichloromethane in a polypropylene tube. Stir the exothermic reaction at room temperature overnight. Add dichloromethane (100 mL) and wash with saturated aqueous sodium bicarbonate (2×20 mL), saturated aqueous sodium chloride (20 mL), dry (sodium sulfate), concentrate and purify (silica gel chromatography, eluting with 5:95 acetone:hexanes to give the title compound as an oil (2.18 g, 58%).

MS (ES): m/z=347 [M+H].

3,3-Difluoropyrrolidine hydrochloride

Stir a solution of 3,3-difluoropyrrolidine-1-carboxylic acid tert-butyl ester (2.18 g, 10.5 mmol) in hydrogen chloride (4 N in 1,4-dioxane, 65 mL) at room temperature. Concentrate to give the title compound (1.5 g, 97%).

5-(3,3-Difluoropyrrolidine-1-carbonyl)-N-methyl-N-propyl-isophthalamic acid ethyl ester Dissolve 5-(methyl-propylcarbamoyl)-isophthalic acid monoethyl ester (667 mg, 2.3 mmol) in a 0.1 N 1-hydroxybenzotriazole solution of 1:1:5 tert-butanol:acetonitrile:dichloromethane (23 mL, 2.3 mmol). Stir the solution at room temperature for 5 min, add 3,3-difluoropyrrolidine hydrochloride (331 mg, 2.3 mmol) and triethylamine (640 μL, 4.6 mmol). Stir the reaction at room temperature for 2 h, add ethyl acetate (100 mL) and wash with saturated aqueous ammonium chloride (2×30 mL), saturated aqueous sodium chloride (30 mL), dry (sodium sulfate), concentrate and purify (silica gel chromatography, eluting with 50:50 ethyl acetate:hexanes) to give the title compound (270 mg, 31%).

MS (ES): m/z=283 [M+H].

5-(3,3-Difluoropyrrolidine-1-carbonyl)-N-methyl-N-propyl-isophthalamic acid

Stir a solution of 5-(3,3-difluoropyrrolidine-1-carbonyl)-N-methyl-N-propyl-isophthalamic acid ethyl ester (270 mg, 0.71 mmol), 1 N lithium hydroxide (1.1 mL, 1.1 mmol) and THF (2.0 mL) at room temperature for 4 h. Add 10 mL water, acidify with 1 N HCl (2 mL), extract with dichloromethane (3×10 mL), dry (sodium sulfate) and concentrate to give the title compound (262 mg, 100%).

Preparation 112

5-Chloro-N-methyl-N-propyl-isophthalamic acid

5-Chloro-N-methyl-N-propyl-isophthalamic acid

Dissolve commercially available 5-chloroisophthalic acid dimethyl ester (1.0 g, 4.37 mmol) in acetone (10 mL) and add a solution of NaOH (192 mg, 4.81 mmol) in methanol (2 mL). Stir 3 h and concentrate. Partition the residue between diethyl ether and water. Acidify the water layer to about pH=1 and collect the precipitate, 5-chloro-isophthalic acid monomethyl ester (675 mg, 72%). Dissolve 5-chloro-isophthalic acid monomethyl ester (459 mg, 2.13 mmol) in DMF (20 mL), add 1-(3-dimethylamino-propyl)-3-ethyl-carbodiimide hydrochloride (513 mg, 2.67 mmol) and 1-hydroxybenzotriazole (360 mg, 2.67 mmol). Stir at room temperature 1 h and add methyl propylamine (584 mg, 8.0 mmol). Stir at room temperature 3 h, dilute with ethyl acetate, wash with 10% aqueous potassium carbonate, 0.1 N citric acid, 1 N lithium chloride and saturated aqueous sodium chloride and concentrate. Dissolve the residue in THF (30 mL) and add 1 N lithium hydroxide (10 mL, 10 mmol). Stir at room temperature 3 h and acidify to about pH=1 by addition of 1 N HCl. Extract with diethyl ether, dry (magnesium sulfate) and concentrate to give the title compound.
MS (ES): m/z=256.1 [M+H].

Preparation 113

N,N-Dipropyl-isophthalamic acid

Dissolve isophthalic acid monomethyl ester (2.25 g, 12.5 mmol), 1-(3-dimethylamino-propyl)-3-ethyl-carbodiimide hydrochloride (2.88 g, 15 mmol), 1-hydroxybenzotriazole (2.02 g, 15 mmol) and triethylamine (3.03 g, 30 mmol) in THF (50 mL) and DMF (20 mL). Stir at room temperature 15 min and add dipropylamine (1.52 g, 15 mmol). Stir at room temperature 16 h and dilute with ethyl acetate. Wash with 10% aqueous potassium carbonate, 0.1 N citric acid, 1 N lithium chloride and saturated aqueous sodium chloride and concentrate. Dissolve the residue in THF (60 mL), methanol (18 mL) and water (9 mL). Add lithium hydroxide (2.1 g, 50 mmol), stir at room temperature 16 h and concentrate. Partition the residue between diethyl ether and 1 N HCl. Dry (magnesium sulfate) and concentrate to give the title compound as a solid.
MS (ES): m/z 250.2 [M+H].

Preparation 114

N-Methyl-5-propoxy-N-propyl-isophthalamic acid

5-Propoxy-isophthalic acid monomethyl ester

Heat commercially available 5-hydroxy-isophthalic acid dimethyl ester (1.0 g, 4.8 mmol), potassium carbonate (5.25 g, 38 mmol) and iodopropane (1.36 g, 8.0 mmol) in DMF (20 mL) at 70° C. for 8 h. Cool to room temperature, partition between ethyl acetate and 10% aqueous potassium carbonate. Wash the ethyl acetate layer with 1 N lithium chloride, saturated aqueous sodium chloride, dry (magnesium sulfate) and concentrate. Dissolve the residue in acetone (10 mL) and add a solution of NaOH (192 mg, 4.80 mmol) in methanol (2 mL). Stir at room temperature 16 h and concentrate. Partition between diethyl ether and 0.1 N citric acid, dry (magnesium sulfate) and concentrate to give the title compound.
MS (ES): m/z=239.0 [M+H].

N-Methyl-5-propoxy-N-propyl-isophthalamic acid

Mix 5-propoxy-isophthalic acid monomethyl ester (500 mg, 2.10 mmol), 1-(3-dimethylamino-propyl)-3-ethylcarbodiimide hydrochloride (403 mg, 2.10 mmol) and 1-hydroxybenzotriazole (283 mg, 2.10 mmol) in DMF (15 mL) at room temperature 1 h. Add methyl-propylamine (438 mg, 6.0 mmol) and stir at room temperature 16 h. Dilute with ethyl acetate, wash with 10% aqueous potassium carbonate, 0.1 N citric acid, 1 N lithium chloride and saturated aqueous sodium chloride. Dry (magnesium sulfate), concentrate and purify (silica gel chromatography, eluting with 20:80 to 30:70 ethyl acetate:hexanes) to give the carboxamide. Dissolve the residue (265 mg, 0.90 mmol) in THF (10 mL) and add 1 N lithium hydroxide (5 mL, 5 mmol) and stir at room temperature 16 h. Acidify the solution to about pH=1 with 1 N HCl, extract with ethyl acetate, dry (magnesium sulfate) and concentrate to give the title compound as a solid.
MS (ES): m/z=280.0 [M+H].

Preparation 115

5-Methanesulfonyl-N-methyl-N-propyl-isophthalamic acid

5-Methanesulfonyl-isophthalic acid dimethyl ester

Dissolve sodium sulfite (1.7 g, 13.51 mmol) and sodium bicarbonate (1.2 g, 14.19 mmol) in water (10 mL). Add 5-chlorosulfonyl-isophthalic acid dimethyl ester (2.0 g, 6.76 mmol) and ethanol (2 mL). Heat to 50° C. for 2 h, concentrate and dry the solid. Add DMF (40 mL) and iodomethane (4.56 g, 32 mmol) and stir at room temperature for 3 h. Dilute with ethyl acetate, wash with 10% aqueous potassium carbonate, 1 N lithium chloride and saturated aqueous sodium chloride. Dry (magnesium sulfate) and concentrate to give the title compound as a solid.
$^1$H NMR (CDCl3) δ 8.93 (s, 1H), 8.76 (s, 2H), 4.00 (s, 6H), 3.13 (s, 3H).

5-Methanesulfonyl-N-methyl-N-propyl-isophthalamic acid

Dissolve 5-methanesulfonyl-isophthalic acid dimethyl ester (1.45 g, 5.33 mmol) in acetone (16 mL) and add a solution of NaOH (210 mg, 5.33 mmol) in methanol (2.5 mL). Stir at room temperature 1 h and concentrate. Partition between diethyl ether and water. Acidify the water layer to about pH=1 with 1 N HCl. Collect and dry the white precipitate. Dissolve the precipitate (500 mg, 1.95 mmol) in DMF (20 mL), add 1-(3-dimethylamino-propyl)-3-ethyl-carbodiimide hydrochloride (374 mg, 1.95 mmol) and 1-hydroxybenzotriazole (263 mg, 1.95 mmol) and stir at room temperature 40 min. Add methyl-propylamine (568 mg, 7.78 mmol) and stir at room temperature 14 h. Dilute with ethyl acetate, wash with 10% aqueous potassium carbonate, 0.1 N citric acid, 1 N lithium chloride and saturated aqueous sodium chloride. Dry (magnesium sulfate), concentrate and purify (silica gel chromatography, eluting with 50:50 to 0:100 ethyl acetate:hexanes) to give the amide ester intermediate (340 mg). Dissolve in THF (10 mL) and add 1 N lithium hydroxide (5 mL, 5 mmol). Stir at room temperature 3 h and pour into 1

N HCl (20 mL). Extract with ethyl acetate, wash with saturated aqueous sodium chloride, dry (magnesium sulfate), filter and concentrate to give the title compound as a solid.

MS (ES): m/z=300.1 [M+H].

Preparation 116

5-Dimethylsulfamoyl-isophthalic acid monomethyl ester

Dissolve commercially available 5-chlorosulfonyl-isophthalic acid dimethyl ester (422 mg, 1.43 mmol) in THF (10 mL) and add dimethylamine (2.0 M in THF, 2.5 mL, 5 mmol). Stir at room temperature 3 h, dilute with ethyl acetate, wash with 10% aqueous potassium carbonate, 0.1 N citric acid and saturated aqueous sodium chloride. Dry (magnesium sulfate), filter and concentrate. Dissolve the residue in acetone (10 mL) and methanol (5 mL). Add a solution of NaOH (60 mg, 1.43 mmol) in methanol (0.7 mL). Stir at room temperature 16 h and acidify with 1 N HCl to about pH=1. Partition between ethyl acetate and water, dry (magnesium sulfate) and concentrate to give the title compound.

MS (ES): m/z=288.0 [M+H].

Preparation 117

N-methyl-5-(2-methylpropenyl)-N-propyl-isophthalamic acid 5-(2-Methylprgopenyl)-isophthalic acid diethyl ester Dissolve commercially available 5-hydroxymethyl-isophthalic acid diethyl ester (2.0 g, 7.91 mmol) in dichloromethane (30 mL) and add this solution to Dess-Martin periodinane (3.69 g, 8.71 mmol) in dichloromethane (30 mL). Stir 30 min at room temperature and pour into saturated aqueous sodium bicarbonate (100 mL) containing sodium thiosulfate (25 g). Extract with diethyl ether (200 mL), dry (magnesium sulfate), concentrate and purify (silica gel plug, washing with 20:80 ethyl acetate:hexanes) to give the aldehyde. Suspend isopropyltriphenylphosphonium iodide (4.76 g, 11 mmol) in THF (40 mL). Add potassium tert-butoxide (1.23 g, 11 mmol), then a solution of the aldehyde prepared above in THF (40 mL). Stir at room temperature for 30 min, dilute with water and ethyl acetate. Wash the organic layer with saturated aqueous sodium chloride, dry (magnesium sulfate), concentrate and purify (silica gel chromatography, eluting with 0:100 to 5:95 ethyl acetate:hexanes) to give the title compound as an oil (535 mg, 25%).

$^1$H NMR (CDCl$_3$) δ 8.49 (s, 1H), 8.07 (s, 2H), 6.31 (s, 1H), 4.40 (q, J=6.8 Hz, 4H), 1.93 (s, 3H), 1.87 (s, 3H), 1.41 (t, J=6.8 Hz, 6H).

N-Methyl-5-(2-methylpropenyl)-N-propyl-isophthalamic acid

Dissolve 5-(2-methylpropenyl)-isophthalic acid diethyl ester (535 mg, 1.94 mmol) in acetone (10 mL) and add a solution of NaOH (77 mg, 1.94 mmol) in methanol (2 mL). Stir at room temperature 2 days and concentrate. Dissolve in water and wash with diethyl ether. Acidify the water layer to about pH=1 with 1 N HCl and extract with dichloromethane. Dry the dichloromethane layer over magnesium sulfate, filter and concentrate. Dissolve the residue in DMF (10 mL) and add 1-(3-dimnethylamino-propyl)-3-ethyl-carbodiimide hydrochloride (409 mg, 2.13 mmol) and 1-hydroxybenzotriazole (288 mg, 2.13 mmol). After 30 min, add methyl-propyl-amine (283 mg, 3.87 mmol) and triethylamine (665 mg, 6.58 mmol) in DMF (2 mL). Stir at room temperature 1 h and dilute with ethyl acetate. Wash with 10% aqueous potassium carbonate, 0.1 N citric acid, 1 N lithium chloride and saturated aqueous sodium chloride and concentrate. Dissolve the residue in THF (20 mL) and add 1 N lithium hydroxide (10 mL, 10 mmol). Stir at room temperature for 4 h and acidify to about pH=1 with 1 N HCl. Extract with dichloromethane, dry (magnesium sulfate), filter and concentrate to give the title compound as a solid (220 mg, 41%).

MS (ES): m/z 276.1=[M+H].

Preparation 118

6-Fluoro-5-methanesulfonyl-N-methyl-N-propyl-isophthalamic acid

3-Bromo-5-chlorosulfonyl-4-fluorobenzoic acid

Heat 3-bromo-4-fluorobenzoic acid (6.25 g, 26.2 mmol) in chlorosulfonic acid (15 mL) at 125° C. for 120 h. Cool to room temperature and add dropwise to about 125 mL ice water. Collect the filtered solid as the title compound.

MS (ES): m/z=317.1 [+H].

3-Bromo-4-fluoro-5-methanesulfonylbenzoic acid

To sodium thiosulfite (2.6 g, 20.7 mmol) and sodium bicarbonate (1.74 g, 20.7 mmol) in water (20 mL) at 75° C. add 3-bromo-5-chlorosulfonyl-4-fluorobenzoic acid (6.25 g, 19.7 mmol) in portions over 5 min. After 1 h, cool to room temperature and add chloroacetic acid (5.29 g, 56 mmol) and NaOH (1.18 g, 29.5 mmol) and reflux 16 h. Cool to room temperature and collect the title compound as a solid MS (ES): m/z=297.1 [M+H].

3-Bromo-4-fluoro-5-methanesulfonyl-N-methyl-N-propyl-benzamide

Mix 3-bromo-4-fluoro-5-methanesulfonylbenzoic acid (1.6 g, 5.04 mmol), 1-(3-dimethylamino-propyl)-3-ethyl-carbodiimide hydrochloride (968 mg, 5.04 mmol) and 1-hydroxybenzotriazole (680 mg, 5.04 mmol) in DMF (20 mL) at room temperature for 20 min. Add methyl-propylamine (368 mg, 5.04 mmol) and triethylamine (520 mg, 15.1 mmol) and stir at room temperature for 1 h. Dilute with ethyl acetate, wash with 10% aqueous potassium carbonate, 0.1 N citric acid, 1 N lithium chloride and saturated aqueous sodium chloride, concentrate and purify (silica gel chromatography, eluting with 10:90 to 50:50 ethyl acetate:hexanes) to give the title compound as an oil.

MS (ES): m/z=352.0, 354.0 [+H].

6-Fluoro-5-methanesulfonyl-N-methyl-N-propyl-isophthalamic acid

Mix 3-bromo-4-fluoro-5-methanesulfonyl-N-methyl-N-propyl-benzamide (1.36 g, 3.86 mmol), palladium acetate (337 mg, 1.5 mmol) and 1,4-bis(diphenylphqsphino)-butane (1.35 g, 3.17 mmol) in DMSO (60 mL), tert-butanol (40 mL), triethylamine (3.88 mL) and water (0.22 mL) under an atmosphere of carbon monoxide (100 psi) at 90° C. for 18 h. Cool to room temperature and filter. Pour the mixture into water and wash thoroughly with ethyl acetate. Extract the organic layer with 10% aqueous potassium carbonate. Acidify the aqueous layer and extract with ethyl acetate. Dry (magnesium sulfate) and concentrate to give the title compound.

MS (ES): m/z=318.0 [M+H].

Preparation 119

5-(Methanesulfonyl-methylamino)-N-methyl-N-propyl-isophthalamic acid

5-Amino-N-methyl-N-propyl-isophthalamic acid methyl ester

Mix 5-nitro-isophthalic acid monomethylester (3.0 g, 13.32 mmol), 1-(3-dimethylaminopropyl)-3-ethylcarbodiimide hydrochloride (3.20 g, 16.65 mmol), and 1-hydroxybenzotriazole (2.25 g, 16.65 mmol) in dichloromethane (100 mL) at room temperature for 20 min. Add propylmethylamine (1.46 g, 16.65 mmol) and triethylamine (3.36 g, 33.3 mmol). Stir at room temperature for 1 h, dilute with ethyl acetate, wash with 10% aqueous potassium carbonate, 1 N citric acid, saturated aqueous sodium chloride and concentrate. Dissolve in ethanol (100 mL), add a slurry of 10% Pd/C (300 mg) in ethanol (10 mL) and place under a hydrogen atmosphere using a balloon and stir overnight. Flush with nitrogen, filter and concentrate to give the title-compound as an oil.

MS (ES): m/z=251.1 [M+H].

5-Methanesulfonylamino-N-methyl-N-propyl-isophthalamic acid methyl ester

Dissolve 5-amino-N-methyl-N-propyl-isophthalamic acid methyl ester (1.64 g, 6.55 mmol) in dichloromethane (20 mL) and add pyridine (620 mg, 6.88 mmol) and methanesulfonyl chloride (788 mg, 6.88 mmol). Stir at room temperature for 72 h, dilute with dichloromethane, wash with 0.1 N citric acid and saturated aqueous sodium chloride. Dry (magnesium sulfate) and concentrate to give the title compound as an oil.

MS (ES): m/z=329.1 [M+H].

5-(Methanesulfonyl-methylamino)-N-methyl-N-propyl-isophthalamic acid methyl ester Mix 5-methanesulfonylamino-N-methyl-N-propyl-isophthalamic acid methyl ester (2.09 g, 6.36 mmol), iodomethane (1.35 g, 9.55 mmol), potassium carbonate (1.38 g, 10 mmol), and tetrabutylammonium bromide (206 mg, 0.64 mmol) in DMF (10 mL) at room temperature for 30 min. Dilute with ethyl acetate and wash with 10% aqueous potassium carbonate, 1 N lithium chloride and saturated aqueous sodium chloride. Dry (magnesium sulfate), concentrate and purify (silica gel chromatography, eluting with 0:100 to 40:60 ethyl acetate:dichloromethane) to give the title compound as an oil.

MS (ES): m/z=343.1 [M+H].

5-(Methanesulfonyl-methylamino)-N-methyl-N-propyl-isophthalamic acid

Dissolve 5-(methanesulfonyl-methylamino)-N-methyl-N-propyl-isophthalamic acid methyl ester (1.09 g, 3.18 mmol) in THF (80 mL) and add 1 N NaOH (16 mL, 16 mmol). Stir at room temperature for 16 h and add 5 N HCl (5 mL). Dilute with ethyl acetate, wash with saturated aqueous sodium chloride, dry (magnesium sulfate) and concentrate to give the title compound.

MS (ES): m/z=329.1 [M+H].

Preparation 120

5-Acetylamino-N-methyl-N-propyl-isophthalamic acid methyl ester

5-Acetylamino-N-methyl-N-propyl-isophthalamic acid methyl ester

Dissolve 5-amino-N-methyl-N-propyl-isophthalamic acid methyl ester (1.64 g, 6.55 mmol) in dichloromethane (20 mL) and add triethylamine (0.993 g, 9.83 mmol), then acetyl chloride (772 mg, 9.83 mmol). Stir at room temperature for 1 h, add N,N-dimethylamino propylamine (0.5 mL), stir 10 min, dilute with dichloromethane, wash with 1 N HCl and saturated aqueous sodium chloride. Dry (magnesium sulfate), filter and concentrate to give the title compound as a solid.

MS (ES): m/z=293.1 [M+H].

5-Acetylamino-N-methyl-N-propyl-isophthalamic acid methyl ester

Dissolve 5-acetylamino-N-methyl-N-propyl-isophthalamic acid methyl ester (1.35 g, 4.62 mmol) in THF (20 mL) and add sodium hydride (0.222 g, 5.54 mmol, 60% dispersion in mineral oil) Add iodomethane (977 mg, 6.93 mmol) and stir at room temperature overnight. Partition between ethyl acetate and 10% aqueous potassium carbonate, wash with saturated aqueous sodium chloride, dry (magnesium sulfate), concentrate and purify (silica gel chromatography, eluting with 0:100 to 5:95 methanol:dichloromethane) to give the N-methyl amide. Dissolve the residue in THF (60 mL) and add 1 N lithium hydroxide (20 mL). Stir at room temperature over the weekend. Acidify to about pH=1 with 1 N HCl and extract with diethyl ether. Dry (magnesium sulfate) and concentrate. Dissolve the residue in dichloromethane (20 mL) and add acetyl chloride (1 mL). Stir 1 h and wash with 0.1 N HCl and saturated aqueous sodium chloride. Dry (magnesium sulfate), and concentrate to give the title compound as a solid.

MS (ES): m/z=293.1 [M+H].

Preparation 121

5-Hydroxymethyl-N-methyl-N-propyl-isophthalamic acid

5-Hydroxymethyl-isophthalic acid monoethyl ester

Add commercially available 5-hydroxymethyl-isophthalic acid diethyl ester (5 g, 19.8 mmol) and NaOH (0.79 g, 19.8 mmol) to ethanol (100 mL). Stir for 4 h at room temperature. Concentrate and pour the residue into water (100 mL) and diethyl ether (100 mL). Separate the aqueous layer and wash it with diethyl ether (40 mL). Acidify the aqueous layer with 5 N HCl to about pH=1. Extract the acidic solution with ethyl acetate (3×40 mL). Wash the combined organic layers with Water, saturated aqueous sodium chloride, dry (sodium sulfate) and concentrate to give the title compound as a solid (3.3 g, 74%).

MS (ES): m/z=225 [M+H].

5-Hydroxymethyl-N-methyl-N-propyl-isophthalamic acid ethyl ester

Mix 5-hydroxymethyl-isophthalic acid monoethyl ester (3.3 g, 14.7 mmol), N-methyl propylamine (1.5 mL, 14.7 mmol), 1-[3-(dimethylamino)propyl]-3-ethylcarbodiimide hydrochloride (2.8 g, 14.7 mmol), and 1-hydroxtbenzotriazole hydrate (2.0 g, 14.7 mmol) in dichloromethane (40 mL) and DMF (4 mL). Stir at room temperature for 3 h. Concentrate and redissolve in ethyl acetate (150 mL). Wash with aqueous sodium bicarbonate solution, aqueous ammonium chloride solution, water, saturated aqueous sodium chloride, dry (sodium sulfate), concentrate and purify (silica gel chromatography, eluting with ethyl acetate and hexanes) to give the title compound (2.5 g, 61%).

MS (ES): m/z=280 [M+H].

5-Hydroxymethyl-N-methyl-N-propyl-isophthalamic acid

Mix 5-hydroxymethyl-N-methyl-N-propyl-isophthalamic acid ethyl ester (1.0 g, 3.6 mmol), 1 N NaOH (25 mL) in THF (5 mL). Stir at room temperature overnight. Wash with diethyl ether (2×20 mL). Acidify the aqueous layer with 5 N HCl to about pH=2. Extract with ethyl acetate (2×20 mL), concentrate and purify (silica gel chromatography eluting with 1% acetic acid in ethyl acetate and hexanes) to give the title compound (0.80 g, 89%).

MS (ES): m/z=252 [M+H].

Preparation 122

5-Isopropoxymethyl-N-methyl-N-propyl-isophthalamic acid

5-Isopropoxymethyl-N-methyl-N-propyl-isophthalamic acid ethyl ester

Mix dichloromethane (1.8 mL), pyridine (56 μL, 0.7 mmol), and trifluomethanesulfonic anhydride (97 μL, 0.58 mmol) to a flask at −35 to −45° C. Add premixed 5-hydroxymethyl-N-methyl-N-propyl-isophthalamic acid ethyl ester (65 mg, 0.23 mmol) in dichloromethane (4 mL) dropwise at −40° C. Stir for 5 min and quench with isopropyl alcohol (2 mL). Dilute the reaction mixture with dichloromethane (10 mL), wash with water (2×10 mL), and concentrate to give the title compound and used directly in the next step without further purification.

MS (ES): m/z=322 [M+H].

5-Isopropoxymethyl-N-methyl-N-propyl-isophthalamic acid

Dissolve the crude 5-isopropoxymethyl-N-methyl-N-propyl-isophthalamic acid ethyl ester (0.23 mmol) in 5 N NaOH (1 mL) and methanol (2 mL). Stir at room temperature for 15 min, concentrate methanol and redissolve the residue in water (20 mL). Wash with diethyl ether (2×10 mL), acidify the aqueous layer with 5 N HCl to about pH=1. Extract with dichloromethane to give the title compound.

MS (ES): m/z=294 [M+H].

Preparation 123

5-Isopropoxy-N-methyl-N-propyl-isophthalamic acid

5-Isopropoxy-isophthalic acid dimethyl ester

Stir 5-hydroxy-isophthalic acid dimethyl ester (4 g, 19.0 mmol), 2-iodopropane (10.2 mL, 101 mmol), and potassium carbonate (4 g, 28.9 mmol) in acetone (20 mL) at 60° C. overnight. Cool to room temperature and pour into ethyl acetate (100 mL) and 5% aqueous ammonium chloride solution (100 mL). Separate the organic layer and wash it with water, saturated aqueous sodium chloride, dry (sodium sulfate), and concentrate to give the title compound and which is used directly in the next step without further purification.

$^1$HNMR (CDCl$_3$) δ 8.24 (d, J=0.8 Hz, 1H), 7.72 (s, 2H), 4.68-4.62 (m, 1H), 3.93 (s, 6H), 1.35 (d, J=6 Hz, 6H).

5-Isopropoxy-isophthalic acid monomethyl ester

Stir 5-isopropoxy-isophthalic acid dimethyl ester (3.7 g, 14.7 mmol) and NaOH (0.56 g, 14 mmol) in methanol (100 mL) and water (2 mL) overnight at room temperature. Concentrate methanol and redissolve the residue in diethyl ether (100 mL) and water (100 mL). Separate the layers and wash with diethyl ether. Concentrate the diethyl ether layer and recover 5-isopropoxy-isophthalic acid dimethyl ester (0.45 g). Acidify the aqueous layer with 5 N HCl to about pH=2, extract with ethyl acetate (3×50 mL). Wash the combined organic layers with saturated aqueous sodium chloride, dry (sodium sulfate) and concentrate to give the title compound (3.0 g, 86%).

MS (ES): m/z=237 [M+H].

5-Isopropoxy-N-methyl-N-propyl-isophthalamic acid methyl ester

Mix 5-isopropoxy-isophthalic acid monomethyl ester (3 g, 12.7 mmol), methyl propyl amine (1.3 mL, 12.7 mmol), 1-[3-(dimethylamino)propyl]-3-ethylcarbodiimide hydrochloride (2.4 g, 12.7 mmol), and 1-hydroxybenzotriazole hydrate (1.7 g, 12.7 mmol) in dichloromethane (50 mL) and stir overnight at room temperature. Dilute with dichloromethane (50 mL), wash with water, 5% aqueous ammonium chloride solution, 5% aqueous sodium bicarbonate solution, dry (sodium sulfate) and concentrate to give the title product which is used directly without further purification.

MS (ES): m/z=294 [M+H].

5-Isopropoxy-N-methyl-N-propyl-isophthalamic acid

Dissolve crude 5-isopropoxy-N-methyl-N-propyl-isophthalamic acid ethyl ester (12.7 mmol) in 1 N lithium hydroxide (50 mL) and THF (50 mL). Stir at room temperature for 4 h. Dilute with water (100 mL). Wash with diethyl ether (3×30 mL), and acidify the aqueous layer with 5 N HCl to about pH=1. Extract with ethyl acetate to give the title compound (3.1 g, 87% over 2 steps).

MS (ES): m/z=280 [M+H].

The compounds of Preparations 124-125 may be prepared essentially as described in Preparation 123 using pyrrolidine or piperidine as the amine.

| Prep | Compound | MS (ES) [M + H] |
|---|---|---|
| 124 | N-Methyl-N-propyl-5-(pyrrolidine-1-carbonyl)-isophthalamic acid | 319 |
| 125 | N-Methyl-5-(piperidine-1-carbonyl)-N-propyl-isophthalamic acid | 333 |

Preparation 126

5-Methoxymethyl-N-methyl-N-propyl-isophthalamic acid

5-Methoxymethyl-N-methyl-N-propyl-isophthalamic acid ethyl ester

Stir 5-hydroxymethyl-N-methyl-N-propyl-isophthalamic acid ethyl ester (1.1 g, 3.9 mmol) in THF (20 mL). Add sodium hydride (0.78 g, 60% in mineral oil) and iodomethane (729 μL, 11.7 mmol). Stir at room temperature for 3 h. Concentrate to give the title product which is used directly in the next step without further purification.
MS (ES): m/z=294 [M+H].

5-Methoxymethyl-N-methyl-N-propyl-isophthalamic acid

Dissolve the crude 5-methoxymethyl-N-methyl-N-propyl-isophthalamic acid ethyl ester (3.9 mmol) in 5 N NaOH (2 mL) and water (10 mL). Stir at room temperature for 30 min. Dilute with water (20 mL). Wash with dichloromethane, and acidify the aqueous layer with 5 N HCl to about pH=2. Extract with dichloromethane and concentrate to give the title compound (0.96 g, 93%). MS (ES): m/z=266 [M+H].

Preparation 127

5-[1,3]Dioxolan-2-yl-N-methyl-N-propyl-isophthalamic acid

5-Formyl-N-methyl-N-propyl-isophthalamic acid ethyl ester

Mix 5-hydroxymethyl-N-methyl-N-propyl-isophthalamic acid ethyl ester (2.8 g, 10 mmol) and Dess-Martin periodinane (5.1 g, 12 mmol) in dichloromethane (50 mL) in an ice-bath. Stir the mixture overnight at room temperature. Dilute with dichloromethane (50 mL) and quench it with premixed sodium thiosulfate (1.5 g) in 5% aqueous sodium bicarbonate solution (50 mL). Filter the slurry through a filtering agent and separate the organic layer. Dry (sodium sulfate), concentrate and purify (silica gel chromatography, eluting with 50:50 ethyl acetate:hexanes) to give the title compound (2.2 g, 79%).
MS (ES): m/z=278 [M+H].

5-[1,3]Dioxolan-2-yl-N-methyl-N-propyl-isophthalamic acid

Mix 5-formyl-N-methyl-N-propyl-isophthalamic acid ethyl ester (580 mg, 2.1 mmol), ethane-1,2-diol (0.35 mL, 6.3 mmol), and boron trifluoride diethyl etherate (0.2 mL, 1.6 mmol) in THF (5 mL) and stir for 1.5 h. Add additional ethane-1,2-diol (0.35 mL, 6.3 mmol) and stir for 20 min. Add 1 N NaOH (10 mL) and stir for 1 h. Add additional 5 N NaOH (1 mL) and stir for 30 min. Dilute the reaction mixture with water (10 mL) and wash with diethyl ether (2×10 mL). Acidify the aqueous layer with 0.5 N HCl to about pH=5. Extract with dichloromethane (3×20 mL), dry (sodium sulfate) and concentrate to give the title compound as a crude residue that is used in the next step without further purification.
MS (ES): m/z=294 [M+H].

The compounds of Preparations 128-131 may be prepared essentially as described in Preparation 127 using the appropriate diols or thiols.

| Prep | Compound | MS (ES) [M + H] |
|---|---|---|
| 128 | 5-[1,3]Dioxan-2-yl-N-methyl-N-propyl-isophthalamic acid | |
| 129 | 5-[1,3]Dithiolan-2-yl-N-methyl-N-propyl-isophthalamic acid | |
| 130 | 5-[1,3]Dithian-2-yl-N-methyl-N-propyl-isophthalamic acid | |
| 131 | N-Methyl-5-[1,3]oxathiolan-2-yl-N-propyl-isophthalamic acid | 310 |

Preparation 132

5-Cyclopropanecarbonyl-N-methyl-N-propyl-isophthalamic acid

5-(Cyclopropyl-hydroxymethyl)-N-methyl-N-propyl-isophthalamic acid ethyl ester Add cyclopropyl magnesium bromide (0.8 M in THF, 1.3 mL, 1.02 mmol) dropwise to a solution of 5-formyl-N-methyl-N-propyl-isophthalamic acid ethyl ester (283 mg, 1.02 mmol) in THF (5 mL) at −10° C. After stirring at 0° C. for 1.5 h, quench the mixture with 5% aqueous ammonium chloride solution while maintaining the temperature below 5° C. Extract with ethyl acetate (3×30 mL), dry (sodium sulfate) concentrate and purify (silica gel chromatography, eluting with ethyl acetate and hexanes) to give the title compound (122 mg, 38%).
MS (ES): m/z=320 [M+H].

5-Cyclopropanecarbonyl-N-methyl-N-propyl-isophthalamic acid ethyl ester

Mix 5-(cyclopropyl-hydroxymethyl)-N-methyl-N-propyl-isophthalamic acid ethyl ester (122 mg, 0.38 mmol) and Dess-Martin periodinane (245 mg, 0.57) in CDCl$_3$ (5 mL) and stir at room temperature for 2 h. Quench the reaction mixture with premixed sodium thiosulfate (500 mg) in 5% aqueous sodium carbonate solution (5 mL). Separate the organic layer and extract the aqueous layer with dichloromethane (2×5 mL). Combine organic layers and concentrate to give the title compound as a crude residue which is used in the next step without further purification.
MS (ES): m/z=318 [M+H].

5-Cyclopropanecarbonyl-N-methyl-N-propyl-isophthalamic acid

Stir the crude 5-cyclopropanecarbonyl-N-methyl-N-propyl-isophthalamic acid ethyl ester (0.38 mmol) in 1 N NaOH (1 mL) and ethanol (1 mL) for 3 h at room temperature. Dilute the mixture with water (5 mL) and wash the aqueous solution with diethyl ether (2×3 mL). Acidify with 1 N HCl (1 mL) and extract with ethyl acetate (3×5 mL). Wash the combined organic layer with saturated aqueous sodium chloride, dry (sodium sulfate) and concentrate to give the title compound as a crude residue which is used in the next step without further purification.
MS (ES): m/z=290 [M+H].

Preparation 133

N-Methyl-5-(2-oxo-pyrrolidin-1-yl)-N-propyl-isophthalamic acid

5-Iodo-isophthalic acid monomethyl ester

Dissolve 5-iodo-isophthalic acid (5 g, 15.6 mmol), NaOH (600 mg, 14.8 mmol) in a mixture of methanol (100 mL), acetone (20 mL) and water (2 mL). Stir at room temperature overnight. Concentrate and redissolve the residue in diethyl ether (100 mL) and water (100 mL). Separate the aqueous layer and wash with diethyl ether (50 mL). Acidify the washed solution with 5 N HCl to about pH=1. Stir for 30 min at room temperature and filter off solid. Wash the solid with water and dry to give the title compound (3.7 g, 77%).

5-Iodo-N-methyl-N-propyl-isophthalamic acid methyl ester

Mix 5-iodo-isophthalic acid monomethyl ester (3.6 g, ), N-methyl propyl amine (1.2 mL, 11.8 mmol), 1-[3-(dimethylamino)propyl]-3-ethylcarbodiimide hydrochloride (2.3 g, 11.8 mmol), and 1-hydroxtbenzotriazole hydrate (1.6 g, 11.8 mmol) in dichloromethane (40 mL) and stir at room temperature for 4 h. Dilute with dichloromethane (20 mL), wash with water, 5% aqueous ammonium chloride solution, 5% aqueous sodium bicarbonate solution. Dry (sodium sulfate); concentrate and purify (silica gel chromatography, eluting with ethyl acetate and hexanes) to give the title compound (3.2 g, 74%).

MS (ES): m/z=362 [M+H].

N-Methyl-5-(2-oxopyrrolidin-1-yl)-N-propyl-isophthalamic acid methyl ester

Mix 5-iodo-N-methyl-N-propyl-isophthalamic acid methyl ester (220 mg, 0.61 mmol), 2-pyrrolidone (56 µL, 0.73 mmol), ethane-1,2-diamine (4 µL, 0.061 mmol), cesium carbonate (398 mg, 1.22) and copper (I) iodide (12 mg, 0.061 mmol) in 1,4-dioxane (4 mL). Heat the mixture to 110° C. for 1 h then stir at room temperature overnight. Dilute with dichloromethane and filter through a filtering agent. Concentrate and purify (silica gel chromatography, eluting with ethyl acetate and hexanes) to give the title compound (100 mg, 52%).

MS (ES): m/z=319 [M+H].

N-Methyl-5-(2-oxopyrrolidin-1-yl)-N-propyl-isophthalamic acid

Stir N-methyl-5-(2-oxopyrrolidin-1-yl)-N-propyl-isophthalamic acid methyl ester (100 mg, 0.314 mmol) in 1 N NaOH (0.5 mL) and methanol (0.5 mL) at room temperature for 3 days. Dilute the mixture with water (1 mL) and wash the aqueous solution with diethyl ether. Acidify with 1 N HCl (0.55 mL) and extract with ethyl acetate (3×2 mL). Concentrate the organic layers to give the title compound as a crude residue which is used in the next step without further purification.

MS (ES): m/z=305 [M+H].

Preparation 134

2'-Fluoro-5-(methyl-propylcarbamoyl)-biphenyl-3-carboxylic acid

2'-Fluoro-5-(methyl-propylcarbamoyl)-biphenyl-3-carboxylic acid methyl ester Add 1,4-dioxane (10 mL), 5-iodo-N-methyl-N-propyl-isophthalamic acid methyl ester (0.720 g, 2.00 mmol), 2-fluorophenylboronic acid (0.364 g, 2.60 mmol), tetrakis(triphenylphosphine)palladium (0) (0.347 g, 0.300 mmol), and potassium carbonate (0.829 g, 6.00 mmol) to a sealed flask flushed with nitrogen. Heat the mixture overnight and cool to room temperature. Filter the mixture though a filtering agent, concentrate and purify (silica gel chromatography, eluting with 4:96 ethyl acetate:hexanes) to give the title compound (0.297 g, 45%).

MS (ES): m/z=329.9 [M+H].

2'-Fluoro-5-(methyl-propylcarbamoyl)-biphenyl-3-carboxylic acid

Chill a solution of 2'-fluoro-5-(methyl-propylcarbamoyl)-biphenyl-3-carboxylic acid methyl ester (0.297 g, 0.903 mmol) in MeOH (2 mL) and THF (2 mL) in an ice bath. Add 2 N NaOH (1.35 mL, 2.70 mmol) to the mixture and stir at room temperature for 3 h. Acidify the solution to about pH=2 and concentrate to one half of the solvent. Partition the residue between ethyl acetate and H$_2$O and extract the aqueous layer with ethyl acetate (2×15 mL). Wash the combined organic extract with saturated aqueous sodium chloride, dry (magnesium sulfate) and concentrate to give the title compound.

MS (ES): m/z=314.2 [M−H].

The compounds of Preparations 135-136 are prepared essentially as described in Preparation 134 using the appropriate difluorophenylboronic acid.

| Prep | Compound | MS (ES) [M − H] |
|---|---|---|
| 135 | 2',6'-Difluoro-5-(methyl-propylcarbamoyl)-biphenyl-3-carboxylic acid | 333.2 |
| 136 | 2',4'-Difluoro-5-(methyl-propylcarbamoyl)-biphenyl-3-carboxylic acid | 332.1 |

Preparation 137

N-Methyl-N-propyl-5-(pyridine-3-carbonyl)-isophthalanic acid

N-Methyl-N-propyl-5-tributylstannanyl-isophthalamic acid methyl ester

Add toluene (40 mL), 5-iodo-N-methyl-N-propyl-isophthalamic acid methyl ester (5.0 g, 13.8 mmol), bis(tributyltin) (8.3 mL, 16.6 mmol), and trans-dichlorobis(triphenylphosphine)palladium (II) (0.968 mg, 1.38 mmol) to a sealed flask flushed with nitrogen. Heat the mixture at 100° C. for 24 h and cool to room temperature. Filter the mixture though a filtering agent, concentrate and purify (silica gel chromatography, eluting with 10:90 to 20:80 ethyl acetate:hexanes) to give the title compound (4.58 g, 63%).

N-Methyl-N-propyl-5-(pyridine-3-carbonyl)-isophthalamic acid methyl ester

Add THF (3 mL), N-methyl-N-propyl-5-tributylstannanyl-isophthalamic acid methyl ester (0.524 g, 1.00 mmol), nicotinoyl chloride hydrochloride (0.232 g, 1.30 mmol), 2-(di-tert-butylphosphino)biphenyl (0.045 g, 0.151 mmol), bis(dibenzylidene-acetone)palladium (0) (029 g, 0.05 mmol) to a sealed tube flushed with nitrogen. Heat the mixture at 50° C. for 16 h and cool to room temperature. Filter the mixture though a filtering agent, concentrate and purify (silica gel chromatography, eluting with 50:50 to 100:0 ethyl acetate:hexanes) to give the title compound (0.070 g, 21%).

MS (ES): m/z=340.9 [M+H].

N-Methyl-N-propyl-5-(pyridine-3-carbonyl)-isophthalamic acid

Chill a solution of N-methyl-N-propyl-5-(pyridine-3-carbonyl)-isophthalamic acid methyl ester (0.070 g, 0.206 mmol) in MeOH (1 mL) and THF (1 mL) in an ice bath. Add 1 N NaOH (0.62 mL, 0.62 mmol) and stir at room temperature for 2 h. Acidify the solution to about pH=2 and concentrate to one half of the solvent. Partition the residue between ethyl acetate and H$_2$O. Extract the aqueous layer with ethyl acetate (2×15 mL). Wash the combined organic extract with saturated aqueous sodium chloride, dry (magnesium sulfate) and concentrate to give the title compound (72%).

MS (ES): m/z=326.9 [M+H].

The compound of Preparation 138 is prepared essentially as described in Preparation 137 using the appropriate nicotinoyl chloride hydrochloride.

| Prep | Compound | MS (ES) [M − H] |
|---|---|---|
| 138 | N-Methyl-N-propyl-5-(pyridine-2-carbonyl)-isophthalamic acid | 333.2 |

Preparation 139

5-(Difluorophenyl-methyl)-N-methyl-N-propyl-isophthalamic acid

N-Methyl-5-(2-phenyl-[1,3]dithian-2-yl)-N-propyl-isophthalamic acid methyl ester Add boron trifluoride diethyl etherate (0.358 mL, 2.83 mmol) to a solution of 5-benzoyl-N-methyl-N-propyl-isophthalamic acid methyl ester (0.192 g, 0.566 mmol) in dichloromethane (3 mL) at 0° C. Add 1,3-propanedithiol (0.114 mL, 1.12 mmol). Stir at room temperature overnight. Partition between water (20 mL) and dichloromethane (20 mL) and extract the aqueous layer with dichloromethane (20 mL). Dry (magnesium sulfate), concentrate and purify (silica gel chromatography, eluting with 30:70 ethyl acetate:hexanes) to give the title compound (51%).

MS (ES): m/z=430.0 [M+H].

5-(Difluorophenyl-methyl)-N-methyl-N-propyl-isophthalamic acid methyl ester Chill a solution of nitrosonium tetrafluoroborate (0.074 g, 0.63 mmol), hydrogen fluoride-pyridine (0.250 mL) in dichloromethane (2 mL) in a plastic bottle. Add a solution of N-methyl-5-(2-phenyl-[1,3]dithian-2-yl)-N-propyl-isophthalamic acid methyl ester (0.123 g, 0.286 mmol) in dichloromethane (1 mL) to the bottle and stir at room temperature for 2 h. Dilute the solution with dichloromethane (5 mL) and filter though a pad of magnesium sulfate and aluminum oxide. Wash solid with ethyl acetate (50 mL), concentrate and purify (silica gel chromatography, eluting with 20:80 to 30:70 ethyl acetate:hexanes) to give the title compound (42%).

MS (ES): m/z=361.9 [M+H].

5-(Difluorophenyl-methyl)-N-methyl-N-propyl-isophthalamic acid

Chill a solution of 5-(difluorophenyl-methyl)-N-methyl-N-propyl-isophthalamic acid methyl ester (0.043 g, 0.119 mmol) in THF (1 mL) in an ice bath. Add 1 N lithium hydroxide (0.18 mL, 0.18 mmol) and stir at room temperature for 3 h. Acidify the solution to about pH=2 and concentrate to one half of the solvent. Partition the residue between ethyl acetate and H$_2$O. Extract the aqueous layer with ethyl acetate (2×10 mL). Wash the combined organic extract with saturated aqueous sodium chloride, dry (magnesium sulfate) and concentrate to give the title compound (95%).

MS (ES): m/z=346.2 [M+H].

Preparation 140

N-Methyl-N-propyl-5-thiazol-2-yl-isophthalamic acid

5-Iodo-isophthalic acid monomethyl ester

Dissolve 5-iodo-isophthalic acid dimethyl ester (10 g, 31.2 mmol) in methanol (90 mL) and cool to 0° C. Add 2 N NaOH (15.6 mL) dropwise and slowly warm up to room temperature. Stir overnight and acidify to about pH=3 with 5 N HCl. Extract with ethyl acetate (2×50 mL). Wash the combined organic layers by water, saturated aqueous sodium chloride, dry (magnesium sulfate) and concentrate to give the title compound as a crude residue which is used in the next step without further purification.

MS (ES): m/z=305.0 [M−H].

5-Iodo-N-methyl-N-propyl-isophthalamic acid methyl ester

Dissolve 5-iodo-isophthalic acid monomethyl ester (9.34 g, 30.5 mmol), 1-hydroxybenzotriazole hydrate (4.86 g, 36 mmol) and a solution of 1,3-dicyclohexylcarbodiimide (1 M in dichloromethane; 36 mL) in THF (70 mL). Cool to 0° C. for 15 min. Add methylpropylamine (3.69 mL, 36 mmol) and stir at room temperature for 12 h. Filter the solution though a filtering agent and wash with ethyl acetate, concentrate and purify (silica gel chromatography, eluting with 20:80 ethyl acetate:hexanes) to give the title compound.

N-Methyl-N-propyl-5-thiazol-2-yl-isophthalamic acid methyl ester

To a previously nitrogen-flushed vessel, add zinc dust (<10 microns, 0.196 g, 3 mmol) and 1,2-dibromoethane (0.023 mL, 0.27 mmol) to THF (0.5 mL). Heat the solution until bubbles appear. Repeat the heating twice and cool to room temperature. Add chlorotrimethylsilane (15 µL) and 2-bromothiazole (90 µL, 1 mmol) in THF (0.4 mL). Stir at room temperature for 15 min. Add 5-iodo-N-methyl-N-propyl-isophthalamic acid methyl ester (541 mg, 1.5 mmol), tetrakis (triphenylphosphine)palladium (0) (15 mg) and flush the mixture with nitrogen again before heating to reflux for 10 h. Cool to room temperature, concentrate and purify (silica gel chromatography, eluting with 0:100 to 40:60 ethyl acetate: hexanes) to give the title compound (95%).

MS (ES): m/z=319.2 [M+H].

N-Methyl-N-propyl-5-thiazol-2-yl-isophthalamic acid

Dissolve N-Methyl-N-propyl-5-thiazol-2-yl-isophthalamic acid methyl ester (150 mg, 0.47 mmol) in methanol (6 mL). Add dropwise 2 N NaOH (0.3 mL) and stir overnight at room temperature. Acidify the mixture to about pH=6 by 5 N HCl and concentrate to near dryness. Dilute with ethyl acetate (20 mL) and wash the organic layer with saturated aqueous sodium chloride solution, dry (magnesium sulfate) and concentrate to give the title compound as an oil.

MS (ES): m/z=305 [M+H].

Preparation 141

N-Methyl-5-(1-methyl-1H-imidazol-2-yl)-N-propyl-isophthalamic acid

N-Methyl-5-(1-methyl-1H-imidazol-2-yl)-N-propyl-isophthalamic acid methyl ester

Add n-butyl lithium (2.0 M in pentane, 0.78 mL, 1.55 mmol) dropwise over 30 min to a previously nitrogen-flushed, flame-dried vessel containing 1-methyl-1H-imidazole (0.12 mL, 1.5 mmol) in THF (10 mL) at −78° C., and stir for 30 min at the same temperature. Warm the solution to 0° C. and add dropwise zinc (II) chloride (1.0 M in diethyl ether, 4.5 mL, 4.5 mmol) over 10 min. Stir the mixture at the same temperature for 1 h and at room temperature for 30 min. Add 5-iodo-N-methyl-N-propyl-isophthalamic acid methyl ester (361 mg, 1.0 mmol) and tetrakis(triphenylphosphine)palladium (0) (12 mg) under nitrogen before heating the reaction to reflux for 20 min. Cool to room temperature, concentrate and purify (silica gel chromatography, eluting with 0:100 to 8:92 methanol:dichloromethane) to give the title compound.

N-Methyl-5-(1-methyl-1H-imidazol-2-yl)-N-propyl-isophthalamic acid

Dissolve N-methyl-5-(1-methyl-1H-imidazol-2-yl)-N-propyl-isophthalamic acid methyl ester (100 mg, 0.32 mmol) in methanol (10 mL). Dropwise add 1 N lithium hydroxide (0.38 mL) and stir overnight at room temperature. Add 2 N NaOH (0.1 mL) and stir for 48 h at room temperature. Acidify the mixture to about pH=6 by DOWEX® 50WX2-100 ion exchange resin and filter. Concentrate filtrate and lyophilize (1:1 acetonitrile:water) to give the title compound.

MS (ES): m/z=300 [M−H].

Preparation 142

5-Benzoyl-N-methyl-N-propyl-isophthalamic acid

N-Methyl-N-propyl-5-tributylstannanyl-isophthalamic acid methyl ester

Dissolve 5-iodo-N-methyl-N-propyl-isophthalamic acid methyl ester (3.0 g, 8.3 mmol), bis(tributyltin) (4.99 mL, 9.97 mmol) and trans-dichlorobis(triphenylphosphine)palladium (II) (582 mg, 0.83 mmol) in toluene (20 mL) in a previously degassed sealed vessel. Flush the mixture with nitrogen and heat the sealed mixture for 24 h at 90° C. Cool the reaction to room temperature and filter though a filtering agent. Concentrate the filtrate and purify (silica gel chromatography, eluting with 0:100 to 20:80 ethyl acetate:hexanes) to give the title compound (66%).

5-Benzoyl-N-methyl-N-propyl-isophthalamic acid methyl ester

Dissolve N-methyl-N-propyl-5-tributylstannanyl-isophthalamic acid methyl ester (480 mg, 0.8 mmol), benzoyl chloride (117 mg), tris(dibenzylideneacetone)dipalladium (0) (19.3 mg) and 2-(di-tert-butylphosphino)biphenyl (34.5 mg) in chloroform (8 mL) in a previously degassed sealed vessel. Flush the mixture with nitrogen and heat the sealed mixture overnight at 60° C. Cool the reaction to room temperature and filter though a filtering agent. Concentrate the filtrate and purify (silica gel chromatography, eluting with 0:100 to 30:70 ethyl acetate:hexanes) to give the title compound (66%).

5-Benzoyl-N-methyl-N-propyl-isophthalamic acid

Dissolve 5-benzoyl-N-methyl-N-propyl-isophthalamic acid methyl ester (60 mg, 0.17 mmol) in methanol (4 mL). Add dropwise 1 N lithium hydroxide (0.23 mL) and stir overnight at room temperature. Acidify the mixture to about pH=6 by 5 N HCl and concentrate to near dryness. Dilute the residue with ethyl acetate and wash with saturated aqueous sodium chloride solution, dry (magnesium sulfate) and concentrate to give the title compound (83%).

MS (ES): m/z=324 [M−H].

Preparation 143

5-(Furan-2-carbonyl)-N-methyl-N-propyl-isophthalamic acid 5-(Furan-2-carbonyl)-N-methyl-N-propyl-isophthalamic acid methyl ester Dissolve N-methyl-N-propyl-5-tributylstannanyl-isophthalamic acid methyl ester (500 mg, 1 mmol), furan-2-carbonyl chloride (0.12 mL), tris(dibenzylideneacetone)-dipalladium (0) (19 mg) and 2-(di-tert-butylphosphino)biphenyl (35 mg) in THF (6 mL) in a previously degassed, sealed vessel. Flush the mixture with nitrogen and heat the sealed mixture overnight at 50° C. Cool the reaction to room temperature and filter though a filtering agent. Concentrate the filtrate and purify (silica gel chromatography, 0:100 to 38:62 ethyl acetate:hexanes) to give the title compound (50%).

5-(Furan-2-carbonyl)-N-methyl-N-propyl-isophthalamic acid

Dissolve 5-(faran-2-carbonyl)-N-methyl-N-propyl-isophthalamic acid methyl ester (100 mg, 0.3 mmol) in methanol (10 mL). Add dropwise 2 N NaOH (0.225 mL) and stir overnight at room temperature. Acidify the mixture to about pH=6 by 5 N HCl and concentrate to near dryness. Dilute the residue with ethyl acetate and wash by saturated aqueous sodium chloride solution, dry (magnesium sulfate) and concentrate.

MS (ES): m/z=314.2 [M−H].

Preparation 144

5-(Difluorofuran-2-ylmethyl)-N-methyl-N-propyl-isophthalamic acid

5-(2-Furan-2-yl-[1,3]dithiolan-2-yl)-N-methyl-N-propyl-isophthalamic acid methyl ester Dissolve 5-(furan-2-carbonyl)-N-methyl-N-propyl-isophthalamic acid methyl ester (290 mg, 0.88 mmol) in dichloromethane (2 mL). Cool to 0° C., add a solution of ethane-1,2-dithiol (0.22 mL, 2.2 mmol) and then add a solution of boron trifluoride dibutyl etherate (0.66 mL, 5.2 mmol) in dichloromethane (5 mL). Warm the mixture to room temperature and stir overnight. Quench with water and dilute with dichloromethane. Wash the organic layer by saturated aqueous sodium chloride, dry (magnesium sulfate), concentrate and purify (silica gel chromatography, eluting with 0:100 to 30:70 ethyl acetate:hexanes) to give the title compound (38%).

5-(Difluorofuran-2-yl-methyl)-N-methyl-N-propyl-isophthalamic acid methyl ester Under nitrogen and in a plastic vessel, dissolve nitrosonium tetrafluoroborate (84.8 µg, 0.72 mmol) and pyridinium poly(hydrogen fluoride) (70% hydrogen fluoride, 30% pyridine, 300 µL) in dichloromethane (2 mL) and cool to 0° C. Add dropwise 5-(2-furan-2-yl-[1,3]dithiolan-2-yl)-N-methyl-N-propyl-isophthalamic acid methyl ester in dichloromethane (1.5 mL) to the mixture, warm up to room temperature and stir for 2 h. Dilute the mixture with dichloromethane (20 mL) and filter the organic liquid though a pad of aluminum oxide and magnesium sulfate mixture. Concentrate the filtrate and purify (silica gel chromatography, 1:99 to 30:70 ethyl acetate:hexanes) to give the title compound (30%).
MS (ES): m/z=352 [M+H].

5-(Difluorofuran-2-yl-methyl)-N-methyl-N-propyl-isophthalamic acid

Dissolve 5-(difluorofuran-2-yl-methyl)-N-methyl-N-propyl-isophthalamic acid methyl ester (30 mg, 0.08 mmol) in methanol (2 mL). Add dropwise 2 N NaOH (0.06 mL) and stir overnight at room temperature. Acidify the mixture to about pH=6 with 5 N HCl and concentrate to near dryness. Dilute the residue with ethyl acetate, wash with saturated aqueous sodium chloride solution, dry (magnesium sulfate) and concentrate to give the title compound (66%).
MS (ES): m/z=335 [M−H].

Preparation 145

N-Methyl-5-(2-methylacryloyl)-N-propyl-isophthalamic acid N-Methyl-5-(2-methylacryloyl)-N-propyl-isophthalamic acid methyl ester Dissolve N-methyl-N-propyl-5-tributylstannanyl-isophthalamic acid methyl ester (885 mg, 168 mmol), 2-methylacryloyl chloride (172 mg, 1.64 mmol), tris(dibenzylideneacetone)dipalladium (46 mg, 0.05 mmol) and tricyclohexylphosphine (46 mg, 0.16 mmol)) in chloroform (15.5 mL) in a previously degassed vessel. Flush the mixture with nitrogen gas and heat the sealed mixture overnight at 60° C. Cool to room temperature and filter though a filtering agent. Concentrate the filtrate and purify (silica gel chromatography, eluting with 0:100 to 20:80 ethyl acetate:hexanes) to give the title compound.

N-Methyl-5-(2-methylacryloyl)-N-propyl-isophthalamic acid

Dissolve N-methyl-5-(2-methylacryloyl)-N-propyl-isophthalamic acid methyl ester (50 mg, 0.16 mmol) in methanol (3 mL). Add 2 N NaOH (0.12 mL) and stir overnight at room temperature. Add 2 N NaOH (0.05 mL ) and stir for an additional 3 h. Acidify the mixture to about pH=6 using DOWEX® 50WX2-100 ion exchange resin and filter. Concentrate filtrate to give the title compound which is used in the next step without further purification.
MS (ES): m/z=288 [M−H].

Preparation 146

5-Isobutyryl-N-methyl-N-propyl-isophthalamic acid

5-(1-Hydroxy-2-methyl-propyl)-N-methyl-N-propyl-isophthalamic acid methyl ester Dissolve N-methyl-5-(2-methylacryloyl)-N-propyl-isophthalamic acid methyl ester (80 mg, 0.26 mmol) in ethyl acetate (25 mL) under nitrogen. Add Raney® nickel (100 mg) and hydrogenate the reaction for 2 h at room temperature under an atmosphere of hydrogen gas (40 psi). Filter the reaction and concentrate to give the crude title product.
MS (ES): m/z=308 [M+H].

5-Isobutyryl-N-methyl-N-propyl-isophthalamic acid methyl ester

Dissolve 5-(1-hydroxy-2-methyl-propyl)-N-methyl-N-propyl-isophthalamic acid methyl ester (70 mg, 0.23 mmol) in dichloromethane (3 mL) and add Dess-Martin periodinane (174 mg, 0.41 mmol) at room temperature. Stir the mixture overnight and quench with 10% aqueous sodium bisulfite solution. Extract the organic layer, wash with saturated aqueous sodium chloride solution, dry (magnesium sulfate), concentrate and purify (silica gel chromatography, eluting with 30:70 ethyl acetate:hexanes) to give the title compound.

-Isobutyryl-N-methyl-N-propyl-isophthalamic acid

Dissolve 5-isobutyryl-N-methyl-N-propyl-isophthalamic acid methyl ester (50 mg, 0.16 mmol) in methanol (3 mL) and add dropwise 2 N NaOH (0.16 mL). Stir the mixture at room temperature for 6 h, store overnight at 4° C. and acidify to about pH=6 by 5 N HCl. Concentrate to near dryness and dilute the residue with ethyl acetate. Wash with saturated aqueous sodium chloride solution and extract the organic layer, dry (magnesium sulfate) and concentrate to give the title compound.
MS (ES): m/z=289[M−H].

Preparation 147

5-Nitro-N,N-dipropyl-isophthalamic acid

5-Nitro-N,N-dipropyl-isophthalamic acid methyl ester

Dissolve commercially available monomethyl 5-nitroisophthalate (3.000 g, 14.07 mmol), 1-(3-dimethylaminopropyl)-3-ethylcarbodiimide hydrochloride (3.238 g, 16.89 mmol), 1-hydroxybenzotriazole hydrate (2.587 g, 16.89 mmol) and 4-dimethylaminopyridine (0.172 g, 1.407 mmol) and triethylamine (5.885 mL, 42.22 mmol) in dichloromethane (309 mL) and stir the mixture at room temperature for 0.5 h. Add dipropylamine (2.026 mL, 14.78 mmol) and triethylamine (5.885 mL, 42.22 mmol) and stir the mixture overnight. Concentrate and redissolve the residue in ethyl acetate and wash with two portions each of 5% aqueous potassium hydrogen sulfate solution, 5% aqueous sodium bicarbonate solution, saturated aqueous sodium chloride, dry (magnesium sulfate) and concentrate to give the title compound (3.885 g, 90%).

MS (ES): m/z=309.1 [M+H].

5-Nitro-N,N-dipropyl-isophthalamic acid

Dissolve 5-nitro-N,N-dipropyl-isophthalamic acid methyl ester (1.000 g, 3.243 mmol) and lithium hydroxide (0.089 g, 3.730 mmol) in a mixture of THF (3.16 mL), water (1.58 mL) and methanol (1.58 mL). Stir the mixture at room temperature until the starting material is consumed. Concentrate and acidify with 1 N HCl. Extract with ethyl acetate, dry (magnesium sulfate) and concentrate to give the title compound (0.874 g, 92%).

MS (ES): m/z=293.1 [M–H].

Preparation 148

5-Acetyl-N-methyl-N-propyl-isophthalamic acid

5-Formyl-N-methyl-N-propyl-isophthalamic acid ethyl ester

Treat a solution 5-hydroxymethyl-N-methyl-N-propyl-isophthalamic acid ethyl ester (5.79 g, 20.7 mmol) in dichloromethane (50 mL) at −78° C. with oxalyly chloride (1.99 mL, 22.8 mmol), DMSO (3.5 mL, 49.5 mmol), and triethylamine (8.6 mL, 62.1mmol). Stir at −78° C. for 30 min, warm to room temperature and stir for 1 h. Quench with ice and extract with dichloromethane (100 mL). Wash with saturated aqueous NaHCO$_3$, saturated aqueous sodium chloride, dry (magnesium sulfate) concentrate and purify (silica gel chromatography, eluting with 40:60 to 50:50 ethyl acetate:hexanes) to give the title compound (4.53 g, 78%).

MS (ES): m/z=278.3 [M+H].

5-(1-Hydroxyethyl)-N-methyl-N-propyl-isohthalamic acid ethyl ester

Treat a solution of 5-formyl-N-methyl-N-propyl-isophthalamic acid ethyl ester (400 mg, 1.44 mmol) in THF (10 mL) at 0° C. with methylmagnesium bromide (3.0 M in diethyl ether, 0.58 mL, 1.73 mmol). Stir at 0° C. for 1 h and quench with saturated aqueous ammonium chloride solution. Extract with ethyl acetate (100 mL), dry (magnesium sulfate), concentrate and purify (silica gel chromatography, eluting with 40:60 to 70:30 ethyl acetate:hexanes) to give the title compound (250 mg, 59%).

MS (ES): m/z=293.9 [M+H].

5-Acetyl-N-methyl-N-propyl-isophthalamic acid ethyl ester

Treat a solution of 5-(1-hydroxyethyl)-N-methyl-N-propyl-isophthalamic acid ethyl ester (250 mg, 0.85 mmol) in dichloromethane (10 mL) with Dess-Martin periodinane (470 mg, 1.11 mmol). Stir at room temperature for 2.5 h, quench with 10% aqueous sodium sulfate, extract with ethyl acetate (50 mL). Wash with 10% aqueous sodium sulfate solution, saturated aqueous sodium chloride, dry (magnesium sulfate), concentrate and purify (silica gel chromatography, eluting with 50:50 ethyl acetate:hexanes) to give the title compound (196 mg, 78%).

MS (ES): m/z=291.9 [M+H].

5-Acetyl-N-methyl-N-propyl-isophthalamic acid

Treat a solution of 5-acetyl-N-methyl-N-propyl-isophthalamic acid ethyl ester (196 mg, 0.67 mmol) in ethanol (7 mL) at room temperature with 2 N NaOH (0.5 mL, 1.0 mmol) for 12 h. Acidify to about pH=3 using 1 N HCl. Extract with ethyl acetate (50 mL), dry (magnesium sulfate) and concentrate to give the title compound (179 mg, 95%).

MS (ES): m/z=263.9 [M+H].

Preparation 149

N-Methyl-N-propyl-5-(2,2,2-trifluoro-acetyl)-isophthalamic acid

N-Methyl-N-propyl-5-(2,2,2-trifluoro-1-hydroxyethyl)-isophthalamic acid

N-Methyl-N-propyl-5-(2,2,2-trifluoro-1-hydroxyethyl)-isophthalamic acid ethyl ester Treat a solution of 5-formyl-N-methyl-N-propyl-isophthalamic acid ethyl ester (500 mg, 1.8 mmol) in THF (10 mL) at 0° C. with trimethyl(trifluoromethyl)silane (0.5 M in THF, 5.4 mL, 2.70 mmol) and tetrabutylammonium fluoride (1.0 M in THF, 2.7 mL, 2.70 mmol). Stir at 0° C. for 2 h and quench with saturated aqueous NaHCO$_3$. Extract with ethyl acetate (100 mL), dry (magnesium sulfate) and concentrate to give the crude title product which is used in the next step without further purification.

MS (ES): m/z=347.9 [M+H].

N-Methyl-N-propyl-5-(2,2,2-trifluoroacetyl)-isophthalamic acid ethyl ester

Treat a solution of N-methyl-N-propyl-5-(2,2,2-trifluoro-1-hydroxyethyl)-isophthalamic acid ethyl ester (1.8 mmol) in dichloromethane (20 mL) with Dess-Martin reagent at room temperature for 2 h. Quench with 10% aqueous sodium sulfite and extract with ethyl acetate (100 mL). Wash the organic layer with 10% aqueous sodium sulfite, saturated aqueous sodium chloride, dry (magnesium sulfate), concentrate and purify (silica gel chromatography, eluting with 60:40 ethyl acetate:hexanes) to give the title compound (330 mg) which is contaminated with recovered N-methyl-N-propyl-5-(2,2,2-trifluoro-1-hydroxyethyl)-isophthalamic acid ethyl ester in a ratio of about 4:1).

MS (ES): m/z=346.3 [M+H].

N-Methyl-N-propyl-5-(2,2,2-trifluoroacetyl)-isophthalamic acid

N-Methyl-N-propyl-5-(2,2,2-trifluoro-1-hydroxyethyl)-isophthalamic acid

Treat a solution of a mixture of N-methyl-N-propyl-5-(2,2,2-trifluoroacetyl)-isophthalamic acid (330 mg, 0.96 mmol) and N-methyl-N-propyl-5-(2,2,2-trifluoro-1-hydroxyethyl)- isophthalamic acid in a ratio of about 4:1 in ethanol (12 mL) with 2 N NaOH (0.72 mL, 1.43 mmol). Stir at room temperature for 12 h, add more 2 N NaOH (1.5 eq.), and stir overnight at room temperature. Acidify to about pH=3 with 1 N HCl. Extract with ethyl acetate (50 mL), dry (magnesium sulfate) and concentrate to give a mixture of the two title products, N-methyl-N-propyl-5-(2,2,2-trifluoroacetyl)-isophthalamic acid (MS (ES): m/z=316.1 [M–H] and N-methyl-N-propyl-5-(2,2,2-trifluoro-1-hydroxyethyl)-isophthalamic acid (MS (ES): m/z=318.1 [M–H]) in a ratio of about 4:1 respectively.

Preparation 150

5-Difluoromethoxy-N-methyl-N-propyl-isophthalamic acid

5-Difluoromethoxy-isophthalic acid dimethyl ester

React 5-hydroxy-isophthalic acid dimethyl ester (5.88 g, 28 mmol), methyl 2-chloro-2,2-difluoroacetate (5.9 mL, 56 mmol), cesium carbonate (18.2 g, 56 mmol) in methyl ethyl ketone at reflux for 2 days. Cool to room temperature, filter though a filtering agent, wash with ethyl acetate, concentrate and purify (silica gel chromatography, eluting with 10:90 to 30:70 ethyl acetate:hexanes) to give the title compound (2.7 g, 37%).
MS (ES): m/z=261.2 [M+H].

5-Difluoromethoxy-isophthalic acid monomethyl ester

Treat a solution of 5-difluoromethoxy-isophthalic acid dimethyl ester (2.7 g, 10.4 mmol) in methanol (35 mL) with 2 N NaOH (5.2 mL, 10.4 mmol) at room temperature for 12 h. Acidify to about pH=3 using 5 N HCl. Extract with ethyl acetate, wash the organic layer with water, saturated aqueous sodium chloride, dry (sodium sulfate) and concentrate to give the crude title product which is used in the next step without further purification.
MS (ES): m/z=245.1 [M–H].

5-Difluoromethoxy-N-methyl-N-propyl-isophthalamic acid methyl ester

Treat a solution containing crude 5-difluoromethoxy-isophthalic acid monomethyl ester (2.5 g, 10 mmol) in THF (20 mL) at room temperature with 1-hydroxybenzotriazole hydrate (1.62 g, 12 mmol), 1,3-dicyclohexylcarbodiimide (12 mL, 1 N, 12 mmol), and n-methylpropylamine (1.23 mL, 12 mmol). Stir at room temperature overnight, filter through a filtering agent, wash with 1:1 ethyl acetate:hexanes (50 mL). Concentrate the combined filtrates and purify (silica gel chromatography, eluting with 0:100 to 30:70 ethyl acetate:hexanes) to give the title compound as a solid (1.6 g, 53%).
MS(ES): m/z=302[M+H].

5-Difluoromethoxy-N-methyl-N-propyl-isophthalamic acid

Treat a solution of 5-difluoromethoxy-N-methyl-N-propyl-isophthalamic acid methyl ester (1.6 g, 5.3 mmol) in methanol (30 mL) with 2 N NaOH (4 mL, 8.0 mmol). Stir at room temperature overnight and acidify to about pH=4 using 1 N HCl. Extract with ethyl acetate (150 mL), wash the organic layer with saturated aqueous sodium chloride, dry (magnesium sulfate) and concentrate to give the title compound which is used in the next step without further purification.
MS (ES): m/z=286.1 [M–H].

Preparation 151

N-Methyl-N-propyl-5-pyridin-4-yl-isophthalamic acid

5-Iodo-N-methyl-N-propyl-isophthalamic acid benzyl ester

Add benzyl chloroformate (5.96 mL, 41.77 mmol) to a solution of 5-iodo-N-methyl-N-propyl-isophthalamic acid (14.5 g, 41.77 mmol), triethylamine (6.4 mL, 45.95 mmol) and 4-dimethylaminopyridine (2.55 g, 20.88 mmol) in dichloromethane (125 mL) at 0° C. and at room temperature for 40 h. Wash the solution twice with a saturated aqueous solution of NaHCO₃, 5% aqueous solution of potassium hydrogen sulfate, saturated aqueous sodium chloride, dry (magnesium sulfate), and concentrate. Dissolve the crude in dichloromethane, wash with a 0.5 N NaOH solution, H₂O, saturated aqueous sodium chloride, dry (magnesium sulfate) and concentrate to give the title compound (6 g, 33%).
MS (ES): m/z=438.1 [M+H].

N-Methyl-N-propyl-5-pyridin-4-yl-isophthalamic acid benzyl ester

Add pyridine-4-boronic acid (2.361 g, 19.21 mmol) and 2 N sodium carbonate (19.21 mL, 38.42 mmol) to a solution of 5-iodo-N-methyl-N-propyl-isophthalamic acid benzyl ester (6.000 g, 13.72 mmol) in ethylene glycol dimethyl ether (206 mL) under nitrogen at room temperature. Add tetrakis(triphenylphosphine)palladium (0) (0.634 g, 0.549 mmol) and reflux for 20 h. Cool to room temperature and concentrate. Add ethyl acetate, separate the organic layer and extract the aqueous layer with ethyl acetate (4×). Wash the combined organic layers with H₂O, saturated aqueous sodium chloride, dry (magnesium sulfate), concentrate and purify (silica gel chromatography, eluting with ethyl acetate) to give the title compound (56%).
MS (ES): m/z=389.2 [M+H].

N-Methyl-N-propyl-5-pyridin-4-yl-isophthalamic acid

Stir a mixture of N-methyl-N-propyl-5-pyridin-4-yl-isophthalamic acid benzyl ester (1.900 g, 4.891 mmol), 10% palladium on carbon (0.208 g) in MeOH (50 mL) under an atmosphere of hydrogen gas (1 atm) for 0.5 h. Filter through a filtering agent and concentrate to give the title compound (quantitative yield).
MS (ES): m/z=299.2 [M+H].

Preparation 152

6-Fluoro-5-(methanesulfonyl-methylamino)-N-methyl-N-propyl-isophthalamic acid 5-Bromo-2-fluorophenylamine Dissolve tin (II) chloride hydrate (86.2 g, 455 mmol), 4-bromo-2-fluoro-1-nitro-benzene (20.0 g, 90.9 mmol) and water (16.4 mL, 909 mmol) in ethanol (475 mL). Reflux the mixture for 6 h. Cool to room temperature and concentrate to a minimal volume. Add ethyl acetate (400 mL) and saturated aqueous sodium bicarbonate solution (1.6 L) to the residue and stir vigorously for 1 h. Filter through a filtering agent and wash with ethyl acetate (2 L). Separate the layers and extract the aqueous layer with ethyl acetate (1 L). Combine the organic layers, wash with saturated aqueous sodium chloride (500 mL), dry (magnesium sulfate) and concentrate to give the title compound as a solid (16.8 g, 97%).

MS (ES): m/z=190 [M+].

Dibenzyl-(5-bromo-2-fluorophenyl)-amine

Stir a slurry of 4-bromo-2-fluorophenylamine (15.0 g, 78.9 mmol), potassium carbonate (43.6 g, 316 mmol) and benzyl bromide (28.2 mL, 237 mmol) in DMF (75 mL) at 100° C. for 18 h. Cool to room temperature and dilute with dichloromethane (200 mL). Filter the slurry and wash with dichloromethane. Wash the filtrate with water (500 mL) and 1 N lithium chloride (250 mL). Dry (magnesium sulfate), concentrate and purify (silica gel chromatography, eluting with 5:95 to 35:65 dichloromethane:hexanes) to give the title compound as a solid (26.2 g, 90%).

MS (ES): m/z=372 [M+2].

5-Bromo-3-dibenzylamino-2-fluorobenzoic acid

Add dropwise a solution of dibenzyl-(5-bromo-2-fluorophenyl)-amine (4.00 g, 10.8 mmol) in THF (12 mL) to a solution of lithium diisopropylamide, freshly prepared by adding n-butyllithium (1.6 M in hexanes, 7.09 mL, 11.3 mmol) to diisopropylamine (1.74 mL, 12.4 mmol) in THF (25 mL) at −78° C. Stir the resulting yellow solution at −78 C. for 45 min. Pour into a dry ice slurry containing about 100 g in dry THF (40 mL). Stir the solution until it reaches room temperature. Concentrate the solution and dissolve the residue in 10% aqueous potassium hydroxide solution (40 mL) and extract with diethyl ether (70 mL). Acidify the aqueous layer to about pH=3 with concentrated HCl. Extract the aqueous layer with diethyl ether (2×200 mL). Combine the organic layers and wash with water (150 mL), dry (magnesium sulfate) and concentrate to give the title compound as a solid (1.81 g, 40%).

MS (ES): m/z=416 [M+2].

5-Bromo-3-dibenzylamino-2-fluorobenzoic acid ethyl ester

Dissolve 5-bromo-3-dibenzylamino-2-fluorobenzoic acid (1.53 g, 3.69 mmol) in ethanol (40 mL). Add concentrated sulfuric acid (0.2 mL) as a catalyst and heat to at reflux for 1 day. Cool to room temperature and concentrate. Dissolve the residue in diethyl ether (30 mL) and wash with 10% aqueous potassium carbonate solution (10 mL) and water (10 mL). Dry (magnesium sulfate) and concentrate to give the title compound as an oil (1.50 g, 92%).

MS (ES): m/z=442 [M].

5-Dibenzylamino-4-fluoro-isophthalic acid 3-ethyl ester

Combine 5-bromo-3-dibenzylamino-2-fluorobenzoic acid ethyl ester (4.74 g, 10.7 mmol), palladium (II) acetate (0.72 g, 3.20 mmol), 1,4-bis(diphenylphosphino)butane (2.84 g, 6.66 mmol), triethylamine (7.90 mL, 56.7 mmol), DMSO (150 mL), tert-butyl alcohol (100 mL), and water (0.50 mL, 27.8 mmol). Place mixture in a container pressurized to 100 psi with carbon monoxide and heat at 80° C. for 24 h. Filter the reaction mixture over a pad of filtering agent. Pour the filtrate into water (500 mL), acidify with 5 N HCl and extract (2×500 mL) with ethyl acetate. Dry (magnesium sulfate), concentrate and purify (silica gel chromatography, eluting with 4:96 methanol:dichloromethane) to give the title compound as a solid (2.40 g, 55%).

MS (ES): m/z=408 [M+H].

5-Dibenzylamino-6-fluoro-N-methyl-N-propyl-isophthalamic acid ethyl ester

Dissolve the 1-hydroxybenzotriazole hydrate (139 mg, 1.03 mmol), 1-[3-(dimethylamino)propyl]-3-ethylcarbodiimide hydrochloride (197 mg, 1.03 mmol) and 5-dibenzylamino-4-fluoro-isophthalic acid 3-ethyl ester (381 mg, 0.934 mmol) in dichloromethane (10.0 mL). Stir for 30 min. Add methylpropyl amine (68.3 mg, 0.93 mmol) to the reaction mixture. Stir the reaction for 4 h. Add 10% aqueous potassium carbonate solution (10 mL). Extract with dichloromethane (2×50 mL). Combine the organic layers, wash with water (20 mL), saturated aqueous sodium chloride (20 mL), dry (magnesium sulfate), concentrate and purify (silica gel chromatography, eluting with 40:60 ethyl acetate:hexanes) to give the title compound (279 mg, 65%).

MS (ES): m/z=463 [M+H].

5-Amino-6-fluoro-N-methyl-N-propyl-isophthalamic acid ethyl ester

Dissolve 5-dibenzylamino-6-fluoro-N-methyl-N-propyl-isophthalamic acid ethyl ester (275 mg, 0.595 mmol) in ethanol (6 mL). Add 10% Pd/C to the solution (50 mg). Stir the black slurry under a balloon containing hydrogen gas for 2.5 days. Filter the slurry through a pad of filtering agent and wash with ethanol. Concentrate the filtrate to give the title compound as a crude product.

MS (ES): m/z=283 [M+H].

6-Fluoro-5-methanesulfonylamino-N-methyl-N-propyl-isophthalamic acid ethyl ester Dissolve 5-amino-6-fluoro-N-methyl-N-propyl-isophthalamic acid ethyl ester (0.162 g, 0.58 mmol) in dichloromethane (1.5 mL). Cool to 0° C. Add pyridine (51.2 µL, 0.63 mmol) and methanesulfonyl chloride (44.5 µL, 0.58 mmol) to the solution. Allow the reaction to warm to room temperature and stir for 2 days. Quench with water (10 mL) and extract with dichloromethane (2×30 mL). Combine the organic layers and wash with saturated aqueous sodium chloride (20 mL), dry (magnesium sulfate), concentrate and purify (silica gel chromatography, eluting with 40:60 ethyl acetate:dichloromethane) to give the title compound as a solid (157 mg, 76%).

MS (ES): m/z=361 [M+H].

6-Fluoro-5-(methanesulfonyl-methylamino)-N-methyl-N-propyl-isophthalamic acid ethyl ester Dissolve 6-fluoro-5-methanesulfonylamino-N-methyl-N-propyl-isophthalamic acid ethyl ester (0.160 g, 0.444 mmol) in DMF (1.0 mL). Add potassium carbonate (44.4 mg, 0.32 mmol), iodomethane (41.5 µL, 0.67 mmol) and tetrabutylammonium bromide (14.3 mg, 0.04 mmol) to the solution. Stir the resulting slurry at room temperature for 16 h. Quench with saturated aqueous sodium sulfate solution (10 mL) and extract with ethyl acetate (3=30 mL). Combine the organic layers and dry (magnesium sulfate). Azeotrope the residue with xylenes to remove residual DMF. Purify (silica gel chromatography, eluting with 40:60 ethyl acetate:dichloromethane) to give the title compound as a solid (111 mg, 67%).

MS (ES): m/z=375 [M+H].

6-Fluoro-5-(methanesulfonyl-methylamino)-N-methyl-N-propyl-isophthalamic acid Dissolve the 6-fluoro-5-(methanesulfonyl-methylamino)-N-methyl-N-propyl-isophthalamic acid ethyl ester (110 mg, 0.30 mmol) in THF (7.5 mL). Add 1 N sodium hydroxide solution (1.48 mL, 1.48 mmol) and stir the resulting biphasic mixture vigorously for 4 h. Acidify with 1 N HCl (1.55 mL, 1.55 mmol) and concentrate the solution to a volume of about 3 mL. Extract the solution with diethyl ether (2×20 mL). Combine the organic layers, dry (magnesium sulfate) and concentrate to give the title compound as a solid (95.2 mg, 93%).
MS (ES): m/z=347 [M+H].

Preparation 153

5-(Methyl-propylcarbamoyl)-1-oxy-nicotinic acid

5-(Methyl-propylcarbamoyl)-1-oxy-nicotinic acid methyl ester

Mix 5-(methyl-propylcarbamoyl)-nicotinic acid methyl ester (396 mg, 1.67 mmol) and 3-chloroperoxybenzoic acid (1.2g, 50-85%) in dichloromethane (50 mL) and stir over the weekend. Dilute with dichloromethane (50 mL) and wash with 5% aqueous sodium bicarbonate solution (20 mL), dry (sodium sulfate), and concentrate to give the crude title compound which is used in the next step without further purification.
MS (ES): m/z=253 [M+H].

5-(Methyl-propylcarbamoyl)-1-oxy-nicotinic acid

Dissolve crude 5-(methyl-propylcarbamoyl)-1-oxy-nicotinic acid methyl ester (0.72 mmol) in 1 N sodium hydroxide (1.4 mL) and methanol (2 mL). Stir at room temperature overnight. Concentrate organic and redissolve the residue in water (15 mL). Wash with dichloromethane (3×10 mL), acidify with 1 N HCl to about pH=2 and concentrate to give the crude title product which is directly in the next step.
MS (ES): m/z=239 [M+H].

Preparation 154

2-Chloro-5-(methyl-propylcarbamoyl)-nicotinic acid

2-Chloro-5-(methyl-propylcarbamoyl)-nicotinic acid methyl ester

Stir 5-(methyl-propylcarbamoyl)-1-oxy-nicotinic acid methyl ester (353 mg, 1.40 mmol) in phosphorus oxychloride (2 mL,) at 100° C. for 1 h. Cool to room temperature and quench with saturated aqueous sodium acetate (50 mL) and ethyl acetate (100 mL). Separate the organic layer, wash with water (50 mL), dry (sodium sulfate), concentrate and purify (silica gel chromatography, eluting with ethyl acetate and hexanes) to give the title compound (208 mg, 55%).
MS (ES): m/z=271 [M+H].

2-Chloro-5-(methyl-propylcarbamoyl)-nicotinic acid

Dissolve 2-chloro-5-(methyl-propylcarbamoyl)-nicotinic acid methyl ester (96 mg, 0.35 mmol) in 1 N sodium hydroxide (0.71 mL, 0.71 mmol) and methanol (2 mL). Stir at room temperature for 2 h. Concentrate organic and redissolve the residue in water (15 mL). Wash with dichloromethane (3×10 mL), acidify the aqueous layer with 1 N HCl to about pH=2. Extract with dichloromethane, dry (sodium sulfate) and concentrate to give the crude title product which is used in the next step without further purification.
MS (ES): m/z=257 [M+H].

Preparation 155

2-Dipropylcarbamoyl-isonicotinic acid

4-Chloropyridine-2-carboxylic acid dipropylamide

Stir a solution of 4-chloro-2-pyridine carboxylic acid (1.0 g, 6.3 mmol), 1-hydroxybenzotriazole (850 mg, 6.3 mmol), 1-(3-dimethylaminopropyl)-3-ethylcarbodimide hydrochloride (1.21 g, 6.3 mmol), dipropyl amine (862 µL, 6.3 mmol), and triethylamine (1.75 mL, 12.6 mmol) in dichloromethane (63 mL) at room temperature over the weekend. Wash the solution with 0.1 N citric acid (2×50 mL), saturated aqueous sodium bicarbonate (50 mL), saturated aqueous sodium chloride (50 mL), dry (sodium sulfate), concentrate and purify (silica gel chromatography, eluting with 10:90 to 20:80 ethyl acetate:hexanes) to give the title compound (1.02 g, 67%).

2-Dipropylcarbamoyl-isonicotinic acid

Heat a mixture of 4-chloropyridine-2-carboxylic acid dipropylamide (1.02 g, 4.2 mmol), palladium (II) acetate (11.3 mg, 0.05 mmol), triethylamine (1.0 mL, 7.1 mmol), 1,1'-bis(3,5-dimethylphenylphosphino)ferrocene (138 mg, 0.55 mmol), DMF (35 mL) and water (5 mL) at 110° C. under an atmosphere of carbon monoxide (200 psi) overnight. Filter the reaction, concentrate and purify (silica gel chromatography, eluting with 0:100 to 10:90 methanol:chloroform) to give the title compound (75 mg, 7%).
MS (ES): m/z=251 [M+H].

Preparation 156

5-(Methyl-propylcarbamoyl)-nicotinic acid

5-(Methyl-propylcarbamoylo-nicotinic acid

Add a solution of pyridine-3,5-dicarboxylic acid (220 mg, 1.32 mmol), diisopropylethylamine (918 mL, 5.28 mmol), and DMF (1.5 mL) in dichloromethane (10 mL) to 2-chlorotritylchloride resin (1.0 g, 1.1 mmol) in a peptide synthesis vessel and mix for 3 h. Filter and wash the resin with a 17:2:1 mixture of dichloromethane:methanol:diisopropylethylamine, followed by dichloromethane. Add a solution of methylpropylamine (225 µL, 2.2 mmol), and benzotriazole-1-yl-oxy-tris-pyrrolidinophosphonium hexafluorophosphate (1.14 g, 2.2 mmol) in dichloromethane (10 mL) to the resin and mix for 1 h. Filter and wash the resin with dichloromethane (2×10 mL). Add a solution of 5% trifluoroacetic acid in dichloromethane (10 mL) to the resin and let stand for 10 min. Filter the resin and wash with dichloromethane (2×10 mL). Combine the filtrates and concentrate to give the title compound (110 mg, 50%).
MS (ES): m/z=223 [M+H].

Preparation 157

4-Dipropylcarbamoyl-pyridine-2-carboxylic acid

2-chloro-N,N-dipropylisonicotinamide

Stir a solution of 2-chloroisonicotinic acid (1.0 g, 6.3 mmol), 1-hydroxybenzotriazole (850 mg, 6.3 mmol), 1-(3- dimethylaminopropyl)-3-ethylcarbodiimide hydrochloride (1.21 g, 6.3 mmol), dipropyl amine (862 µL, 6.3 mmol), and triethylamine (1.75 mL, 12.6 mmol) in dichloromethane (63 mL) at room temperature over the weekend. Wash the solution with 0.1 N citric acid (2×50 mL), saturated aqueous sodium bicarbonate (50 mL), saturated aqueous sodium chloride (50 mL), dry (sodium sulfate), concentrate and purify (silica gel chromatography, eluting with 10:90 to 20:80 ethyl acetate:hexanes) to give the title compound (1.16 g, 76%).

MS (ES): m/z=241 [M+H].

4-Dipropylcarbamoyl-pyridine-2-carboxylic acid

Heat a mixture of 2-chloro-N,N-dipropylisonicotinamide (0.91 g, 3.8 mmol), palladium (II) acetate (13.2 mg), triethylamine (1.0 mL, 7.1 mmol), 1,1'-bis(3,5-dimethylphenylphosphino)ferrocene (161 mg, 0.64 mmol), DMF (35 mL) and water (5 mL) at 110° C. under an atmosphere of carbon monoxide (200 psi) overnight. Filter the reaction, concentrate and purify (silica gel chromatography, eluting with 0:100 to 10:90 methanol:chloroform) to give the title compound (486 mg, 51%).

MS (ES): m/z=251.1 [M+H].

Preparation 158

3-(Methanesulfonyl-methylamino)-benzoic acid

Prepare the title compound starting from ethyl 3-aminobenzoate according to the procedure described in WO 00/55153.

MS (ES): m/z=228.1 [M−H].

Preparation 159

2-(2-(S)-Amino-1-(S)-hydroxy-3-phenylpropyl)-homopiperidine (S)-2-Dibenzylamino-3-1henylpropionaldehyde Dissolve (S)-2-dibenzylamino-3-phenylpropan-1-ol (5.00 g, 15.1 mmol) in dimethyl sulfoxide (19 mL) and cool in an ice bath. Add triethylamine (12 mL, 192 mmol) followed by sulfur trioxide-pyridine complex (4.8 g, 30.3 mmol), stir 30 min then slowly add water (7 mL). Dilute with ethyl acetate and wash with 5% aqueous citric acid (3×), saturated aqueous sodium chloride, dry (magnesium sulfate) and evaporate to give a light yellow residue (4.9 g, 100%).

MS (ES): m/z=330.2 [+H].

(2S,3 S)-2-Dibenzylamino-4-nitro-1-phenyl-oct-7-en-3-ol

Cool to −10° C. a well stirred mixture of O-allyl-N-(9-anthracenylmethyl)-cinchonidinium bromide (0.480 g, 0.8 mmol), potassium fluoride (3 gr, 51 mmol), THF (150 mL) and 5-nitropent-1-ene (2.34 g, 20 mmol) and treat with a solution of (S)-2-dibenzylamino-3-phenylpropionaldehyde (2.640 gr, 8 mmol). Allow mixture to warm to room temperature and stir for two days. Concentrate under reduced pressure. Purify on silica gel with hexane/ethyl ether mixtures to give a mixture of two products (2.7 g, 75%).

MS (ES): m/z=445.2 [M+H].

(2S,3R)-4-Amino-2-dibenzylamino-1-phenyloct-7-en-3-ol

Add powdered Zn (1.56 g, 24 mmol) portionwise at 0-5° C. to a stirred suspension of the (2S,3S)-2-dibenzylamino-4-nitro-1-phenyloct-7-en-3-ol mixture (2.7 g, 6 mmol) in a mixture of ethanol (20 mL) and concentrated HCl (20 mL). Stir for 1 h. Filter the reaction mixture and concentrate the filtrate under reduced pressure. Dilute residue with water and add concentrated ammonium hydroxide. Extract with dichloromethane. Wash the organic layer with water, dry (magnesium sulfate), and concentrate under reduced pressure to give the mixture of amines (1.5 g, 60%).

MS (ES): m/z =415.3 [M+H].

N-[1-((1R,2S)-2-Dibenzylamino-1-hydroxy-3-phenyl-propyl)-pent-4-enyl]-acrylamide Add sodium carbonate (0.324 g, 3.96 mmol) and acryloyl chloride (356 mg, 3.96 mmol) to a solution of (2S,3R)-4-Amino-2-dibenzylamino-1-phenyloct-7-en-3-ol (1.5 g, 3.6 mmol) in dichloromethane. Stir the reaction overnight. Concentrate under reduced pressure. Purify on silica gel with hexane/ethyl acetate mixtures to give a mixture of two products (0.8 g, 48%).

MS (ES): in/z=469.3 [M+H].

7-((1R,2S)-2-Dibenzylamino-1-hydroxy-3-phenyl-propyl)-1,5,6,7-tetrahydro-azepin-2-one Dissolve N-[1-((1R,2S)-2-dibenzylamino-1-hydroxy-3-phenyl-propyl)-pent-4-enyl]-acrylamide (0.5 g, 1.06 mmol) in dichloromethane (50 mL) under nitrogen atmosphere and add Grubb's second generation catalyst (20% mol). Stir the reaction at 50° C. for one day. Concentrate under reduced pressure. Purify on silica gel with hexane/ethyl acetate mixtures to give a mixture of two products. (0, 210 g, 45%) that may be separated using HPLC-MS (19×300 mm, 7 µm, C-18 column; flow rate=20 mL/min; mobile phase gradient 5%-95% over 26 minutes; Solvent A: acetonitrile; Solvent B: 0.1% trifluoroacetic acid in water).

Isomer 1 (MS (ES): m/z=441.3 [M+H]) has a retention time of: 3.21 min and Isomer 2 (MS (ES): m/z=441.3 [M+H]) has a retention time of: 3.41 min using the following conditions:

Column: Waters, XTerra MS $C_{18}$, 3.5 µm, 2.1 mm i.d.×50 mm.
1. Mobile Phase
   A: 0.2% Formic/$H_2O$ [pH 2.2]
   B: 0.2% Formic/ACN
2. Gradient profile:

| Time (min) | Buffer | |
| --- | --- | --- |
| | A(%) | B(%) |
| 0 | 95 | 5 |
| 5.00 | 5 | 95 |
| 6.00 | 5 | 95 |
| 6.05 | 95 | 5 |

(1R,2S)-1-Homopiperidin-2-yl-2-dibenzylamino-3-phenylpropan-1-ol (Isomer 1)

Dissolve 7-((1R,2S)-2-dibenzylamino-1-hydroxy-3-phenylpropyl)-1,5,6,7-tetrahydroazepin-2-one (Isomer 1) (40 mg, 0.09 mmol) in THF (5 mL) and add $BH_3SMe_2$ (2 M in diethyl ether, 0.14 mL, 0.27 mmol). Stir the reaction at 50° C. for 3 hour. Add saturated aqueous citric acid (10 mL). Extract aqueous twice with ethyl acetate, combine organics and wash with saturated sodium chloride, dry (magnesium sulfate) and concentrate under reduced pressure. Add 20% palladium hydroxide on carbon (90 mg) and methanol (10 mL) and stir under 1 atmosphere of hydrogen overnight. Filter and evaporate to give a foam. Purify the product using a SCX column to give a thick residue (0.007 g, 40%).

MS (ESI) m/z=249.19 [M+H].

(1R,2S)-1-Homopiperidin-2-yl-2-dibenzylamino-3-phenyl-propan-1-ol (Isomer 2)

This product may be prepared as described for (Isomer 2) beginning with 7-((1R,2S)-2-dibenzylamino-1-hydroxy-3-phenylpropyl)-1,5,6,7-tetrahydroazepin-2-one (Isomer 2).

MS (ES): m/z=249.19 [M+H].

Preparation 160

(2R, 5R)-2-[(1R, 2S)-2-Acetylamino-3-(3,5-difluoro-phenyl)-1-hydroxy-propyl]-5-benzyloxy-piperidine-1-carboxylic acid tert-butyl ester

(2R, 5R)-5-Benzyloxy-piperidine-1,2-dicarboxylic acid 1-tert-butyl ester 2-ethyl Add benzyltrichloroacetimidate (0.82 mL, 4.4 mmol) and boron trifluoride etherate (0.04 mL, 0.3 mmol) to (2R, 5R)-5-hydroxy-piperidine-1,2-dicarboxylic acid 1-tert-butyl ester 2-ethyl ester (0.80 g, 2.9 mmol) in 15 mL dichloromethane at 0° C. and stir at room temperature overnight. Concentrate under vacuum. Subject residue to flash silica gel chromatography, eluting with from 20:1 to 2:1 hexane: ethyl acetate) to provide the desired compound as an oil (0.46 g, 43%).

$^1$H-NMR (CDCl$_3$, 300 MHz): δ1.20-1.40 (m, 4H), 1.40-1.50 (d, 9H), 1.60-1.80 (m, 1H), 1.95-2.15 (m, 1H), 2.20-2.40 (m, 1H), 2.60-2.85 (m, 1H), 3.30-3.47 (m, 1H), 4.10-4.26 (m, 3H), 4.37-4.90 (m, 3H) and 7.23-7.40 (m, 5H) ppm.

(2R, 5R)-5-Benzyloxy-2-hydroxymethyl-piperidine-1-carboxylic acid tert-butyl ester Add lithium borohydride (0.041 g, 1.9 mmol) to (2R, 5R)-5-Benzyloxy-piperidine-1,2-dicarboxylic acid 1-tert-butyl ester 2-ethyl (0.460 g, 1.3 mmol) in 5 mL diethyl lether at room temperature and stir overnight. Quench with saturated aqueous ammonium chloride and extract with diethyl ether. Combine the organic layers and dry over magnesium sulfate and concentrate. Subject the residue to silica gel flash chromatography, eluting with 2:1 to 1:2 hexane:ethyl acetate to provide the desired compound (0.270 g, 66%).

MS(ESI): m/z=222 (M+H -Boc)$^+$.

(2R, 5R)-5-Benzyloxy-2-formyl-piperidine-1-carboxylic acid tert-butyl ester

Add sulfur trioxide pyridine complex (0.27 g, 1.7 mmol) in dimethylsulfoxide (0.95 mL, 13.0 mmol) to (2R, 5R)-5-Benzyloxy-2-hydroxymethyl-piperidine-1-carboxylic acid tert-butyl ester (0.27 g, 0.84 mmol) in triethylamine (0.70 mL, 5.0 mmol) at 10° C. and stir at room temperature for 30 minutes. Quench with water and extract with diethyl ether. Combine the organic layers, wash with 5% aqueous citric acid followed by saturated aqueous sodium chloride, dry over magnesium sulfate and concentrate. The residue may be used without further purification.

(2R, 5R)-5-Benzyloxy-2-[3-(3,5-difluoro-phenyl)-1-hydroxy-2-nitro-propyl]-piperidine -1-carboxylic acid tert-butyl ester Add tetrabutylammonium fluoride (0.08 mL, 0.08 mmol, 1.0 M in tetrahydro-furan) to (2R, 5R)-5-Benzyloxy-2-formyl-piperidine-1-carboxylic acid tert-butyl ester (0.27 mg, 0.84 mmol) and 1,3-difluoro-5-(2-nitro-ethyl)-benzene (0.17 g, 0.93 mmol) in 5 mL tetrahydrofuran. Stir at room temperature overnight and concentrate. Subject the residue to silica gel chromatography, eluting with from 100% hexane to 90:10 hexane:ethyl acetate to provide the desired compound as a mixture of 3 isomers (0.286 g, 67%).

MS(ESI): m/z=507 (M+H)$^+$

(2R, 5R)-2-[Amino-3-(3,5-difluoro-phenyl)-1-hydroxy-propyl]-5-benzyloxy-piperidine-1-carboxylic acid tert-butyl ester Add nickel (II) chloride (0.08 g, 0.62 mmol) and sodium borohydride (0.08 g, 2.07 mmol) to (2R, 5R)-5-Benzyloxy-2-[3-(3,5-difluoro-phenyl)-1-hydroxy-2-nitro -propyl]-piperidine-1-carboxylic acid tert-butyl ester (0.210 g, 0.41 mmol) in 10 mL methanol at room temperature and stir for 30 minutes. Quench with water and concentrate. Add ethyl acetate and water and filter through a pad of filtering agent, wash with ethyl acetate. Dry the organic layer over magnesium sulfate and concentrate. The residue may be used without further purification.

MS(ESI): m/z=477 (M+H)$^+$

(2R, 5R)-2-[(1R, 2S)-2-Acetylamino-3-(3,5-difluoro-phenyl)-1-hydroxy-propyl]-5-benzloxy-piperidine-1-carboxylic acid tert-butyl ester Add acetic anhydride (0.04 mL, 0.46 mmol) to (2R, 5R)-2-[Amino-3-(3,5-difluoro-phenyl)-1-hydroxy-propyl]-5-benzyloxy-piperidine-1-carboxylic acid tert-butyl ester (0.20 g, 0.46 mmol) and triethylamine (0.06mL, 0.46 mmol) in 4 mL tetrahydro-furan at 0° C. and stir at room temperature for 1 hour. Add ethyl acetate and wash with water followed by saturated aqueous sodium chloride, dry over magnesium sulfate and concentrate. Subject the residue to silica gel flash chromatography, eluting with from 4:1 to 1:2 hexane:ethyl acetate to provide the desired compound as a mixture of 3 isomers (0.10 g, 45%). Separate the major diastereomer (0.06 g) using semi-preparative HPLC under acidic conditions with TFA 0.05% at pH 2.5.

Column: Kromasil C18 (21×100 mm, 5 um).

Gradient mode: from 50 to 90% CH3CN (TFA 0.05%) in 7 min.

Flow rate: 25 mL/min, 230 nm

MS(ESI): m/z=419 (M+H-Boc)$^+$

EXAMPLE 1

2-(S)-sec-Butylamino-N-[1-(S)-(3,5-difluorobenzyl)-2-(R)-hydroxy-2-(R)-piperidin-2-yl-ethyl]-6-(methanesulfonyl-methylamino)-isonicotinamide hydrochloride

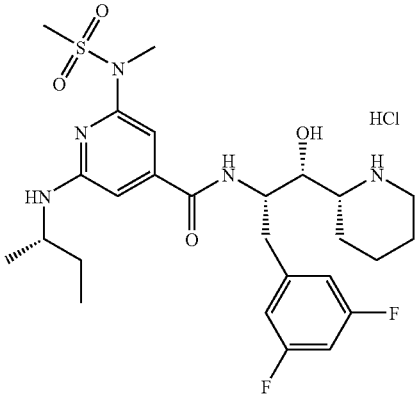

2-(R)-[2-(S)-{[2-(S)-sec-Butylamino-6-(methanesulfonyl-methylamino)-pyridine-4-carbonyl]-amino}-3-(3,5-difluorophenyl)-1-(S)-hydroxypropyl]-piperidine-1-carboxylic acid tert-butyl ester Cool a solution of 2-(R)-[2-(S)-amino-3-(3,5-difluorophenyl)-1-(S)-hydroxypropyl]-piperidine-1-carboxylic acid tert-butyl ester (0.096 g, 0.258 mmol) and 2-(S)-sec-butylamino-6-(methanesulfonyl-methylamino)-isonicotinic acid (0.0856 g, 0.284 mmol) in dichloromethane (2 mL) in an ice bath. Add 4-methylmorpholine (0.17 mL, 1.55 mmol) and n-propylphosphonic anhydride (0.227 mL, 0.387 mmol, 50 wt % in ethyl acetate). Stir 30 min, warm to room temperature and stir 30 min. Add water (3 mL) and ethyl acetate (20 mL). Wash with 5% aqueous citric acid, water, saturated aqueous sodium bicarbonate, saturated aqueous sodium chloride, dry (magnesium sulfate), concentrate and purify (silica gel chromatography, eluting with dichloromethane and ethyl acetate) to give the title compound as a solid (0.13 g, 78%).

MS (ES): m/z=654.4 [M+H].

2-(S)-sec-Butylamino-N-[1-(S)-(3,5-difluorobenzyl)-2-(R)-hydroxy-2-(R)-piperidin-2-yl-ethyl]-6-(methanesulfonyl-methylamino)-isonicotinamide hydrochloride Cool a solution of 2-(R)-[2-(S)-{[2-(S)-sec-butylamino-6-(methanesulfonyl-methylamino)-pyridine-4-carbonyl]-amino} 3-(3,5-difluorophenyl)-1-(S)-5 hydroxypropyl]-piperidine-1-carboxylic acid tert-butyl ester (0.082 g, 0.125 mmol) in dichloromethane (3 mL) in an ice bath. Add 4 M hydrogen chloride in 1,4-dioxane (6 mL), warm to room temperature, stir 1 h and concentrate to give the title compound as a foam (0.08 g, 100%).

MS (ES): m/z=554.2 [M+H].

The compound of EXAMPLE 2 may be prepared essentially as described in EXAMPLE 1.

| EX | Compound | MS [M + H] |
|---|---|---|
| 2 | N-(1-(S)-Benzyl-2-(R)-hydroxy-2-piperidin-2-(R)-ylethyl)-2-(S)-sec-butylamino-6-(methanesulfonyl-methylamino)-isonicotinamide hydrochloride | 518.2 |

EXAMPLE 3

N-[1-(S)-Benzyl-2-hydroxy-2-(4-methyl-3-oxopiperazin-2-yl)-ethyl]-2-(S)-sec-butylamino-6-(methylsulfonyl-methylamino)-isonicotinamide hydrochloride Stir overnight at room temperature a solution of 2-sec-butylamino-6-(methylsulfonyl-methylamino)-pyridine-4-carboxylic acid (115 mg, 0.38 mmol), 3-(2-amino-1-hydroxy-3-phenylpropyl)-1-methylpiperazin-2-one (101 mg, 0.38 mmol), 1-(3-dimethylaminopropyl)-3-ethylcarbodiimide hydrochloride (EDCI) (87.4 mg, 0.45 mmol), triethylamine (0.16 mL, 1.14 mmol) and 4-(dimethylamino)pyridine (4.6 mg, 0.04 mmol) in dichloromethane (10 mL). Dilute with more dichloromethane and wash with 5% aqueous sodium bicarbonate. Separate organic layer and wash with saturated aqueous sodium chloride, dry (magnesium sulfate concentrate and purify (silica gel chromatography, eluting with 9:1 dichloromethane:methanol) to give a white solid. Suspend the solid in 4 M HCl in 1,4-dioxane and stir for 10 min. Concentrate the solution to give the title compound as a yellow solid (Isomer 2, 47 mg, 21%).

MS (ES): m/z=547 [M+H].

The compounds of EXAMPLES 4-7 may be prepared essentially as described in EXAMPLE 3 beginning with the appropriate acids.

| EX | Compound | MS [M + H] |
|---|---|---|
| 4 | N-[1-(S)-Benzyl-2-hydroxy-2-(4-methyl-3-oxopiperazin-2-yl)-ethyl]-2-sec-butylamino-6-(methylsulfonyl-methylamino)-isonicotinamide hydrochloride Isomer 1 | 547 |
| 5 | N-[1-(S)-Benzyl-2-hydroxy-2-(4-methyl-3-oxopiperazin-2-yl)-ethyl]-2-sec-butylamino-6-(methylsulfonyl-methylamino)-isonicotinamide hydrochloride Isomer 3 | 547 |
| 6 | N-[1-(S)-Benzyl-2-hydroxy-2-(4-methyl-3-oxopiperazin-2-yl)-ethyl]-2-sec-butylamino-6-(methylsulfonyl-methylamino)-isonicotinamide hydrochloride Isomer 4 | 547 |
| 7 | N-[(1S,2R)-2-(R)-(4-Acetylpiperazin-2-yl)-1-benzyl-2-hydroxyethyl]-2-sec-butylamino-6-(methanesulfonyl-methylamino)-isonicotinamide hydrochloride | 561 |

EXAMPLE 8

2-(S)-(2-{[2-(S)-sec-Butylamino-6-(methanesulfonyl-methylamino)-pyridine-4-carbonyl]-amino}-1-(S)-hydroxy-3-phenylpropyl)-3-(S)-fluoropyrrolidine-1-carboxylic acid hydrochloride and 2-(S)-(2-{[2-(S)-sec-Butylamino-6-(methanesulfonyl-methylamino)-pyridine-4-carbonyl]-amino}-1-(S)-hydroxy-3-phenylpropyl)-3,3-difluoropyrrolidine-1-carboxylic acid hydrochloride

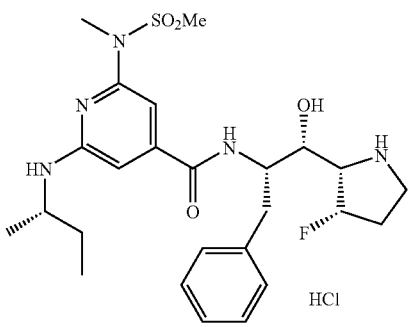

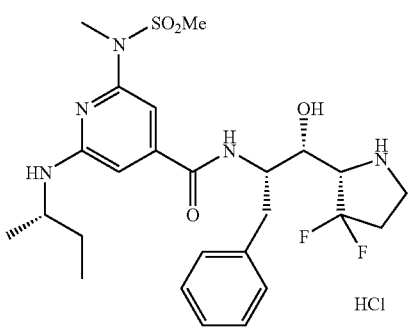

Dissolve a mixture of 2-(S)-(2-(S)-amino-1-(S)-hydroxy-3-phenylpropyl)-3-(S)-fluoropyrrolidine-1-carboxylic acid tert-butyl ester and 2-(S)-(2-(S)-amino-1-(S)-hydroxy-3-phenylpropyl)-3,3-difluoropyrrolidine-1-carboxylic acid tert-butyl ester (822 mg, 2.43 mmol) in dichloromethane (10 mL). Add 2-(S)-sec-butylamino-6-(methanesulfonyl-methylamino)-isonicotinic acid potassium salt (822 mg, 2.43 mmol), 1-(3-dimethylaminopropyl)-3-ethylcarbodiimide hydrochloride (EDCI) (512 mg, 2.67 mmol), 1-hydroxybenzotriazole hydrate (HOBt) (361 mg, 2.67 mmol) and diisopropylethylamine (0.93 mL, 5.34 mmol). Stir the reaction for 18 h at room temperature. Dilute the reaction with dichloromethane, wash with 5% aqueous potassium carbonate, dry (sodium sulfate), concentrate and purify (silica gel chromatography, eluting with 2:98 methanol:dichloromethane) to give the 2 separate title compounds (97 mg and 32 mg respectively).

MS (ES): m/z=622.3 [M+H], MS (ES): m/z=640.4 [M+H].

N-[1-Benzyl-2-(S)-(3-(S)-fluoropyrrolidin-2-yl)-2-(S)-hydroxyethyl]-2-(S)-sec-butylamino-6-(methanesulfonyl-methylamino)-isonicotinamide hydrochloride Add 4 M HCl in 1,4-dioxane (6 mL) to 2-(S)-(2-{[2-(S)-sec-butylamino-6-(methanesulfonyl-methylamino)-pyridine-4-carbonyl]-amino}-1-(S)-hydroxy-3-phenylpropyl)-3-(S)-fluoropyrrolidine-1-carboxylic acid tert-butyl ester (97 mg, 0.16 mmol) and stir at room temperature for 20 min. Concentrate the reaction to give the title compound. MS (ES): m/z=522.2 [M+H].

N-[1-Benzyl-2-(S)-(3,3-difluoropyrrolidin-2-yl)-2-(S)-hydroxyethyl]-2-(S)-sec-butylamino-6-(methanesulfonyl-methylamino)-isonicotinamide hydrochloride Add 4 M HCl in 1,4-dioxane (5 mL) to 2-(S)-(2-{[2-(S)-sec-butylamino-6-(methanesulfonyl-methylamino)-pyridine-4-carbonyl]-amino}-1-(S)-hydroxy-3-phenylpropyl)-3-difluoropyrrolidine-1-carboxylic acid tert-butyl ester (32 mg, 0.05 mmol) and stir at room temperature for 15 min. Concentrate the reaction to a residue and purify (silica gel chromatography, eluting with 4:96 methanol:dichloromethane) to give the title compound (18 mg, 62%).

MS (ES): m/z=540.3 [M+H].

The compounds of EXAMPLES 9-14 may be prepared essentially as described in EXAMPLE 8.

| EX | Compound | MS [M + H] |
|---|---|---|
| 9 | N-[1-(S)-Benzyl-2-(R)-hydroxy-2-(1,2,3,4-tetrahydro-isoquinolin-3-(R)-yl)-ethyl]-2-(S)-sec-butylamino-6-(methanesulfonyl-methylamino)-isonicotinamide hydrochloride | 666.3 |
| 10 | 2'-Fluorobiphenyl-3-carboxylic acid [1-(S)-benzyl-2-(R)-2-hydroxy(1,2,3,4-tetrahydroisoquinolin-3-(R)-yl)-ethyl]-amide hydrochloride | 481.2 |
| 11 | N-[1-Benzyl-2-(6-ethylpiperidin-2-yl)-2-hydroxyethyl]-2-sec-butyl-amino-6-(methanesulfonylmethylamino)-isonicotinamide hydrochloride-Isomer 2 | 546 |
| 12 | N-[1-Benzyl-2-(6-ethylpiperidin-2-yl)-2-hydroxyethyl]-2-sec-butyl-amino-6-(methanesulfonylmethylamino)-isonicotinamide hydrochloride-Isomer 1 | 546 |
| 13 | N-[(1S)-1-Benzyl-2-hydroxy-2-(6-methylpiperidin-2-yl)-ethyl]-2-sec-butylamino-6-(methanesulfonyl-methyl-amino)-isonicotinamide hydrochloride-Isomer 1 | 532 |
| 14 | N-[(1S)-1-Benzyl-2-hydroxy-2-(6-methylpiperidin-2-yl)-ethyl]-2-sec-butylamino-6-(methanesulfonyl-methylamino)-isonicotinamide hydrochloride-Isomer 2 | 532 |

EXAMPLE 15

N-[(1S,2R)-1-(3,5-Difluorobenzyl)-2-hydroxy-2-(R)-piperidin-2-ylethyl]-acetamide Dissolve (R)-2-[(1S,2S)-2-Acetylamino-3-(3,5-difluorophenyl)-1-hydroxypropyl]-piperidine-1-carboxylic acid tert-butyl ester (0.085 g, 0.21 mmol) in hydrogen chloride (4 M in 1,4-dioxane, 3 mL). Stir 1 h and concentrate to give the title compound as a foam 10 (0.077 g, 100%).

MS (ES): m/z=313.2 [M+H].

The compounds of EXAMPLE 16-20 may be prepared essentially as described in EXAMPLE 15.

| EX | Compound | MS [M + H] |
|---|---|---|
| 16 | N-((1S,2R)-1-Benzyl-2-hydroxy-2-(R)-piperidin-2-ylethyl)-acetamide hydrochloride | 277.2 |
| 17 | N-[2-(2-Azabicyclo[2.2.1]hept-3-yl)-1-benzyl-2-hydroxyethyl]-acetamide trifluoroacetate Isomer 1 | 289.2 |
| 18 | N-[2-(2-Azabicyclo[2.2.1]hept-3-yl)-1-benzyl-2-hydroxyethyl]-acetamide trifluoroacetate Isomer 2 | 289.2 |
| 19 | N-{(1S,2R)-2-[(5R,2R)-5-Benzyloxy-2-piperidin-2-yl]-1-(3,5-difluoro-benzyl)-2-hydroxy-ethyl}-acetamide hydrochloride | 419 |
| 20 | N-((1S,2R)-1-Benzyl-2-hydroxy-2-(R)-(4-(4-methylpentanoyl)piperazin-2-ylethyl)-acetamide dihydrochloride | 376 | pared as described in Preparation 5, Isomer 2) (120 mg, 0.45 mmol), 1-(3-dimethylaminopropyl)-3-ethylcarbodiimide hydrochloride (EDCI) (112 mg, 0.58 mmol), triethylamine (0.12 mL, 0.9 mmol), dimethylaminopyridine (5.5 mg, 0.04 mmol) and 1-hydroxybenzotriazole hydrate (HOBt) (79 mg, 0.58 mmol) in dichloromethane (10 mL/mmol). Dilute with more dichloromethane and wash with 5% aqueous sodium bicarbonate solution, saturated aqueous sodium chloride. Dry (magnesium sulfate), concentrate and purify (silica gel chromatography, eluting with 9:1 dichloromethane:methanol) to provide a white solid. Suspend the solid in 4 M HCl in 1,4-dioxane and stir for 10 min and concentrate the solution to give the title compound as a white solid (15 mg, 10%).

The compounds of EXAMPLES 22-25 may be prepared essentially as described in EXAMPLE 21.

| EX | Compound | MS [M + H] |
|---|---|---|
| 22 | N-[(1S)-1-Benzyl-2-(6-ethylpiperidin-2-yl)-2-hydroxyethyl]-acetamide hydrochloride Isomer 1 | 305 |
| 23 | N-[(1S)-1-Benzyl-2-(6-ethylpiperidin-2-yl)-2-hydroxyethyl]-acetamide hydrochloride Isomer 2 | 305 |
| 24 | N-[(1S)-1-Benzyl-2-hydroxy-2-(6-methylpiperidin-2-yl)-ethyl]-acetamide hydrochloride Isomer 1 | 291 |
| 25 | N-[(1S)-1-Benzyl-2-hydroxy-2-(6-methylpiperidin-2-yl)-ethyl]-acetamide hydrochloride Isomer 2 | 291 |

EXAMPLE 21

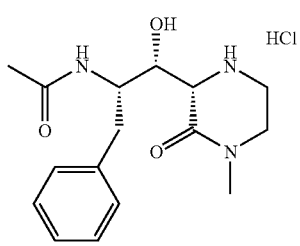

N-[1(S),2(S)-Benzyl-2-hydroxy-2-(S)-(4-methyl-3-oxopiperazin-2-yl)-ethyl]-acetamide hydrochloride Stir overnight at room temperature under a nitrogen atmosphere a solution of acetic acid (25 μl, 0.45), 3-(2-(S)-amino-1-hydroxy-3-phenylpropyl)-1-methylpiperazin-2-one (pre-

EXAMPLE 26

N-{2-[2-Aza-(1R,4R)bicyclo[2.2.2]oct-3R-yl]-1S-benzyl-2-(S)-hydroxyethyl}-2-(S)-sec-butylamino-6-(methanesulfonyl-methylamino)-isonicotinamide trifluoroacetate

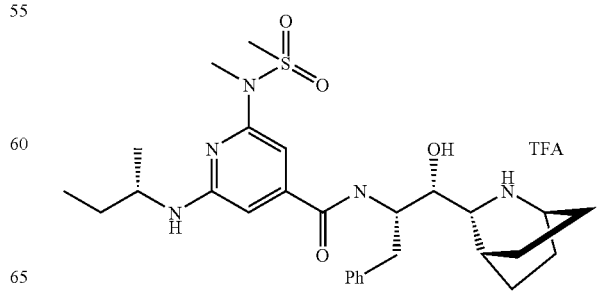

3-(R)-(2S)-{[2-(S)-sec-Butylamino-6-(methanesulfonyl-methylamino)-pyridine-4-carbonyl]-amino}-1-(S)-hydroxy-3-phenylpropyl)-2-aza-(1R44R)-bicyclo[2.2.2]octane-2-carboxylic acid tert-butyl ester Dissolve 2-(S)-sec-butylamino-6-(methanesulfonyl-methylamino)-isonicotinate potassium salt (47 mg, 0.138 mmol) in THF (2 mL) at room temperature. Add 1-hydroxy-7-azabenzotriazole (HOAt) (0.5 M in DMF, 0.28 mL,) and 1-(3-dimethylaminopropyl)-3-ethylcarbodiimide hydrochloride (EDCI) (27 mg, 0.138 mmol) to the solution. After 10 min add 3-(R)-[2-(S)-amino-1-(S)-hydroxy-3-phenylpropyl]-2-aza-(1R,4R)-bicyclo[2.2.2]octane-2-carboxylic acid tert-butyl ester (50 mg, 0.14 mmol) to the reaction and stir at room temperature overnight. Quench the reaction by saturated aqueous sodium bicarbonate solution and dilute with dichloromethane. Extract the organic layer and wash with saturated aqueous sodium chloride solution, dry (magnesium sulfate), filter and concentrate to give the crude title compound which is used in the next step without further purification.

N-{2-[2-Aza-(1R,4R)bicyclo[2.2.2]oct-3-(R)-yl]-1-(S)-benzyl-2-(S)-hydroxyethyl}-2-(S)-sec-butylamino-6-(methanesulfonyl-methylamino)-isonicotinamide trifluoroacetate Dissolve 3-(R)-(2-(S)-{[2-(S)-sec-butylamino-6-(methanesulfonyl-methylamino)-pyridine-4-carbonyl]-amino}-1-(S)-hydroxy-3-phenylpropyl)-2-aza-(1R,4R)-bicyclo[2.2.2]octane-2-carboxylic acid tert-butyl ester (87 mg, 0.14 mmol) in THF (3 mL) at 0° C. and add dropwise 4 N HCl in 1,4-dioxane (0.17 mL, 0.67 mmol). Stir the mixture from 0° C. to room temperature overnight. Concentrate most solvent and excess HCl and purify (reverse phase HPLC, gradient of water and acetonitrile with 1% trifluoroacetic acid buffer) to give the title compound.

MS (ES): n/z=544.3 [M+H], MS (ES): m/z=656.3 [M−H·TFA].

The compounds of EXAMPLE 27-29 may be prepared essentially as described in EXAMPLE 26.

| EX | Compound | MS [M + H] |
|---|---|---|
| 27 | N-{2-[2-Aza-(1R,4R)bicyclo[2.2.2]oct-3-(R)-yl]-1-(S)-benzyl-2-(R)-hydroxyethyl}-2-(S)-sec-butylamino-6-(methanesulfonyl-methylamino)-isonicotinamide trifluoroacetate | 544.3 |
| 28 | N-[2-(2-Aza-bicyclo[2.2.1]hept-3-yl)-1-benzyl-2-hydroxyethyl]-2-sec-butylamino-6-(methanesulfonyl-methylamino)-isonicotinamide trifluoroacetate Isomer 1 | 530.3 |
| 29 | N-[2-(2-Aza-bicyclo[2.2.1]hept-3-yl)-1-benzyl-2-hydroxyethyl]-2-sec-butylamino-6-(methanesulfonyl-methylamino)-isonicotinamide trifluoroacetate Isomer 2 | 530.3 |

EXAMPLE 30

N-((1S,2R)-2-Homopiperidin-2-yl-1-benzyl-2-hydroxy-ethyl)-2-((S)-sec-butylamino)-6-(methanesulfonyl-methyl-amino)-isonicotinamide hydrochloride Isomer 1

Dissolve 2-((S)-sec-butylamino)-6-(ethyl-methyl-amino)-isonicotinic acid (2.5 mg, 0.007 mmol) in a 1:1:5 mixture of tert-butanol:acetonitrile:dichloromethane (0.5 ml). Add 1-hydroxybenzotriazole (4.2 mg, 0.01 mmol) followed by 1-(3-dimethylamino-propyl)-3-ethylcarbodiimide hydrochloride (1.92 mg, 2.05 mmol). Add dropwise to a solution of 1-(S)-homopiperidin-2-yl-2-(R)-dibenzylamino-3-phenyl-propan-1-ol (Isomer I) (7 mg, 0.03 mmol) and triethylamine (12 ul, 0.09 mmol) in the solvent mixture (0.5 ml) with rapid stirring over 10 minutes at room temperature. Add 2 mL dichloromethane, extract with water (2 ml), saturated aqueous sodium bicarbonate (3 ml), saturated aqueous sodium chloride (3 ml), and dry (sodium sulfate), filter, and concentrate under reduced pressure. Purify using HPLC-MS to isolate product (19×300 mm, 7 μm, C-18 column;

flow rate=20 mL/min; mobile phase gradient 5%-95% over 26 minutes; Solvent A: acetonitrile; Solvent B: 0.1% trifluoroacetic acid in water). Add 1 mL of ethyl acetate and 0.01 ml of 1 N HCl in diethyl ether. Evaporate the solvent to obtain the product (4 mg, 0.83 mmol, 95% yield). MS (ESI) m/z 532.3 (M+H).

The compound of EXAMPLE 31 may be prepared essentially as described in EXAMPLE 30.

| EX | Compound | MS [M + H] |
|---|---|---|
| 31 | N-((1S,2R)-2-Homopiperidin-2-yl-1-benzyl-2-hydroxy-ethyl)-2-((S)-sec-butyl-amino)-6-(methanesulfonyl-methyl-amino)-isonicotinamide hydrochloride Isomer 2 | 532.3 |

EXAMPLE 32

N-[(1S,2R)-2-(R)-(4-Acetylpiperazin-2-yl)-1-benzyl-2-hydroxyethyl]-acetamide

Dissolve 2-(R)-[(2-(R)-amino-1-(S)-hydroxy-3-phenyl-propyl)]-piperazine-1-carboxylic acid tert-butyl ester (106 mg, 0.3 mmol) in dichloromethane (6 mL)and add 1-acetyl-imidazole (76 mg, 0.69 mmol) in one portion, followed by triethylamine (0.19 mL, 1.36 mmol). Stir at room temperature for 48 h, dilute with dichloromethane, wash with 5% aqueous sodium bicarbonate solution, saturated aqueous sodium chloride solution, dry (magnesium sulfate), concentrate and purify (silica gel cartridge (5 g), eluting with 9:1 dichloromethane:methanol) to obtain a colorless oil (45 mg). Dissolve this oil in of 4 N HCl in 1,4-dioxane (0.5 mL), stir for 1 h at room temperature and concentrate to give the title compound as a white solid (38 mg, 34% yield).

MS (ES): m/z=320 [M+H].

The compounds of EXAMPLES 33-41 may be prepared essentially as described in EXAMPLE 32.

| EX | Compound | MS [M + H] |
|---|---|---|
| 33 | N-{(1S,2R)-1-Benzyl-2-hydroxy-2-(R)-[4-(3-methyl-butyl)-piperazin-2-yl]-ethyl}-acetamide hydrochloride | 348 |
| 34 | N-{(1S,2R)-1-Benzyl-2-hydroxy-2-(R)-[4-(5-methyl-hexanoyl)-piperazin-2-yl]-ethyl}-acetamide dihydrochloride | 390 |
| 35 | N-{(1S,2R)-1-Benzyl-2-hydroxy-2-(R)-[4-(2-propylpentanoyl)-piperazin-2-yl]-ethyl}-acetamide dihydrochloride | 404 |
| 36 | N-{(1S,2R)-1-Benzyl-2-hydroxy-2-(R)-[4-(3-methoxybenzoyl)-piperazin-2-yl]-ethyl}-acetamide dihydrochloride | 412 |
| 37 | N-{(1S,2R)-1-Benzyl-2-hydroxy-2-(R)-[4-(5-cyclohexylpentanoyl)-piperazin-2-yl]-ethyl}-acetamide dihydrochloride | 444 |
| 38 | N-{(1S,2R)-1-(3,5-Difluoro-benzyl)-2-hydroxy-2-(S)-[4-(4-methoxy-phenyl)-3-oxo-piperazin-2-yl]-ethyl}-acetamide hydrochloride | 470 |
| 39 | N-{(1S,2R)-1-Benzyl-2-hydroxy-2-(S)-[4-(4-methoxy-phenyl)-3-oxo-piperazin-2-yl]-ethyl}-acetamide hydrochloride | 398 |
| 40 | N-{(1S,2R)-1-(3,5-Difluoro-benzyl-2-hydroxy-2-(S)-[4-(2-(3-methyl-butyl-phenyl)-3-oxo-piperazin-2-yl]-ethyl}-acetamide hydrochloride | 474 |
| 41 | N-{(1S,2R)-1-(3,5-Difluoro-benzyl)-2-hydroxy-2-(R)-[1,2,3,4-tetrahydro-isoquinolin-3-yl]-ethyl}-acetamide hydrochloride | 361 |

EXAMPLE 42

N-{(1S,2S)-1-Benzyl-2-hydroxy-2-(S)-[4-propyl-3-oxopiperazin-2-yl]-ethyl}-acetamide dihydrochloride Dissolve 3-(2-(S)-amino-1-(S)-hydroxy-3-(S)-phenylpropyl)-1-propylpiperazin-2-one (127 mg, 0.43 mmol) in dry dichloromethane (4 mL) and add N-acetyl-N-(2-trifluoromethylphenyl)-acetamide (116 mg, 0.48 mmol). Stir at room temperature for two days and purify (silica gel chromatography, eluting with 9:1 dichloromethane:methanol) to give the free amine compound (37 mg, 26% yield). Stir with of HCl (0.1 mL, 4 N in 1,4-dioxane) for 10 min and concentrate to give the title compound as a white solid (39 mg, 95% yield).

MS (ES): m/z=334 [M+H].

The compound of EXAMPLE 43 may be prepared essentially as described in EXAMPLE 42.

| EX | Compound | MS [M + H] |
|---|---|---|
| 43 | (1S, 2S, 2'S) N-{1-Benzyl-2-hydroxy-2-[4-(4-methoxybenzyl)-3-oxopiperazin-2-yl]-ethyl}-acetamide dihydrochloride | 412 |

EXAMPLE 44

N-[1-(S)-Benzyl-2-(S)-hydroxy-2-(S)-(4-(4-methoxybenzyl)-3-oxopiperazin-2-yl)ethyl]-2-(S)-sec-butylamino-6-(methylsulfonyl-methylamino)-isonicotinamide hydrochloride Stir overnight at room temperature under nitrogen a solution of 2-(S)-sec-butylamino-6-(methylsulfonyl-methylamino)pyridine-4-carboxylic acid (90 mg, 0.29 mmol), (2-(S)-amino-1-(S)-hydroxy-3-(S)-phenylpropyl)1-(-methoxybenzyl)-piperazin-2-one (110 mg, 0.29 mmol), 1-(3-dimethylaminopropyl)-3-ethylcarbodiimide hydrochloride (EDCI) (66.7 mg, 0.34 mmol), triethylamine (0.12 mL, 0.87 mmol) and dimethylaminopyridine (3.5 mg, 0.029 mmol) in dry dichloromethane (10 mL/mmol). Dilute with more dichloromethane and wash with 5% aqueous sodium bicarbonate solution. Separate layers, wash with saturated aqueous sodium chloride solution, dry (magnesium sulfate), concentrate and purify (silica gel chromatography, eluting with 100% dichloromethane to 9:1 dichloromethane:methanol) to give a white solid. Suspend the solid in HCl (4 M in 1,4-dioxane) and stir for 10 min. Concentrate the solution to give the title compound as a yellow solid (Isomer-1) (28 mg, 14%).

MS (ES): m/z=653 [M+H].

Follow same procedure for Isomer-2 and 4:

MS (ES): m/z=653 [M+H] (Isomer-2)

MS (ES): m/z=653 [M+H] (Isomer-4)

EXAMPLE 45

N-[(1S,2S)-1-Benzyl-2-hydroxy-2-(S)-(4-propyl-3-oxopiperazin-2-yl)-ethyl]-2-(S)-sec-butylamino-6-(methylsulfonyl-methylamino)-isonicotinamide hydrochloride Stir overnight at room temperature under nitrogen a solution of 2-(S)-sec-butylamino-6-(methylsulfonyl-methylamino)-pyridine-4-carboxylic acid (97 mg, 0.32 mmol), (2-(S)-amino-1-(S)-hydroxy-3-(S)-phenylpropyl)-1-propylpiperazin-2-one (94 mg, 0.32 mmol), 1-(3-dimethylaminopropyl)-3-ethylcarbodiimide hydrochloride (EDCI) (73.6 mg, 0.38 mmol), triethylamine (0.13 mL, 0.96 mmol) and dimethylaminopyridine (3.9 mg, 0.032 mmol) in dry dichloromethane (10 mL/mmol). Dilute with dichloromethane and wash with 5% aqueous sodium bicarbonate. Separate layers and wash with saturated aqueous sodium chloride solution, dry (magnesium sulfate), concentrate and purify (silica gel chromatography, eluting with a gradient of 100% dichloromethane to 9:1 dichloromethane:methanol) to give a white solid. Suspend the solid in HCl (4 M in 1,4-dioxane) and stir for 10 min. Concentrate the solution to give the title compound as a yellow solid (Isomer-2) (58 mg, 30%).

MS (ES): m/z 575 [M+H].

EXAMPLE 46

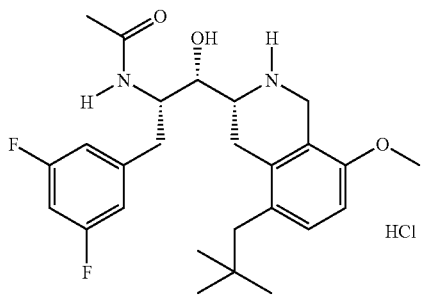

N-(1S,2R)-1-(3,5-Difluorobenzyl)-2-[3(R)-5-(2,2-dimethylpropyl)-8-methoxy-1,2,3,4-tetrahydroisoquinolin-3-yl]-2-hydroxyethylacetamide hydrochloride tert-Butyl 3(R)-[(1S,2S)-2-(Acetylamino)-3-(3,5-difluorophenyl)-1-hydroxypropyl]-5-bromo-8-methoxy-3,4-dihydroisoquinoline-2(1H)-carboxylate Slurry tert-butyl (3R)-3-[(1S,2S)-2-amino-3-(3,5-difluorophenyl)-1-hydroxy-propyl]-5-bromo-8-methoxy-3,4-dihydroisoquinoline-2(1H)-carboxylate (59.4 mg, 0.000113 mol) in tetrahydrofuran (1.00 mL). Add triethylamine (15.7 uL, 0.000113 mol) and acetic anhydride (10.6 uL, 0.000113 mol) and stir for 45 minutes. Dilute dichloro-methane (25 mL) and wash with water (1×10 mL), 0.1N HCl (1×10 mL), saturated aqueous sodium bicarbonate (1×10 mL), saturated aqueous sodium chloride (1×10 mL) and dry over magnesium sulfate. Concentrate the filtrate to give the desired product (57.9, 88%) as a white solid.
MS (ES): m/z=571 [M+2].

tert-Butyl 3(R)-[(1S,2S)-2-(Acetylamino)-3-(3,5-difluorophenyl)-1-hydroxypropyl]-5-(2,2-dimethylpropyl)-8-methoxy-3,4-dihydroisoquinoline-2(1H)-carboxylate Dissolve tert-butyl 3(R)-[(1S,2S)-2-(acetylamino)-3-(3,5-difluorophenyl)-1-hydroxypropyl]-5-bromo-8-methoxy-3,4-dihydroisoquinoline-2(1H)-carboxylate (46.0 mg, 0.0808 mmol) in tetrahydrofuran (1.00 mL) in a sealed tube flushed with nitrogen. Add [1,1'-bis(diphenylphosphino)ferrocene]dichloropalladium(II) complex with dichloromethane (1:1) (3.3 mg, 0.0040 mmol) and 0.500 M of neopentyl zinc iodide in tetrahydrofuran (0.808 mL) dropwise at room temperature. Stir the resulting green solution at room temperature for six hours. Heat to 50° C. for three days. Add saturated ammonium chloride solution (2 mL) and dilute with ethyl acetate (30 mL). Add water (10 mL) and separate the layers. Extract the aqueous layer (1×30 mL) with ethyl acetate. Combine the organic layers and dry over magnesium sulfate. Purify (Biotage medium pressure chormatography eluting with 1.5% methanol:dichloromethane) to give desired product (21.8 mg, 46%) as an off-white foam.
MS(ES): m/z=561 [M+H].

Deprotection

Dissolve tert-butyl (3R)-3-[(1 S,2S)-2-(acetylamino)-3-(3,5-difluorophenyl)-1-hydroxypropyl]-5-(2,2-dimethylpropyl)-8-methoxy-3,4-dihydroisoquinoline-2(1H)-carboxylate (21.8 mg, 0.0389 mmol) in 4.0 M of hydrogen chloride in 1,4-dioxane (2.00 mL). Stir for 16 hours. Concentrate to dryness and place under high vacuum to obtain desired product.
MS(ES): 7m/z=461 [M+H].

The compound of EXAMPLE 47 may be prepared following the acetylation and deprotection steps essentially as described in EXAMPLE 46, substituting trifluoroacetic acid for hydrogen chloride.

| EX | Compound | MS [M + H] |
|---|---|---|
| 47 | 3-(R)-[2-(R,S)-Acetylamino-3-(3,5-difluorophenyl)-1-(S)-hydroxyprop-yl]-piperazine-1-carboxylic acid benzyl ester trifluoroacetate | 448.2 |

EXAMPLE 48

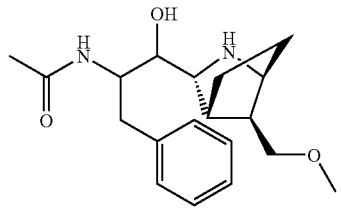

N-[1-Benzyl-2-hydroxy-2-(7-methoxymethyl-2-azabicyclo[2.2.1]hept-3-yl)-ethyl]-acetamide hydrochloride (Isomer 1)

3-(2-Acetylamino-1-hydroxy-3-phenylpropyl)-7-methoxymethyl-2-azabicyclo[2.2.1]heptane-2-carboxylic acid tert-butyl ester (Isomer 1 and Isomer 2)

Dissolve 3-(2-amino-1-hydroxy-3-phenylpropyl)-7-methoxymethyl-2-azabicyclo[2.2.1]heptane-2-carboxylic acid tert-butyl ester (0.243 mg, 0.622 mmol) in tetrahydrofuran (3 mL) and cool the mixture in an ice bath. Add triethylamine (0.091 mL, 0.653 mmol) and acetic anhydride (0.059 mL, 0.622 mmol) in tetrahydrofuran (2 mL). Stir the mixture at room temperature for 1 h. Add dichloromethane (30 mL) and water (10 mL). Separate layers and wash the organic layer with 0.5 N HCl, saturated aqueous sodium bicarbonate, dry (magnesium sulfate), concentrate and purify (silica gel chromatography, eluting with 3-5% isopropyl alcohol/47-45% dichlomethane in 50% hexanes) to give the title compound Isomer-1 (0.044 g, 16%) and Isomer-2 (0.077 mg, 29%).
MS (ES): m/z=433.3 [M+H].

N-[1-Benzyl-2-hydroxy-2-(7-methoxymethyl-2-azabicyclo[2,2,1]hept-3-yl)-ethyl]-acetamide hydrochloride (Isomer-1)

Cool a solution of 3-(2-acetylamino-1-hydroxy-3-phenylpropyl)-7-methoxymethyl-2-azabicyclo[2.2.1]heptane-2-carboxylic acid tert-butyl ester (Isomer 1) (0.044 g, 0.102 mmol) in tetrahydrofuran (1 mL) and add a solution of hydrochloric acid (2.0 mL, 4 M in 1,4-dioxane). Stir the mixture for 5 h at room temperature, concentrate and purify (silica gel chromatography, eluting with 2 M ammonia in 5:95 to 10:90 methanol:dichloromethane) to give the title compound after treatment with the same equivalent of hydrochloric acid in diethyl ether (16 mg, 43%).

MS (ES): m/z=333.3 [M+H].

The compounds of EXAMPLES 49-54 may be prepared essentially as described in EXAMPLE 48. EXAMPLE 54 is purified using reverse phase HPLC, eluting with 0.1% trifluoroacetic acid in acetonitrile/water.

| EX | Compound | MS [M + H] |
|---|---|---|
| 49 | N-[1-Benzyl-2-hydroxy-2-(7-methoxymethyl-2-azabicyclo[2.2.1]hept-3-yl)-ethyl]-acetamide hydrochloride (Isomer 2) | 333.3 |
| 50 | N-[1-(3,5-Difluorobenzyl)-2-hydroxy-2-(7-methoxymethyl-2-azabicyclo[2.2.1]hept-3-yl)-ethyl]-acetamide hydrochloride (Isomer 1) | 369.3 |
| 51 | N-[1-(3,5-Difluoro-benzyl)-2-hydroxy-2-(7-methoxymethyl-2-azabicyclo[2.2.1]hept-3-yl)-ethyl]-acetamide hydrochloride (Isomer 2) | 369.3 |
| 52 | N-{1-(3,5-Difluorobenzyl)-2-hydroxy-2-[7-(3-methylbutyl)-2-azabicyclo[2.2.1]hept-3-yl]-ethyl}-acetamide hydrochloride (Isomer 1) | 395.3 |
| 53 | N-{1-(3,5-Difluorobenzyl)-2-hydroxy-2-[7-(3-methylbutyl)-2-azabicyclo[2.2.1]hept-3-yl]-ethyl}-acetamide hydrochloride (Isomer 2) | 395.4 |
| 54 | N-[1-Benzyl-2-hydroxy-2-(7-isopropyl-5-methyl-2-azabicyclo[2.2.2]oct-3-yl)-ethyl]-acetamide trifluoroacetate | 359.3 |

EXAMPLE 55

N-(1S, 2R)-{1-(3,5-Difluoro-benzyl)-2-hydroxy-2-[(5R,2R)-5-(3-methyl-butoxy)-piperidin-2-yl]-ethyl}-acetamide hydrochloride (2R, 5R)-5-Benzyloxymethoxy-piperidine-1,2-dicarboxylic acid 1-tert-butyl ester 2-ethyl Add diisopropylethylamine (12.1 mL, 69.51 mmol) and 60% benzylchloromethyl ether (12.1 mL, 52.13 mmol) to (2R, 5R)-5-hydroxy-piperidine-1,2-dicarboxylic acid 1-tert-butyl ester 2-ethyl ester in 140 mL dichloromethane and reflux for 3 h. Cool to room temperature, add ethyl acetate and wash with 5% aqueous citric acid, saturated aqueous sodium bicarbonate and saturated aqueous sodium chloride, dry over magnesium sulfate and concentrate.

MS(ESI): m/z=294 (M+H-Boc)+

(2R, 5R)-5-Benzyloxymethoxy-2-hydroxymethyl-piperidine-1-carboxylic acid 1-tert-butyl ester Add lithium borohydride (1.13 g, 52.12 mmol) to (2R, 5R)-5-Benzyloxymethoxy-piperidine-1,2-dicarboxylic acid 1-tert-butyl ester 2-ethyl (18.0 g, 34.75 mmol) in 140 mL diethylether at room temperature and stir overnight. Quench with saturated ammonium chloride and extract with diethylether. Combine the organic layers and dry over magnesium sulfate and concentrate. Subject the residue to silica gel flash chromatography, eluting with from 2:1 to 1:2 hexane: ethyl acetate to provide the desired compound (8.40 g, 60% overall yield).

MS(ESI): m/z=252 (M+H-Boc)+ and 374 (M+Na)+

(2R, 5R)-5-Benzyloxymethoxy-2-formyl-piperidine-1-carboxylic acid 1-tert-butyl ester Add sulfur trioxide pyridine complex (7.6 g, 47.8 mmol) in dimethylsulfoxide (27.0 mL, 382.4 mmol) to (2R, 5R)-5-Benzyloxymethoxy-2-hydroxymethyl-piperidine-1-carboxylic acid 1-tert-butyl ester (8.4 g, 23.90 mmol) in triethylamine (20.0 mL, 143.4 mmol) at 10° C. and stir at room temperature for 30 minutes. Add water and extract with diethyl ether. Combine the organic layers, wash with 5% citric acid followed by saturated aqueous sodium chloride. Dry over magnesium sulfate and concentrate to provide the desired compound. (8.0 g crude)

(2R, 5R)-5-Benzyloxymethoxy-2-[3-(3,5-difluoro-phenyl)-1-hydroxy-2-nitro-propyl]-piperidine-1-carboxylic acid tert-butyl ester Add tetrabutylammonium fluoride (12.0 mL, 11.9 mmol, 1.0 M in tetrahydro-furan) to (2R, 5R)-5-Benzyloxymethoxy-2-formyl-piperidine-1-carboxylic acid 1-tert-butyl ester (8.0 g, 23.90 mmol) and 1,3-difluoro-5-(2-nitro-ethyl)-benzene (4.92 g, 26.30 mmol) in 150 mL tetrahydrofuran at room temperature, stir overnight and concentrate. Subject to silica gel chromatography, eluting with 100% hexane to 90:10 hexane: ethyl acetate) to provide the desired compound as a mixture of 3 isomers (8.0 g, 62% overall yield).

MS(ESI): m/z=537 (M+H)+

(2R, 5R)-[2-Acetylamino-3-(3,5-difluoro-phenyl)-1-hydroxy-propyl]-5-Benzyloxymeth-oxypiperidine-1-carboxylic acid tert-butyl ester Add nickel (II) chloride (1.4 g, 11.18 mmol) and sodium borohydride (1.4 g, 32.27 mmol) to (2R, 5R)-5-Benzyloxymethoxy-2-[3-(3,5-difluoro-phenyl)-1-hydroxy-2-nitro-propyl]-piperidine-1-carboxylic acid tert-butyl ester (4.0 g, 7.45 mmol) in 150 mL methanol at room temperature and stir until all starting material is consumed. Add acetic anhydride and stir at room temperature for 30 minutes and concentrate. Quench with water, add ethyl acetate and filter through a pad of filtering agent. Wash the organic layer saturated aqueous sodium chloride. Dry the organic layer over magnesium sulfate and concentrate. Subject the residue to silica gel chromatography, eluting with 70:30 to 100% hexane: ethyl acetate) to provide the desired compound as a mixture of 3 isomers (2.2 g, 54%).

MS(ESI): m/z=549 (M+H)+

(2R, 5R)-2-{(4S, 5S)-3-Acetyl-4-[3,5-difluoro-benzyl]-2,2-dimethyl-oxazolidin-5-yl}-5-Benzyloxymethoxy-piperidine-1-carboxylic acid tert-butyl Add pyridinium p-toluenesulfonate (PPTS) (0.18 g, 0.72 mmol) and 2-methoxypropene (6.9 mL, 71.80 mmol) to (2R, 5R)-[2-Acetylamino-3-(3,5-difluoro-phenyl)-1-hydroxy-propyl]-5-Benzyloxymethoxy-piperidine-1-carboxylic acid tert-butyl ester (3.94 g, 7.18 mmol) in 50 mL dichloromethane and 50 mL acetone at room temperature, stir overnight and concentrate. Subject residue to silica gel chromatography, eluting with 90:10 to 50:50 hexane: ethyl acetate) to provide the desired compound as a white solid (2.50 g, 60%).

MS(ESI): m/z=589 (M+H)$^+$ (2R, 5R)-2{(4S, 5S)-3-Acetyl-4-[3,5-difluoro-benzyl]-2,2-dimethyl-oxazolidin-5-yl}-5-hydroxy-piperidine-1-carboxylic acid tert-butyl ester Stir (21R, 5R)-2-{(4S, 5S)-3-Acetyl-4-[3,5-difluoro-benzyl]-2,2-dimethyl-oxazolidin-5-yl}-5-Benzyloxymethoxy-piperidine-1-carboxylic acid tert-butyl ester (2.50 g, 4.25 mmol) and 10% Palladium on carbon (0.45 g, 0.42 mmol) in 50 mL methanol under a balloon of hydrogen at room temperature until all starting material is consumed. Filter the suspension through a pad of filtering agent and wash with methanol. Concentrate under reduced pressure to give the desired compound (1.9 g, 95%).

MS(ESI): m/z=469 (M+H)$^+$ (2R, 5R)-2-{(4S, 5S)-3-Acetyl-4-[3,5-difluoro-benzyl]-2,2-dimethyl-oxazolidin-5-yl}-5-(3-methyl-butoxy)-piperidine-1-carboxylic acid tert-butyl ester Add (2R, 5R)-2-{(4S, 5S)-3-Acetyl-4-[3,5-difluoro-benzyl]-2,2-dimethyl-oxazolidin-5-yl}-5-hydroxy-piperidine-1-carboxylic acid tert-butyl ester (0.06 g, 0.13 mmol) in 1.0 mL dimethylformamide to 60% sodium hydride (0.006 g, 0.15 mmol) in 0.5 mL dimethylformamide at room temperature and stir for 15 minutes. Add 1-bromo-3-methylbutane (0.023 mL, 0.19 mmol) and stir at room temperature overnight. Add 60% sodium hydride (0.006 g, 0.15 mmol) and 1-bromo-3-methylbutane (0.023 mL, 0.19 mmol) and stir for 4 h at room temperature. Quench with water and extract with diethyl ether, dry the organic layer over magnesium sulfate and concentrate. Subject the residue to silica gel chromatography, eluting with 100% dichloromethane to 90:10 dichloromethane: ethyl acetate to provide the desired compound (0.05 g, 75%).

MS(ESI): m/z=539 (M+H)$^+$

N-(1S,2R)-{1-(3,5-Difluoro-benzyl)-2-hydroxy-2-[(5R,2R)-5-(3-methyl-butoxy)-piperidin-2-yl]-ethyl}-acetamide hydrochloride Add 4.0 M hydrogen chloride in dioxane (0.46 mL, 1.86 mmoles) to (2R, 5R)-2-{(4S, 5S)-3-Acetyl-4-[3,5-difluoro-benzyl]-2,2-dimethyl-oxazolidin-5-yl}-5-(3-methyl-butoxy)-piperidine-1-carboxylic acid tert-butyl ester (0.05 g, 0.09 mmol) and stir until all starting material is consumed. Concentrate to afford the title product as a white solid (0.04 g, 92%).

MS(ESI): m/z=399 (M+H)$^+$

The compounds of EXAMPLES 56-83 may be prepared essentially as described in EXAMPLE 55 using (2R, 5R)-2-{(4S, 5S)-3-Acetyl-4-[3,5-difluoro-benzyl]-2,2-dimethyl-oxazolidin-5-yl}-5-hydroxy-piperidine-1-carboxylic acid tert-butyl ester and the corresponding alkylating agent.

| EX | COMPOUND | MS(ES) (M + H) |
|---|---|---|
| 56 | N-(1S,2R)-{2-[(5R,2R)-5-Butoxy-piperidin-2-yl]-1-(3,5-Difluoro-benzyl)-2-hydroxy-ethyl}-acetamide hydrochloride | 385 |
| 57 | N-(1S,2R)-{2-[(5R,2R)-5-Allyloxy-piperidin-2-yl]-1-(3,5-Difluoro-benzyl)-2-hydroxy-ethyl}-acetamide hydrochloride | 369 |
| 58 | N-(1S,2R)-{1-(3,5-fluoro-benzyl)-2-hydroxy-2-[(5R,2R)-5-isobutoxy-piperidin-2-yl]-ethyl}-acetamide hydrochloride | 385 |
| 59 | N-(1S,2R)-{1-(3,5-Difluoro-benzyl)-2-[(5R,2R)-5-hexyloxy-piperidin-2-yl]-2-hydroxy-ethyl}-acetamide hydrochloride | 413 |
| 60 | N-(1S,2R)-{1-(3,5-Difluoro-benzyl)-2-[(5R,2R)-5-((3-chlorobenzothien-2-yl)methoxy)-piperidin-2-yl]-2-hydroxy-ethyl}-acetamide hydrochloride | 509 |
| 61 | N-(1S,2R)-{1-(3,5-Difluoro-benzyl)-2-hydroxy-2-[(5R,2R)-5-pent-4-enyloxy-piperidin-2-yl]-ethyl}-acetamide hydrochloride | 397 |
| 62 | N-(1S,2R)-{1-(3,5-Difluoro-benzyl)-2-hydroxy-2-[(5R,2R)-5-((5-chlorobenzothien-2-yl)methoxy)-piperidin-2-yl]-2-hydroxy-ethyl}-acetamide hydrochloride | 509 |
| 63 | N-(1S,2R)-{1-(3,5-Difluoro-benzyl)-2-hydroxy-2-[(5R,2R)-5-((5-chlorothien-2-yl)methoxy)-piperidin-2-yl]-2-hydroxyethyl}acetamide hydrochloride | 459 |
| 64 | N-(1S,2R)-{1-(3,5-Difluoro-benzyl)-2-hydroxy-2-](5R,2R)-5-(2-ethylbutyloxy)-piperidin-2-yl]-ethyl}-acetamide hydrochloride | 413 |
| 65 | N-(1S,2R)-{1-(3,5-Difluoro-benzyl)-2-hydroxy-2-[(5R,2R)-5-(2-cyclohexylethyloxy)-piperidin-2-yl]-ethyl}-acetamide hydrochloride | 439 |
| 66 | N-(1S,2R)-{1-(3,5-Difluoro-benzyl)-2-hydroxy-2-[(5R,2R)-5-(cyclopentylmethyloxy)-piperidin-2-yl]-ethyl}-acetamide hydrochloride | 411 |
| 67 | N-(1S,2R)-{1-(3,5-Difluoro-benzyl)-2-hydroxy-2-[(5R,2R)-5-(3,3-dimethylbutoxy)-piperidin-2-yl]-ethyl}-acetamide hydrochloride | 413 |
| 68 | N-(1S,2R)-{1-(3,5-Difluoro-benzyl)-2-hydroxy-2-[(5R,2R)-5-(2-methylbenzyloxy)-piperidin-2-yl]-ethyl}-acetamide hydrochloride | 433 |
| 69 | N-(1S,2R)-{1-(3,5-Difluoro-benzyl)-2-hydroxy-2-[(5R,2R)-5-((2-methylthiazol-2-yl)methoxy)-piperidin-2-yl]-2-hydroxyethyl-acetamide hydrochloride | 440 |
| 70 | N-(1S,2R)-{1-(3,5-Difluoro-benzyl)-2-hydroxy-2-[(5R,2R)-5-(4-methylbenzyloxy)-piperidin-2-yl]-ethyl}acetamide hydrochloride | 433 |
| 71 | N-(1S,2R)-{1-(3,5-Difluoro-benzyl)-2-hydroxy-2-[(5R,2R)-5-(2-chlorobenzyloxy)-piperidin-2-yl]-ethyl}-acetamide hydrochloride | 453 |
| 72 | N-(1S,2R)-{1-(3,5-Difluoro-benzyl)-2-hydroxy-2-[(5R,2R)-5-(3-chlorobenzyloxy)-piperidin-2-yl]-ethyl}-acetamide hydrochloride | 453 |
| 73 | N-(1S,2R)-{1-(3,5-Difluoro-benzyl)-2-hydroxy-2-[(5R,2R)-5-(4-chlorobenzyloxy)-piperidin-2-yl]-ethyl}-acetamide hydrochloride | 453 |

-continued

| EX | COMPOUND | MS(ES) (M + H) |
|---|---|---|
| 74 | N-(1S,2R)-{1-(3,5-Difluoro-benzyl)-2-hydroxy-2-[(5R,2R)-5-(2-trifluoromethylbenzyloxy)-piperidin-2-yl]-ethyl}-acetamide hydrochloride | 487 |
| 75 | N-(1S,2R)-{1-(3,5-Difluoro-benzyl)-2-hydroxy-2-[(5R,2R)-5-(3-trifluoromethylbenzyloxy)-piperidin-2-yl]-ethyl}-acetamide hydrochloride | 487 |
| 76 | N-(1S,2R)-{1-(3,5-Difluoro-benzyl)-2-hydroxy-2-[(5R,2R)-5-(4-trifluoromethylbenzyloxy)-piperidin-2-yl]-ethyl}-acetamide hydrochloride | 487 |
| 77 | N-(1S,2R)-{1-(3,5-Difluoro-benzyl)-2-hydroxy-2-[(5R,2R)-5-(4-tert-butylbenzyloxy)-piperidin-2-yl]-ethyl}-acetamide hydrochloride | 475 |
| 78 | N-(1S,2R)-{1-(3,5-Difluoro-benzyl)-2-hydroxy-2-[(5R,2R)-5-(2,6-difluorobenzyloxy)-piperidin-2-yl]-ethyl}-acetamide hydrochloride | 455 |
| 79 | N-(1S,2R)-{1-(3,5-Difluoro-benzyl)-2-hydroxy-2-[(5R,2R)-5-(2,6-dichlorobenzyloxy)-piperidin-2-yl]-ethyl}-acetamide hydrochloride | 487 |
| 80 | N-(1S,2R)-{1-(3,5-Difluoro-benzyl)-2-hydroxy-2-[(5R,2R)-5-(2-fluorobenzyloxy)-piperidin-2-yl]-ethyl}-acetamide hydrochloride | 437 |
| 81 | N-(1S,2R)-{1-(3,5-Difluoro-benzyl)-2-hydroxy-2-[(5R,2R)-5-(3-fluorobenzyloxy)-piperidin-2-yl]-ethyl}-acetamide hydrochloride | 437 |
| 82 | N-(1S,2R)-{1-(3,5-Difluoro-benzyl)-2-hydroxy-2-[(5R,2R)-5-(4-fluorobenzyloxy)-piperidin-2-yl]-ethyl}-acetamide hydrochloride | 437 |
| 83 | N-(1S,2R)-{1-(3,5-Difluoro-benzyl)-2-[(5R,2R)-5-(cyclohexylmethoxy)-piperidin-2-yl]-2-hydroxy-ethyl}-acetamide hydrochloride | 425 |
| 84 | N-(1S,2R)-{1-(3,5-Difluoro-benzyl)-2-[(5R,2R)-5-(cyclobutylmethoxy)-piperidin-2-yl]-2-hydroxy-ethyl}-acetamide hydrochloride | 397 |

EXAMPLE 85

N-(1S, 2R)-{1-(3,5-Difluoro-benzyl)-2-hydroxy-2-[(5R,2R)-5-pentyloxy-piperidin-2-yl]-ethyl}-acetamide hydrochloride Stir N-(1S,2R)-{1-(3,5-Difluoro-benzyl)-2-hydroxy-2-[(5R,2R)-5-pent-4-enyloxy-piperdin-2-yl]-ethyl}-acetamide hydrochloride (0.02 g, 0.04 mmol) and 10% Palladium on carbon (0.004 g, 0.004 mmol) in 2 mL methanol under a balloon of hydrogen at room temperature until all starting material is consumed. Filter the suspension through a pad of filtering agent and wash with methanol. Concentrate under reduced pressure to give the desired compound (0.015 g, 88%).

MS(ESI): m/z=399 (+H)$^+$

The compound of EXAMPLE 86 may be prepared essentially as described in EXAMPLE 85 beginning with N-(1S, 2R)-{2-[(5R,2R)-5-Allyloxy-piperidin-2-yl]-1-(3,5-Difluoro-benzyl)-2-hydroxy-ethyl}-acetamide hydrochloride.

| EX | COMPOUND | MS(ES) (M + H) |
|---|---|---|
| 86 | N-(1S,2R)-{1-(3,5-Difluoro-benzyl)-2-hydroxy-2-[(5R,2R)-5-propoxy-piperidin-2-yl]-ethyl}acetamide hydrochloride | 371 |

EXAMPLE 87

N-(1S, 2R)-{1-(3,5-Difluoro-benzyl)-2-hydroxy-2-[(2R)-4-(4-methylpentanoyl)-piperazin-2-yl]-ethyl}-4-methylpentanamide hydrochloride Combine 4-methyl-pentanoic acid (0.047 mL, 0.37 mmol), 2-(R)-[(2-(R)-amino-1-(S)-hydroxy-3-(3,5-difluoro-phenyl) propyl)]piperzine-1-carboxylic acid tert-butyl ester (63 mg, 0.17 mmol), 1-(3-dimethylaminopropyl)-3-ethylcarbodiimide hydrochloride (78 mg, 0.41 mmol), hydroxybenzotriazole (50 mg, 0.41 mmol), triethylamine (0.095 mL, 0.68 mmol), and 4-dimethylaminopyridine (4.6 mg, 0.04 mmol) in 2 mL dichloromethane. Stir at room temperature over night. Subject reaction mixture to silica gel chromatography, eluting with 97:3 dichloromethane:methanol. Stir residue in 4M HCl in 1,4-dioxane over night. Concentrate under reduced pressure to provide the title compound (39 mg, 49%) as a white solid.

MS(ES): m/z=468 (M+H)

The compounds of Formula I are inhibitors of BACE and thereby inhibit the production of A-β peptide which has been implicated in the pathology and progression of a number of neurodegenerative disorders, including Alzheimer's disease (See: Cumming, et al., *Current Opinion in Drug Discovery and Development,* 7(4), 536-556, (2004); and Varghese, et al., *Journal of Medicinal Chemistry,* 46(22), 4625 (2003)). Methods for determining the BACE inhibitory activity of compounds are well known in the art (See: Sinha, et al., *Science,* 286, 735 (1999); Turner, et al., Biochemistry, 40, 10001 (2001); Hom, et al., *Journal of Medicinal Chemistry,* 46, 1799 (2003); U.S. Pat. Nos. 5,744,346; 5,942,400; WO00/17369; WO00/03819; WO 03/040096; and WO 04/024081).

In vitro Assay Procedures:

For in vitro enzymatic and cellular assays, test compounds are prepared in DMSO to make up a 10 millimolar stock solution. The stock solution is serially diluted (in a 1:3, 1:2.5, 1:2, or 1:1 dilution series) in DMSO to obtain a final compound concentration of 10 millimolar to 1 micromolar at the first highest concentration of a ten-point dilution curve in a 96-well round-bottom plate right before conducting the in vitro enzymatic and whole assays.

In vitro Protease Inhibition Assays:

BACE1 mcaFRET Assay

Serial dilutions of test compounds are prepared as described above. Two microliter of each dilution is added to each well on row A to H of a corresponding low protein binding black plate to which 50 microliter of 50 millimolar ammonium acetate, pH 4.6, 1 mM Triton X-100, 1 mg/ml Bovine Serum Albumin, and 15 micromolar of FRET substrate (sequence: (MCA)-S-E-V-N-L-D-A-E-F-R-K(Dnp)-R-R-R-R-NH$_2$) for BACE1 activity are pre-added. The content is mixed well on a plate shaker for 10 min. Fifty microliter of two hundred picomolar human BACE1(1-460):Fc (See: Vasser, et al., *Science*, 286, 735-741 (1999)) in the same reaction buffer described above is added to the plate containing substrate and test compounds to initiate the reaction. The relative fluorescence unit (RFU) of the mixture at time 0 is recorded at excitation wavelength 330 nm and emission wavelength 400 nm, after brief mixing on a plate shaker. The reaction plate is covered with aluminum foil and kept in a dark humidified oven at room temperature for 16 to 24 hours. The RFU at the end of incubation is recorded with the same excitation and emission setting. The difference of the RFU at time 0 and the end of incubation represents the activity of BACE1 under the compound-treatment. The 10-point inhibition curve was plotted and fitted with the four-parameter logistic equation to obtain the $EC_{50}$ and $IC_{50}$ values. (See: Sinha, et al., *Nature*, 402, 537-540 (2000)). Representation compounds of Formula I were tested essentially as described above and exhibited an $IC_{50}$ for BACE1 of at least 15 µM. Data for selected compounds of the invention tested in this assay are contained in the following table.

| EXAMPLE | $IC_{50}$ (µM) |
|---|---|
| 3 | .001 |
| 7 | .003 |
| 19 | 13.1 |
| 55 | 6.9 |
| 58 | 6.8 |

BACE2 mcaFRET Assay

Serial dilutions of test compounds are prepared as described above. Two microliter of each dilution is added to each well on row A to H of a corresponding low protein binding black plate to which 50 microliter of 50 millimolar ammonium acetate, pH 4.6, 1 mM Triton X-100, 1 mg/ml Bovine Serum Albumin, and 15 micromolar of FRET substrate (sequence: (MCA)-S-E-V-N-L-D-A-E-F-R-K(Dnp)-R-R-R-R-$NH_2$) for BACE2 activity are pre-added. The content is mixed well on a plate shaker for 10 min. Fifty microliter of four hundred picomolar purified recombinant human BACE2(1-460):Fc in the same reaction buffer described above is added to the plate containing substrate and test compounds to initiate the reaction. The relative fluorescence unit (RFU) of the mixture at time 0 is recorded at excitation wavelength 330 nm and emission wavelength 400 nm brief mixing on a plate shaker. The reaction plate is covered with aluminum foil and kept in a dark humidified oven at room temperature for 16 to 24 hours. The RFU at the end of incubation is recorded with the same excitation and emission setting. The difference of the RFU at time 0 and the end of incubation represents the activity of BACE2 under the compound treatment. The 10-point inhibition curve was plotted and fitted with the four-parameter logistic equation to obtain the $EC_{50}$ and $IC_{50}$ values. Representative compounds of Formula I were tested essentially as described above and exhibited an $IC_{50}$ for BACE2 of at least 15 µM.

Expression of Human and Murine BACE1.

Both human (accession number: AF190725) and murine (accession number: NM_011792) BACE1 were cloned from total brain cDNA by room temperature-PCR. The nucleotide sequences corresponding to amino acid sequences #1 to 460 were inserted into the cDNA encoding human $IgG_1$ (Fc) polypeptide (Vassar et al. 1999). This fusion protein of BACE1(1-460) and human Fc, named huBACE1:Fc, was constructed into the pJB02 vector. Human BACE1(1-460):Fc (huBACE1:Fc) and murine BACE1(1-460):Fc (muBACE1:Fc) were transiently expressed in HEK293 cells. 250 µg cDNA of each construct was mixed with Fugene 6 and added to 1 liter HEK293 cells. Four days after the transfection, conditioned media were harvested for purification. Purification of huBACE1:Fc and muBACE1:Fc.

Conditioned media of HEK93 cell transiently transfected with huBACE1:Fc or muBACE1:Fc cDNA were collected. Cell debris was removed by filtering the conditioned media through 0.22 µm sterile filter. 5 ml Protein A-agarose (bed volume) was added to 4 liter conditioned media. This mixture was gently stirred overnight at 40° C. The Protein A-agarose resin was collected and packed into a low-pressure chromatography column. The column was washed with 20× bed volumes of PBS at flow rate 20 ml per hour. Bound huBACE1:Fc or muBACE1:Fc protein was eluted with 50 mM acetic acid, pH 3.6, at flow rate 20 ml per hour. 1 ml fractions of eluate were neutralized immediately with 0.5 ml 200 mM ammonium acetate, pH 6.5. The purity of final product was assessed by electrophoresis in 4-20% Tris-Glycine SDS-PAGE. The enzyme was stored at –80C in small aliquots.

Whole Cell Assay for Measuring the Inhibition of Beta-Secretase Activity

The routine whole cell assay for the measurement of inhibition of beta-secretase activity utilizes the human embryonic kidney cell line HEK293p (ATCC Accession No. CRL-1573) stably expressing a human APP751 cDNA containing the naturally occurring double mutation Lys651Met52 to Asn651Leu652, commonly called the Swedish mutation (noted HEK293/APP751sw) and shown to overproduce Abeta (Citron et al., 1992, *Nature* 360:672-674). Human embryonic kidney HEK293p cells stably expressing wild-type human APP751 cDNA (noted HEK293/APP751wt) are also used to assess the inhibition of beta-secretase activity. In vitro Aβ reduction assays have been described in the literature (See: Dovey, et al., *Journal of Neurochemistry*, 76, 173-181 (2001); Seubert, et al., *Nature*, 361, 260 (1993); and Johnson-Wood, et al., *Proc. Natl. Acad. Sci. USA*, 94, 1550-1555 (1997))

Cells (HEK293/APP751sw or HEK293/APP751wt, at $3 \times 10^4$ cells/well, containing 200 microliters culture media, DMEM containing 10% FBS) are incubated at 37C for 4 to 6 hours in the presence/absence of inhibitors (diluted in DMSO) at the desired concentration. At the end of the incubation, conditioned media are analyzed for beta-secretase activity, for example, by analysis of cleavage fragments, Abeta peptide and sAPPbeta. Abeta peptides are measured by a sandwich ELISA, using monoclonal 266 as a capture antibody and biotinylated 3D6 as reporting antibody. The sAPP-beta fragments are analyzed by a sandwich ELISA, using monoclonal 8E5 antibody as a capture antibody and rabbit polyclonal 192sw or 192wt as a reporting antibody. Note that sAPPbeta is the cleavage product of full length APP by BACE 1. The concentration of sAPPbeta released in the conditioned media following the compound treatment corresponds to the activity of BACE1 under such conditions. The 10-point inhibition curve was plotted and fitted with the four-parameter logistic equation to obtain the $EC_{50}$ and $IC_{50}$ values for the Abeta, sAPPbeta-lowering effect. Data for selected compounds of the invention tested in this assay are contained in the following table.

| EXAMPLE | IC$_{50}$ (µM) |
|---------|----------------|
| 3 | .041 |
| 7 | .045 |
| 19 | 17.1 |
| 55 | 6.1 |

In vivo Inhibition of Beta-Secretase

Several animal models, including mouse, guinea pig, dog, and monkey, may be used to screen for inhibition of beta-secretase activity in vivo following compound treatment. Animals used in this invention can be wild type, transgenic, or gene knockout animals. For example, the PDAPP mouse model, prepared as described in Ganes et al., 1995, *Nature* 373:523-527, and other non-transgenic or gene knockout animals are useful to analyze in vivo inhibition of Abeta and sAPPbeta production in the presence of inhibitory compounds. Generally, 4 to 12 month old PDAPP mice, gene knockout mice or non-transgenic animals are administered compound formulated in vehicles, such as corn oil, cyclodextran, phosphate buffers, Pharmasolve, or other suitable vehicles. One to twenty-four hours following the administration of compound, animals are sacrificed, and brains as well as plasma are removed for analysis of Abeta and sAPP fragments. (See: Dovey, et al., *Journal of Neurochemistry*, 76, 173-181 (2001); and Johnson-Wood, et al., *Proc. Natl. Acad. Sci. USA*, 94, 1550-1555 (1997))

Beginning at time 0, brain tissue, plasma or cerebrospinal fluid is obtained from selected animals and analyzed for the presence of APP cleavage peptides, including Abeta peptides, sAPPbeta and other APP fragments, for example, by specific sandwich ELISA assays. At the end of the test period, animals are sacrificed and brain tissues, plasma or cerebrospinal fluid are analyzed for the presence of Abeta peptide and sAPPbeta. Brain tissues of APP transgenic animals are also analyzed for the amount of beta-amyloid plaques following compound treatment.

Animals (PDAPP or other APP transgenic mice) administered an inhibitory compound may demonstrate the reduction of Abeta or sAPPbeta in brain tissues, plasma or cerebrospinal fluids and decrease of beta amyloid plaques in brain tissue, as compared with vehicle-treated controls. Animals (PDAPP or other APP transgenic mice) administered the inhibitory compounds of the invention may also show improvement in cognitive behavioral assessments for learning and memory tasks.

Oral administration of the compounds of the present invention is preferred. However, oral administration is not the only route or even the only preferred route. For example, transdermal administration may be very desirable for patients who are forgetful or petulant about taking oral medicine, and the intravenous route may be preferred as a matter of convenience or to avoid potential complications related to oral administration. Compounds of Formula I may also be administered by the percutaneous, intramuscular, intranasal or intrarectal route in particular circumstances. The route of administration may be varied in any way, limited by the physical properties of the drugs, the convenience of the patient and the caregiver, and other relevant circumstances (*Remington's Pharmaceutical Sciences*, 18th Edition, Mack Publishing Co. (1990)).

The pharmaceutical compositions are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations of the present invention may be determined by methods well known to the skilled artisan.

The tablets, pills, capsules, troches, and the like may also contain one or more of the following adjuvants: binders such as povidone, hydroxypropyl cellulose, microcrystalline cellulose, or gelatin; excipients or diluents such as: starch, lactose, microcrystalline cellulose or dicalcium phosphate, disintegrating agents such as: croscarmellose, crospovidone, sodium starch glycolate, corn starch and the like; lubricants such as: magnesium stearate, stearic acid, talc or hydrogenated vegetable oil; glidants such as colloidal silicon dioxide; wetting agents such as: sodium lauryl sulfate and polysorbate 80; and sweetening agents such as: sucrose, aspartame or saccharin may be added or a flavoring agent such as: peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, as coatings. Thus, tablets or pills may be coated with sugar, hydroxypropyl methylcellulose, polymethacrylates, or other coating agents. Syrups may contain, in addition to the present compounds, sucrose as a sweetening agent and certain preservatives, dyes and colorings and flavors. Materials used in preparing these various compositions should be pharmaceutically pure and non-toxic in the amounts used.

The compounds of Formula I are generally effective over a wide dosage range. For example, dosages per day normally fall within the range of about 0.0001 to about 30 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

In order to achieve or maintain appropriate levels of the compounds of Formula I in the brain of an afflicted mammal, it may be necessary or desirable to co-administer an effective amount of an inhibitor of P-glycoprotein (P-gp). P-gp inhibitors and the use of such compounds are known to those skilled in the art. (See: *Cancer Research*, 53, 4595 (1993); *Clin. Cancer Res.*, 2, 7 (1996); *Cancer Research*, 56, 4171 (1996); WO99/64001; and WO01/10387).

The P-gp inhibitor may be administered in any manner that achieves a sufficient degree of inhibition of P-gp to achieve or maintain sufficient levels of the compounds of Formula I for effective BACE inhibition in the brain of an afflicted mammal. As such, the P-gp inhibitor may be administered separately before, during, or after the administration of a compound of Formula I. Furthermore, if desirable, the P-gp inhibitor may be formulated with a compound of Formula I. These formulations and methods represent further embodiments of the present invention.

Many suitable P-gp inhibitors are known today and undoubtably others will be identified in the future. Suitable P-gp inhibitors include cyclosporin A, verapamil, tamoxifen, quinidine, Vitamin E-TGPS, ritonavir, megestrol acetate, progesterone, rapamycin, 10, 11-methanodibenzosuberane, phenothiazines, acridine derivatives such as GF120918, FK506, VX-710, LY355979, PSC-833, GF-102,918 and other steroids.

We claim:

1. A compound of Formula I:

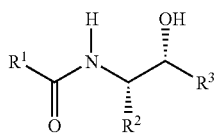

where:
$R^1$ is $C_1$-$C_6$ alkyl
$R^2$ is benzyl optionally monosubstituted in the phenyl ring with a substituent selected from the group consisting of halo, or benzyl optionally disubstituted in the phenyl ring with a first substituent independently selected from halo and a second substituent independently selected from halo,
$R^3$ is:
  i) a piperidin-2-yl moiety of formula:

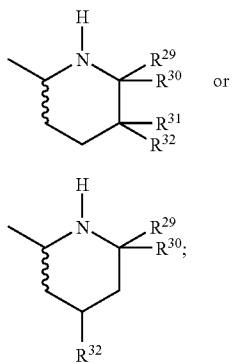

ii) a tetrahydropyridin-2-yl moiety of formula:

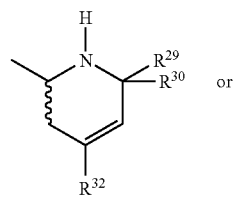

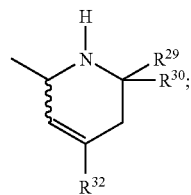

$R^{29}$ is hydrogen or $C_1$-$C_6$ alkyl;
$R^{30}$ is hydrogen or $C_1$-$C_6$ alkyl;
$R^{29}$ and $R^{30}$ taken together with the carbon to which they are attached form a $C_3$-$C_6$ cycloalkyl ring;
$R^{31}$ is hydrogen, $C_1$-$C_6$ alkyl, $C_3$-$C_6$ cycloalkyl, or phenyl optionally monosubstituted with $C_1$-$C_6$ alkyl;
$R^{32}$ is hydrogen, $R^{33}$, or —$(CH_2)_{0-2}$—$OR^{33}$;
$R^{33}$ is $C_1$-$C_{10}$ alkyl optionally substituted with 1-6 fluorine atoms, $C_2$-$C_6$ alkenyl, $C_2$-$C_6$ alkynyl, or —$(CH_2)_{0-3}$—$R^{34}$;
$R^{34}$ is $C_3$-$C_7$ cycloalkyl or phenyl each optionally substituted with one or two substituents independently selected from the group consisting of halo, $C_1$-$C_6$ alkyl, $C_1$-$C_6$ alkoxy, hydroxy, trifluoromethyl, and trifluoromethoxy, thienyl optionally substituted with halo, benzothienyl optionally substituted with halo, or thiazolyl optionally substituted with $C_1$-$C_4$ alkyl, or adamantyl;

or a pharmaceutically acceptable salt thereof.

2. A pharmaceutical composition comprising a compound of claim 1, in combination with a pharmaceutically acceptable carrier, diluent, or excipient.

3. A compound of claim 1 wherein $R^1$ is methyl.

4. A compound of claim 1 wherein $R^2$ is benzyl optionally monosubstituted or disubstituted in the phenyl ring with fluoro.

* * * * *

UNITED STATES PATENT AND TRADEMARK OFFICE
CERTIFICATE OF CORRECTION

| | |
|---|---|
| PATENT NO. | : 7,618,978 B2 |
| APPLICATION NO. | : 10/599125 |
| DATED | : November 17, 2009 |
| INVENTOR(S) | : Bueno Melendo et al. |

Page 1 of 1

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 398 days.

Delete the phrase "by 398 days" and insert -- by 423 days --

Signed and Sealed this

Eleventh Day of May, 2010

David J. Kappos
*Director of the United States Patent and Trademark Office*